(12) United States Patent
Dever et al.

(10) Patent No.: US 11,634,732 B2
(45) Date of Patent: *Apr. 25, 2023

(54) PHARMACEUTICAL COMPOSITIONS COMPRISING GENE-CORRECTED PRIMARY CELLS

(71) Applicant: The Board of Trustees of the Leland Stanford Junior University, Stanford, CA (US)

(72) Inventors: Daniel P. Dever, Stanford, CA (US); Rasmus O. Bak, Stanford, CA (US); Ayal Hendel, Stanford, CA (US); Waracharee Srifa, Stanford, CA (US); Matthew H. Porteus, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/502,479

(22) Filed: Oct. 15, 2021

(65) Prior Publication Data

US 2022/0064676 A1 Mar. 3, 2022

Related U.S. Application Data

(63) Continuation of application No. 15/927,750, filed on Mar. 21, 2018, now Pat. No. 11,193,141, which is a continuation of application No. PCT/US2016/053344, filed on Sep. 23, 2016.

(60) Provisional application No. 62/357,832, filed on Jul. 1, 2016, provisional application No. 62/332,431, filed on May 5, 2016, provisional application No. 62/232,713, filed on Sep. 25, 2015.

(51) Int. Cl.

| | |
|---|---|
| *C12N 15/85* | (2006.01) |
| *C12N 15/90* | (2006.01) |
| *C12N 9/22* | (2006.01) |
| *C07K 14/805* | (2006.01) |
| *A61K 35/28* | (2015.01) |
| *A61K 48/00* | (2006.01) |
| *C12N 5/0789* | (2010.01) |
| *A61P 7/00* | (2006.01) |
| *A61K 31/7115* | (2006.01) |
| *C12N 5/0781* | (2010.01) |
| *C12N 5/0783* | (2010.01) |
| *C12N 5/0775* | (2010.01) |
| *C12N 15/113* | (2010.01) |
| *C12N 15/864* | (2006.01) |

(52) U.S. Cl.
CPC ........ *C12N 15/907* (2013.01); *A61K 31/7115* (2013.01); *A61K 35/28* (2013.01); *A61K 48/00* (2013.01); *A61P 7/00* (2018.01); *C07K 14/805* (2013.01); *C12N 5/0635* (2013.01); *C12N 5/0636* (2013.01); *C12N 5/0647* (2013.01); *C12N 5/0665* (2013.01); *C12N 9/22* (2013.01); *C12N 15/113* (2013.01); *C12N 15/85* (2013.01); *C12N 15/8645* (2013.01); *C12N 2310/20* (2017.05); *C12N 2310/311* (2013.01); *C12N 2310/313* (2013.01); *C12N 2310/3125* (2013.01); *C12N 2750/14143* (2013.01)

(58) Field of Classification Search
None
See application file for complete search history.

(56) References Cited

U.S. PATENT DOCUMENTS

| | | |
|---|---|---|
| 8,349,810 B2 | 1/2013 | Miller et al. |
| 8,673,557 B2 | 3/2014 | Scharenberg et al. |
| 8,865,406 B2 | 10/2014 | Zhang et al. |
| 8,889,418 B2 | 11/2014 | Zhang et al. |
| 8,895,308 B1 | 11/2014 | Zhang et al. |
| 9,434,776 B2 | 9/2016 | Ando et al. |
| 9,605,277 B2 | 3/2017 | Angel et al. |

(Continued)

FOREIGN PATENT DOCUMENTS

| | | |
|---|---|---|
| WO | 2012018726 A1 | 2/2012 |
| WO | 2014189781 A1 | 11/2014 |

(Continued)

OTHER PUBLICATIONS

Translation of WO 2014/188043 pp. 1-25 (Year: 2014).*
Cord-Blood Cells Made Plentiful, Research Highlights, Nature, vol. 513, Sep. 25, 2014, pp. 462-463.
Hendel et al., "Chemically Modified Guide RNAS Enhance CRISPR-Cas Genome Editing in Human Primary Cells," Nature Biotechnology, vol. 33, No. 9, Sep. 2015, pp. 985-989.

(Continued)

*Primary Examiner* — Marcia S Noble
(74) *Attorney, Agent, or Firm* — Kilpatrick Townsend & Stockton LLP

(57) ABSTRACT

In certain aspects, the present invention provides methods for inducing a stable gene modification of a target nucleic acid via homologous recombination in a primary cell, such as a primary blood cell and/or a primary mesenchymal cell. In certain other aspects, the present invention provides methods for enriching a population of genetically modified primary cells having targeted integration at a target nucleic acid. The methods of the present invention rely on the introduction of a DNA nuclease such as a Cas polypeptide and a homologous donor adeno-associated viral (AAV) vector into the primary cell to mediate targeted integration of the target nucleic acid. Also provided herein are methods for preventing or treating a disease in a subject in need thereof by administering to the subject any of the genetically modified primary cells or pharmaceutical compositions described herein to prevent the disease or ameliorate one or more symptoms of the disease.

15 Claims, 74 Drawing Sheets

Specification includes a Sequence Listing.

(56) References Cited

U.S. PATENT DOCUMENTS

| | | | |
|---|---|---|---|
| 9,616,090 | B2 | 4/2017 | Conway et al. |
| 9,631,186 | B2 | 4/2017 | Wang |
| 9,822,370 | B2 | 11/2017 | Musunuru et al. |
| 9,877,988 | B2 | 1/2018 | Rebar |
| 9,956,247 | B2 | 5/2018 | Rebar |
| 9,957,526 | B2 | 5/2018 | Holmes et al. |
| 10,006,052 | B2 | 6/2018 | Jarjour et al. |
| 10,006,053 | B2 | 6/2018 | Baltimore et al. |
| 10,072,066 | B2 | 9/2018 | Liu et al. |
| 10,196,651 | B2 | 2/2019 | Conway et al. |
| 10,208,319 | B2 | 2/2019 | Musunuru et al. |
| 10,293,000 | B2 | 5/2019 | Rebar |
| 10,337,001 | B2 | 7/2019 | Ryan et al. |
| 10,369,232 | B2 | 8/2019 | Chivukula et al. |
| 10,385,359 | B2 | 8/2019 | Lee et al. |
| 10,435,677 | B2 | 10/2019 | Cost et al. |
| 10,604,771 | B2 | 3/2020 | Cannon et al. |
| 10,738,305 | B2 | 8/2020 | Porteus |
| 10,745,714 | B2 | 8/2020 | Gersbach et al. |
| 10,767,175 | B2 | 9/2020 | Dellinger et al. |
| 10,820,580 | B2 | 11/2020 | Shen et al. |
| 10,900,034 | B2 | 1/2021 | Ryan et al. |
| 11,193,141 | B2 | 12/2021 | Dever et al. |
| 11,492,646 | B2 | 11/2022 | Dever et al. |
| 2005/0244970 | A1 | 11/2005 | Zhang et al. |
| 2013/0280222 | A1 | 10/2013 | Kay et al. |
| 2014/0068797 | A1 | 3/2014 | Doudna et al. |
| 2014/0186919 | A1 | 7/2014 | Zhang et al. |
| 2014/0271573 | A1 | 9/2014 | Brandan et al. |
| 2014/0273226 | A1 | 9/2014 | Wu |
| 2014/0302563 | A1 | 10/2014 | Doudna et al. |
| 2014/0356959 | A1 | 12/2014 | Church et al. |
| 2015/0059010 | A1 | 2/2015 | Cigan et al. |
| 2016/0024474 | A1 | 1/2016 | Conway et al. |
| 2016/0289675 | A1 | 10/2016 | Ryan et al. |
| 2018/0051281 | A1 | 2/2018 | Ryan et al. |
| 2018/0119140 | A1 | 5/2018 | Porteus et al. |
| 2019/0032091 | A1 | 1/2019 | Dever et al. |
| 2019/0144888 | A1 * | 5/2019 | Townes .................. A61P 7/00 424/93.21 |
| 2020/0131539 | A1 | 4/2020 | Bak et al. |
| 2022/0025408 | A1 | 1/2022 | Dever et al. |
| 2022/0025409 | A1 | 1/2022 | Dever et al. |

FOREIGN PATENT DOCUMENTS

| | | | | |
|---|---|---|---|---|
| WO | WO-2014188043 | A2 * | 11/2014 | ........... A61K 31/138 |
| WO | 2015057980 | A1 | 4/2015 | |
| WO | 2016089433 | A1 | 6/2016 | |
| WO | 2016094880 | A1 | 6/2016 | |
| WO | 2016164356 | A1 | 10/2016 | |
| WO | 2017053729 | A1 | 3/2017 | |

OTHER PUBLICATIONS

Application No. PCT/US2016/053344, International Search Report and Written Opinion, dated Jan. 19, 2017, 18 pages.
Vasileva et al., "Homologous Recombination is Required for AAV-Mediated Gene Targeting," Nucleic Acids Research, vol. 34, No. 11, 2006, pp. 3345-3360.
Threlfall et al., "Synthesis and Biological Activity of Phosphonoacetate- and Thiophosphonoacetate-modified 2'-O-methyl Oligoribonucleotides," Org. Biomol. Chem., vol. 10, 2012, pp. 746-754.
Yoo et al., "2'-O-Methyl-Modified Phosphorothioate Antisense Oligonucleotides have Reduced Non-specific Effects in Vitro," Nucleic Acid Research, vol. 32, No. 6, Apr. 2, 2004, pp. 2008-2016.
Park et al., Therapeutic Crispr/Cas9 Genome Editing for Treating Sickle Cell Disease, Blood, Dec. 2016, 128(22):4703, 3 pages.
Park et al., CRISPR/Cas9 gene editing for curing sickle cell disease, Transfus Apher Sci., Feb. 2021, 60(1):103060, pp. 1-18.
Zeballos et al., Next-Generation CRISPR Technologies and Their Applications in Gene and Cell Therapy, Trends in Biotechnology, Jul. 2021, vol. 39, No. 7, pp. 692-705.
Sun et al., "Seamless Correction of the Sickle Cell Disease Mutation of the HBB Gene in Human Induced Pluripotent Stem Cells Using TALENs," Biotechnology and Bioengineering; vol. 111; Issue 5, Aug. 2013, pp. 1048-1053.

* cited by examiner

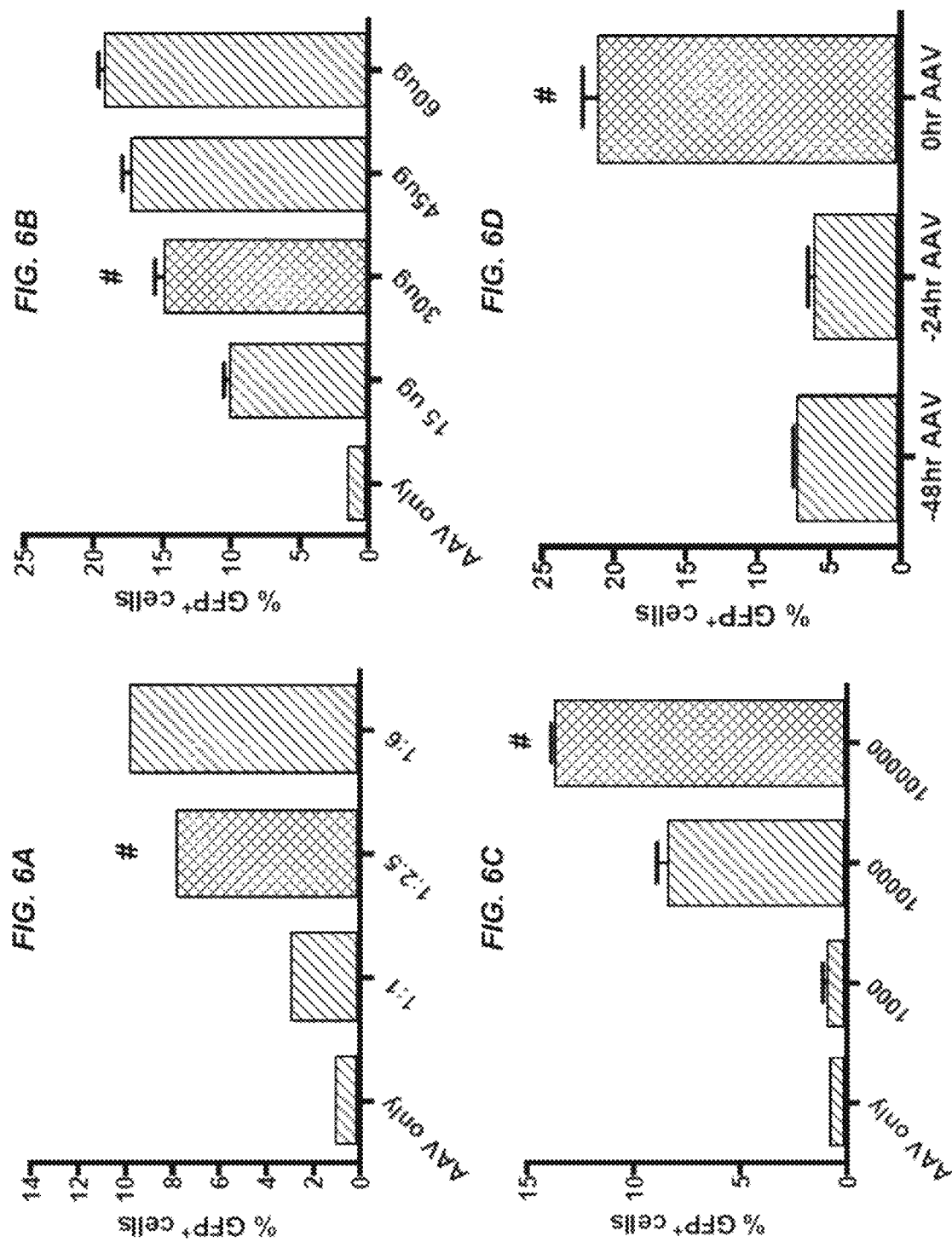

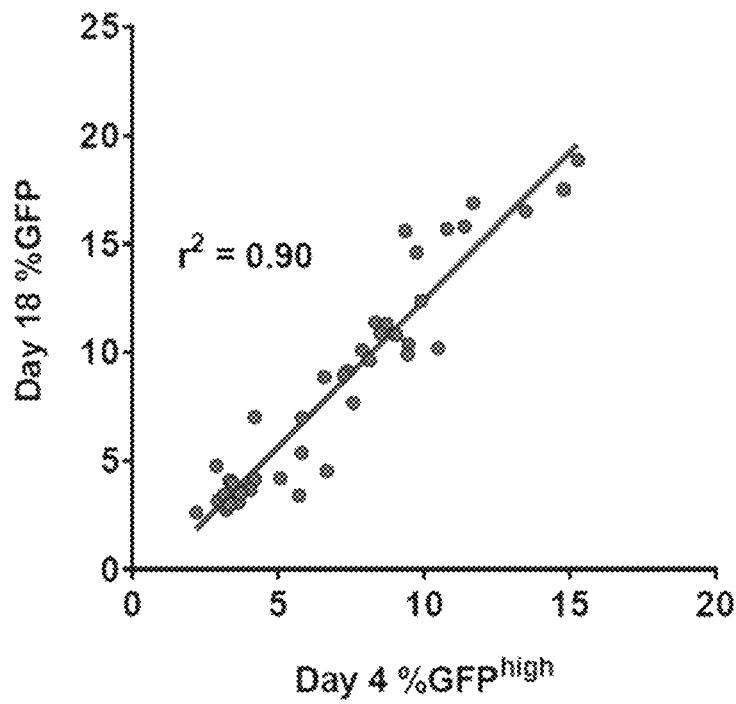
FIG. 13A  HBB
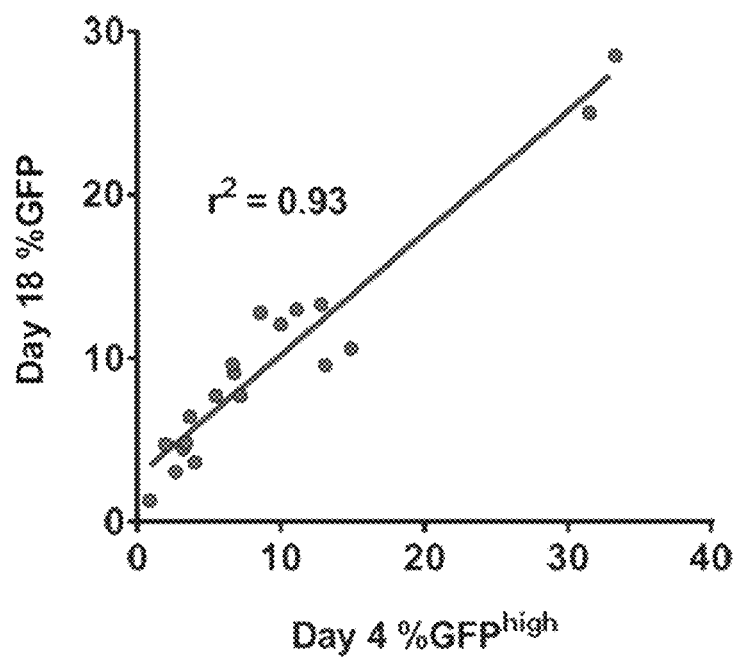
FIG. 13B  CCR5

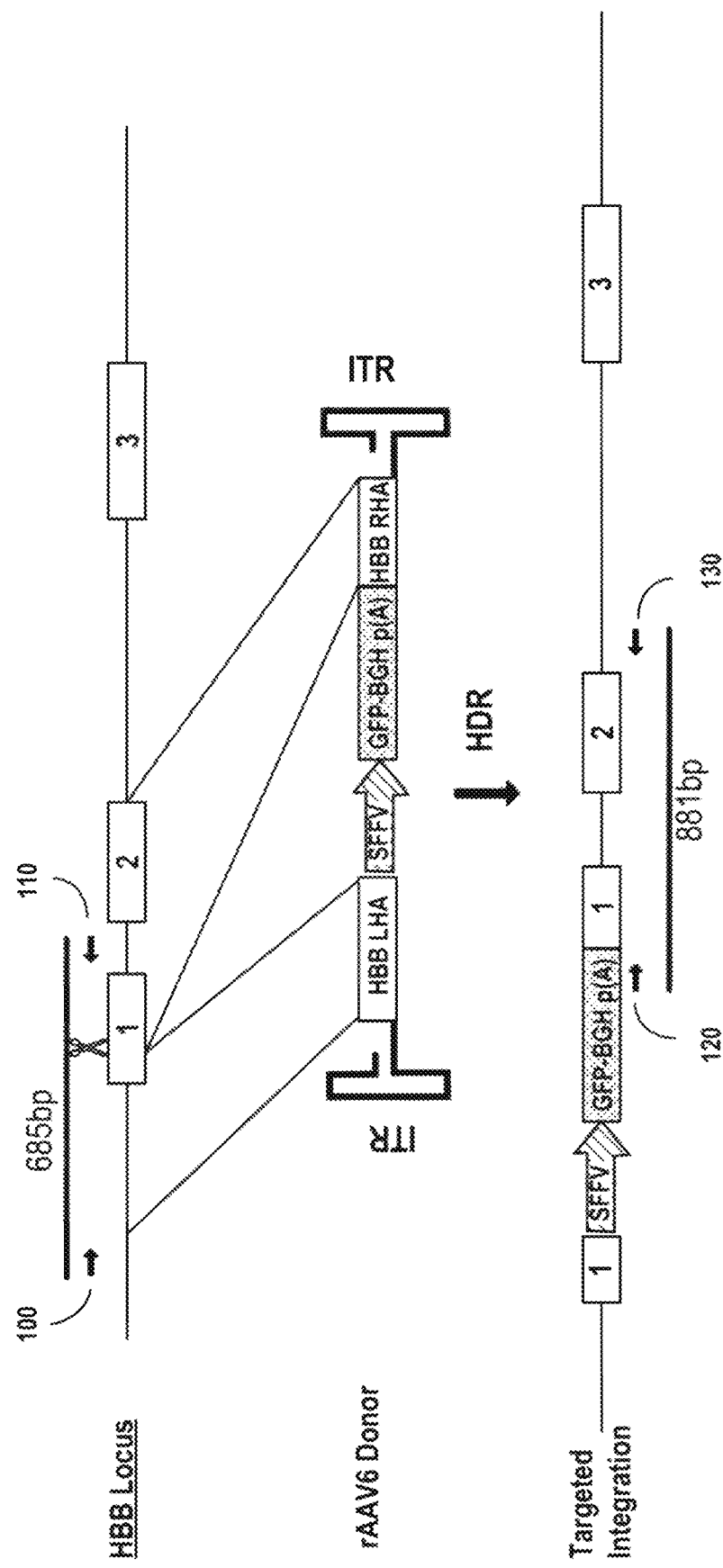

FIG. 19A
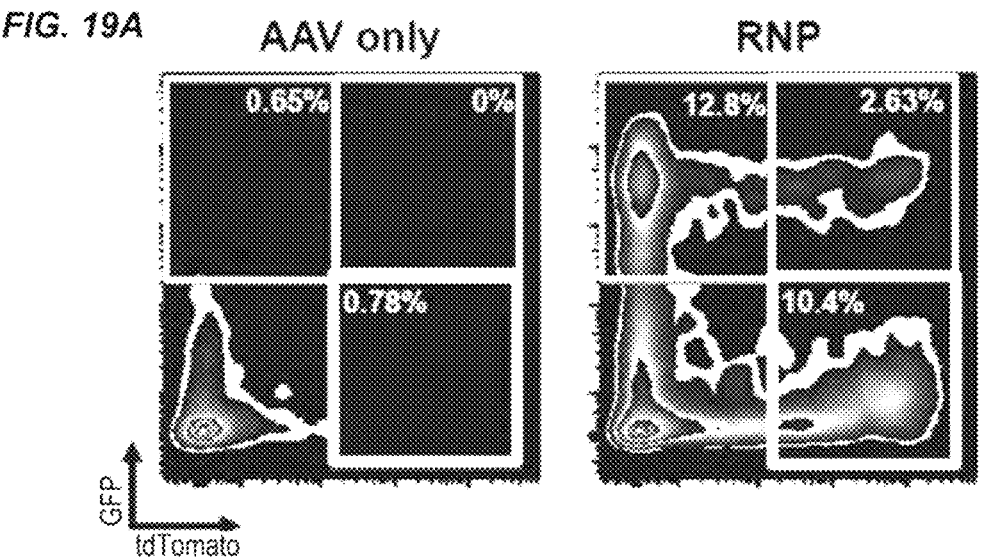
FIG. 19B
Total targeting frequency = 25.8%
Green/Red + Red/Green = 2.63%
Assumption: Green/Green + Red/Red = 2.63%
% biallelic in targeted cells: (5.26/25.8) x 100 = 20.4%
FIG. 19C
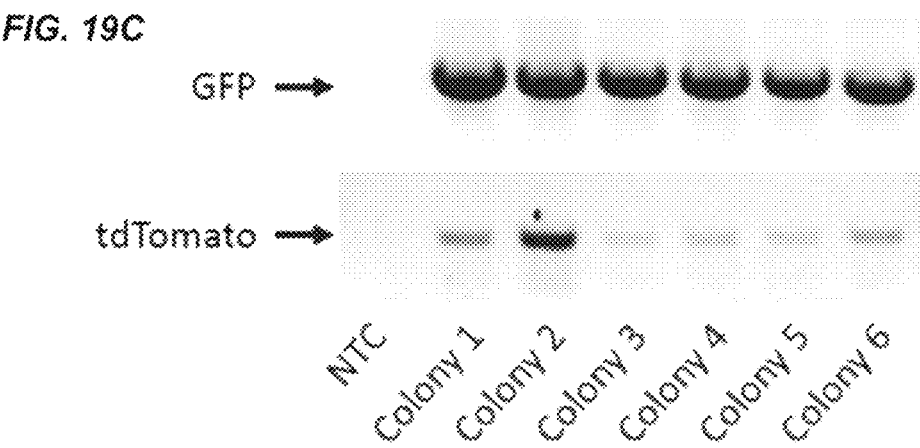

| Locus | Transgene | # of clones with DNA | # of clones with on-target HDR event | # of clones with no HR event | # of clones with unknown event | % of Clones with on-target integration |
|---|---|---|---|---|---|---|
| HBB | GFP | 95 | 87 | 4 | 4 | 91.6% |
| CCR5 | GFP | 115 | 115 | 0 | 0 | 100% |
| CCR5 | tNGFR | 223 | 221 | 0 | 2 | 99.1% |
| IL2RG | GFP | 177 | 164 | 4 | 13 | 92.9% |
| Dual (HBB and CCR5) | GFP and mCherry | 57 | 50 (both loci) | 6 (at least 1 locus) | 1 | 87.7% |

*FIG. 20*

| Sample Name | % engraftment (average per mouse) | % GFP+ cells in human cells (average per mouse) | Total live cells injected per mouse (average per mouse) | Average total HSCs injected per mouse (CD34+/CD38-/CD90+/CD45RA-) | Estimated total modified human cells in BM per mouse at week 16 |
|---|---|---|---|---|---|
| RNP | 6.99 (+/-1.8) | 3.46 (+/-0.82) | 500,000 | 24,000 (+/-1100) | 270,000 (+/-33,000) |
| RNP GFP high | 1.67 (+/-1.0) | 78.8 (+/-10.6) | 350,000 100,000 x1 250,000 x2 500,000 x3 | 2,900 (+/-770) | 1,460,000 (+/-390,000) |

*FIG. 24*

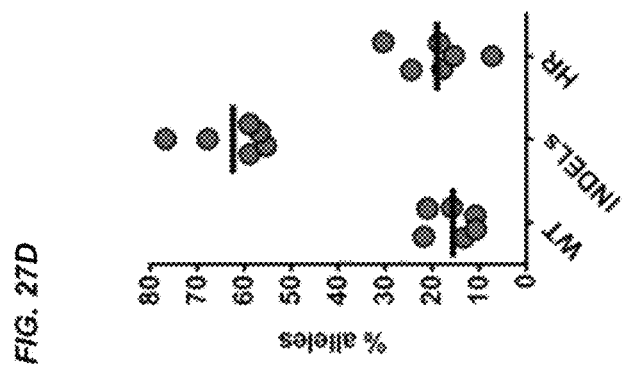
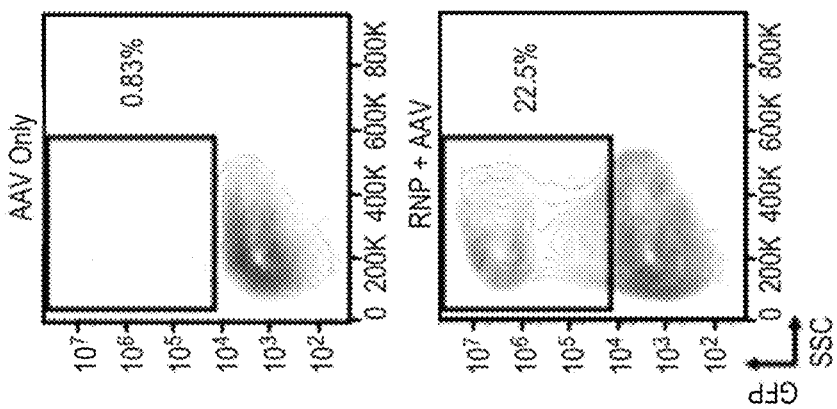
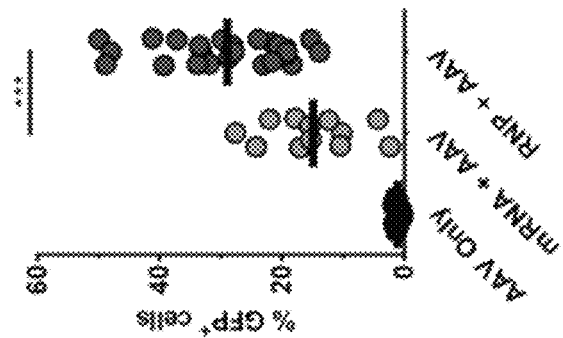

HBB: CTTGCCCCACAGGGCAGTAACGG
Off: TCAGCCCCACAGGGCAGTAAGGG

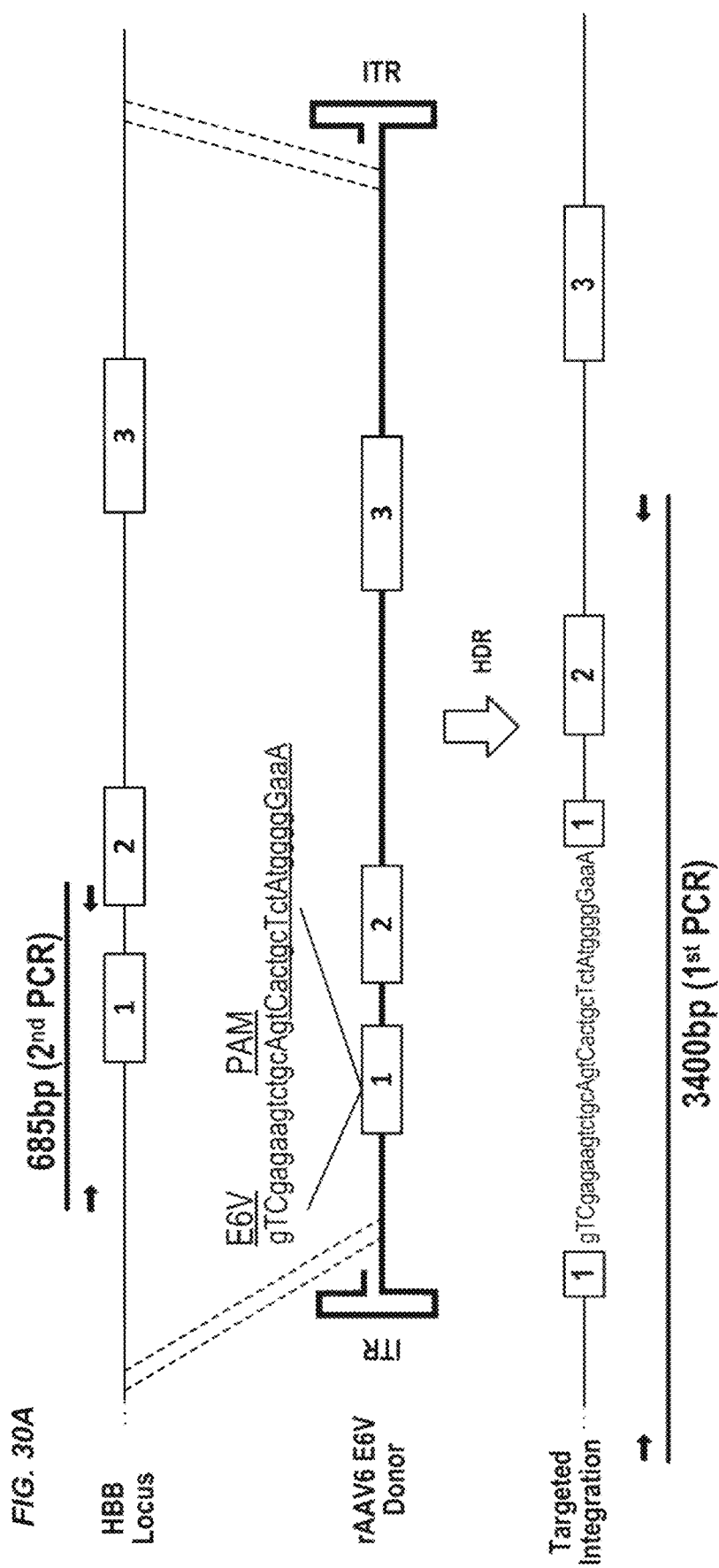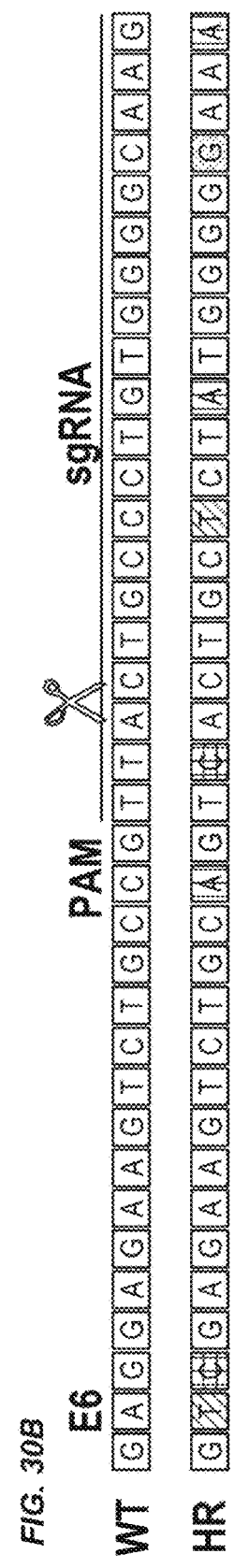
FIG. 30A
FIG. 30B

| Sample Name | % engraftment (average per mouse) | % GFP+ cells among human cells (average per mouse) | Total live cells injected per mouse (average per mouse) | Average total HSCs injected per mouse (CD34+/CD38-/CD90+/CD45RA-) | Estimated total modified human cells in BM per mouse at Week 16 |
|---|---|---|---|---|---|
| RNP+AAV | 6.99 (+/-1.8) | 3.46 (+/-0.82) | 500,000 | 24,000 (+/-1100) | 270,000 (+/-33,000) |
| RNP+AAV GFPhigh | 1.67 (+/-1.0) | 78.8 (+/-10.6) | 350,000 100,000 x 1 250,000 x 2 500,000 x 3 | 2,900 (+/-770) | 1,460,000 (+/-390,000) |

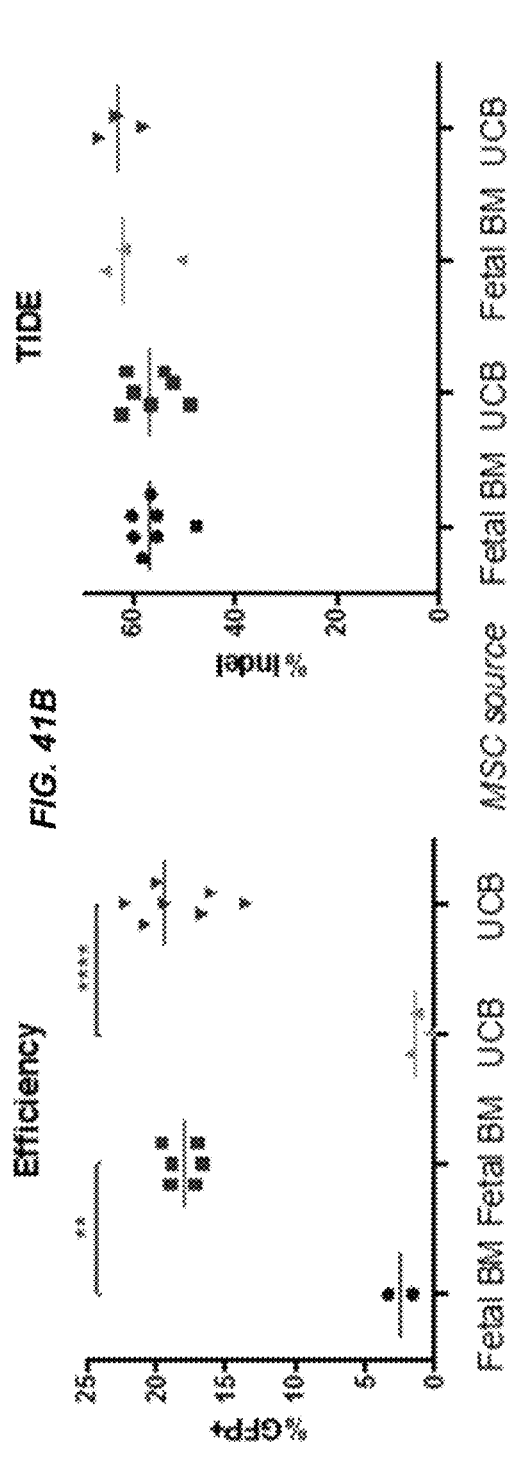

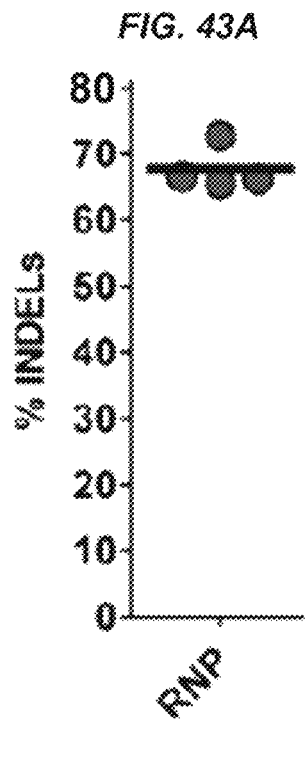 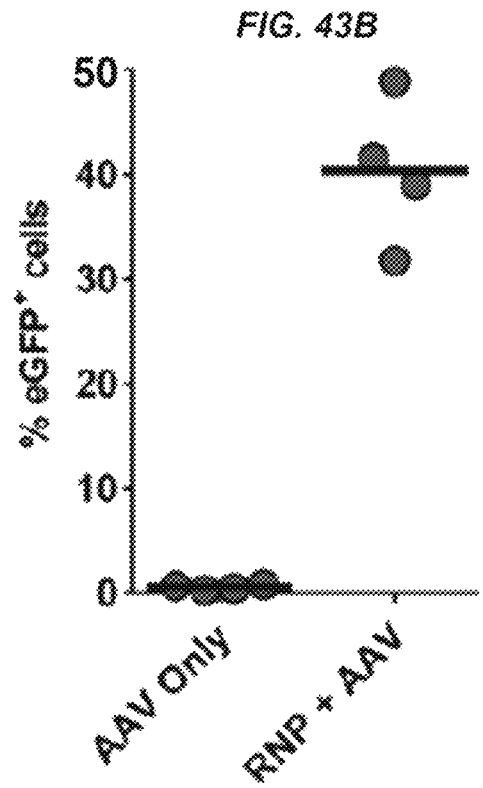
FIG. 43A   FIG. 43B
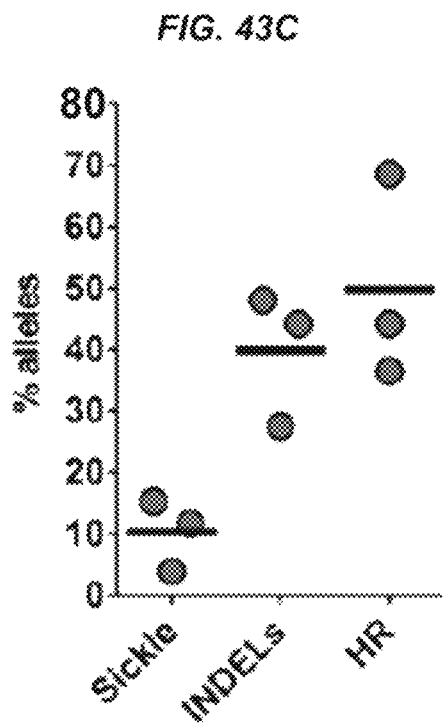 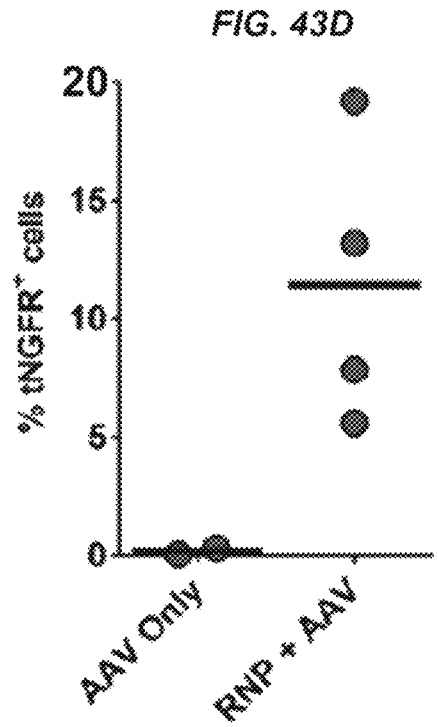
FIG. 43C   FIG. 43D

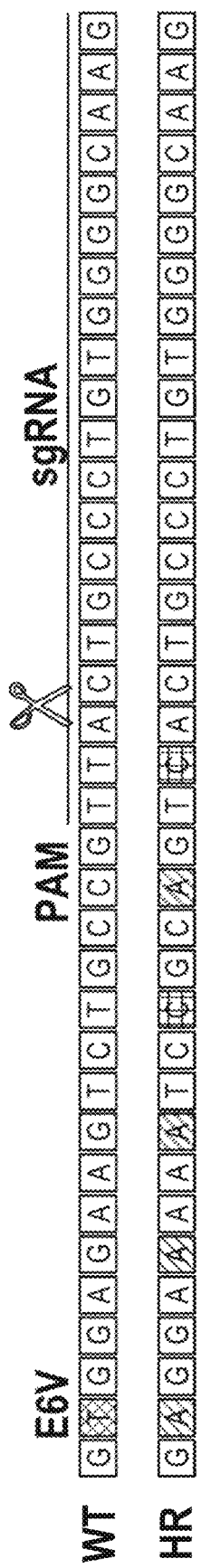
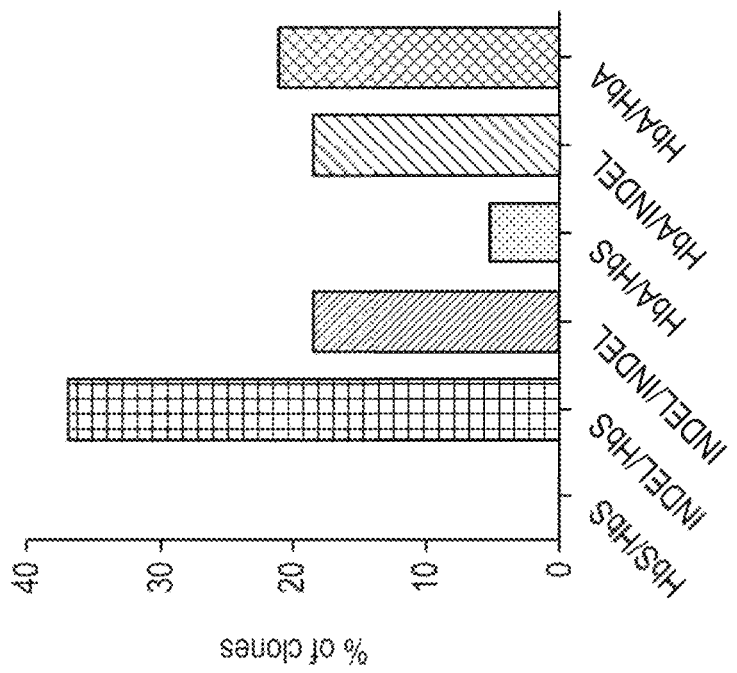
FIG. 45A
FIG. 45B

FIG. 47

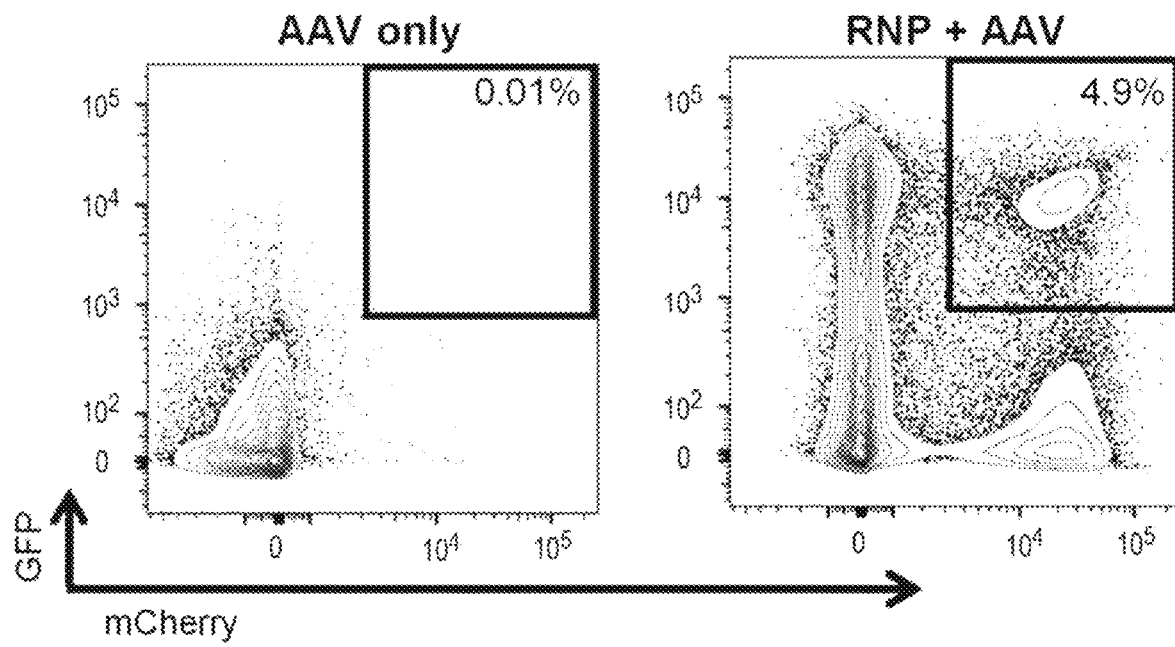
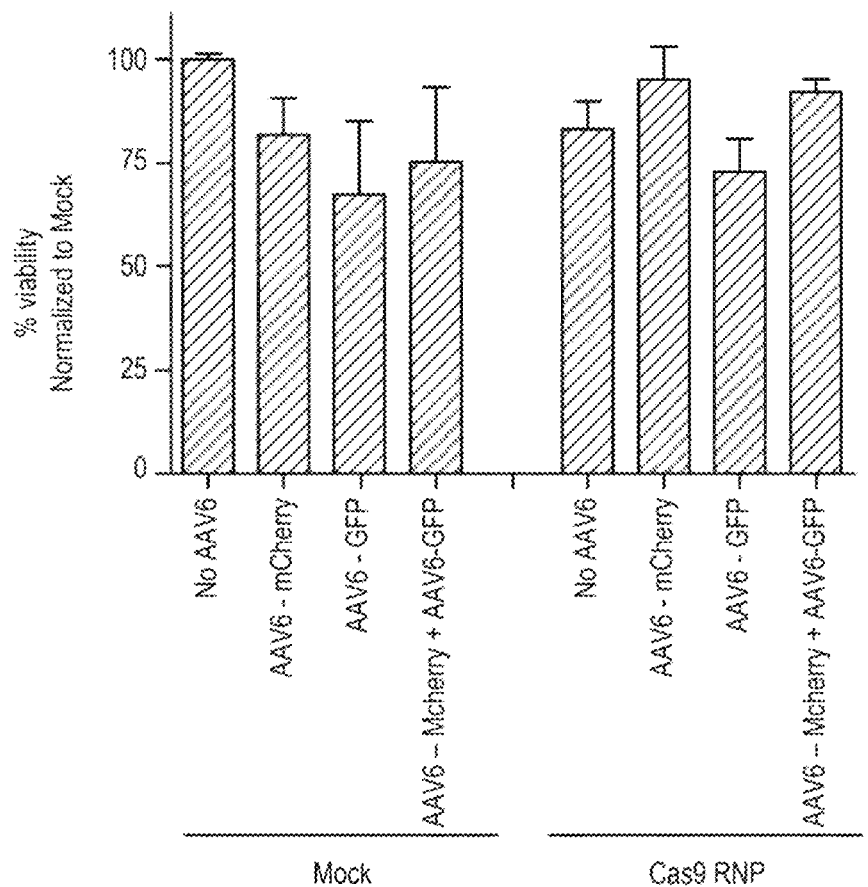

PHARMACEUTICAL COMPOSITIONS COMPRISING GENE-CORRECTED PRIMARY CELLS

CROSS-REFERENCE TO RELATED APPLICATIONS

The present application is a continuation of U.S. application Ser. No. 15/927,750 filed Mar. 21, 2018, which is a continuation of International Application No. PCT/US2016/053344 filed Sep. 23, 2016, which claims priority to U.S. Provisional Application No. 62/232,713 filed Sep. 25, 2015, U.S. Provisional Application No. 62/332,431 filed May 5, 2016, and U.S. Provisional Application No. 62/357,832 filed Jul. 1, 2016, the disclosures of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support under contracts A1097320 and EY018244 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Oct. 8, 2021, is named 079445-000760US-1271467 SL.txt and is 38,118 bytes in size.

BACKGROUND OF THE INVENTION

The development of genome editing using engineered nucleases is the foundation for the idea that ex vivo gene correction constitutes a viable therapeutic strategy for both genetic and non-genetic diseases (Naldini, *Nature Reviews. Genetics,* 12, 301-315 (2011)). While construction of zinc-finger nucleases (ZFNs), transcription-activator-like effector nucleases (TALENs), and meganuclease/TALEN hybrids (megaTALs) is possible (Carroll, *Annual Review of Biochemistry,* 83, 409-439 (2014); Porteus, *Genome Biology* 16, 286 (2015)), the RNA-guided endonuclease of the CRISPR/Cas9 system can be easily engineered to create site-specific double-strand breaks (Jinek et al., *Science,* 337, 816-821 (2012); Mali et al., *Science,* 339, 823-826 (2013); Cong et al., *Science,* 339, 819-823 (2013)) (DSBs). CRISPR/Cas9 consists of the Cas9 endonuclease and a 100-nucleotide (nt) single guide RNA (sgRNA). Target identification relies on RNA-DNA Watson-Crick hybridization between a 20-nucleotide stretch of the sgRNA and the DNA target site, which then guides Cas9 to cleave both DNA strands. DSB formation subsequently triggers one of two highly conserved competing repair mechanisms, canonical non-homologous end-joining (NHEJ) or homologous recombination (HR) (Kass and Jasin, *FEBS Letters,* 584, 3703-3708 (2010)). Through the iterative cycle of break and NHEJ repair, insertions and/or deletions (INDELs) can be created at the site of the break. In contrast, genome editing by HR requires the delivery of a donor molecule to serve as an undamaged DNA molecule that the HR machinery uses to repair the break by a 'copy and paste' method (Porteus, *Genome Biology,* 16, 286 (2015)). For gene editing purposes, the HR pathway can be exploited to make precise nucleotide changes in the genome (Porteus and Baltimore, *Science,* 300, 763 (2003)). Using this strategy, disease-causing mutations can be replaced or entire open reading frames (ORFs) can be inserted at specific sites. One of the attractive features of precise genome editing rather than lentiviral gene transfer is that endogenous promoters, regulatory elements, and enhancers can be preserved to mediated precise spatiotemporal gene expression (Naldini, *Nature Reviews Genetics,* 12, 301-315 (2011); Woods et al., *Nature,* 440, 1123 (2006)).

Hematopoietic stem cells (HSCs) have the ability to repopulate an entire hematopoietic system (Baum et al., *Proceedings of the National Academy of Sciences USA,* 89, 2804-2808 (1992)), and several genetic diseases of the blood (Mukherjee and Thrasher, Gene, 525, 174-181 (2013); Cavazzana-Calvo et al., *Nature,* 467, 318-322 (2010); Naldini, *Nature,* 526, 351-360 (2015)) and acquired (Jenq & van den Brink, *Nature Reviews Cancer,* 10, 213-221 (2010)) could potentially be cured by genome editing of HSCs. Recent studies have demonstrated efficient targeted integration in hematopoietic stem and progenitor cells (HSPCs) derived from mobilized peripheral blood, fetal liver, or cord blood by combining ZFN expression with exogenous HR donors delivered via single stranded oligonucleotides (ssODN) (Hoban et al., Blood 125, 2597-2604 (2015)), integrase-defective lentiviral vectors (IDLV) (Genovese et al., Nature 510, 235-240 (2014)), or recombinant adeno-associated viral vectors serotype 6 (rAAV6) (Wang et al., *Nature Biotechnology,* 33, 1256-1263 (2015)). However, the high editing frequencies in vitro did not result in high frequencies of edited cells following transplantation into immunodeficient mice.

BRIEF SUMMARY OF THE INVENTION

In a first aspect, provided herein is a method for inducing a stable gene modification of a target nucleic acid via homologous recombination in a primary cell. The method includes introducing into the primary cell: (a) a modified single guide RNA (sgRNA) comprising a first nucleotide sequence that is complementary to the target nucleic acid and a second nucleotide sequence that interacts with a CRISPR-associated protein (Cas) polypeptide, wherein one or more of the nucleotides in the first nucleotide sequence and/or the second nucleotide sequence are modified nucleotides; (b) a Cas polypeptide, an mRNA encoding a Cas polypeptide, and/or a recombinant expression vector comprising a nucleotide sequence encoding a Cas polypeptide, wherein the modified sgRNA guides the Cas polypeptide to the target nucleic acid; and (c) a homologous donor adeno-associated viral (AAV) vector comprising a recombinant donor template comprising two nucleotide sequences comprising two non-overlapping, homologous portions of the target nucleic acid, wherein the nucleotide sequences are located at the 5' and 3' ends of a nucleotide sequence corresponding to the target nucleic acid to undergo homologous recombination.

In a second aspect, provided herein is a genetically modified primary cell produced by the homologous recombination-mediated gene targeting method described herein.

In a third aspect, provided herein is a pharmaceutical composition comprising a genetically modified primary cell described herein, and a pharmaceutically acceptable carrier. In some embodiments, the pharmaceutical composition comprises one type of genetically modified primary cell. In other embodiments, the pharmaceutical composition comprises two or more different types of genetically modified primary cells, e.g., 2, 3, 4, 5, 6, 7, 8, 9, 10 or more different types of genetically modified primary cells.

In a fourth aspect, provided herein is a kit comprising (a) a modified single guide RNA (sgRNA) comprising a first nucleotide sequence that is complementary to the target nucleic acid and a second nucleotide sequence that interacts with a CRISPR-associated protein (Cas) polypeptide, wherein one or more of the nucleotides in the first nucleotide sequence and/or the second nucleotide sequence are modified nucleotides; (b) a Cas polypeptide, an mRNA encoding a Cas polypeptide, and/or a recombinant expression vector comprising a nucleotide sequence encoding a Cas polypeptide, wherein the modified sgRNA guides the Cas polypeptide to the target nucleic acid; (c) a homologous donor adeno-associated viral (AAV) vector comprising a recombinant donor template comprising two nucleotide sequences comprising two non-overlapping, homologous portions of the target nucleic acid, wherein the nucleotide sequences are located at the 5' and 3' ends of a nucleotide sequence corresponding to the target nucleic acid to undergo homologous recombination, and an instruction manual.

In a fifth aspect, provided herein is a method for preventing or treating a disease in a subject in need thereof. The method comprises administering to the subject a genetically modified primary cell described herein, or a pharmaceutical composition comprising a genetically modified primary cell described herein, to prevent the disease or ameliorate one or more symptoms of the disease.

In a sixth aspect, provided herein is a method for enriching a population of genetically modified primary cells having targeted integration at a target nucleic acid. The method includes: (a) introducing a DNA nuclease and a homologous donor adeno-associated viral (AAV) vector comprising a recombinant donor template into a population of primary cells, wherein the recombinant donor template comprises a nucleotide sequence encoding a selectable marker; (b) culturing the population of primary cells for a period of time (e.g., 2 to 4 days) sufficient to produce a population of genetically modified primary cells and a population of unmodified primary cells; and (c) separating the population of genetically modified primary cells from the population of unmodified primary cells based upon a higher expression of the selectable marker in the population of genetically modified primary cells compared to a population of primary cells to which only the homologous donor AAV vector has been introduced, thereby generating an enriched population of genetically modified primary cells.

In a seventh aspect, provided herein is an enriched population of genetically modified primary cells produced by the enrichment method described herein.

In an eighth aspect, provided herein is a pharmaceutical composition comprising an enriched population of genetically modified primary cells described herein, and a pharmaceutically acceptable carrier. In some embodiments, the pharmaceutical composition comprises one type of an enriched population of genetically modified primary cells. In other embodiments, the pharmaceutical composition comprises two or more different types of enriched populations of genetically modified primary cells, e.g., 2, 3, 4, 5, 6, 7, 8, 9, 10 or more different types of enriched populations of genetically modified primary cells.

In a ninth aspect, provided herein is a method for preventing or treating a disease in a subject in need thereof. The method comprises administering to the subject an enriched population of genetically modified primary cells described herein, or a pharmaceutical composition comprising an enriched population of genetically modified primary cells described herein, to prevent the disease or ameliorate one or more symptoms of the disease.

Other objects, features, and advantages of the present invention will be apparent to one of skill in the art from the following detailed description and figures.

BRIEF DESCRIPTION OF THE DRAWINGS

FIG. 1D provides a schematic of dual-genic targeting of GFP into HBB and mCherry into CCR5. 500,000 HSPCs were electroporated with CCR5-RNP and HBB-RNP complexes (2×15 μg rCas9 protein and 2×8 μg MS sgRNA), and then transduced with HBB-GFP (top AAV) and CCR5-mCherry (bottom AAV) rAAV6 at an MOI of 50,000 each. (1) boxes: HBB homology arms, (2) boxes: GFP expression cassette, (3) boxes: CCR5 homology arms, (4) boxes: mCherry expression cassette. FIG. 1E provides representative FACS images from day 18 post-electroporation showing cells with either GFP (HBB), mCherry (CCR5), or GFP/mCherry double-targeted integration. FIG. 1F shows compiled data from dual-genic targeting experiments showing percent fluorescent cells at day 18 post-electroporation. Each data point within each experimental group represents a different CD34$^+$ HSPC donor (N=4).

FIG. 3G shows the percent GFP$^+$ cells in the total human population, CD19$^+$ B cells, and CD33$^+$ myeloid cells. Three different HSPC donors were used for engraftment studies (N=number of data points within group), *p<0.05, ****p<0.0001, one-way ANOVA and Tukey's multiple comparison test for total human cells and unpaired t test with Welch's correction for B and Myeloid cells.

FIGS. 6A-6D show optimization of HR at the HBB locus in CD34$^+$ HSPCs with RNP delivery of Cas9 and homologous donor delivery via rAAV6. CD34$^+$ HSPCs were electroporated with RNPs at different molar ratios of rCas9 (15 µg):sgRNA(x) and then transduced with rAAV6 donor at an MOI of 100,000 (FIG. 6A). HSPCs were electroporated with RNPs at different rCas9 concentrations while keeping Cas9:sgRNA ratio (1:2.5) constant, and then transduced with rAAV6 as described above (FIG. 6B). HSPCs were electroporated as described above with optimal parameters identified in FIGS. 6A and 6B, and then transduced at indicated MOIs of HBB rAAV6 donor (FIG. 6C). Timing of rAAV6 delivery was tested relative to electroporation of RNPs (FIG. 6D). HSPCs were either transduced 48 or 24 hours before, or 15 min after electroporation. For all experiments, GFP percentages were analyzed by flow cytometry 18 days post-electroporation. Bars labeled with a hashtag indicate the parameter chosen for the remainder of the studies, which were chosen based on cost-benefit or benefit-toxicity evaluations. Error bars represent S.E.M from 2 independent experiments.

FIGS. 13A and 13B provide linear regression models showing that the day 4 GFP$^{high}$ population is a reliable predictor of targeting frequencies. Day 4 GFP$^{high}$ percentages (x-axis) were plotted against day 18 total GFP+ percentages (y-axis), and $r^2$ correlation coefficient values were generated from a total of 38 and 19 CD34+ HSPC donors from HBB (FIG. 13A) and CCR5 (FIG. 13B), respectively.

(FIG. 14A) FIG. 14B shows the percent of tNGFR+ HSPCs at day 18 post-electroporation from three CD34+ HSPC donors. FACS plot highlighting the tNGFR expression shift following addition of the CRISPR/Cas9 system in HSPCs at day 4 post-electroporation (FIG. 14C). FIG. 14D shows the percentage of tNGFR+ cells every 4 days. tNGFR$^{high}$ (1), tNGFR$^{low}$ (2), and tNGFR$^{neg}$ (3) were sorted, cultured for 20 days, and analyzed every 4 days by flow cytometry to monitor tNGFR expression over time (FIGS. 14C and 14D). Error bars represent S.E.M from three CD34+ HSPC donors.

FIGS. 17A-17C provide an overview of PCR analyses of methylcellulose colonies with HR of GFP donors at the HBB, CCR5, and IL2RG loci. The HBB locus was targeted by creating a DSB in exon 1 via Cas9 (scissors) and supplying a rAAV6 GFP donor template (SEQ ID NO:38) (FIG. 17A). Alleles with integrations were identified by PCR (881 bp) using an In (arrow; 120)—Out (arrow; 130) primer set. Wildtype alleles were identified by PCR (685 bp) using primers flanking the sgRNA target site (arrow; 100 and arrow; 110). The CCR5 locus was targeted in exon 3 as described above (FIG. 17B). CCR5 Donor template sequence is provided in SEQ ID NO:39. A 3-primer PCR identified integrated (1200 bp) and WT (1415 bp) alleles using In (arrow; 220)—Out (arrow; 210)—WT (arrow; 200) primers. HR at exon 1 of the IL2RG locus was performed as above and analyzed by a similar strategy as HBB with two primer sets to pick up WT (arrow; 300 and arrow; 310) and integrated alleles (arrow; 320 and arrow; 330) separately (FIG. 17C). IL2RG donor template sequence is provided in SEQ ID NO:40.

FIG. 18D provides a schematic of targeted integration ((1): homology arms; (2): integrated expression cassette). Representative Sanger sequence chromatograms for junctions between right homology arm (middle section) and insert (left section) or genomic locus (right section) highlighting seamless homology-directed repair at the HBB, CCR5, and IL2RG loci (FIG. 18D). The nucleic acid sequences for: the insert-3' homology arm for the HBB loci is set forth in SEQ ID NO:10; the 3' homology arm-genomic locus for the HBB loci is set forth in SEQ ID NO:11; the insert-3' homology arm for the CCR5 loci is set forth in SEQ ID NO:12; the 3' homology arm-genomic locus for the CCR5 loci is set forth in SEQ ID NO:13; the insert-3' homology arm for the IL2RG loci is set forth in SEQ ID NO:14; and the 3' homology arm-genomic locus for the IL2RG loci is set forth in SEQ ID NO:15.

FIGS. 19A-19C show biallelic HR at the HBB locus using CRISPR/Cas9 and rAAV6. Representative FACS plots at day 4 post-electroporation of CD34+ HSPCs targeted with HBB-GFP and HBB-tdTomato rAAV6 donors (FIG. 19A). Gates encompass the following populations: GFP$^{high}$ (upper left quadrant; "Green"), tdTomato$^{high}$ (lower right quadrant; "Red"), and GFP$^{high}$/tdTomato$^{high}$ (upper right quadrant). Overview of calculations used to estimate biallelic HR frequencies from the FACS results (FIG. 19B). Total targeting frequency is the sum of GFP$^{high}$+tdTomato$^{high}$+GFP$^{high}$/tdTomato$^{high}$ and half of biallelic targeting events is assumed to be Green/Red+Red/Green. Therefore, 5.26/25.8 are the estimated biallelic integration rate (20.4%). Representative genotyping gel images of GFP$^{high}$/tdTomato$^{high}$ clones confirming each allele has on-target integration of GFP or tdTomato cassette (FIG. 19C).

FIG. 20 provides a summary of the allele modifications found in transgene$^{high}$ methylcellulose clones. Targeted HSPCs in the transgene$^{high}$ gate were single-cell sorted into 96-well plates containing methylcellulose at day 4 post-electroporation and then cultured for 14 days to form colonies. Colonies were then isolated, gDNA was extracted, and PCRs were performed on each colony to identify type of allele modification (see FIGS. 17A-17C for PCR strategies). Methylcellulose clones were derived from at least two CD34+ HSPC donors from independent experiments.

FIG. 24 shows that engrafted HSPCs enriched for targeted integration produces more human cells than non-enriched cells. Average engraftment frequencies and percent GFP$^+$ human cells +/−S.E.M are shown. Total number of cells transplanted was the same (500,000) for all mice in the RNP group, whereas in the GFP$^{high}$ group, one mouse was transplanted with 100,000 cells, two mice with 250,000 cells, and three mice with 500,000 cells. The total number of HSCs transplanted per mouse (+/−S.E.M.) was calculated based on the frequencies of GFP$^+$ cells in the CD34$^+$/CD38$^-$/CD90$^+$/CD45RA$^-$ subset analyzed by flow cytometry (see FIG. 3C) directly before injection. The total number of modified human cells in the bone marrow (BM) at week 16 post-transplant per mouse (+/−S.E.M.) was estimated based on calculations presented in the materials and methods.

FIGS. 27A-27D show CRISPR/Cas9 and rAAV6-mediated targeted integration at the HBB locus in human CD34+ hematopoietic stem and progenitor cells (HSPCs). FIG. 27A: Schematic of targeted genome editing at the HBB locus (SEQ ID NO:1) using CRISPR/Cas9 and rAAV6. Site-specific double strand breaks (DSBs) are created by Cas9 (scissors) mainly between nucleotide 17-18 of the 20 bp target site, which is followed by the 'NGG' Protospacer adjacent motif (PAM). A DSB stimulates homologous recombination (HR) using rAAV6 homologous donor as repair template. Boxes (1-3): HBB exons, boxes (4-5): homology arms, boxes (6-7): GFP expression cassette. FIG. 27B: 500,000 CD34$^+$ HSPCs, isolated from cord blood or mobilized peripheral blood, were electroporated with 15 µg Cas9 mRNA and 10 µg MS sgRNA (mRNA) or 30 µg rCas9 protein and 16 µg MS sgRNA precomplexed (RNP). HSPCs were grown for 4 days and gDNA was harvested and INDELs were analyzed via TIDE software. All data points within experimental groups represent different HSPC donors (N=number of data points within group). FIG. 27C: HSPCs were nucleofected as described above and then HBB-specific rAAV6s were added at an MOI of 100,000 vector genomes per cell and cells were analyzed by flow cytometry 18-21 days post-electroporation when GFP levels were found to be constant. Left panel shows compiled data from multiple independent experiments showing percent cells stably expressing GFP at day 18-21 post-electroporation. Right panel shows representative FACS plots. All data points within experimental groups represent different HSPC donors (N=number of data points within group). FIG. 27D: CD34$^+$ HSPCs (isolated from cord blood or adult bone marrow) were treated as above with HBB-specific Cas9 RNP and rAAV6 E6V donor (see, FIGS. 30A and 30B). Targeted integration frequencies were analyzed at day 4 post-electroporation by sequencing of TOPO-cloned PCR fragments derived from In-Out PCR. 100 TOPO clones were analyzed from each of six different HSPC donors (N=6).

FIG. 28A: CD34$^+$ HSPCs were electroporated with the CRISPR system (mRNA or RNP delivery) or without (AAV only), and then transduced with rAAV6 at an MOI of 100,000. Day 4 post-electroporation, cells were analyzed by flow cytometry and live cells were gated in high forward scatter (FSC) and low side scatter (SSC). Percent cells in FSC/SSC gate is shown relative to that of mock-electroporated (Mock) cells. Each dot represents a unique CD34$^+$ HSPC donor. FIG. 28B: Upper panel: sgRNA target sequences at the HBB on-target site (SEQ ID NO:42) and a highly complementary off-target site (SEQ ID NO:49) (Chr9:101833584-101833606) are shown. PAM sequences are underlined and the "TCA" sequence at the left end of "Off" (bold) highlight the three mismatches of the off-target site. Lower panel: HSPCs were electroporated with either the "All RNA" or RNP-based CRISPR system, and 4 days post-electroporation gDNA was extracted and analyzed for INDEL frequencies using TIDE on the on-target HBB and the off-target site. Results are graphed as a ratio of on to off-target activity highlighting the increased specificity of the RNP system. Averages from three different CD34$^+$ HSPC donors are shown and error bars represent S.E.M. p<0.01, **p<0.0001, ns=p≥0.05, unpaired Student's t-test. FIG. 28C: INDEL frequencies for the data presented in FIG. 28B. * p<0.05, paired Student's t-test.

FIG. 29A: Representative FACS plots showing stable GFP rates at day 18 post-electroporation in donor-nuclease mismatch experiments. Mismatching nuclease and donor (middle box) leads to infrequent end-capture events compared to on-target HR events observed with matched nuclease and homologous rAAV6 donor (bottom box). HSPCs were electroporated with 15 µg Cas9 mRNA and either HBB MS sgRNA or IL2RG MS sgRNA, then transduced with HBB-GFP rAAV6 or IL2RG-GRP rAAV6 donor followed by 18 days of culture. FIG. 29B: End-capture experiments were performed in three replicate experiments each in three unique CD34+HSPC donors. ns=p≥0.05, paired Student's t-test. FIG. 29C: Activity of the IL2RG CRISPR was confirmed by quantification of INDELs at the IL2RG target site using TIDE analysis.

FIGS. 30A-30C show a schematic of targeting rAAV6 E6V homologous donor to the HBB locus. FIG. 30A: The human HBB locus on chromosome 11 is depicted at the top of the schematic and consists of three exons (black boxes) and two introns. The rAAV6 E6V donor includes the glutamine (E) to valine (V) mutation at codon 6, which is responsible for acquiring sickle cell anemia (SEQ ID NO:48). Other SNPs were introduced to PAM region and sgRNA binding site to prevent recutting following HR in HSPCs. To analyze targeted integration frequencies in HSPCs, a 2-step PCR was performed. First, a 3.4 kb In-Out PCR ("1st PCR") was performed followed by a nested 685 bp PCR ("2nd PCR") on gel-purified fragment from the first PCR. This $2^{nd}$ PCR fragment was cloned into TOPO vectors, which were sequenced to determine the allele genotype (WT, INDEL, or HR). FIG. 30B: The sequence of a wild-type HBB allele (SEQ ID NO:5) aligned with the sequence of an allele that has undergone HR (SEQ ID NO:50). FIG. 30C: Representative INDELs from the data represented in FIG. 27D (SEQ ID NO:52-69). The HBB reference sequence is shown at the top (SEQ ID NO:51).

FIG. 31A: 500,000 HSPCs were electroporated with Cas9 RNP and then transduced with GFP rAAV6 donor. Left panel: representative FACS plots from day 4 post-electroporation highlight the GFP$^{high}$ population (gate (top boxes)) generated by the addition of Cas9 RNP. Right panel: at day 4 post-electroporation, HBB-targeted HSPCs from GFP$^{high}$ (1), GFP$^{low}$ (2), and GFP$^{neg}$ (3) fractions were sorted and cultured for 15-20 days while monitoring GFP expression by flow cytometry. Error bars represent S.E.M. (N=11, all from unique mPB or CB donors) FIG. 31B: HSPCs were targeted with GFP rAAV6 as described above. At day 4 post-electroporation, the GFP$^{high}$ population was single-cell sorted into 96-well plates containing methylcellulose to promote colony formation. After 14 days, gDNA was isolated from formed colonies and PCR was performed to detect targeted integration at the 3' end (see, FIGS. 33A-C). A total of 95 HBB colonies were screened from three different CD34+ HSPC donors. FIG. 31C: HSPCs were nucleofected as described above and then transduced with tNGFR rAAV6 donor. Left panel: representative FACS plots from day 4 post-electroporation highlight the tNGFR$^{high}$ population (gate (top boxes)) generated by the addition of Cas9 RNP. Right panel: tNGFR$^{high}$ (1) HSPCs were enriched using CD271 (LNGFR) magnetic microbeads and cultured for 18 days while monitoring tNGFR expression. Error bars represent S.E.M. (N=5, all from unique CB donors). FIG. 31D: HSPCs were targeted with the tNGFR donor as described above. At day 4 post-electroporation, the tNGFR$^{high}$ population was single-cell sorted into 96-well plates containing methylcellulose to promote colony formation. After 14 days, gDNA was isolated from formed colonies and PCR was performed to detect targeted integrations at the 5' end (see, FIGS. 34A-34C).

FIG. 33A: The HBB locus was targeted by creating a DSB in exon 1 via Cas9 (scissors) and supplying a rAAV6 GFP donor template. Alleles with integrations were identified by PCR performed on methylcellulose-derived colonies using an In—Out primer set (881 bp). Wildtype alleles were identified by PCR using primers flanking the sgRNA target site (685 bp). FIG. 33B: Representative genotyping PCRs showing mono- and bi-allelic clones as well as a clone derived from Mock cells. NTC=non-template control. FIG. 33C: Representative Sanger sequence chromatograms for junctions between right homology arm and insert (SEQ ID NO:10), and between homology arm and genomic locus (SEQ ID NO:11), highlighting seamless homologous recombination.

FIG. 34A: The HBB locus was targeted by creating a DSB in exon 1 via Cas9 (scissors) and supplying an rAAV6 tNGFR donor template. Genotypes were assessed by a 3-primer genotyping PCR performed on methylcellulose-derived colonies using an In-Out primer set (793 bp) and a primer set flanking the sgRNA target site (685 bp). Note that the two forward primers are the same. FIG. 34B: Representative genotyping PCRs showing a WT/unknown, mono-, and bi-allelic clone. FIG. 34C: Representative Sanger sequence chromatograms for junctions between right homology arm and insert (SEQ ID NO:71), and between homology arm and genomic locus (SEQ ID NO:70), highlighting seamless homologous recombination.

FIG. 35A: GFP$^{high}$ HSPCs were single cell-sorted into 96-well plates containing methylcellulose. Representative images from fluorescence microscopy show lineage-restricted progenitors (BFU-E, CFU-E, CFU-GM) and multipotent progenitors (CFU-GEMM) with GFP expression. FIG. 35B: Colony forming units (CFUs) derived as described above were counted 14 days post-sort and shown relative to the total number of cells sorted (% cloning efficiency). Error bars represent S.E.M. (N=3 different HSPC donors), *p<0.05, ns=p≥0.05, Student's t-test. FIG. 35C: Colonies from above were scored according to their morphology: 1) CFU-Erythroid (CFU-E), 2) Burst Forming Unit-Erythroid (BFU-E), 3) CFU-Granulocyte/Macrophage (CFU-GM), and 4) CFU-Granulocyte/Erythrocyte/Macrophage/Megakaryocyte (CFU-GEMM). Error bars represent S.E.M. (N=3 different HSPC donors), p<0.01, one-way ANOVA and Tukey's multiple comparison test. FIG. 35D: 500,000 HSPCs isolated from mobilized peripheral blood (mPB), adult bone marrow (ABM), or cord blood (CB) were electroporated with RNP and transduced with GFP rAAV6 donor. At day 4 post-electroporation, cells were phenotyped by flow cytometry for the cell surface markers CD34, CD38, CD90, and CD45RA (FIGS. 36A and 36B). Percent GFP$^{high}$ cells in the indicated subpopulations are shown. Error bars represent S.E.M. (data points represent unique donors, N=3 per HSPC source), p<0.0001, paired Student's t-test. FIG. 35E: CD34+ or CD34+/CD38−/CD90+ cells were sorted directly from freshly isolated cord blood CD34+ HSPCs, cultured overnight, and then electroporated with RNP and transduced with GFP rAAV6. Bars show average percent GFP⁺ cells at day 18 post-electroporation. Error bars represent S.E.M. (N=3 from different HSPC donors), p<0.01, paired Student's t-test.

FIG. 36A: Cells were immunophenotyped for CD34, CD38, CD90, and CD45RA expression and relevant FACS gates are indicated. FIG. 36B: Representative FACS plots showing GFP$^{high}$ cells in the CD34⁺/CD38⁻/CD90⁺/CD45RA⁻ population of HSPCs derived from mobilized peripheral blood, bone marrow, or cord blood.

FIG. 37A: 500,000 HBB-targeted HSPCs were injected into the tail vein of sublethally irradiated NSG mice except for the GFP$^{high}$ group, for which 100,000-500,000 cells were injected. 16 weeks post-transplantation, mononuclear cells (MNCs) were isolated by Ficoll density gradient centrifugation from the bone marrow, and human chimerism and GFP expression was analyzed by flow cytometry. Top panel: Representative FACS plot from a mouse transplanted with HBB RNP+AAV GFP$^{high}$ HSPCs showing engrafted human cells in the box with asterisk (huCD45⁺/HLA-ABC⁺). Bottom panel: Representative FACS plot showing GFP expression in human cells. CD19⁺ B cells and CD33⁺ myeloid cells were backgated and shown in (1) and (2), respectively. FIG. 37B: Human engraftment in NSG mice from all experimental groups determined as described above. Three different HSPC donors were used for engraftment studies (N=number of data points within group), ****p<0.0001, ns=p≥0.05, one-way ANOVA and Tukey's multiple comparison test. Bars represent median. FIG. 37C: Percent GFP⁺ cells in the total human population ("Total human cells"), CD19⁺ B cells ("B cells"), and CD33⁺ myeloid cells ("Myeloid cells"). Three different HSPC donors were used for engraftment studies (N=number of data points within group), *p<0.05, ****p<0.0001, one-way ANOVA and Tukey's multiple comparison test for total human cells and unpaired t test with Welch's correction for B and Myeloid cells. Bars represent median. FIG. 37D: 12-14 weeks post-secondary transplantation, MNCs were isolated by Ficoll density gradient centrifugation from the bone marrow, and human chimerism and GFP expression was analyzed by flow cytometry. Left panel: Representative FACS plot from a secondary mouse transplanted with RNP+AAV (top) or RNP+AAV GFP$^{high}$ (bottom) cells showing engrafted human cells in the gate (boxes with asterisks) (huCD45⁺/HLA-ABC⁺). Right panel: Percent GFP⁺ human cells in the BM of secondary recipients transplanted with either RNP+AAV or RNP+AAV GFP$^{High}$ cells from the BM of primary recipients. FIG. 37E: Human cells were sorted from the BM of RNP+AAV or RNP+AAV GFP$^{high}$ secondary NSG recipients, gDNA was harvested, and then In/Out PCR was carried out to analyze on-target integrations at the 5' and 3' ends of SFFV-GFP-polyA cassette at the HBB locus. Input control was a PCR carried out to amplify a 400 bp region of the human CCR5 gene. Positive control was from an HSPC sample confirmed to have targeted integration at HBB with SFFV-GFP-PolyA. FIG. 37F: 80 million mPB-derived CD34+ cells isolated from one HSPC donor were electroporated with HBB-RNPs and transduced with HBB AAV6s. Four days post-electroporation, 400,000-700,000 bulk HSPCs or HSPCs enriched for targeting (by FACS or bead-enrichment) were transplanted into the tail veins of sublethally irradiated mice. 16 weeks post-transplant, cells were harvested from the bone marrow as described above and human cell chimerism (hCD45⁺/HLA-ABC⁺ double positive) was analyzed by flow cytometry. FIG. 37G: Percent GFP⁺ and tNGFR⁺ in the total human population was analyzed by flow cytometry. Bars represent median.

FIG. 38A: Representative FACS plot from the analysis of the bone marrow of a control mouse not transplanted with human cells. Human engraftment was delineated as huCD45/HLA-ABC double positive. 4 out of 157,898 cells were found within the human cell gate. FIG. 38B: Representative FACS gating scheme from one mouse from the RNP+rAAV6 experimental group. As above, human engraftment was delineated as huCD45/HLA-ABC double positive. B cells were marked by CD19 expression, and myeloid cells identified by CD33 expression. GFP expression was analyzed in total human cells (2.4%), B-cells (1.9%) and myeloid cells (2.8%).

FIG. 39 shows that engrafted HSPCs enriched for targeted integration produces more human cells than non-enriched cells. Average engraftment frequencies and percent GFP⁺ human cells +/−S.E.M are shown. Total number of cells transplanted was the same (500,000) for all mice in the RNP group, whereas in the GFP$^{high}$ group, one mouse was transplanted with 100,000 cells, two mice with 250,000 cells, and three mice with 500,000 cells. The total number of HSCs transplanted per mouse (+/−S.E.M.) was calculated based on the frequencies of GFP⁺ cells in the CD34⁺/CD38⁻/CD90⁺/CD45RA⁻ subset analyzed by flow cytometry (see, FIG. 35D) directly before injection. The total number of modified human cells in the bone marrow (BM) at week 16 post-transplant per mouse (+/−S.E.M.) was estimated based on calculations presented in the materials and methods.

FIG. 40C: Collective data from the analysis of GFP+ cells in the human CD34+/CD10⁻ population from the RNP+AAV (RNP) (N=11) and RNP+AAV GFP$^{high}$ (RNP GFp$^{high}$) (N=6) experimental groups. For the RNP+AAV GFP$^{high}$ group, cells from all six mice were pooled before analysis and thus, no error bar is available. Error bar on RNP group represents S.E.M.

FIGS. 41A-41D show gene editing using MS-modified sgRNA, Cas9 mRNA, and AAV6 donor at the HBB and CCR5 loci in mesenchymal stromal cells (MSCs). FIG. 41A: Efficiency of targeted integration at HBB as indicated by % GFP⁺ cells analyzed by flow cytometry after at least 7 days of targeting. FIG. 41B: Rate of INDELs at the HBB and CCR5 loci on day 4 after delivery of MS-modified sgRNA and Cas9 mRNA. FIG. 41C: FACS-enriched targeted fetal bone marrow (BM)-MSCs display surface markers CD73/CD90/CD105 and not CD14/CD19/CD34/CD45, as described by the ISCT requirements. FIG. 41D: Fetal BM-MSCs retain MSC morphology and overexpress GFP after targeting and enrichment by FACS.

FIGS. 43A-43F show the correction of the E6V mutation in sickle cell disease (SCD) patient-derived CD34$^+$ HSPCs. FIG. 43A: 500,000 CD34$^+$ HSPCs isolated from peripheral blood of SCD patients were electroporated with precomplexed rCas9 protein and MS sgRNA (RNP). Four days post-electroporation, gDNA was harvested and INDELs were analyzed via TIDE software (N=4 different SCD patient donors). FIG. 43B: HSPCs were nucleofected as described above, followed by transduction with an HBB-specific SFFV-GFP rAAV6 donor (SEQ ID NO:38). Cells were analyzed by flow cytometry 10-14 days post-electroporation when GFP levels were found to be constant (N=4 different SCD patient donors). FIG. 43C: SCD CD34$^+$ HSPCs were treated as above with HBB-specific Cas9 RNP and rAAV6 corrective SNP donor (see FIG. 45A). HBB editing frequencies were analyzed at day 4 post-electroporation by sequencing of TOPO-cloned PCR fragments derived from In-Out PCR. 50-100 TOPO clones were analyzed from each of three different HSPC donors (N=3 different SCD patient donors). FIG. 43D: SCD CD34+ HSPCs were electroporated with HBB-RNPs and transduced with anti-sickling HBB cDNA-EF1-tNGFR correction donor (SEQ ID NO:37). Frequencies of tNGFR$^+$ cells were analyzed by flow cytometry at day 4 post-electroporation (N=3 different SCD patient donors). FIG. 43E: SCD Mock HSPCs (bottom) and tNGFR$^{high}$ cells sorted from SCD HSPCs targeted with the cDNA donor (top) were differentiated into erythrocytes in vitro at day 4 post-electroporation. Representative FACS plots from day 21 of differentiation show cell surface markers associated with erythrocytes (GPA$^+$/CD45$^-$/CD71$^+$/CD34$^-$). FIG. 43F: HbS, HbA, and HbAS3 mRNA expression was analyzed in erythrocytes differentiated from HBB-edited or Mock SCD HSPCs. All mRNA transcript levels were normalized to the RPLP0 input control (N=2 different SCD patient donors).

FIGS. 45A and 45B show correction of the sickle cell mutation in patient-derived CD34+ HSPCs. FIG. 45A: Schematic overview of the sequence of the sickle allele aligned (SEQ ID NO:72) with the sequence of an allele that has undergone HR (SEQ ID NO:73) using the corrective SNP donor. The sgRNA recognition sequence, the PAM site, and the cut site (scissors) are shown. The donor carries synonymous mutations between the sickle nucleotide and the cut site to avoid premature cross-over during HR. Synonymous mutations were also added to the PAM and the sgRNA target site to prevent re-cutting of the corrected allele by Cas9. FIG. 45B: HSPCs from two different sickle cell patients were targeted with the corrective SNP donor and seeded in methylcellulose. After 14 days, In-Out PCR amplicons from a total of 38 clones were sequenced and genotypes were extracted from sequence chromatograms.

FIG. 47 shows the integration of full diverged HBB cDNA (SEQ ID NO:74). Provided is a chromatogram obtained from sequencing of an In-Out PCR amplicon on sickle cell disease patient-derived CD34+ cells electroporated with HBB Cas9 RNP and transduced with rAAV6 HBB cDNA donor (see FIG. 45 for donor design). PCR was performed on genomic DNA extracted four days after electroporation of a bulk sample. The chromatogram shows the sequence of the full HBB cDNA with labeled boxes indicating the positions of the start codon, sickle cell codon position, and stop codon.

FIG. 49A shows FACS plots of CD34+ HSPCs following electroporation with Cas9 RNP targeting three genes (IL2RG, HBB, and CCR5), followed by transduction with rAAV6 donors homologous to each of the three genes (IL2RG-GFP, HBB-tdTomato, and CCR5-tNGFR, respectively). FIG. 49B shows FACS plots of trigenic-targeted cells that were identified as reporter$^{high}$ for all three reporters. FIG. 49C shows gel images illustrating targeted integration at all three genes in nine of eleven colonies of methylcellulose clones derived from the triple-positive cells in FIG. 49B.

FIGS. 50A and 50B show dual-allelic integration in primary human T cells. FIG. 50A shows FACS plots of GFP$^{high}$/mCherry$^{high}$ cells at day 4 post-electroporation (cells were electroporated with CCR5-targeting Cas9 RNP, followed by transduction with CCR5-specific rAAV6 donors encoding GFP and mCherry). FIG. 50B shows the viabilities of T cells at day 2 post-electroporation, measured by a Trypan Blue exclusion assay (N=2 different buffy coat-derived T cells).

DETAILED DESCRIPTION OF THE INVENTION

I. Introduction

Figure 1A:
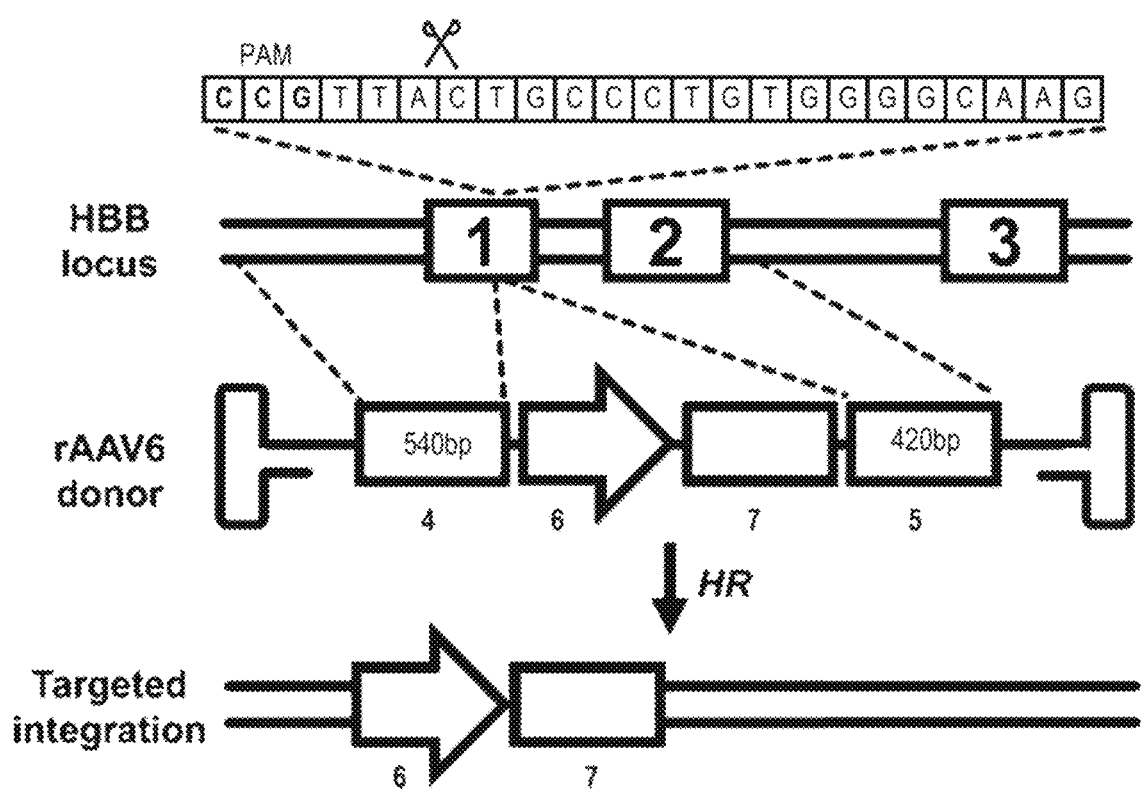
FIGS. 1A-1F show CRISPR/Cas9 and rAAV6-mediate targeted integration at the CCR5, IL2RG and HBB loci in human CD34+ hematopoietic stem and progenitor cells (HSPCs). Schematic of targeted genome editing at the HBB locus using CRISPR/Cas9 and rAAV6 (FIG. 1A). Site-specific double strand breaks (DSBs) are created by Cas9 (scissors) mainly between nucleotide 17-18 of the 20 bp target site, which is followed by the 'NGG' Protospacer adjacent motif (PAM) (gray); SEQ ID NO:1 refers to 5'-CCGTTACTGCCCTGTGGGGCAAG-3'. A DSB stimulates homologous recombination (HR) using rAAV6 homologous donor as repair template. White boxes (1-3): HBB exons, blue boxes (4-5): 540 bp and 420 bp homology arms, orange boxes (6-7): transgene expression cassette between homology arms. 500,000 CD34+ HSPCs, isolated from cord blood or mobilized peripheral blood, were electroporated with 15 μg Cas9 mRNA and 10 μg MS sgRNA (mRNA) or 30 μg rCas9 protein and 16 μg MS sgRNA precomplexed (RNP). Gene-specific rAAV6s were added at an MOI of 100,000 and cells were analyzed 18-21 days post-electroporation by flow cytometry. Compiled data from multiple independent experiments showing percent cells stably expressing GFP at day 18-21 post-electroporation (FIG. 1B, left panel). Representative FACS images from day 18-21 post-electroporation showing targeted integration of GFP at the HBB, CCR5, and IL2RG loci (FIG. 1B, right panel). All data points within experimental groups represent different HSPC donors (N=number of data points within group). CD34+ HSPCs (isolated from cord blood or adult bone marrow) were treated as above with HBB-specific Cas9 RNP and rAAV6 E6V donor (FIG. 1C). See FIG. 10 for additional details. Targeted integration frequencies were analyzed at day 4 post-electroporation by sequencing of TOPO-cloned PCR fragments spanning the target site. 100 TOPO clones were analyzed from each of six different HSPC donors (N=6) (FIG. 1C).

Precise nuclease-mediated gene modification via homologous recombination (HR) in primary cells such as hematopoietic stem and progenitor cells (HSPCs) and mesenchymal stem cells (MSCs) has the power to reveal gene-function relationships and potentially transform curative genetic therapies. However, no gene-editing platform exists for achieving clinically-relevant efficiencies of HR in primary cells. By combining delivery of Cas9 protein complexed with chemically modified sgRNAs with transduction of a donor via recombinant adeno-associated viral vectors, serotype 6 (rAAV6) into HSPCs and MSCs, the present inventors have achieved high frequencies of HR-mediated genome editing at different loci. Importantly, a distinct shift from episomal to chromosomal reporter transgene expression resulting from successful HR allowed for early identification and enrichment of a population of HSPCs with targeted integration in greater than 90% of cells. These cells can be identified because HR-mediated integration causes the reporter gene to be expressed at log-fold higher levels than the non-integrated reporter. Notably, this enriched population of genetically modified HSPCs displayed long-term multi-lineage engraftment when transplanted into immunodeficient mice, confirming the presence of long-term repopulating hematopoietic stem cells (LT-HSCs). Furthermore, the frequency is high enough that it is possible to multiplex HR-mediated genome editing in primary cells.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "gene" refers to a combination of polynucleotide elements, that when operatively linked in either a native or recombinant manner, provide some product or function. The term "gene" is to be interpreted broadly, and can encompass mRNA, cDNA, cRNA and genomic DNA forms of a gene.

The term "homology-directed repair" or "HDR" refers to a mechanism in cells to accurately and precisely repair double-strand DNA breaks using a homologous template to guide repair. The most common form of HDR is homologous recombination (HR).

The term "homologous recombination" or "HR" refers to a genetic process in which nucleotide sequences are exchanged between two similar molecules of DNA. Homologous recombination (HR) is used by cells to accurately repair harmful breaks that occur on both strands of DNA, known as double-strand breaks or other breaks that generate overhanging sequences.

The term "single guide RNA" or "sgRNA" refer to a DNA-targeting RNA containing a guide sequence that targets the Cas nuclease to the target genomic DNA and a scaffold sequence that interacts with the Cas nuclease (e.g., tracrRNA), and optionally, a donor repair template The term "Cas polypeptide" or "Cas nuclease" refers to a Clustered Regularly Interspaced Short Palindromic Repeats-associated polypeptide or nuclease that cleaves DNA to generate blunt ends at the double-strand break at sites specified by a 20-nucleotide guide sequence contained within a crRNA transcript. A Cas nuclease requires both a crRNA and a tracrRNA for site-specific DNA recognition and cleavage. The crRNA associates, through a region of partial complementarity, with the tracrRNA to guide the Cas nuclease to a region homologous to the crRNA in the target DNA called a "protospacer."

The term "ribonucleoprotein complex" or "RNP complex" refers to a complex comprising an sgRNA and a Cas polypeptide.

The term "homologous donor adeno-associated viral vector" or "donor adeno-associated viral vector" refers to an adeno-associated viral particle that can express a recombinant donor template for CRISPR-based gene editing via homology-directed repair in a host cell, e.g., primary cell.

The term "recombinant donor template" refers to a nucleic acid stand, e.g., DNA strand that is the recipient strand during homologous recombination strand invasion that is initiated by the damaged DNA, in some cases, resulting from a double-stranded break. The donor polynucleotide serves as template material to direct the repair of the damaged DNA region.

The terms "sequence identity" or "percent identity" in the context of two or more nucleic acids or polypeptides refer to two or more sequences or subsequences that are the same ("identical") or have a specified percentage of amino acid residues or nucleotides that are identical ("percent identity") when compared and aligned for maximum correspondence with a second molecule, as measured using a sequence comparison algorithm (e.g., by a BLAST alignment, or any other algorithm known to persons of skill), or alternatively, by visual inspection.

The term "homologous" refers to two or more amino acid sequences when they are derived, naturally or artificially, from a common ancestral protein or amino acid sequence. Similarly, nucleotide sequences are homologous when they are derived, naturally or artificially, from a common ancestral nucleic acid.

The term "primary cell" refers to a cell isolated directly from a multicellular organism. Primary cells typically have undergone very few population doublings and are therefore more representative of the main functional component of the tissue from which they are derived in comparison to continuous (tumor or artificially immortalized) cell lines. In some cases, primary cells are cells that have been isolated and then used immediately. In other cases, primary cells cannot divide indefinitely and thus cannot be cultured for long periods of time in vitro.

The term "gene modified primary cell" or "genome edited primary cell" refers to a primary cell into which a heterologous nucleic acid has been introduced in some cases, into its endogenous genomic DNA.

The term "primary blood cell" refers to a primary cell obtained from blood or a progeny thereof. A primary blood cell can be a stem cell or progenitor cell obtained from blood. For instance, a primary blood cell can be a hematopoietic stem cell or a hematopoietic progenitor cell.

The term "primary immune cell" or "primary leukocyte" refers to a primary white blood cell including but not limited to a lymphocyte, granulocyte, monocyte, macrophage, natural killer cell, neutrophil, basophil, eosinophil, macrophage, stem cell thereof, or progenitor cell thereof. For instance, a primary immune cell can be a hematopoietic stem cell or a hematopoietic progenitor cell. A hematopoietic stem cell or a hematopoietic progenitor cell can give rise to blood cells, including but not limited to, red blood cells, B lymphocytes, T lymphocytes, natural killer cells, neutrophils, basophils, eosinophils, monocytes, macrophages, and all types thereof.

The term "primary mesenchymal cell" refers to a primary cell of a mesenchymal lineage including those that can differentiate to become a cell of a mesenchymal lineage. Mesenchymal cells include stem cells (stromal cells), progenitor cells and differentiated cells of bone, cartilage, fat, muscle, etc.

The term "pharmaceutical composition" refers to a composition that is physiologically acceptable and pharmacologically acceptable. In some instances, the composition includes an agent for buffering and preservation in storage, and can include buffers and carriers for appropriate delivery, depending on the route of administration.

The term "pharmaceutical acceptable carrier" refers to a substance that aids the administration of an agent (e.g., Cas nuclease, modified single guide RNA, gene modified primary cell, etc.) to a cell, an organism, or a subject. "Pharmaceutically acceptable carrier" refers to a carrier or excipient that can be included in a composition or formulation and that causes no significant adverse toxicological effect on the patient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical carriers are useful in the present invention.

The term "administering or "administration" refers to the process by which agents, compositions, dosage forms and/or combinations disclosed herein are delivered to a subject for treatment or prophylactic purposes. Compositions, dosage forms and/or combinations disclosed herein are administered in accordance with good medical practices taking into account the subject's clinical condition, the site and method of administration, dosage, subject age, sex, body weight, and other factors known to the physician. For example, the terms "administering" or "administration" include providing, giving, dosing and/or prescribing agents, compositions, dosage forms and/or combinations disclosed herein by a clinician or other clinical professional.

The term "treating" refers to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The terms "culture," "culturing," "grow," "growing," "maintain," "maintaining," "expand," "expanding," etc., when referring to cell culture itself or the process of culturing, can be used interchangeably to mean that a cell (e.g., primary cell) is maintained outside its normal environment under controlled conditions, e.g., under conditions suitable for survival. Cultured cells are allowed to survive, and culturing can result in cell growth, stasis, differentiation or division. The term does not imply that all cells in the culture survive, grow, or divide, as some may naturally die or senesce. Cells are typically cultured in media, which can be changed during the course of the culture.

The terms "subject," "patient," and "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

Unless defined otherwise, all technical and scientific terms used herein have the same meanings as commonly understood by one of ordinary skill in the art to which this technology belongs. Although exemplary methods, devices and materials are described herein, any methods and materials similar or equivalent to those expressly described herein can be used in the practice or testing of the present technology. For example, the reagents described herein are merely exemplary and that equivalents of such are known in the art. The practice of the present technology can employ, unless otherwise indicated, conventional techniques of tissue culture, immunology, molecular biology, microbiology, cell biology, and recombinant DNA, which are within the skill of the art. See, e.g., Sambrook and Russell eds. (2001) *Molecular Cloning: A Laboratory Manual,* 3rd edition; the series Ausubel et al. eds. (2007) *Current Protocols in Molecular Biology; the series Methods in Enzymology* (Academic Press, Inc., N.Y.); MacPherson et al. (1991) *PCR I: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Miller and Calos eds. (1987) *Gene Transfer Vectors for Mammalian Cells* (Cold Spring Harbor Laboratory); and Makrides ed. (2003) *Gene Transfer and Expression in Mammalian Cells* (Cold Spring Harbor Laboratory).

III. Detailed Description of the Embodiments

In certain aspects, the present invention provides methods for inducing a stable gene modification of a target nucleic acid via homologous recombination in a primary cell, such as a primary blood cell and/or a primary mesenchymal cell. In certain other aspects, the present invention provides methods for enriching a population of genetically modified primary cells having targeted integration at a target nucleic acid. The methods of the present invention rely on the introduction of a DNA nuclease such as a Cas polypeptide and a homologous donor adeno-associated viral (AAV) vector into the primary cell to mediate targeted integration of the target nucleic acid. Also provided herein are methods for preventing or treating a disease in a subject in need thereof by administering to the subject any of the genetically modified primary cells or pharmaceutical compositions described herein to prevent the disease or ameliorate one or more symptoms of the disease.

A. Gene Targeting in Primary Cells

In some aspects, provided herein is a method for inducing a stable gene modification of a target nucleic acid via homologous recombination in a primary cell. The method includes introducing into the primary cell: (a) a modified single guide RNA (sgRNA) comprising a first nucleotide sequence that is complementary to the target nucleic acid and a second nucleotide sequence that interacts with a CRISPR-associated protein (Cas) polypeptide, wherein one or more of the nucleotides in the first nucleotide sequence and/or the second nucleotide sequence are modified nucleotides; (b) a Cas polypeptide, an mRNA encoding a Cas polypeptide, and/or a recombinant expression vector comprising a nucleotide sequence encoding a Cas polypeptide, wherein the modified sgRNA guides the Cas polypeptide to the target nucleic acid; and (c) a homologous donor adeno-associated viral (AAV) vector comprising a recombinant donor template comprising two nucleotide sequences comprising two non-overlapping, homologous portions of the target nucleic acid, wherein the nucleotide sequences are located at the 5' and 3' ends of a nucleotide sequence corresponding to the target nucleic acid to undergo homologous recombination.

In some embodiments, the primary cell is selected from the group consisting of a primary blood cell, a primary mesenchymal cell, and a combination thereof. In some embodiments, the primary blood cell is selected from the group consisting of an immune cell, a red blood cell, a progenitor or stem cell thereof, and a combination thereof. In some instances, the immune cell is selected from the group consisting of a T cell, a B cell, a dendritic cell, a natural killer cell, a macrophage, a neutrophil, an eosinophil, a basophil, a mast cell, a precursor thereof, and a combination thereof. The progenitor or stem cell can be selected from the group consisting of a hematopoietic progenitor cell, a hematopoietic stem cell, and a combination thereof. In some cases, the red blood cell is a blood stem cell. In some instances, the primary mesenchymal cell is selected from the group consisting of a mesenchymal stem cell, a mesenchymal progenitor cell, a mesenchymal precursor cell, a differentiated mesenchymal cell, and a combination thereof. The differentiated mesenchymal cell can be selected from the group consisting of a bone cell, a cartilage cell, a muscle cell, an adipose cell, a stromal cell, a fibroblast, a dermal cell, and a combination thereof.

In some embodiments, the primary cell is isolated from a mammal prior to introducing the modified sgRNA, the Cas polypeptide, and the homologous donor AAV vector into the primary cell. For instance, the primary cell can be harvested from a human subject. In some instances, the primary cell or a progeny thereof is returned to the mammal after introducing the modified sgRNA, the Cas polypeptide, and the homologous donor AAV vector into the primary cell. In other words, the genetically modified primary cell undergoes autologous transplantation. In other instances, the genetically modified primary cell undergoes allogeneic transplantation. For example, a primary cell that has not undergone stable gene modification is isolated from a donor subject, and then the genetically modified primary cell is transplanted into a recipient subject who is different than the donor subject.

The primary cell can comprise a population of primary cells. In some cases, the population of primary cells comprises a heterogeneous population of primary cells. In other cases, the population of primary cells comprises a homogeneous population of primary cells.

In some embodiments, the homologous donor AAV vector is selected from a wild-type AAV serotype 1 (AAV1), wild-type AAV serotype 2 (AAV2), wild-type AAV serotype 3 (AAV3), wild-type AAV serotype 4 (AAV4), wild-type AAV serotype 5 (AAV5), wild-type AAV serotype 6 (AAV6), wild-type AAV serotype 7 (AAV7), wild-type AAV serotype 8 (AAV8), wild-type AAV serotype 9 (AAV9), wild-type AAV serotype 10 (AAV10), wild-type AAV serotype 11 (AAV11), wild-type AAV serotype 12 (AAV12), a variant thereof, and any shuffled chimera thereof. In some instances, the homologous donor AAV vector has at least about 90% sequence identity to any one selected from the group consisting of an AAV1, AAV2, AAV3, AAV4, AAV3, AAV5, AAV6, AAV7, AAV8, AAV9, AAV10, AAV11 and AAV12. In other instances, the homologous donor AAV vector is a wild-type AAV6 or an AAV6 variant having at least 95% sequence identity to wild-type AAV6, e.g., 95%, 96%, 97%, 98%, 99%, or 100% sequence identity to wild-type AAV6.

In some embodiments, the stable gene modification of the target nucleic acid is induced in greater than about 70% of the population of primary cells, e.g., about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the population of primary cells. In other embodiments, the stable gene modification of the target nucleic acid is induced in greater than about 80% of the population of primary cells, e.g., about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the population of primary cells. In yet other embodiments, the stable gene modification of the target nucleic acid is induced in greater than about 90% of the population of primary cells, e.g., about 90%, about 91%, about 92%, about 93%, about 94%, about 95%, about 96%, about 97%, about 98%, about 99%, or about 100% of the population of primary cells.

In other embodiments, the stable gene modification of the target nucleic acid comprises the replacement of a genetic mutation in the target nucleic acid (e.g., to correct a point mutation or a single nucleotide polymorphism (SNP) in the target nucleic acid that is associated with a disease) or the insertion of an open reading frame (ORF) comprising a normal copy of the target nucleic acid (e.g., to knock in a wild-type cDNA of the target nucleic acid that is associated with a disease). As a non-limiting example, the stable gene modification comprises the correction of the sickle cell disease-causing E6V mutation in the HBB gene by either editing the nucleotide mutation (e.g., by introducing a homologous donor AAV vector comprising the sickle cell disease nucleotide correction donor template set forth in SEQ ID NO:36, wherein a "T" nucleotide at position 1194 has been changed to an "A" nucleotide to correct the E6V mutation) or knocking in a wild-type HBB cDNA.

In some embodiments, the modified nucleotides comprise a modification in a ribose group, a phosphate group, a nucleobase, or a combination thereof. In some instances, the modification in the ribose group comprises a modification at the 2' position of the ribose group. In some cases, the modification at the 2' position of the ribose group is selected from the group consisting of 2'-O-methyl, 2'-fluoro, 2'-deoxy, 2'-O-(2-methoxy ethyl), and a combination thereof. In other instances, the modification in the phosphate group comprises a phosphorothioate modification. In other embodiments, the modified nucleotides are selected from the group consisting of a 2'-O-methyl (M) nucleotide, a 2'-O-methyl 3'-phosphorothioate (MS) nucleotide, a 2'-O-methyl 3'-thioPACE (MSP) nucleotide, and a combination thereof.

In some embodiments, the modified sgRNA comprises one, two, or three consecutive or non-consecutive modified nucleotides at or near the 5'-end of the first nucleotide sequence and/or one, two, or three consecutive or non-consecutive modified nucleotides at or near the 3'-end of the second nucleotide sequence. In some instances, the modified sgRNA comprises three consecutive modified nucleotides at the 5'-end of the first nucleotide sequence and three consecutive modified nucleotides at the 3'-end of the second nucleotide sequence. The modified sgRNA can be chemically synthesized. In other embodiments, the modified sgRNA comprises at least two different modified sgRNAs, wherein each modified sgRNA is directed to different target nucleic acids. In further embodiments, the modified sgRNA is based on a truncated sgRNA sequence.

In some embodiments, the Cas polypeptide is a Cas9 polypeptide, a variant thereof, or a fragment thereof. In certain instances, the Cas polypeptide variant comprises a high-fidelity or enhanced specificity Cas9 polypeptide variant. In certain embodiments, the modified sgRNA and the Cas polypeptide are introduced into the primary cell concomitantly. In other embodiments, the modified sgRNA and the Cas polypeptide are introduced into the primary cell sequentially. In some cases, the modified sgRNA is introduced first, and the Cas polypeptide thereafter. In other cases, the Cas polypeptide is introduced first, and the modified sgRNA thereafter.

In some embodiments, the modified sgRNA and the Cas polypeptide can be incubated together to form a ribonucleoprotein (RNP) complex prior to introducing into the primary cell. For instance, the modified sgRNA and the Cas polypeptide can be mixed together in a vessel to form an RNP complex, and then the RNP complex is introduced into the primary cell. In other embodiments, the Cas polypeptide described herein can be an mRNA encoding the Cas polypeptide, which Cas mRNA is introduced into the primary cell together with the modified sgRNA as an "All RNA" CRISPR system. In certain instances, the modified sgRNA and the Cas mRNA are introduced into the primary cell concomitantly. In other instances, the modified sgRNA and the Cas mRNA are introduced into the primary cell sequentially. In some cases, the modified sgRNA is introduced first, and the Cas mRNA thereafter. In other cases, the Cas mRNA is introduced first, and the modified sgRNA thereafter.

In some embodiments, the RNP complex and the homologous donor AAV vector are concomitantly introduced into the primary cell. In other embodiments, the RNP complex and the homologous donor AAV vector are sequentially introduced into the primary cell. In some instances, the RNP complex is introduced into the primary cell before the homologous donor AAV vector. In other instances, the homologous donor AAV vector is introduced into the primary cell before the RNP complex. For example, the RNP complex can be introduced into the primary cell about 1, 2, 3, 4, 5, 6, 7, 8, 9, 10, 11, 12, 13, 14, 15, 16, 17, 18, 19, 20, 25, 30, 35, 40, 45, 50, 55, 60, 90, 120, 150, 180, 210, or 240 minutes or more before the homologous donor AAV vector, or vice versa. In particular embodiments, the RNP complex is introduced into the primary cell about 15 minutes (e.g., from about 10 to about 20 minutes) before the homologous donor AAV vector.

In some embodiments, the "All RNA" CRISPR system and the homologous donor AAV vector are concomitantly introduced into the primary cell. In other embodiments, the "All RNA" CRISPR system and the homologous donor AAV vector are sequentially introduced into the primary cell. In some instances, the "All RNA" CRISPR system is introduced into the primary cell before the homologous donor AAV vector. In other instances, the homologous donor AAV vector is introduced into the primary cell before the "All RNA" CRISPR system. For example, the "All RNA" CRISPR system can be introduced into the primary cell about 1, 2, 3, 4, 5, 6, 7, 8, 9, 10, 11, 12, 13, 14, 15, 16, 17, 18, 19, 20, 25, 30, 35, 40, 45, 50, 55, 60, 90, 120, 150, 180, 210, or 240 minutes or more before the homologous donor AAV vector, or vice versa. In particular embodiments, the "All RNA" CRISPR system is introduced into the primary cell about 15 minutes (e.g., from about 10 to about 20 minutes) before the homologous donor AAV vector.

In some embodiments, the recombinant donor template also contains a nucleotide sequence encoding a marker selected from the group consisting of a selectable marker, a detectable marker, a cell surface marker, or a combination thereof.

In some embodiments, any of the methods described herein can also include purifying the primary cell having the stable gene modification of the target nucleic acid using the marker. In some cases, the composition isolated by the purifying step includes at least about 80% primary cells having the stable gene modification of the target nucleic acid, e.g., about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more primary cells having the stable gene modification of the target nucleic acid.

In some embodiments, the step of introducing the modified sgRNA and the Cas polypeptide into the primary cell comprises electroporating the modified sgRNA and the Cas polypeptide into the primary cell. In some embodiments, the step of introducing the homologous donor AAV vector into the primary cell comprises transducing the primary cell.

In some embodiments, any of the methods described herein can also include culturing the primary cell in a culture medium comprising a small molecule that increases targeting efficiency of gene modification via homologous recombination. In some instances, the small molecule comprises UM171, any other pyrimidoindole derivative, a variant thereof, or a derivative thereof. The compound UM171 is described in, e.g., Fares et al., Science, 2014, 345 (6203): 1509-12.

In other aspects, provided herein is a genetically modified primary cell produced by any of the methods described herein. In some embodiments, the genetically modified primary cell is selected from the group consisting of a genetically modified primary blood cell, a genetically modified primary mesenchymal cell, and a combination thereof. In some embodiments, the genetically modified primary blood cell is selected from the group consisting of a genetically modified immune cell, a genetically modified red blood cell, a genetically modified progenitor or stem cell thereof, and a combination thereof. In some instances, the genetically modified immune cell is selected from the group consisting of a genetically modified T cell, a genetically modified B cell, a genetically modified dendritic cell, a genetically modified natural killer cell, a genetically modified macrophage, a genetically modified neutrophil, a genetically modified eosinophil, a genetically modified basophil, a genetically modified mast cell, a precursor thereof, and a combination thereof. The genetically modified progenitor or stem cell can be selected from the group consisting of a genetically modified hematopoietic progenitor cell, a genetically modified hematopoietic stem cell, and a combination thereof. In some cases, the genetically modified red blood cell is a genetically modified blood stem cell. In some instances, the genetically modified primary mesenchymal cell is selected from the group consisting of a genetically modified mesenchymal stem cell, a genetically modified mesenchymal progenitor cell, a genetically modified mesenchymal precursor cell, a genetically modified differentiated mesenchymal cell, and a combination thereof. The genetically modified differentiated mesenchymal cell can be selected from the group consisting of a genetically modified bone cell, a genetically modified cartilage cell, a genetically modified muscle cell, a genetically modified adipose cell, a genetically modified stromal cell, a genetically modified fibroblast, a genetically modified dermal cell, and a combination thereof.

In yet other aspects, provided herein is a pharmaceutical composition comprising any of the genetically modified primary cells described herein, and a pharmaceutically acceptable carrier. In other embodiments, the pharmaceutical composition comprises one type of genetically modified primary cell. In other embodiments, the pharmaceutical composition comprises two or more different types of genetically modified primary cells, e.g., 2, 3, 4, 5, 6, 7, 8, 9, 10 or more different types of genetically modified primary cells.

In further aspects, provided herein is a kit comprising (a) a modified single guide RNA (sgRNA) comprising a first nucleotide sequence that is complementary to the target nucleic acid and a second nucleotide sequence that interacts with a CRISPR-associated protein (Cas) polypeptide, wherein one or more of the nucleotides in the first nucleotide sequence and/or the second nucleotide sequence are modified nucleotides; (b) a Cas polypeptide, an mRNA encoding a Cas polypeptide, and/or a recombinant expression vector comprising a nucleotide sequence encoding a Cas polypeptide, wherein the modified sgRNA guides the Cas polypeptide to the target nucleic acid; (c) a homologous donor adeno-associated viral (AAV) vector comprising a recombinant donor template comprising two nucleotide sequences comprising two non-overlapping, homologous portions of the target nucleic acid, wherein the nucleotide sequences are located at the 5' and 3' ends of a nucleotide sequence corresponding to the target nucleic acid to undergo homologous recombination, and an instruction manual.

In some embodiments, the kit further includes a primary cell selected from the group consisting of a primary blood cell, a primary mesenchymal cell, and a combination thereof. In some instances, the kit also contains a reagent for harvesting or isolating a primary cell from a subject. The primary cell can be selected from the group consisting of a primary blood cell, a primary mesenchymal cell, and a combination thereof. The subject can be a mammalian subject, e.g., a human subject.

In yet further aspects, provided herein is method of preventing or treating a disease in a subject in need thereof, the method comprising administering to the subject any of the genetically modified primary cells described herein, or any of the pharmaceutical compositions described herein, to prevent the disease or ameliorate one or more symptoms of the disease.

In some embodiments, the step of administering comprises a delivery route selected from the group consisting of intravenous, intraperitoneal, intramuscular, intradermal, subcutaneous, intrathecal, intraosseous, or a combination thereof. The disease can be selected from the group consisting of a hemoglobinopathy, a viral infection, X-linked severe combined immune deficiency, Fanconi anemia, hemophilia, neoplasia, cancer, amyotrophic lateral sclerosis, Alzheimer's disease, Parkinson's disease, cystic fibrosis, blood diseases and disorders, inflammation, immune system diseases or disorders, metabolic diseases, liver diseases and disorders, kidney diseases and disorders, muscular diseases and disorders, bone or cartilage diseases and disorders, neurological and neuronal diseases and disorders, cardiovascular diseases and disorders, pulmonary diseases and disorders, and lysosomal storage disorders. In some instances, the hemoglobinopathy is sickle cell disease, α-thalassemia, β-thalassemia, or δ-thalassemia. In other instances, the viral infection is selected from the group consisting of a hepatitis B virus infection, hepatitis C virus infection, human papilloma virus infection, human immunodeficiency virus (HIV) infection, human T-lymphotrophic virus (HTLV) infection, Epstein-Barr virus infection, herpes virus infection, cytomegalovirus infection, and any other chronic viral infection. In yet other instances, the muscular diseases and disorders are selected from the group consisting of Becker muscular dystrophy, Duchenne muscular dystrophy, Emery-Dreifuss muscular dystrophy, facioscapulohumeral muscular dystrophy, any other muscular dystrophy, and muscular atrophy.

In particular embodiments, the genetically modified primary cells or pharmaceutical compositions of the present invention are administered to the subject in a sufficient amount to correct a mutation in the target nucleic acid that is associated with the disease. In some instances, the mutation is corrected by replacing a mutant allele in the target nucleic acid with the wild-type allele. In other instances, the mutation is corrected by inserting an open reading frame (ORF) that corresponds to a wild-type cDNA of the target nucleic acid. As a non-limiting example, the method of the present invention can be used to prevent or treat sickle cell disease by administering genetically modified primary cells or pharmaceutical compositions thereof wherein the sickle cell disease-causing E6V mutation in the HBB gene has been corrected via editing the nucleotide mutation (e.g., by introducing a homologous donor AAV vector comprising the sickle cell disease nucleotide correction donor template set forth in SEQ ID NO:36, wherein a "T" nucleotide at position 1194 has been changed to an "A" nucleotide to correct the E6V mutation) or knocking in a wild-type HBB cDNA.

B. Multiplexed Gene Targeting

The methods of the present invention enable targeted integration frequencies that are high enough to allow multiplexed gene targeting. Multiplexing can be used, for example, to simultaneously modify both alleles of the same gene, modify one allele of two or more different genes, or a combination thereof.

In some embodiments, multiplexing comprises introducing two or more different modified sgRNAs into a primary cell. Any number of modified sgRNAs can be introduced. In some instances, between about two and ten (i.e., about 2, 3, 4, 5, 6, 7, 8, 9, or 10) different modified sgRNAs are introduced into the primary cell. In other instances, between about 10 and 100 (i.e., about 10, 15, 20, 25, 30, 35, 40, 45, 50, 55, 60, 65, 70, 75, 80, 85, 90, 95, or 100) different modified sgRNAs are introduced into the primary cell. In other instances, between about 100 and 1,000 (i.e., about 100, 150, 200, 250, 300, 350, 400, 450, 500, 550, 600, 650, 700, 750, 800, 850, 900, 950, or 1,000) different modified sgRNAs are introduced into the primary cell. In some instances, at least about 1,000 to 10,000 (i.e., about 1,000, 1500, 2,000, 2,500, 3,000, 3,500, 4,000, 4,500, 5,000, 5,500, 6,000, 6,500, 7,000, 7,500, 8,000, 8,500, 9,000, 9,500, 10,000, or more) different modified sgRNAs are introduced into the primary cell. In particular embodiments, each different modified sgRNA is directed to a different target nucleic acid. Introducing two or more different modified sgRNAs is useful, for example, in targeting multiple different genes (i.e., each different modified sgRNA can be used to target a different nucleic acid or gene). In some instances, at least some of the different modified sgRNAs are introduced concomitantly. In other instances, all of the modified sgRNAs are introduced concomitantly. In yet other instances, each of the different modified sgRNAs is introduced sequentially.

In other embodiments, multiplexing comprises introducing two or more different homologous donor adeno-associated viral (AAV) vectors into a primary cell. Any number of donor AAV vectors can be introduced. In some instances, between about two and ten (i.e., about 2, 3, 4, 5, 6, 7, 8, 9, or 10) different donor AAV vectors are introduced into the primary cell. In other instances, between about 10 and 100 (i.e., about 10, 15, 20, 25, 30, 35, 40, 45, 50, 55, 60, 65, 70, 75, 80, 85, 90, 95, or 100) different donor AAV vectors are introduced into the primary cell. In other instances, between about 100 and 1,000 (i.e., about 100, 150, 200, 250, 300, 350, 400, 450, 500, 550, 600, 650, 700, 750, 800, 850, 900, 950, or 1,000) different donor AAV vectors are introduced into the primary cell. In some instances, at least about 1,000 to 10,000 (i.e., about 1,000, 1500, 2,000, 2,500, 3,000, 3,500, 4,000, 4,500, 5,000, 5,500, 6,000, 6,500, 7,000, 7,500, 8,000, 8,500, 9,000, 9,500, 10,000, or more) different donor AAV vectors are introduced into the primary cell. In particular embodiments, each different donor AAV vector is directed to a different target nucleic acid. Introducing donor AAV vectors that are directed to different nucleic acids is useful, for example, in targeting multiple genes or nucleic acids (i.e., each different donor AAV vector can be used to target a different nucleic acid or gene). As a non-limiting example, three different recombinant AAV6 donor vectors, each targeting a different gene (e.g., IL2RG, HBB, and CCR5), can be introduced into a primary cell. In other embodiments, at least two of the different donor AAV vectors are directed to the same target nucleic acid. Introducing two different donor AAV vectors that are directed to the same target nucleic acid is useful, as a non-limiting example, in targeting two different alleles of the same gene or nucleic acid. Furthermore, each of the vectors directed to the same target nucleic acid can comprise a different reporter. As a non-limiting example, two different recombinant AAV6 donor vectors, both directed to the same gene (e.g., CCR5) but comprising sequences encoding two different reporters (e.g., GFP and mCherry) can be introduced into a primary cell. This allows one to determine that integration has occurred at each allele, as each allele is reported on by a different marker.

In some instances, at least some of the different donor AAV vectors are introduced concomitantly. In other instances, all of the donor AAV vectors are introduced concomitantly. In yet other instances, each of the different donor AAV vectors is introduced sequentially. In some embodiments, each of the donor AAV vectors is of the same serotype (e.g., AAV6, AAV7, AAV8, or another serotype described herein or known to one of skill in the art). In other embodiments, at least some of the donor AAV vectors are of a different serotype. In certain embodiments, each of the different donor AAV vectors is of a different serotype.

In certain other embodiments, multiplexing comprises introducing a plurality of different recombinant donor templates into a primary cell. Any number of recombinant donor templates can be introduced. In some instances, the plurality comprises between about two and ten (i.e., about 2, 3, 4, 5, 6, 7, 8, 9, or 10) different recombinant donor templates. In other instances, the plurality comprises between about 10 and 100 (i.e., about 10, 15, 20, 25, 30, 35, 40, 45, 50, 55, 60, 65, 70, 75, 80, 85, 90, 95, or 100) different recombinant donor templates. In other instances, the plurality comprises between about 100 and 1,000 (i.e., about 100, 150, 200, 250, 300, 350, 400, 450, 500, 550, 600, 650, 700, 750, 800, 850, 900, 950, or 1,000) different recombinant donor templates. In some instances, the plurality comprises at least about 1,000 to 10,000 (i.e., about 1,000, 1500, 2,000, 2,500, 3,000, 3,500, 4,000, 4,500, 5,000, 5,500, 6,000, 6,500, 7,000, 7,500, 8,000, 8,500, 9,000, 9,500, 10,000, or more) different recombinant donor templates. The plurality of recombinant donor templates can all be included in the same donor AAV vector, or each different recombinant donor template can be included in a separate donor AAV vector. A combination thereof is also useful in some applications.

In some embodiments, the recombinant donor template or plurality of different recombinant donor templates further comprises a nucleotide sequence encoding a selectable marker, a detectable marker, a cell surface marker, or a combination thereof. Non-limiting examples of selectable markers, detectable markers, and cell surface markers are described below. In some instances, each of the different donor templates in the plurality thereof further comprises a different nucleotide sequence encoding a selectable marker, a detectable marker, a cell surface marker, or a combination thereof. As a non-limiting example, such an arrangement is useful for detecting modification of different genes or nucleic acids (e.g., by introducing two different recombinant donor templates, each comprising IL2RG-GFP or HBB-tdTomato, one can use detection of GFP and tdTomato to detect or confirm modification of the IL2RG and HBB genes, respectively).

In other instances, at least two of the different recombinant donor templates comprise the same nucleotide sequence encoding a selectable marker, a detectable marker, a cell surface marker, or a combination thereof. Such an arrangement is useful in scenarios wherein a large number of genes or nucleic acids are being modified and a limited number of markers are available, and/or it only necessary to select at least for one modification event. As a non-limiting example, if three genes are being targeted for modification, and it is only necessary to identify or select cells wherein at least one (i.e., 1, 2, or 3) gene has been modified, then using the same marker is acceptable and economical.

In some other embodiments, multiplexing comprises a combination of one or more of the multiplexing approaches described above (i.e., introducing into the primary cell two or more different sgRNAs, two or more different donor AAV vectors, two or more different recombinant donor templates and/or one or more marker-encoding nucleotide sequences, or a combination thereof).

C. Enriching Genetically Modified Primary Cells

In some aspects, provided herein is a method for enriching a population of genetically modified primary cells having targeted integration at a target nucleic acid. The method includes: (a) introducing a DNA nuclease and a homologous donor adeno-associated viral (AAV) vector comprising a recombinant donor template into a population of primary cells, wherein the recombinant donor template comprises a nucleotide sequence encoding a selectable marker; (b) culturing the population of primary cells for a period of time sufficient to produce a population of genetically modified primary cells and a population of unmodified primary cells; and (c) separating the population of genetically modified primary cells from the population of unmodified primary cells based upon a higher expression of the selectable marker in the population of genetically modified primary cells compared to a population of primary cells to which only the homologous donor AAV vector has been introduced, thereby generating an enriched population of genetically modified primary cells.

In some embodiments, the population of primary cells is selected from the group consisting of primary blood cells, primary mesenchymal cells, and a combination thereof. In some embodiments, the primary blood cells are selected from the group consisting of immune cells, red blood cells, progenitors or stem cells thereof, and a combination thereof. In some instances, the immune cells are selected from the group consisting of T cells, B cells, dendritic cells, natural killer cells, macrophages, neutrophils, eosinophils, basophils, mast cells, precursors thereof, and a combination thereof. The progenitors or stem cells can be selected from the group consisting of hematopoietic progenitor cells, hematopoietic stem cells (HSCs), and a combination thereof. In some cases, the red blood cells are a blood stem cells. In some instances, the primary mesenchymal cells are selected from the group consisting of mesenchymal stem cells (MSCs), mesenchymal progenitor cells, mesenchymal precursor cells, differentiated mesenchymal cells, and a combination thereof. The differentiated mesenchymal cells can be selected from the group consisting of bone cells, cartilage cells, muscle cells, adipose cells, stromal cells, fibroblasts, dermal cells, and a combination thereof.

In certain embodiments, the DNA nuclease is selected from the group consisting of a CRISPR-associated protein (Cas) polypeptide, a zinc finger nuclease (ZFN), a transcription activator-like effector nuclease (TALEN), a meganuclease, a variant thereof, a fragment thereof, and a combination thereof. In some instances, the DNA nuclease is a polypeptide, an mRNA encoding the polypeptide, and/or a recombinant expression vector comprising a nucleotide sequence encoding the polypeptide.

In some embodiments, step (a) further comprises introducing into the population of primary cells a DNA-targeting RNA, a truncated DNA-targeting RNA, or a nucleotide sequence encoding the DNA-targeting RNA or truncated DNA-targeting RNA. In certain instances, the DNA-targeting RNA comprises a single guide RNA (sgRNA) or a truncated sgRNA. In some cases, the sgRNA (e.g., truncated sgRNA) comprises a first nucleotide sequence that is complementary to the target nucleic acid and a second nucleotide sequence that interacts with a Cas polypeptide. In other instances, the sgRNA comprises one or more modified nucleotides. In some cases, one or more of the nucleotides in the first nucleotide sequence and/or the second nucleotide sequence are modified nucleotides.

In some embodiments, the modified nucleotides comprise a modification in a ribose group, a phosphate group, a nucleobase, or a combination thereof. In some instances, the modification in the ribose group comprises a modification at the 2' position of the ribose group. In some cases, the modification at the 2' position of the ribose group is selected from the group consisting of 2'-O-methyl, 2'-fluoro, 2'-deoxy, 2'-O-(2-methoxyethyl), and a combination thereof. In other instances, the modification in the phosphate group comprises a phosphorothioate modification. In other embodiments, the modified nucleotides are selected from the group consisting of a 2'-O-methyl (M) nucleotide, a 2'-O-methyl 3'-phosphorothioate (MS) nucleotide, a 2'-O-methyl 3'-thioPACE (MSP) nucleotide, and a combination thereof.

In some embodiments, the modified sgRNA comprises one, two, or three consecutive or non-consecutive modified nucleotides at or near the 5'-end of the first nucleotide sequence and/or one, two, or three consecutive or non-consecutive modified nucleotides at or near the 3'-end of the second nucleotide sequence. In some instances, the modified sgRNA comprises three consecutive modified nucleotides at the 5'-end of the first nucleotide sequence and three consecutive modified nucleotides at the 3'-end of the second nucleotide sequence. The modified sgRNA can be chemically synthesized. In other embodiments, the modified sgRNA comprises at least two different modified sgRNAs, wherein each modified sgRNA is directed to different target nucleic acids.

In some embodiments, the Cas polypeptide is a Cas9 polypeptide, a variant thereof, or a fragment thereof. In certain instances, the Cas polypeptide variant comprises a high-fidelity or enhanced specificity Cas9 polypeptide variant. In certain embodiments, the sgRNA (e.g., modified sgRNA) and the Cas polypeptide are introduced into the population of primary cells concomitantly. In other embodiments, the sgRNA (e.g., modified sgRNA) and the Cas polypeptide are introduced into the population of primary cells sequentially. In some cases, the sgRNA is introduced first, and the Cas polypeptide thereafter. In other cases, the Cas polypeptide is introduced first, and the sgRNA thereafter.

In certain embodiments, the sgRNA (e.g., modified sgRNA) and the Cas polypeptide are incubated together to form a ribonucleoprotein (RNP) complex prior to introducing into the population of primary cells. For instance, the sgRNA and the Cas polypeptide can be mixed together in a vessel to form an RNP complex, and then the RNP complex is introduced into the population of primary cells. In particular embodiments, in order to facilitate multiplexing, a plurality of different RNP complexes (i.e., two or more different RNP complexes) is formed, wherein each different RNP complex is formed by incubating the Cas polypeptide with a different sgRNA. The plurality of different RNP complexes is then introduced into the primary cell or population thereof. This approach is useful, for example, to modify multiple genes or nucleic acids at once. In other embodiments, the Cas polypeptide described herein can be an mRNA encoding the Cas polypeptide, which Cas mRNA is introduced into the population of primary cells together with the sgRNA as an "All RNA" CRISPR system. In certain instances, the sgRNA (e.g., modified sgRNA) and the Cas mRNA are introduced into population of primary cells concomitantly. In other instances, the sgRNA (e.g., modified sgRNA) and the Cas mRNA are introduced into the population of primary cells sequentially. In some cases, the sgRNA is introduced first, and the Cas mRNA thereafter. In other cases, the Cas mRNA is introduced first, and the sgRNA thereafter.

In some embodiments, the RNP complex and the homologous donor AAV vector are concomitantly introduced into the population of primary cells. In other embodiments, the RNP complex and the homologous donor AAV vector are sequentially introduced into the population of primary cells. In some instances, the RNP complex is introduced into the population of primary cells before the homologous donor AAV vector. In other instances, the homologous donor AAV vector is introduced into the population of primary cells before the RNP complex. For example, the RNP complex can be introduced into the population of primary cells about 1, 2, 3, 4, 5, 6, 7, 8, 9, 10, 11, 12, 13, 14, 15, 16, 17, 18, 19, 20, 25, 30, 35, 40, 45, 50, 55, 60, 90, 120, 150, 180, 210, or 240 minutes or more before the homologous donor AAV vector, or vice versa. In particular embodiments, the RNP complex is introduced into the population of primary cells about 15 minutes (e.g., from about 10 to about 20 minutes) before the homologous donor AAV vector.

In some embodiments, the "All RNA" CRISPR system and the homologous donor AAV vector are concomitantly introduced into the population of primary cells. In other embodiments, the "All RNA" CRISPR system and the homologous donor AAV vector are sequentially introduced into the population of primary cells. In some instances, the "All RNA" CRISPR system is introduced into the population of primary cells before the homologous donor AAV vector. In other instances, the homologous donor AAV vector is introduced into the population of primary cells before the "All RNA" CRISPR system. For example, the "All RNA" CRISPR system can be introduced into the population of primary cells about 1, 2, 3, 4, 5, 6, 7, 8, 9, 10, 11, 12, 13, 14, 15, 16, 17, 18, 19, 20, 25, 30, 35, 40, 45, 50, 55, 60, 90, 120, 150, 180, 210, or 240 minutes or more before the homologous donor AAV vector, or vice versa. In particular embodiments, the "All RNA" CRISPR system is introduced into the population of primary cells about 15 minutes (e.g., from about 10 to about 20 minutes) before the homologous donor AAV vector.

In some embodiments, the step of introducing the DNA nuclease (e.g., Cas polypeptide) and optionally the DNA-targeting RNA (e.g., sgRNA) into the population of primary cells comprises electroporating the population of primary cells. In some embodiments, the step of introducing the homologous donor AAV vector into the population of primary cells comprises transducing the population of primary cells.

In certain embodiments, the recombinant donor template comprises two nucleotide sequences comprising two non-overlapping, homologous portions of the target nucleic acid, wherein the nucleotide sequences are located at the 5' and 3' ends of a nucleotide sequence corresponding to the target nucleic acid.

In some embodiments, the homologous donor AAV vector is selected from a wild-type AAV serotype 1 (AAV1), wild-type AAV serotype 2 (AAV2), wild-type AAV serotype 3 (AAV3), wild-type AAV serotype 4 (AAV4), wild-type AAV serotype 5 (AAV5), wild-type AAV serotype 6 (AAV6), wild-type AAV serotype 7 (AAV7), wild-type AAV serotype 8 (AAV8), wild-type AAV serotype 9 (AAV9), wild-type AAV serotype 10 (AAV10), wild-type AAV serotype 11 (AAV11), wild-type AAV serotype 12 (AAV12), a variant thereof, and any shuffled chimera thereof. In some instances, the homologous donor AAV vector has at least about 90% sequence identity to any one selected from the group consisting of an AAV1, AAV2, AAV3, AAV4, AAV3, AAV5, AAV6, AAV7, AAV8, AAV9, AAV10, AAV11 and AAV12. In other instances, the homologous donor AAV vector is a wild-type AAV6 or an AAV6 variant having at least 95% sequence identity to wild-type AAV6, e.g., 95%, 96%, 97%, 98%, 99%, or 100% sequence identity to wild-type AAV6.

In some embodiments, greater than about 70% of the primary cells in the enriched population are genetically modified, e.g., about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the primary cells in the enriched population. In other embodiments, greater than about 80% of the primary cells in the enriched population are genetically modified, e.g., about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the primary cells in the enriched population. In yet other embodiments, greater than about 85% of the primary cells in the enriched population are genetically modified, e.g., about 85%, about 86%, about 87%, about 88%, about 89%, about 90%, about 91%, about 92%, about 93%, about 94%, about 95%, about 96%, about 97%, about 98%, about 99%, or about 100% of the primary cells in the enriched population. In further embodiments, greater than about 90% of the primary cells in the enriched population are genetically modified, e.g., about 90%, about 91%, about 92%, about 93%, about 94%, about 95%, about 96%, about 97%, about 98%, about 99%, or about 100% of the primary cells in the enriched population. In yet further embodiments, greater than about 95% of the primary cells in the enriched population are genetically modified, e.g., about 95%, about 96%, about 97%, about 98%, about 99%, or about 100% of the primary cells in the enriched population.

In some embodiments, the population of primary cells is cultured for a period of 2 to 4 days (e.g., 2, 3, or 4 days) after the DNA nuclease and/or the homologous donor AAV vector is introduced. In particular embodiments, the population of primary cells is cultured for a period of 2 to 4 days (e.g., 2, 3, or 4 days) after the DNA nuclease is introduced as a ribonucleoprotein (RNP) complex via electroporation. In other embodiments, the population of primary cells is cultured for a period of less than 2 days (e.g., 12, 24, or 36 hours) or more than 4 days (e.g., 5, 6, 7, or more days) after the DNA nuclease and/or the homologous donor AAV vector is introduced. The population of primary cells can be cultured for a period of time sufficient to produce a population of genetically modified primary cells and a population of unmodified primary cells, such that the primary cells (e.g., greater than about 50%, 55%, 60%, 65%, 70%, 75%, 80%, 85%, 90%, or 95% of the primary cells) do not differentiate and/or lose their long-term repopulating capacity upon culturing.

In some embodiments, step (b) further comprises culturing the population of primary cells in a culture medium comprising a small molecule that increases targeting efficiency of gene modification via homologous recombination. In some instances, the small molecule comprises UM171, any other pyrimidoindole derivative, a variant thereof, or a derivative thereof. The compound UM171 is described in, e.g., Fares et al., Science, 2014, 345 (6203): 1509-12.

In some embodiments, the selectable marker is a detectable marker or a cell surface marker. In certain instances, the detectable marker is a fluorescent protein such as green fluorescent protein (GFP), enhanced green fluorescent protein (EGFP), red fluorescent protein (RFP), blue fluorescent protein (BFP), cyan fluorescent protein (CFP), yellow fluorescent protein (YFP), mCherry, tdTomato, DsRed-Monomer, DsRed-Express, DSRed-Express2, DsRed2, AsRed2, mStrawberry, mPlum, mRaspberry, HcRedl, E2-Crimson, mOrange, mOrange2, mBanana, ZsYellowl, TagBFP, mTagBFP2, Azurite, EBFP2, mKalamal, Sirius, Sapphire, T-Sapphire, ECFP, Cerulean, SCFP3A, mTurquoise, mTurquoise2, monomeric Midoriishi-Cyan, TagCFP, mTFP1, Emerald, Superfolder GFP, Monomeric Azami Green, TagGFP2, mUKG, mWasabi, Clover, mNeonGreen, Citrine, Venus, SYFP2, TagYFP, Monomeric Kusabira-Orange, mKOk, mKO2, mTangerine, mApple, mRuby, mRuby2, HcRed-Tandem, mKate2, mNeptune, NiFP, mKeima Red, LSS-mKate1, LSS-mKate2, mBeRFP, PA-GFP, PAmCherry1, PATagRFP, TagRFP6457, IFP1.2, iRFP, Kaede (green), Kaede (red), KikGR1 (green), KikGR1 (red), PS-CFP2, mEos2 (green), mEos2 (red), mEos3.2 (green), mEos3.2 (red), PSmOrange, Dronpa, Dendra2, Timer, AmCyan1, or a combination thereof. In other instances, the cell surface marker is a marker not normally expressed on the primary cells such as a truncated nerve growth factor receptor (tNGFR), a truncated epidermal growth factor receptor (tEGFR), CD8, truncated CD8, CD19, truncated CD19, a variant thereof, a fragment thereof, a derivative thereof, or a combination thereof.

In certain embodiments, the genetically modified primary cells are separated from the population of unmodified primary cells using flow cytometry. In some instances, the flow cytometry comprises fluorescence-activated cell sorting (FACS). In certain other embodiments, the genetically modified primary cells are separated from the population of unmodified primary cells using magnetic bead separation. In some instances, the magnetic bead separation comprises magnetic-activated cell sorting (MACS).

In some embodiments, the expression of the selectable marker is at least about 1-fold higher in the population of genetically modified primary cells compared to the population of primary cells to which only the homologous donor AAV vector has been introduced. For example, the expression of the selectable marker can be (at least) about 1-fold, about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, or about 100-fold higher in the population of genetically modified primary cells compared to the population of primary cells to which only the homologous donor AAV vector has been introduced. For example, the expression of the selectable marker can be about 1-fold to about 100-fold, about 1-fold to about 50-fold, about 1-fold to about 25-fold, about 1-fold to about 10-fold, about 5-fold to about 100-fold, about 5-fold to about 50-fold, about 5-fold to about 25-fold, about 5-fold to about 20-fold, about 5-fold to about 15-fold, about 5-fold to about 10-fold, about 10-fold to about 100-fold, about 10-fold to about 50-fold, about 10-fold to about 25-fold, about 10-fold to about 20-fold, about 10-fold to about 15-fold, about 15-fold to about 100-fold, about 15-fold to about 50-fold, about 15-fold to about 25-fold, about 15-fold to about 20-fold, about 25-fold to about 100-fold, about 25-fold to about 50-fold, or about 50-fold to about 100-fold higher in the population of genetically modified primary cells compared to the population of primary cells to which only the homologous donor AAV vector has been introduced. In particular embodiments, the expression of the selectable marker is about 10-fold to about 25-fold higher in the population of genetically modified primary cells compared to the population of primary cells to which only the homologous donor AAV vector has been introduced.

In particular embodiments, the enriched population of genetically modified primary cells has long-term repopulating capacity.

In some embodiments, the method further comprises expanding the enriched population of genetically modified primary cells. In other embodiments, the method further comprises culturing the population of primary cells in a culture medium comprising a cytokine cocktail for 1 to 2 days prior to step (a). In yet other embodiments, step (b) further comprises culturing the population of primary cells in a culture medium comprising a cytokine cocktail.

In some embodiments, the population of primary cells is isolated from a mammal prior to introducing the DNA nuclease and the homologous donor AAV vector into the population of primary cells. For instance, the population of primary cells can be harvested from a human subject. In some instances, the enriched population of genetically modified primary cells is administered to the mammal. In other words, the enriched population of genetically modified primary cells undergoes autologous transplantation. In other instances, the enriched population of genetically modified primary cells undergoes allogeneic transplantation. For example, a population of primary cells that has not undergone stable gene modification is isolated from a donor subject, and then the enriched population of genetically modified primary cells is transplanted into a recipient subject who is different than the donor subject.

In other aspects, provided herein is an enriched population of genetically modified primary cells produced by the enrichment method described herein.

In yet other aspects, provided herein is a pharmaceutical composition comprising an enriched population of genetically modified primary cells described herein, and a pharmaceutically acceptable carrier. In some embodiments, the pharmaceutical composition comprises one type of an enriched population of genetically modified primary cells. In other embodiments, the pharmaceutical composition comprises two or more different types of enriched populations of genetically modified primary cells, e.g., 2, 3, 4, 5, 6, 7, 8, 9, 10 or more different types of enriched populations of genetically modified primary cells.

In further aspects, provided herein is a method for preventing or treating a disease in a subject in need thereof. The method comprises administering to the subject an enriched population of genetically modified primary cells described herein, or a pharmaceutical composition comprising an enriched population of genetically modified primary cells described herein, to prevent the disease or ameliorate one or more symptoms of the disease.

In some embodiments, the step of administering comprises a delivery route selected from the group consisting of intravenous, intraperitoneal, intramuscular, intradermal, subcutaneous, intrathecal, intraosseous, or a combination thereof. The disease can be selected from the group consisting of a hemoglobinopathy, a viral infection, X-linked severe combined immune deficiency, Fanconi anemia, hemophilia, neoplasia, cancer, amyotrophic lateral sclerosis, Alzheimer's disease, Parkinson's disease, cystic fibrosis, blood diseases and disorders, inflammation, immune system diseases or disorders, metabolic diseases, liver diseases and disorders, kidney diseases and disorders, muscular diseases and disorders, bone or cartilage diseases and disorders, neurological and neuronal diseases and disorders, cardiovascular diseases and disorders, pulmonary diseases and disorders, and lysosomal storage disorders. In some instances, the hemoglobinopathy is sickle cell disease, α-thalassemia, β-thalassemia, or δ-thalassemia. In other instances, the viral infection is selected from the group consisting of a hepatitis B virus infection, hepatitis C virus infection, human papilloma virus infection, human immunodeficiency virus (HIV) infection, human T-lymphotrophic virus (HTLV) infection, Epstein-Barr virus infection, herpes virus infection, cytomegalovirus infection, and any other chronic viral infection. In yet other instances, the muscular diseases and disorders are selected from the group consisting of Becker muscular dystrophy, Duchenne muscular dystrophy, Emery-Dreifuss muscular dystrophy, facioscapulohumeral muscular dystrophy, any other muscular dystrophy, and muscular atrophy.

D. Nuclease-Mediated Genome Editing

The present invention includes using a DNA nuclease such as an engineered (e.g., programmable or targetable) DNA nuclease to induce genome editing of a target nucleic acid sequence. Any suitable DNA nuclease can be used including, but not limited to, CRISPR-associated protein (Cas) nucleases, zinc finger nucleases (ZFNs), transcription activator-like effector nucleases (TALENs), meganucleases, other endo- or exo-nucleases, variants thereof, fragments thereof, and combinations thereof.

In some embodiments, a nucleotide sequence encoding the DNA nuclease is present in a recombinant expression vector. In certain instances, the recombinant expression vector is a viral construct, e.g., a recombinant adeno-associated virus construct, a recombinant adenoviral construct, a recombinant lentiviral construct, etc. For example, viral vectors can be based on vaccinia virus, poliovirus, adenovirus, adeno-associated virus, SV40, herpes simplex virus, human immunodeficiency virus, and the like. A retroviral vector can be based on Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, mammary tumor virus, and the like. Useful expression vectors are known to those of skill in the art, and many are commercially available. The following vectors are provided by way of example for eukaryotic host cells: pXT1, pSG5, pSVK3, pBPV, pMSG, and pSVLSV40. However, any other vector may be used if it is compatible with the host cell. For example, useful expression vectors containing a nucleotide sequence encoding a Cas9 polypeptide are commercially available from, e.g., Addgene, Life Technologies, Sigma-Aldrich, and Origene.

Depending on the target cell/expression system used, any of a number of transcription and translation control elements, including promoter, transcription enhancers, transcription terminators, and the like, may be used in the expression vector. Useful promoters can be derived from viruses, or any organism, e.g., prokaryotic or eukaryotic organisms. Suitable promoters include, but are not limited to, the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human H1 promoter (H1), etc.

In other embodiments, a nucleotide sequence encoding the DNA nuclease is present as an RNA (e.g., mRNA). The RNA can be produced by any method known to one of ordinary skill in the art. As non-limiting examples, the RNA can be chemically synthesized or in vitro transcribed. In certain embodiments, the RNA comprises an mRNA encoding a Cas nuclease such as a Cas9 polypeptide or a variant thereof. For example, the Cas9 mRNA can be generated through in vitro transcription of a template DNA sequence such as a linearized plasmid containing a Cas9 open reading frame (ORF). The Cas9 ORF can be codon optimized for expression in mammalian systems. In some instances, the Cas9 mRNA encodes a Cas9 polypeptide with an N- and/or C-terminal nuclear localization signal (NLS). In other instances, the Cas9 mRNA encodes a C-terminal HA epitope tag. In yet other instances, the Cas9 mRNA is capped, polyadenylated, and/or modified with 5-methylcytidine. Cas9 mRNA is commercially available from, e.g., TriLink BioTechnologies, Sigma-Aldrich, and Thermo Fisher Scientific.

In yet other embodiments, the DNA nuclease is present as a polypeptide. The polypeptide can be produced by any method known to one of ordinary skill in the art. As non-limiting examples, the polypeptide can be chemically synthesized or in vitro translated. In certain embodiments, the polypeptide comprises a Cas protein such as a Cas9 protein or a variant thereof. For example, the Cas9 protein can be generated through in vitro translation of a Cas9 mRNA described herein. In some instances, the Cas protein such as a Cas9 protein or a variant thereof can be complexed with a single guide RNA (sgRNA) such as a modified sgRNA to form a ribonucleoprotein (RNP). Cas9 protein is commercially available from, e.g., PNA Bio (Thousand Oaks, Calif., USA) and Life Technologies (Carlsbad, Calif., USA).

1. CRISPR/Cas System

The CRISPR (Clustered Regularly Interspaced Short Palindromic Repeats)/Cas (CRISPR-associated protein) nuclease system is an engineered nuclease system based on a bacterial system that can be used for genome engineering. It is based on part of the adaptive immune response of many bacteria and archaea. When a virus or plasmid invades a bacterium, segments of the invader's DNA are converted into CRISPR RNAs (crRNA) by the "immune" response. The crRNA then associates, through a region of partial complementarity, with another type of RNA called tracrRNA to guide the Cas (e.g., Cas9) nuclease to a region homologous to the crRNA in the target DNA called a "protospacer." The Cas (e.g., Cas9) nuclease cleaves the DNA to generate blunt ends at the double-strand break at sites specified by a 20-nucleotide guide sequence contained within the crRNA transcript. The Cas (e.g., Cas9) nuclease can require both the crRNA and the tracrRNA for site-specific DNA recognition and cleavage. This system has now been engineered such that the crRNA and tracrRNA can be combined into one molecule (the "single guide RNA" or "sgRNA"), and the crRNA equivalent portion of the single guide RNA can be engineered to guide the Cas (e.g., Cas9) nuclease to target any desired sequence (see, e.g., Jinek et al. (2012) Science 337:816-821; Jinek et al. (2013) eLife 2:e00471; Segal (2013) eLife 2:e00563). Thus, the CRISPR/Cas system can be engineered to create a double-strand break at a desired target in a genome of a cell, and harness the cell's endogenous mechanisms to repair the induced break by homology-directed repair (HDR) or nonhomologous end-joining (NHEJ).

In some embodiments, the Cas nuclease has DNA cleavage activity. The Cas nuclease can direct cleavage of one or both strands at a location in a target DNA sequence. For example, the Cas nuclease can be a nickase having one or more inactivated catalytic domains that cleaves a single strand of a target DNA sequence.

Non-limiting examples of Cas nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, variants thereof, mutants thereof, and derivatives thereof. There are three main types of Cas nucleases (type I, type II, and type III), and 10 subtypes including 5 type I, 3 type II, and 2 type III proteins (see, e.g., Hochstrasser and Doudna, *Trends Biochem Sci*, 2015:40(1):58-66). Type II Cas nucleases include Cas1, Cas2, Csn2, and Cas9. These Cas nucleases are known to those skilled in the art. For example, the amino acid sequence of the *Streptococcus pyogenes* wild-type Cas9 polypeptide is set forth, e.g., in NBCI Ref. Seq. No. NP_269215, and the amino acid sequence of *Streptococcus thermophilus* wild-type Cas9 polypeptide is set forth, e.g., in NBCI Ref. Seq. No. WP_011681470. CRISPR-related endonucleases that are useful in the present invention are disclosed, e.g., in U.S. Application Publication Nos. 2014/0068797, 2014/0302563, and 2014/0356959.

Cas nucleases, e.g., Cas9 polypeptides, can be derived from a variety of bacterial species including, but not limited to, *Veillonella* atypical, *Fusobacterium nucleatum, Filifactor alocis, Solobacterium moorei, Coprococcus catus, Treponema denticola, Peptomphilus duerdenii, Catenibacterium mitsuokai, Streptococcus mutans, Listeria innocua, Staphylococcus pseudintermedius, Acidaminococcus intestine, Olsenella uli, Oenococcus kitaharae, Bifidobacterium bifidum, Lactobacillus rhamnosus, Lactobacillus gasseri, Finegoldia magna, Mycoplasma mobile, Mycoplasma gallisepticum, Mycoplasma ovipneumoniae, Mycoplasma canis, Mycoplasma synoviae, Eubacterium rectale, Streptococcus thermophilus, Eubacterium dolichum, Lactobacillus coryniformis* subsp. *Torquens, Ilyobacter polytropus, Ruminococcus albus, Akkermansia muciniphila, Acidothermus cellulolyticus, Bifidobacterium longum, Bifidobacterium dentium, Corynebacterium diphtheria, Elusimicrobium minutum, Nitratifractor salsuginis, Sphaerochaeta globus, Fibrobacter succinogenes* subsp. *Succinogenes, Bacteroides fragilis, Capnocytophaga ochracea, Rhodopseudomonas palustris, Prevotella micans, Prevotella ruminicola, Flavobacterium columnare, Aminomonas paucivorans, Rhodospirillum rubrum, Candidatus Puniceispirillum marinum, Verminephrobacter eiseniae, Ralstonia syzygii, Dinoroseobacter shibae, Azospirillum, Nitrobacter hamburgensis, Bradyrhizobium, Wolinella succinogenes, Campylobacter jejuni* subsp. *Jejuni, Helicobacter mustelae, Bacillus cereus, Acidovorax ebreus, Clostridium perfringens, Parvibaculum lavamentivorans, Roseburia intestinalis, Neisseria meningitidis, Pasteurella multocida* subsp. *Multocida, Sutterella wadsworthensis, proteobacterium, Legionella pneumophila, Parasutterella excrementihominis, Wolinella succinogenes,* and *Francisella novicida.*

"Cas9" refers to an RNA-guided double-stranded DNA-binding nuclease protein or nickase protein. Wild-type Cas9 nuclease has two functional domains, e.g., RuvC and HNH, that cut different DNA strands. Cas9 can induce double-strand breaks in genomic DNA (target DNA) when both functional domains are active. The Cas9 enzyme can comprise one or more catalytic domains of a Cas9 protein derived from bacteria belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor,* and *Campylobacter*. In some embodiments, the Cas9 is a fusion protein, e.g., the two catalytic domains are derived from different bacteria species.

Useful variants of the Cas9 nuclease can include a single inactive catalytic domain, such as a RuvC$^-$ or HNH$^-$ enzyme or a nickase. A Cas9 nickase has only one active functional domain and can cut only one strand of the target DNA, thereby creating a single strand break or nick. In some embodiments, the mutant Cas9 nuclease having at least a D10A mutation is a Cas9 nickase. In other embodiments, the mutant Cas9 nuclease having at least a H840A mutation is a Cas9 nickase. Other examples of mutations present in a Cas9 nickase include, without limitation, N854A and N863A. A double-strand break can be introduced using a Cas9 nickase if at least two DNA-targeting RNAs that target opposite DNA strands are used. A double-nicked induced double-strand break can be repaired by NHEJ or HDR (Ran et al., 2013, *Cell*, 154:1380-1389). This gene editing strategy favors HDR and decreases the frequency of INDEL mutations at off-target DNA sites. Non-limiting examples of Cas9 nucleases or nickases are described in, for example, U.S. Pat. Nos. 8,895,308; 8,889,418; and 8,865,406 and U.S. Application Publication Nos. 2014/0356959, 2014/0273226 and 2014/0186919. The Cas9 nuclease or nickase can be codon-optimized for the target cell or target organism.

In some embodiments, the Cas nuclease can be a Cas9 polypeptide that contains two silencing mutations of the RuvC1 and HNH nuclease domains (D10A and H840A), which is referred to as dCas9 (Jinek et al., *Science*, 2012, 337:816-821; Qi et al., *Cell*, 152(5):1173-1183). In one embodiment, the dCas9 polypeptide from *Streptococcus pyogenes* comprises at least one mutation at position D10, G12, G17, E762, H840, N854, N863, H982, H983, A984, D986, A987 or any combination thereof. Descriptions of such dCas9 polypeptides and variants thereof are provided in, for example, International Patent Publication No. WO 2013/176772. The dCas9 enzyme can contain a mutation at D10, E762, H983 or D986, as well as a mutation at H840 or N863. In some instances, the dCas9 enzyme contains a D10A or D10N mutation. Also, the dCas9 enzyme can include a H840A, H840Y, or H840N. In some embodiments, the dCas9 enzyme of the present invention comprises D10A and H840A; D10A and H840Y; D10A and H840N; D10N and H840A; D10N and H840Y; or D10N and H840N substitutions. The substitutions can be conservative or non-conservative substitutions to render the Cas9 polypeptide catalytically inactive and able to bind to target DNA.

For genome editing methods, the Cas nuclease can be a Cas9 fusion protein such as a polypeptide comprising the catalytic domain of the type IIS restriction enzyme, FokI, linked to dCas9. The FokI-dCas9 fusion protein (fCas9) can use two guide RNAs to bind to a single strand of target DNA to generate a double-strand break.

In some embodiments, the Cas nuclease can be a high-fidelity or enhanced specificity Cas9 polypeptide variant with reduced off-target effects and robust on-target cleavage. Non-limiting examples of Cas9 polypeptide variants with improved on-target specificity include the SpCas9 (K855A), SpCas9 (K810A/K1003A/R1060A) [also referred to as eSpCas9(1.0)], and SpCas9 (K848A/K1003A/R1060A) [also referred to as eSpCas9(1.1)] variants described in Slaymaker et al., *Science*, 351(6268):84-8 (2016), and the SpCas9 variants described in Kleinstiver et al., *Nature*, 529(7587): 490-5 (2016) containing one, two, three, or four of the following mutations: N497A, R661A, Q695A, and Q926A (e.g., SpCas9-HF1 contains all four mutations).

2. Zinc Finger Nucleases (ZFNs)

"Zinc finger nucleases" or "ZFNs" are a fusion between the cleavage domain of FokI and a DNA recognition domain containing 3 or more zinc finger motifs. The heterodimerization at a particular position in the DNA of two individual ZFNs in precise orientation and spacing leads to a double-strand break in the DNA. In some cases, ZFNs fuse a cleavage domain to the C-terminus of each zinc finger domain. In order to allow the two cleavage domains to dimerize and cleave DNA, the two individual ZFNs bind opposite strands of DNA with their C-termini at a certain distance apart. In some cases, linker sequences between the zinc finger domain and the cleavage domain requires the 5' edge of each binding site to be separated by about 5-7 bp. Exemplary ZFNs that are useful in the present invention include, but are not limited to, those described in Urnov et al., *Nature Reviews Genetics,* 2010, 11:636-646; Gaj et al., *Nat Methods,* 2012, 9(8):805-7; U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; and U.S. Application Publication Nos. 2003/0232410 and 2009/0203140.

ZFNs can generate a double-strand break in a target DNA, resulting in DNA break repair which allows for the introduction of gene modification. DNA break repair can occur via non-homologous end joining (NHEJ) or homology-directed repair (HDR). In HDR, a donor DNA repair template that contains homology arms flanking sites of the target DNA can be provided.

In some embodiments, a ZFN is a zinc finger nickase which can be an engineered ZFN that induces site-specific single-strand DNA breaks or nicks, thus resulting in HDR. Descriptions of zinc finger nickases are found, e.g., in Ramirez et al., *Nucl Acids Res,* 2012, 40(12):5560-8; Kim et al., *Genome Res,* 2012, 22(7):1327-33.

3. TALENs

"TALENs" or "TAL-effector nucleases" are engineered transcription activator-like effector nucleases that contain a central domain of DNA-binding tandem repeats, a nuclear localization signal, and a C-terminal transcriptional activation domain. In some instances, a DNA-binding tandem repeat comprises 33-35 amino acids in length and contains two hypervariable amino acid residues at positions 12 and 13 that can recognize one or more specific DNA base pairs. TALENs can be produced by fusing a TAL effector DNA binding domain to a DNA cleavage domain. For instance, a TALE protein may be fused to a nuclease such as a wild-type or mutated FokI endonuclease or the catalytic domain of FokI. Several mutations to FokI have been made for its use in TALENs, which, for example, improve cleavage specificity or activity. Such TALENs can be engineered to bind any desired DNA sequence.

TALENs can be used to generate gene modifications by creating a double-strand break in a target DNA sequence, which in turn, undergoes NHEJ or HDR. In some cases, a single-stranded donor DNA repair template is provided to promote HDR.

Detailed descriptions of TALENs and their uses for gene editing are found, e.g., in U.S. Pat. Nos. 8,440,431; 8,440,432; 8,450,471; 8,586,363; and U.S. Pat. No. 8,697,853; Scharenberg et al., *Curr Gene Ther,* 2013, 13(4):291-303; Gaj et al., *Nat Methods,* 2012, 9(8):805-7; Beurdeley et al., *Nat Commun,* 2013, 4:1762; and Joung and Sander, *Nat Rev Mol Cell Biol,* 2013, 14(1):49-55.

4. Meganucleases

"Meganucleases" are rare-cutting endonucleases or homing endonucleases that can be highly specific, recognizing DNA target sites ranging from at least 12 base pairs in length, e.g., from 12 to 40 base pairs or 12 to 60 base pairs in length. Meganucleases can be modular DNA-binding nucleases such as any fusion protein comprising at least one catalytic domain of an endonuclease and at least one DNA binding domain or protein specifying a nucleic acid target sequence. The DNA-binding domain can contain at least one motif that recognizes single- or double-stranded DNA. The meganuclease can be monomeric or dimeric.

In some instances, the meganuclease is naturally-occurring (found in nature) or wild-type, and in other instances, the meganuclease is non-natural, artificial, engineered, synthetic, rationally designed, or man-made. In certain embodiments, the meganuclease of the present invention includes an I-CreI meganuclease, I-CeuI meganuclease, I-MsoI meganuclease, I-SceI meganuclease, variants thereof, mutants thereof, and derivatives thereof.

Detailed descriptions of useful meganucleases and their application in gene editing are found, e.g., in Silva et al., *Curr Gene Ther,* 2011, 11(1):11-27; Zaslavoskiy et al., *BMC Bioinformatics,* 2014, 15:191; Takeuchi et al., *Proc Natl Acad Sci USA,* 2014, 111 (11): 4061-4066, and U.S. Pat. Nos. 7,842,489; 7,897,372; 8,021,867; 8,163,514; 8,133,697; 8,021,867; 8,119,361; 8,119,381; 8,124,36; and 8,129,134.

E. DNA-Targeting RNA

In some embodiments, the methods of the present invention comprise introducing into a primary cell a guide nucleic acid, e.g., DNA-targeting RNA (e.g., a single guide RNA (sgRNA) or a double guide nucleic acid) or a nucleotide sequence encoding the guide nucleic acid (e.g., DNA-targeting RNA). In particular embodiments, a modified single guide RNA (sgRNA) comprising a first nucleotide sequence that is complementary to a target nucleic acid and a second nucleotide sequence that interacts with a CRISPR-associated protein (Cas) polypeptide is introduced into a primary cell, wherein one or more of the nucleotides in the first nucleotide sequence and/or the second nucleotide sequence are modified nucleotides.

The DNA-targeting RNA (e.g., sgRNA) can comprise a first nucleotide sequence that is complementary to a specific sequence within a target DNA (e.g., a guide sequence) and a second nucleotide sequence comprising a protein-binding sequence that interacts with a DNA nuclease (e.g., Cas9 nuclease) or a variant thereof (e.g., a scaffold sequence or tracrRNA). The guide sequence ("first nucleotide sequence") of a DNA-targeting RNA can comprise about 10 to about 2000 nucleic acids, for example, about 10 to about 100 nucleic acids, about 10 to about 500 nucleic acids, about 10 to about 1000 nucleic acids, about 10 to about 1500 nucleic acids, about 10 to about 2000 nucleic acids, about 50 to about 100 nucleic acids, about 50 to about 500 nucleic acids, about 50 to about 1000 nucleic acids, about 50 to about 1500 nucleic acids, about 50 to about 2000 nucleic acids, about 100 to about 500 nucleic acids, about 100 to about 1000 nucleic acids, about 100 to about 1500 nucleic acids, about 100 to about 2000 nucleic acids, about 500 to about 1000 nucleic acids, about 500 to about 1500 nucleic acids, about 500 to about 2000 nucleic acids, about 1000 to about 1500 nucleic acids, about 1000 to about 2000 nucleic acids, or about 1500 to about 2000 nucleic acids at the 5' end that can direct the DNA nuclease (e.g., Cas9 nuclease) to the target DNA site using RNA-DNA complementarity base pairing. In some embodiments, the guide sequence of a DNA-targeting RNA comprises about 100 nucleic acids at the 5' end that can direct the DNA nuclease (e.g., Cas9 nuclease) to the target DNA site using RNA-DNA complementarity base pairing. In some embodiments, the guide sequence comprises 20 nucleic acids at the 5' end that can direct the DNA nuclease (e.g., Cas9 nuclease) to the target DNA site using RNA-DNA complementarity base pairing. In other embodiments, the guide sequence comprises less than 20, e.g., 19, 18, 17, 16, 15 or less, nucleic acids that are complementary to the target DNA site. The guide sequence can include 17 nucleic acids that can direct the DNA nuclease (e.g., Cas9 nuclease) to the target DNA site. In some instances, the guide sequence contains about 1 to about 10 nucleic acid mismatches in the complementarity region at the 5' end of the targeting region. In other instances, the guide sequence contains no mismatches in the complementarity region at the last about 5 to about 12 nucleic acids at the 3' end of the targeting region.

The protein-binding scaffold sequence ("second nucleotide sequence") of the DNA-targeting RNA (e.g., sgRNA) can comprise two complementary stretches of nucleotides that hybridize to one another to form a double-stranded RNA duplex (dsRNA duplex). The protein-binding scaffold sequence can be between about 30 nucleic acids to about 200 nucleic acids, e.g., about 40 nucleic acids to about 200 nucleic acids, about 50 nucleic acids to about 200 nucleic acids, about 60 nucleic acids to about 200 nucleic acids, about 70 nucleic acids to about 200 nucleic acids, about 80 nucleic acids to about 200 nucleic acids, about 90 nucleic acids to about 200 nucleic acids, about 100 nucleic acids to about 200 nucleic acids, about 110 nucleic acids to about 200 nucleic acids, about 120 nucleic acids to about 200 nucleic acids, about 130 nucleic acids to about 200 nucleic acids, about 140 nucleic acids to about 200 nucleic acids, about 150 nucleic acids to about 200 nucleic acids, about 160 nucleic acids to about 200 nucleic acids, about 170 nucleic acids to about 200 nucleic acids, about 180 nucleic acids to about 200 nucleic acids, or about 190 nucleic acids to about 200 nucleic acids. In certain aspects, the protein-binding sequence can be between about 30 nucleic acids to about 190 nucleic acids, e.g., about 30 nucleic acids to about 180 nucleic acids, about 30 nucleic acids to about 170 nucleic acids, about 30 nucleic acids to about 160 nucleic acids, about 30 nucleic acids to about 150 nucleic acids, about 30 nucleic acids to about 140 nucleic acids, about 30 nucleic acids to about 130 nucleic acids, about 30 nucleic acids to about 120 nucleic acids, about 30 nucleic acids to about 110 nucleic acids, about 30 nucleic acids to about 100 nucleic acids, about 30 nucleic acids to about 90 nucleic acids, about 30 nucleic acids to about 80 nucleic acids, about 30 nucleic acids to about 70 nucleic acids, about 30 nucleic acids to about 60 nucleic acids, about 30 nucleic acids to about 50 nucleic acids, or about 30 nucleic acids to about 40 nucleic acids.

In some embodiments, the DNA-targeting RNA (e.g., sgRNA) is a truncated form thereof comprising a guide sequence having a shorter region of complementarity to a target DNA sequence (e.g., less than 20 nucleotides in length). In certain instances, the truncated DNA-targeting RNA (e.g., sgRNA) provides improved DNA nuclease (e.g., Cas9 nuclease) specificity by reducing off-target effects. For example, a truncated sgRNA can comprise a guide sequence having 17, 18, or 19 complementary nucleotides to a target DNA sequence (e.g., 17-18, 17-19, or 18-19 complementary nucleotides). See, e.g., Fu et al., Nat. Biotechnol., 32(3): 279-284 (2014).

The DNA-targeting RNA (e.g., sgRNA) can be selected using any of the web-based software described above. As a non-limiting example, considerations for selecting a DNA-targeting RNA can include the PAM sequence for the Cas9 nuclease to be used, and strategies for minimizing off-target modifications. Tools, such as the CRISPR Design Tool, can provide sequences for preparing the DNA-targeting RNA, for assessing target modification efficiency, and/or assessing cleavage at off-target sites.

The DNA-targeting RNA (e.g., sgRNA) can be produced by any method known to one of ordinary skill in the art. In some embodiments, a nucleotide sequence encoding the DNA-targeting RNA is cloned into an expression cassette or an expression vector. In certain embodiments, the nucleotide sequence is produced by PCR and contained in an expression cassette. For instance, the nucleotide sequence encoding the DNA-targeting RNA can be PCR amplified and appended to a promoter sequence, e.g., a U6 RNA polymerase III promoter sequence. In other embodiments, the nucleotide sequence encoding the DNA-targeting RNA is cloned into an expression vector that contains a promoter, e.g., a U6 RNA polymerase III promoter, and a transcriptional control element, enhancer, U6 termination sequence, one or more nuclear localization signals, etc. In some embodiments, the expression vector is multicistronic or bicistronic and can also include a nucleotide sequence encoding a fluorescent protein, an epitope tag and/or an antibiotic resistance marker. In certain instances of the bicistronic expression vector, the first nucleotide sequence encoding, for example, a fluorescent protein, is linked to a second nucleotide sequence encoding, for example, an antibiotic resistance marker using the sequence encoding a self-cleaving peptide, such as a viral 2A peptide. Viral 2A peptides including foot-and-mouth disease virus 2A (F2A); equine rhinitis A virus 2A (E2A); porcine teschovirus-1 2A (P2A) and Thoseaasigna virus 2A (T2A) have high cleavage efficiency such that two proteins can be expressed simultaneously yet separately from the same RNA transcript.

Suitable expression vectors for expressing the DNA-targeting RNA (e.g., sgRNA) are commercially available from Addgene, Sigma-Aldrich, and Life Technologies. The expression vector can be pLQ1651 (Addgene Catalog No. 51024) which includes the fluorescent protein mCherry. Non-limiting examples of other expression vectors include pX330, pSpCas9, pSpCas9n, pSpCas9-2A-Puro, pSpCas9-2A-GFP, pSpCas9n-2A-Puro, the GeneArt® CRISPR Nuclease OFP vector, the GeneArt® CRISPR Nuclease OFP vector, and the like.

In certain embodiments, the DNA-targeting RNA (e.g., sgRNA) is chemically synthesized. DNA-targeting RNAs can be synthesized using 2'-O-thionocarbamate-protected nucleoside phosphoramidites. Methods are described in, e.g., Dellinger et al., *J. American Chemical Society* 133, 11540-11556 (2011); Threlfall et al., *Organic & Biomolecular Chemistry* 10, 746-754 (2012); and Dellinger et al., *J. American Chemical Society* 125, 940-950 (2003).

In particular embodiments, the DNA-targeting RNA (e.g., sgRNA) is chemically modified. As a non-limiting example, the DNA-targeting RNA is a modified sgRNA comprising a first nucleotide sequence complementary to a target nucleic acid (e.g., a guide sequence or crRNA) and a second nucleotide sequence that interacts with a Cas polypeptide (e.g., a scaffold sequence or tracrRNA).

Without being bound by any particular theory, sgRNAs containing one or more chemical modifications can increase the activity, stability, and specificity and/or decrease the toxicity of the modified sgRNA compared to a corresponding unmodified sgRNA when used for CRISPR-based genome editing, e.g., homologous recombination. Non-limiting advantages of modified sgRNAs include greater ease of delivery into target cells, increased stability, increased duration of activity, and reduced toxicity. The modified sgRNAs described herein as part of a CRISPR/Cas9 system provide higher frequencies of on-target genome editing (e.g., homologous recombination), improved activity, and/or specificity compared to their unmodified sequence equivalents.

One or more nucleotides of the guide sequence and/or one or more nucleotides of the scaffold sequence can be a modified nucleotide. For instance, a guide sequence that is about 20 nucleotides in length may have 1 or more, e.g., 1, 2, 3, 4, 5, 6, 7, 8, 9, 10, 11, 12, 13, 14, 15, 16, 17, 18, 19, or 20 modified nucleotides. In some cases, the guide sequence includes at least 2, 3, 4, 5, 6, 7, 8, 9, 10, or more modified nucleotides. In other cases, the guide sequence includes at least 2, 3, 4, 5, 6, 7, 8, 9, 10, 11, 12, 13, 14, 15, 16, 17, 19, 20, or more modified nucleotides. The modified nucleotide can be located at any nucleic acid position of the guide sequence. In other words, the modified nucleotides can be at or near the first and/or last nucleotide of the guide sequence, and/or at any position in between. For example, for a guide sequence that is 20 nucleotides in length, the one or more modified nucleotides can be located at nucleic acid position 1, position 2, position 3, position 4, position 5, position 6, position 7, position 8, position 9, position 10, position 11, position 12, position 13, position 14, position 15, position 16, position 17, position 18, position 19, and/or position 20 of the guide sequence. In certain instances, from about 10% to about 30%, e.g., about 10% to about 25%, about 10% to about 20%, about 10% to about 15%, about 15% to about 30%, about 20% to about 30%, or about 25% to about 30% of the guide sequence can comprise modified nucleotides. In other instances, from about 10% to about 30%, e.g., about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% of the guide sequence can comprise modified nucleotides.

In certain embodiments, the modified nucleotides are located at the 5'-end (e.g., the terminal nucleotide at the 5'-end) or near the 5'-end (e.g., within 1, 2, 3, 4, or 5 nucleotides of the terminal nucleotide at the 5'-end) of the guide sequence and/or at internal positions within the guide sequence.

In some embodiments, the scaffold sequence of the modified sgRNA contains one or more modified nucleotides. For example, a scaffold sequence that is about 80 nucleotides in length may have 1 or more, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 76, 77, 78, 79, or 80 modified nucleotides. In some instances, the scaffold sequence includes at least 2, 3, 4, 5, 6, 7, 8, 9, 10, or more modified nucleotides. In other instances, the scaffold sequence includes at least 2, 3, 4, 5, 6, 7, 8, 9, 10, 11, 12, 13, 14, 15, 16, 17, 19, 20, or more modified nucleotides. The modified nucleotides can be located at any nucleic acid position of the scaffold sequence. For example, the modified nucleotides can be at or near the first and/or last nucleotide of the scaffold sequence, and/or at any position in between. For example, for a scaffold sequence that is about 80 nucleotides in length, the one or more modified nucleotides can be located at nucleic acid position 1, position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28, position 29, position 30, position 31, position 32, position 33, position 34, position 35, position 36, position 37, position 38, position 39, position 40, position 41, position 42, position 43, position 44, position 45, position 46, position 47, position 48, position 49, position 50, position 51, position 52, position 53, position 54, position 55, position 56, position 57, position 58, position 59, position 60, position 61, position 62, position 63, position 64, position 65, position 66, position 67, position 68, position 69, position 70, position 71, position 72, position 73, position 74, position 75, position 76, position 77, position 78, position 79, and/or position 80 of the sequence. In some instances, from about 1% to about 10%, e.g., about 1% to about 8%, about 1% to about 5%, about 5% to about 10%, or about 3% to about 7% of the scaffold sequence can comprise modified nucleotides. In other instances, from about 1% to about 10%, e.g., about 1%, about 2%, about 3%, about 4%, about 5%, about 6%, about 7%, about 8%, about 9%, or about 10% of the scaffold sequence can comprise modified nucleotides.

In certain embodiments, the modified nucleotides are located at the 3'-end (e.g., the terminal nucleotide at the 3'-end) or near the 3'-end (e.g., within 1, 2, 3, 4, or 5 nucleotides of the 3'-end) of the scaffold sequence and/or at internal positions within the scaffold sequence.

In some embodiments, the modified sgRNA comprises one, two, or three consecutive or non-consecutive modified nucleotides starting at the 5'-end (e.g., the terminal nucleotide at the 5'-end) or near the 5'-end (e.g., within 1, 2, 3, 4, or 5 nucleotides of the terminal nucleotide at the 5'-end) of the guide sequence and one, two, or three consecutive or non-consecutive modified nucleotides starting at the 3'-end (e.g., the terminal nucleotide at the 3'-end) or near the 3'-end (e.g., within 1, 2, 3, 4, or 5 nucleotides of the 3'-end) of the scaffold sequence.

In some instances, the modified sgRNA comprises one modified nucleotide at the 5'-end (e.g., the terminal nucleotide at the 5'-end) or near the 5'-end (e.g., within 1, 2, 3, 4, or 5 nucleotides of the terminal nucleotide at the 5'-end) of the guide sequence and one modified nucleotide at the 3'-end (e.g., the terminal nucleotide at the 3'-end) or near the 3'-end (e.g., within 1, 2, 3, 4, or 5 nucleotides of the 3'-end) of the scaffold sequence.

In other instances, the modified sgRNA comprises two consecutive or non-consecutive modified nucleotides starting at the 5'-end (e.g., the terminal nucleotide at the 5'-end) or near the 5'-end (e.g., within 1, 2, 3, 4, or 5 nucleotides of the terminal nucleotide at the 5'-end) of the guide sequence and two consecutive or non-consecutive modified nucleotides starting at the 3'-end (e.g., the terminal nucleotide at the 3'-end) or near the 3'-end (e.g., within 1, 2, 3, 4, or 5 nucleotides of the 3'-end) of the scaffold sequence.

In yet other instances, the modified sgRNA comprises three consecutive or non-consecutive modified nucleotides starting at the 5'-end (e.g., the terminal nucleotide at the 5'-end) or near the 5'-end (e.g., within 1, 2, 3, 4, or 5 nucleotides of the terminal nucleotide at the 5'-end) of the guide sequence and three consecutive or non-consecutive modified nucleotides starting at the 3'-end (e.g., the terminal nucleotide at the 3'-end) or near the 3'-end (e.g., within 1, 2, 3, 4, or 5 nucleotides of the 3'-end) of the scaffold sequence.

In particular embodiments, the modified sgRNA comprises three consecutive modified nucleotides at the 5'-end of the guide sequence and three consecutive modified nucleotides at the 3'-end of the scaffold sequence.

The modified nucleotides of the sgRNA can include a modification in the ribose (e.g., sugar) group, phosphate group, nucleobase, or any combination thereof. In some embodiments, the modification in the ribose group comprises a modification at the 2' position of the ribose.

In some embodiments, the modified nucleotide includes a 2'fluoro-arabino nucleic acid, tricycle-DNA (tc-DNA), peptide nucleic acid, cyclohexene nucleic acid (CeNA), locked nucleic acid (LNA), ethylene-bridged nucleic acid (ENA), a phosphodiamidate morpholino, or a combination thereof.

Modified nucleotides or nucleotide analogues can include sugar- and/or backbone-modified ribonucleotides (i.e., include modifications to the phosphate-sugar backbone). For example, the phosphodiester linkages of a native or natural RNA may be modified to include at least one of a nitrogen or sulfur heteroatom. In some backbone-modified ribonucleotides, the phosphoester group connecting to adjacent ribonucleotides may be replaced by a modified group, e.g., a phosphothioate group. In preferred sugar-modified ribonucleotides, the 2' moiety is a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In some embodiments, the modified nucleotide contains a sugar modification. Non-limiting examples of sugar modifications include 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-5'-triphosphate), 2'-O-alkyl oligoribonucleotide, 2'-deoxy-2'-C-alkyl oligoribonucleotide (2'-O-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-5'-triphosphate), azidotriphosphate (2'-azido-2'-deoxycytidine-5'-triphosphate, 2'-azido-2'-deoxyuridine-5'-triphosphate), and combinations thereof.

In some embodiments, the modified sgRNA contains one or more 2'-fluoro, 2'-amino and/or 2'-thio modifications. In some instances, the modification is a 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, 5-amino-allyl-uridine, 5-bromo-uridine, 5-iodo-uridine, 5-methyl-cytidine, ribo-thymidine, 2-aminopurine, 2'-amino-butyryl-pyrene-uridine, 5-fluoro-cytidine, and/or 5-fluoro-uridine.

There are more than 96 naturally occurring nucleoside modifications found on mammalian RNA. See, e.g., Limbach et al., *Nucleic Acids Research*, 22(12):2183-2196 (1994). The preparation of nucleotides and modified nucleotides and nucleosides are well-known in the art, e.g., from U.S. Pat. Nos. 4,373,071, 4,458,066, 4,500,707, 4,668,777, 4,973,679, 5,047,524, 5,132,418, 5,153,319, 5,262,530, and 5,700,642. Numerous modified nucleosides and modified nucleotides that are suitable for use as described herein are commercially available. The nucleoside can be an analogue of a naturally occurring nucleoside. In some cases, the analogue is dihydrouridine, methyladenosine, methylcytidine, methyluridine, methylpseudouridine, thiouridine, deoxycytodine, and deoxyuridine.

In some cases, the modified sgRNA described herein includes a nucleobase-modified ribonucleotide, i.e., a ribonucleotide containing at least one non-naturally occurring nucleobase instead of a naturally occurring nucleobase. Non-limiting examples of modified nucleobases which can be incorporated into modified nucleosides and modified nucleotides include m5C (5-methylcytidine), m5U (5-methyluridine), m6A (N6-methyladenosine), s2U (2-thiouridine), Um (2'-O-methyluridine), m1A (1-methyl adenosine), m2A (2-methyladenosine), Am (2-1-O-methyl-adenosine), ms2m6A (2-methylthio-N6-methyladenosine), i6A (N6-isopentenyl adenosine), ms2i6A (2-methylthio-N6isopentenyladenosine), io6A (N6-(cis-hydroxyisopentenyl) adenosine), ms2io6A (2-methylthio-N6-(cis-hydroxyisopentenyl)adenosine), g6A (N6-glycinylcarbamoyladenosine), t6A (N6-threonyl carbamoyladenosine), ms2t6A (2-methylthio-N6-threonyl carbamoyladenosine), m6t6A (N6-methyl-N6-threonylcarbamoyladenosine), hn6A (N6.-hydroxynorvalylcarbamoyl adenosine), ms2hn6A (2-methylthio-N6-hydroxynorvalyl carbamoyladenosine), Ar(p) (2'-O-ribosyladenosine(phosphate)), I (inosine), m1I (1-methylinosine), m'Im (1,2'-O-dimethylinosine), m3C (3-methylcytidine), Cm (2T-O-methylcytidine), s2C (2-thiocytidine), ac4C (N4-acetylcytidine), f5C (5-fonnylcytidine), m5Cm (5,2-O-dimethylcytidine), ac4Cm (N4acetyl2TOmethylcytidine), k2C (lysidine), m1G (1-methylguanosine), m2G (N2-methylguanosine), m7G (7-methylguanosine), Gm (2'-O-methylguanosine), m22G (N2,N2-dimethylguanosine), m2Gm (N2,2'-O-dimethylguanosine), m22Gm (N2,N2,2'-O-trimethylguanosine), Gr(p) (2'-O-ribosylguanosine(phosphate)), yW (wybutosine), o2yW (peroxywybutosine), OHyW (hydroxywybutosine), OHyW* (undermodified hydroxywybutosine), imG (wyosine), mimG (methylguanosine), Q (queuosine), oQ (epoxyqueuosine), galQ (galtactosyl-queuosine), manQ (mannosyl-queuosine), preQo (7-cyano-7-deazaguanosine), preQi (7-aminomethyl-7-deazaguanosine), G (archaeosine), D (dihydrouridine), m5Um (5,2'-O-dimethyluridine), s4U (4-thiouridine), m5s2U (5-methyl-2-thiouridine), s2Um (2-thio-2'-O-methyluridine), acp3U (3-(3-amino-3-carboxypropyl)uridine), ho5U (5-hydroxyuridine), mo5U (5-methoxyuridine), cmo5U (uridine 5-oxyacetic acid), mcmo5U (uridine 5-oxyacetic acid methyl ester), chm5U (5-(carboxyhydroxymethyl)uridine)), mchm5U (5-(carboxyhydroxymethyl)uridine methyl ester), mcm5U (5-methoxycarbonyl methyluridine), mcm5Um (S-methoxycarbonylmethyl-2-O-methyluridine), mcm5 s2U (5-methoxycarbonylmethyl-2-thiouridine), nm5 s2U (5-aminomethyl-2-thiouridine), mnm5U (5-methylaminomethyluridine), mnm5s2U (5-methylaminomethyl-2-thiouridine), mnm5se2U (5-methylaminomethyl-2-selenouridine), ncm5U (5-carbamoylmethyl uridine), ncm5Um (5-carbamoylmethyl-2'-O-methyluridine), cmnm5U (5-carboxymethylaminomethyluridine), cnmm5Um (5-carboxymethylaminomethyl-2-L-Omethyluridine), cmnm5s2U (5-carboxymethylaminomethyl-2-thiouridine), m62A (N6, N6-dimethyladenosine), Tm (2'-O-methylinosine), m4C (N4-methylcytidine), m4Cm (N4,2-O-dimethylcytidine), hm5C (5-hydroxymethylcytidine), m3U (3-methyluridine), cm5U (5-carboxymethyluridine), m6Am (N6,T-O-dimethyladenosine), m62Am (N6,N6,O-2-trimethyladenosine), m2'7G (N2,7-dimethylguanosine), m2'2'7G (N2,N2,7-trimethylguanosine), m3Um (3,2T-O-dimethyluridine), m5D (5-methyldihydrouridine), f5Cm (5-formyl-2'-O-methylcytidine), m1Gm (1,2'-O-dimethylguanosine), m'Am (1,2-O-dimethyl adenosine)irinomethyluridine), tm5s2U (S-taurinomethyl-2-thiouridine)), imG-14 (4-demethyl guanosine), imG2 (isoguanosine), or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyOuracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-($C_2$-$C_6$) alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, and combinations thereof.

In some embodiments, the phosphate backbone of the modified sgRNA is altered. The modified sgRNA can include one or more phosphorothioate, phosphoramidate (e.g., N3'-P5'-phosphoramidate (NP)), 2'-O-methoxy-ethyl (2'MOE), 2'-O-methyl-ethyl (2'ME), and/or methylphosphonate linkages. In certain instances, the phosphate group is changed to a phosphothioate, 2'-O-methoxy-ethyl (2'MOE), 2'-O-methyl-ethyl (2'ME), N3'-P5'-phosphoramidate (NP), and the like.

In particular embodiments, the modified nucleotide comprises a 2'-O-methyl nucleotide (M), a 2'-O-methyl, 3'-phosphorothioate nucleotide (MS), a 2'-O-methyl, 3'thioPACE nucleotide (MSP), or a combination thereof.

In some instances, the modified sgRNA includes one or more MS nucleotides. In other instances, the modified sgRNA includes one or more MSP nucleotides. In yet other instances, the modified sgRNA includes one or more MS nucleotides and one or more MSP nucleotides. In further instances, the modified sgRNA does not include M nucleotides. In certain instances, the modified sgRNA includes one or more MS nucleotides and/or one or more MSP nucleotides, and further includes one or more M nucleotides. In certain other instances, MS nucleotides and/or MSP nucleotides are the only modified nucleotides present in the modified sgRNA.

It should be noted that any of the modifications described herein may be combined and incorporated in the guide sequence and/or the scaffold sequence of the modified sgRNA.

In some cases, the modified sgRNAs also include a structural modification such as a stem loop, e.g., M2 stem loop or tetraloop.

The chemically modified sgRNAs can be used with any CRISPR-associated or RNA-guided technology. As described herein, the modified sgRNAs can serve as a guide for any Cas9 polypeptide or variant thereof, including any engineered or man-made Cas9 polypeptide. The modified sgRNAs can target DNA and/or RNA molecules in isolated cells or in vivo (e.g., in an animal).

F. Recombinant Donor Adeno-Associated Viral (AAV) Vectors

Provided herein is a homologous donor adeno-associated viral (AAV) vector comprising a recombinant donor template comprising two nucleotide sequences comprising two non-overlapping, homologous portions of the target nucleic acid ("homology arms"), wherein the nucleotide sequences are located at the 5' and 3' ends of a nucleotide sequence corresponding to the target nucleic acid to undergo homologous recombination. The donor template can further comprise a selectable marker, a detectable marker, and/or a cell purification marker.

In some embodiments, the homology arms are the same length. In other embodiments, the homology arms are different lengths. The homology arms can be at least about 10 base pairs (bp), e.g., at least about 10 bp, 15 bp, 20 bp, 25 bp, 30 bp, 35 bp, 45 bp, 55 bp, 65 bp, 75 bp, 85 bp, 95 bp, 100 bp, 150 bp, 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 950 bp, 1000 bp, 1.1 kilobases (kb), 1.2 kb, 1.3 kb, 1.4 kb, 1.5 kb, 1.6 kb, 1.7 kb, 1.8 kb, 1.9 kb, 2.0 kb, 2.1 kb, 2.2 kb, 2.3 kb, 2.4 kb, 2.5 kb, 2.6 kb, 2.7 kb, 2.8 kb, 2.9 kb, 3.0 kb, 3.1 kb, 3.2 kb, 3.3 kb, 3.4 kb, 3.5 kb, 3.6 kb, 3.7 kb, 3.8 kb, 3.9 kb, 4.0 kb, or longer. The homology arms can be about 10 bp to about 4 kb, e.g., about 10 bp to about 20 bp, about 10 bp to about 50 bp, about 10 bp to about 100 bp, about 10 bp to about 200 bp, about 10 bp to about 500 bp, about 10 bp to about 1 kb, about 10 bp to about 2 kb, about 10 bp to about 4 kb, about 100 bp to about 200 bp, about 100 bp to about 500 bp, about 100 bp to about 1 kb, about 100 bp to about 2 kb, about 100 bp to about 4 kb, about 500 bp to about 1 kb, about 500 bp to about 2 kb, about 500 bp to about 4 kb, about 1 kb to about 2 kb, about 1 kb to about 2 kb, about 1 kb to about 4 kb, or about 2 kb to about 4 kb.

The recombinant donor template can be introduced or delivered into a primary cell via viral gene transfer. In some embodiments, the donor template is delivered using an adeno-associated virus (AAV). Any AAV serotype, e.g., human AAV serotype, can be used including, but not limited to, AAV serotype 1 (AAV1), AAV serotype 2 (AAV2), AAV serotype 3 (AAV3), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), AAV serotype 11 (AAV11), AAV serotype 11 (AAV11), a variant thereof, or a shuffled variant thereof (e.g., a chimeric variant thereof). In some embodiments, an AAV variant has at least 90%, e.g., 90%, 91%, 92%, 93%, 94%, 95%, 96%, 97%, 98%, 99% or more amino acid sequence identity to a wild-type AAV. An AAV1 variant can have at least 90%, e.g., 90%, 91%, 92%, 93%, 94%, 95%, 96%, 97%, 98%, 99% or more amino acid sequence identity to a wild-type AAV1. An AAV2 variant can have at least 90%, e.g., 90%, 91%, 92%, 93%, 94%, 95%, 96%, 97%, 98%, 99% or more amino acid sequence identity to a wild-type AAV2. An AAV3 variant can have at least 90%, e.g., 90%, 91%, 92%, 93%, 94%, 95%, 96%, 97%, 98%, 99% or more amino acid sequence identity to a wild-type AAV3. An AAV4 variant can have at least 90%, e.g., 90%, 91%, 92%, 93%, 94%, 95%, 96%, 97%, 98%, 99% or more amino acid sequence identity to a wild-type AAV4. An AAV5 variant can have at least 90%, e.g., 90%, 91%, 92%, 93%, 94%, 95%, 96%, 97%, 98%, 99% or more amino acid sequence identity to a wild-type AAV5. An AAV6 variant can have at least 90%, e.g., 90%, 91%, 92%, 93%, 94%, 95%, 96%, 97%, 98%, 99% or more amino acid sequence identity to a wild-type AAV6. An AAV7 variant can have at least 90%, e.g., 90%, 91%, 92%, 93%, 94%, 95%, 96%, 97%, 98%, 99% or more amino acid sequence identity to a wild-type AAV7. An AAV8 variant can have at least 90%, e.g., 90%, 91%, 92%, 93%, 94%, 95%, 96%, 97%, 98%, 99% or more amino acid sequence identity to a wild-type AAV8. An AAV9 variant can have at least 90%, e.g., 90%, 91%, 92%, 93%, 94%, 95%, 96%, 97%, 98%, 99% or more amino acid sequence identity to a wild-type AAV9. An AAV10 variant can have at least 90%, e.g., 90%, 91%, 92%, 93%, 94%, 95%, 96%, 97%, 98%, 99% or more amino acid sequence identity to a wild-type AAV10. An AAV11 variant can have at least 90%, e.g., 90%, 91%, 92%, 93%, 94%, 95%, 96%, 97%, 98%, 99% or more amino acid sequence identity to a wild-type AAV11. An AAV12 variant can have at least 90%, e.g., 90%, 91%, 92%, 93%, 94%, 95%, 96%, 97%, 98%, 99% or more amino acid sequence identity to a wild-type AAV12.

In some instances, one or more regions of at least two different AAV serotype viruses are shuffled and reassembled to generate an AAV chimera virus. For example, a chimeric AAV can comprise inverted terminal repeats (ITRs) that are of a heterologous serotype compared to the serotype of the capsid. The resulting chimeric AAV virus can have a different antigenic reactivity or recognition, compared to its parental serotypes. In some embodiments, a chimeric variant of an AAV includes amino acid sequences from 2, 3, 4, 5, or more different AAV serotypes.

Descriptions of AAV variants and methods for generating thereof are found, e.g., in Weitzman and Linden. Chapter 1-Adeno-Associated Virus Biology in *Adeno-Associated Virus: Methods and Protocols Methods in Molecular Biology*, vol. 807. Snyder and Moullier, eds., Springer, 2011; Potter et al., *Molecular Therapy—Methods & Clinical Development*, 2014, 1, 14034; Bartel et al., *Gene Therapy*, 2012, 19, 694-700; Ward and Walsh, *Virology*, 2009, 386 (2):237-248; and Li et al., *Mol Ther*, 2008, 16(7):1252-1260. AAV virions (e.g., viral vectors or viral particle) described herein can be transduced into primary cells to introduce the recombinant donor template into the cell. A recombinant donor template can be packaged into an AAV viral vector according to any method known to those skilled in the art. Examples of useful methods are described in McClure et al., *J Vis Exp*, 2001, 57:3378.

The recombinant donor template may comprise two nucleotide sequences that include two non-overlapping, homologous region of the target nucleic acid. The nucleotide sequences are sequences that are homologous to the genomic sequences flanking the site-specific double-strand break (DSB) generated by the engineered nuclease system of the present invention, e.g., an sgRNA and a Cas polypeptide. The two nucleotide sequences are located at the 5' and 3' ends of a nucleotide sequence that corresponds to the target nucleic acid. The donor template is used by the engineered nuclease to repair the DSB and provide precise nucleotide changes at the site of the break.

The recombinant donor template of interest can also include one or more nucleotide sequences encoding a functional polypeptide or a fragment thereof. The donor template can be used to introduce a precise and specific nucleotide substitution or deletion in a pre-selected gene, or in some cases, a transgene. Any of a number of transcription and translation control elements, including promoter, transcription enhancers, transcription terminators, and the like, may be used in the donor template. In some embodiments, the recombinant donor template of interest includes a promoter. In other embodiments, the recombinant donor template of interest is promoterless. Useful promoters can be derived from viruses, or any organism, e.g., prokaryotic or eukaryotic organisms. Suitable promoters include, but are not limited to, the spleen focus-forming virus promoter (SFFV), elongation factor-1 alpha promoter (EF1a), Ubiquitin C promoter (UbC), phosphoglycerate kinase promoter (PGK), simian virus 40 (SV40) early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human H1 promoter (H1), etc.

In some embodiments, the recombinant donor template further comprises one or more sequences encoding polyadenylation (polyA) signals. Suitable polyA signals include, but are not limited to, SV40 polyA, thymidine kinase (TK) polyA, bovine growth hormone (BGH) polyA, human growth hormone (hGH) polyA, rabbit beta globin (rbGlob) polyA, or a combination thereof. The donor template can also further comprise a non-polyA transcript-stabilizing element (e.g., woodchuck hepatitis virus posttranscriptional regulatory element (WPRE)) or a nuclear export element (e.g., constitutive transport element (CTE)).

In some embodiments, the transgene is a detectable marker or a cell surface marker. In certain instances, the detectable marker is a fluorescent protein such as green fluorescent protein (GFP), enhanced green fluorescent protein (EGFP), red fluorescent protein (RFP), blue fluorescent protein (BFP), cyan fluorescent protein (CFP), yellow fluorescent protein (YFP), mCherry, tdTomato, DsRed-Monomer, DsRed-Express, DSRed-Express2, DsRed2, AsRed2, mStrawberry, mPlum, mRaspberry, HcRedl, E2-Crimson, mOrange, mOrange2, mBanana, ZsYellowl, TagBFP, mTagBFP2, Azurite, EBFP2, mKalamal, Sirius, Sapphire, T-Sapphire, ECFP, Cerulean, SCFP3A, mTurquoise, mTurquoise2, monomeric Midoriishi-Cyan, TagCFP, mTFP1, Emerald, Superfolder GFP, Monomeric Azami Green, TagGFP2, mUKG, mWasabi, Clover, mNeonGreen, Citrine, Venus, SYFP2, TagYFP, Monomeric Kusabira-Orange, mKOk, mKO2, mTangerine, mApple, mRuby, mRuby2, HcRed-Tandem, mKate2, mNeptune, NiFP, mKeima Red, LSS-mKate1, LSS-mKate2, mBeRFP, PA-GFP, PAmCherry1, PATagRFP, TagRFP6457, IFP1.2, iRFP, Kaede (green), Kaede (red), KikGR1 (green), KikGR1 (red), PS-CFP2, mEos2 (green), mEos2 (red), mEos3.2 (green), mEos3.2 (red), PSmOrange, Dronpa, Dendra2, Timer, AmCyan1, or a combination thereof. In other instances, the cell surface marker is a marker not normally expressed on the primary cells such as a truncated nerve growth factor receptor (tNGFR), a truncated epidermal growth factor receptor (tEGFR), CD8, truncated CD8, CD19, truncated CD19, a variant thereof, a fragment thereof, a derivative thereof, or a combination thereof.

G. Primary Cells

The present invention can be used to induce targeted integration of a target nucleic acid via homologous recombination in any primary cell of interest. A population of the genetically modified primary cells can be enriched in accordance with the methods of the present invention. The primary cell can be a cell isolated from any multicellular organism, e.g., a plant cell (e.g., a rice cell, a wheat cell, a tomato cell, an *Arabidopsis thaliana* cell, a *Zea mays* cell, and the like), a cell from a multicellular protist, a cell from a multicellular fungus, an animal cell such as a cell from an invertebrate animal (e.g., fruit fly, cnidarian, echinoderm, nematode, etc.) or a cell from a vertebrate animal (e.g., fish, amphibian, reptile, bird, mammal, etc.), a cell from a human, a cell from a healthy human, a cell from a human patient, a cell from a cancer patient, etc. In some cases, the genetically modified primary cell or an enriched population thereof can be transplanted to a subject (e.g., patient). For instance, the primary cell or a population thereof can be derived from the subject (e.g., patient) to be treated.

Any type of primary cell may be of interest, such as a stem cell, e.g., embryonic stem cell, induced pluripotent stem cell, adult stem cell (e.g., hematopoietic stem cell, mesenchymal stem cell, neural stem cell, organ stem cell), a progenitor cell, a somatic cell (e.g., fibroblast, hepatocyte, heart cell, liver cell, pancreatic cell, muscle cell, skin cell, blood cell, neural cell, immune cell), and any other cell of the body, e.g., human body. The cells can be primary cells or primary cell cultures derived from a subject, e.g., an animal subject or a human subject, and allowed to grow in vitro for a limited number of passages. In some embodiments, the cells are disease cells or derived from a subject with a disease. For instance, the cells can be cancer or tumor cells.

In particular embodiments, the primary cell of interest is a primary blood cell, a primary mesenchymal cell, or a combination thereof. In certain instances, the primary blood cell is selected from the group consisting of an immune cell (e.g., leukocyte), a red blood cell, a progenitor or stem cell thereof, and a combination thereof. In some cases, the immune cell is selected from the group consisting of a T cell, a B cell, a dendritic cell, a natural killer cell, a macrophage, a neutrophil, an eosinophil, a basophil, a mast cell, a precursor thereof, and a combination thereof. In other cases, the progenitor or stem cell is selected from the group consisting of a hematopoietic progenitor cell, a hematopoietic stem cell, and a combination thereof. In yet other cases, the red blood cell is a blood stem cell. In other instances, the primary mesenchymal cell is selected from the group consisting of a mesenchymal stem cell (i.e., mesenchymal stromal cell or MSC), a mesenchymal progenitor cell, a mesenchymal precursor cell, a differentiated mesenchymal cell, and a combination thereof. In some cases, the differentiated mesenchymal cell is selected from the group consisting of a bone cell, a cartilage cell, a muscle cell, an adipose cell, a stromal cell, a fibroblast, a dermal cell, and a combination thereof. The primary cells can be obtained from peripheral blood, cord blood, bone marrow, or any tissue that is a source of the primary cells of interest. The primary cells can be mobilized by administering a mobilizing agent (e.g., granulocyte colony-stimulating factor or GCSF) to a subject (e.g., a donor of the cells), and harvested directly from the subject. In some embodiments, the cells from the subject (the donor) are harvested, purified, in vitro cultured, or any combination thereof. The primary cells may be a heterogeneous population of cells. Alternatively, the primary cell may be a homogeneous population of cells.

Primary blood cells include primary immune cells such as leukocytes. Non-limiting examples of primary immune cells include T lymphocytes (T cells), B lymphocytes (B cells), small lymphocytes, natural killer cells (NK cells), natural killer T cells, macrophages, monocytes, monocyte-precursor cells, eosinophils, neutrophils, basophils, megakaryocytes, myeloblasts, mast cells, progenitors thereof, and stem cells thereof. Non-limiting examples of subsets of primary immune cells include peripheral blood mononuclear cells (PBMC), lymphocytes (e.g., T cells, B cells, NK cells, etc.), and the like.

The primary immune cell can be at any stage of its development. For example, the primary B cell can be a common lymphoid progenitor cell, a progenitor B cell, a precursor B cell, an immature B cell, a naïve B cell, a mature B cell, an activated B cell, and the like. The primary T cell can be a common lymphoid progenitor cell, a progenitor T cell, a precursor T cell, an immature T cell, a naïve T cell, a mature T cell, an effector T cell, a memory T cell, a memory stem T cell, a tumor infiltrating cell (TIL), a CD3$^+$ T cell, a CD4$^+$ T cell, a CD8$^+$ T cell, and the like. The primary T cell can also be skewed towards particular populations and phenotypes. For example, the primary T cell can be skewed to phenotypically comprise CD45RO(−), CCR7 (+), CD45RA(+), CD62L(+), CD27(+), CD28(+) and/or IL-7Rα(+).

In some embodiments, the primary progenitor or stem cell is a hematopoietic stem cell, a hematopoietic progenitor cell, a myeloid progenitor cell, a lymphoid progenitor cell, a multipotent progenitor, an oligopotent progenitor, or a lineage-restricted progenitor. In certain instances, the hematopoietic stem cell and the hematopoietic progenitor cell are CD34$^+$ cells. In some cases, the primary progenitor or stem cell is a hematopoietic stem and progenitor cell (HSPC) such as a CD34$^+$ HSPC. Hematopoietic stem cells and hematopoietic progenitor cells can be isolated as a heterogeneous population of cells that express the cell surface antigen CD34. CD34$^+$ cells that are CD38$^-$ (CD34$^+$/CD38$^-$) are primitive, immature CD34$^+$ multipotent hematopoietic progenitor cells. CD34$^+$ cells that are CD38$^-$ and CD90$^+$ (CD34+/CD38$^-$/CD90$^+$) are long-term repopulating hematopoietic progenitor cells. CD34$^+$ cells that are CD38$^-$, CD90+, and CD45RA$^-$ (CD34+/CD38$^-$/CD90$^+$/CD45RA$^-$) are a population of cells highly enriched for HSCs. Cells that are CD34$^+$/CD38$^+$ are known as short-term hematopoietic progenitor cells. Hematopoietic stem cells include those described in, e.g., U.S. Pat. Nos. 5,061,620 and 5,716,827. Detailed descriptions of hematopoietic stem cells, hematopoietic progenitor cells, blood cells, and immune cells are found in, e.g., Seita and Weissman, *Wiley Interdescip Rev Syst Biol Med,* 2010, 2(6):640-653.

Primary blood cells also include primary erythrocytes (e.g., red blood cells) and any type of cell that can become an erythrocyte such as a mature erythrocyte that does not contain a nucleus. Non-limiting examples of cells that can become erythrocytes include hemocytoblasts (e.g., blood stem cells or hematopoietic stem cells), hematopoietic progenitor cells, common myeloid progenitor cells, proerythroblasts (pronormoblasts), basophilic erythroblasts, intermediate erythroblasts, late erythroblasts, reticulocyte, and the like.

Primary mesenchymal cells include primary cells of a mesenchymal lineage that can differentiate to become cells of bone, cartilage, fat, muscle, etc. Non-limiting examples include mesenchymal stem cells (i.e., mesenchymal stromal cells or MSCs), mesenchymal progenitor cells, and mesenchymal precursor cells, as well as differentiated mesenchymal cells such as bone cells, cartilage cells, muscle cells, adipose cells, stromal cells, fibroblasts, dermal cells, and combinations thereof. Bone marrow-derived mesenchymal stem cells (BM-MSCs) can display one or more cell surface antigens such as CD73, CD90, and/or CD105 (e.g., CD73$^+$/CD90$^+$/CD105$^+$ BM-MSCs), and can optionally not express one or more of the following cell surface antigens: CD14, CD19, CD34, and/or CD45 (e.g., CD14$^-$/CD19$^-$/CD34$^-$/CD45$^-$ BM-MSCs).

Primary cells can be harvested from a subject by any standard method. For instance, cells from tissues, such as skin, muscle, bone marrow, spleen, liver, kidney, pancreas, lung, intestine, stomach, etc., can be harvested by a tissue biopsy or a fine needle aspirate. Blood cells and/or immune cells can be isolated from whole blood, plasma, or serum. Induced pluripotent stem cells can be generated from differentiated cells according to standard protocols described in, for example, U.S. Pat. Nos. 7,682,828, 8,058,065, 8,530, 238, 8,871,504, 8,900,871 and 8,791,248.

In some embodiments, the primary cell is in vitro. In other embodiments, the primary cell is ex vivo.

H. Introducing DNA Nucleases, Modified sgRNAs, and Homologous Donor AAV Vectors into Primary Cells Methods for introducing polypeptides, nucleic acids, and viral vectors (e.g., viral particles) into a primary cell, target cell, or host cell are known in the art. Any known method can be used to introduce a polypeptide or a nucleic acid (e.g., a nucleotide sequence encoding the DNA nuclease or a modified sgRNA) into a primary cell, e.g., a human primary cell. Non-limiting examples of suitable methods include electroporation (e.g., nucleofection), viral or bacteriophage infection, transfection, conjugation, protoplast fusion, lipofection, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Any known method can be used to introduce a viral vector (e.g., viral particle) into a primary cell, e.g., a human primary cell. In some embodiments, the homologous donor adeno-associated viral (AAV) vector described herein is introduced into a primary cell by viral transduction or infection. Useful methods for viral transduction are described in, e.g., Wang et al., *Gene Therapy*, 2003, 10: 2105-2111.

In some embodiments, the polypeptide and/or nucleic acids of the gene modification system can be introduced into a primary cell using a delivery system. In certain instances, the delivery system comprises a nanoparticle, a microparticle (e.g., a polymer micropolymer), a liposome, a micelle, a virosome, a viral particle, a nucleic acid complex, a transfection agent, an electroporation agent (e.g., using a NEON transfection system), a nucleofection agent, a lipofection agent, and/or a buffer system that includes a nuclease component (as a polypeptide or encoded by an expression construct) and one or more nucleic acid components such as an sgRNA and/or a donor template. For instance, the components can be mixed with a lipofection agent such that they are encapsulated or packaged into cationic submicron oil-in-water emulsions. Alternatively, the components can be delivered without a delivery system, e.g., as an aqueous solution.

Methods of preparing liposomes and encapsulating polypeptides and nucleic acids in liposomes are described in, e.g., *Methods and Protocols, Volume 1: Pharmaceutical Nanocarriers: Methods and Protocols.* (ed. Weissig). Humana Press, 2009 and Heyes et al. (2005) *J Controlled Release* 107:276-87. Methods of preparing microparticles and encapsulating polypeptides and nucleic acids are described in, e.g., Functional Polymer Colloids and Microparticles volume 4 (Microspheres, microcapsules & liposomes). (eds. Arshady & Guyot). Citus Books, 2002 and *Microparticulate Systems for the Delivery of Proteins and Vaccines.* (eds. Cohen & Bernstein). CRC Press, 1996.

I. Methods for Isolating and Purifying Genetically Modified Primary Cells

Selectable markers, detectable markers, cell surface markers, and cell purification markers, alone or in combination, can be used to isolate and/or purify genetically modified primary cells, e.g., genetically modified human primary cells. Expression of a selectable marker gene encoding an antibiotic resistance factor can provide for preferential survival of genetically modified cells in the presence of the corresponding antibiotic, whereas other cells present in the culture will be selectively killed. Alternatively, expression of a fluorescent protein such as GFP or expression of a cell surface marker not normally expressed on the primary cells may permit genetically modified primary cells to be identified, purified, or isolated by fluorescence-activated cell sorting (FACS), magnetic-activated cell sorting (MACS), or analogous methods. Suitable cell surface markers include CD8, truncated CD8, CD19, truncated CD19, truncated nerve growth factor receptor (tNGFR), and truncated epidermal growth factor receptor (tEGFR), although other cell surface markers can also fulfill the same function.

Methods for isolating or purifying the genetically modified primary cells are known in the art. In some embodiments, a population of genetically modified primary cells is isolated or purified (e.g., separated) from a population of unmodified primary cells in accordance with the enrichment scheme of the present invention. For example, FACS or MACS methods can be used to enrich genetically modified human primary cells expressing a fluorescent protein such as GFP or a cell surface marker such as truncated nerve growth factor receptor (tNGFR) as described herein.

Methods for culturing or expanding the genetically modified cells are known in the art. Methods for culturing primary cells and their progeny are known, and suitable culture media, supplements, growth factors, and the like are both known and commercially available. Typically, human primary cells are maintained and expanded in serum-free conditions. One suitable medium for culturing primary human CD3+ T cells includes 5% human serum (Sigma-Aldrich, St. Louis, Mo., USA), 10 ng/ml human rIL-7 (BD Biosciences, San Jose, Calif., USA), and 100 IU/ml human rIL-2 (Peprotech, Rocky Hill, N.J., USA). Alternative media, supplements and growth factors and/or alternative concentrations can readily be determined by the skilled person and are extensively described in the literature. In some embodiments, the isolated or purified gene modified cells can be expanded in vitro according to standard methods known to those of ordinary skill in the art.

IV. Examples

The following examples are offered to illustrate, but not to limit, the claimed invention.

Example 1. Genome Editing by Homologous Recombination Using CRISPR/Cas9 and rAAV6 in Hematopoietic Stem and Progenitor Cells with Enrichment and Multiplexing Precise nuclease-mediated gene modification via homologous recombination (HR) in hematopoietic stem and progenitor cells (HSPCs) has the power to reveal gene-function relationships and potentially transform curative genetic therapies. While using chemically modified sgRNAs dramatically enhanced the activity of the CRISPR/Cas9 system in HSPCs, translating these high efficiencies into elevated HR frequencies has remained challenging. By combining delivery of Cas9 protein complexed with chemically modified sgRNAs with transduction of a donor via recombinant adeno-associated viral vectors, serotype 6 (rAAV6) into HSPCs, high frequencies of HR-mediated genome editing were achieved at three different loci. Importantly, a distinct shift from episomal to chromosomal reporter transgene expression resulting from successful HR allowed for early identification and enrichment of an HSPC population in which targeted integration in greater than 90% of cells was consistently observed. Notably, this enriched population displayed long-term multi-lineage engraftment in immunodeficient mice, implying that the enriched population contained long-term repopulating hematopoietic stem cells (HSCs). Furthermore, the frequency is high enough that it is possible to multiplex HR-mediated genome editing in HSPCs.

The development of genome editing using engineered nucleases is the foundation for the idea that ex vivo gene correction constitutes a viable therapeutic strategy for both genetic and non-genetic diseases (Naldini, *Nature Reviews Genetics* 12, 301-315 (2011)). While construction of zinc-finger nucleases (ZFNs), transcription-activator-like effector nucleases (TALENs), and meganuclease/TALEN hybrids (megaTALs) is possible (Carroll, *Annual review of Biochemistry* 83, 409-439 (2014); Porteus, MH, *Genome Biology* 16, 286 (2015)), the RNA-guided endonuclease of the CRISPR/Cas9 system can be easily engineered to create site-specific double-strand breaks (Jinek et al., *Science* 337, 816-821 (2012); Mali et al., *Science* 339, 823-826 (2013); Cong et al., *Science* 339, 819-823 (2013)) (DSBs). CRISPR/Cas9 consists of the Cas9 endonuclease and a 100-nucleotide (nt) single guide RNA (sgRNA). Target identification relies on RNA-DNA Watson-Crick hybridization between a 20-nucleotide stretch of the sgRNA and the DNA target site, which then guides Cas9 to cleave both DNA strands. DSB formation subsequently triggers one of two highly conserved competing repair mechanisms, canonical non-homologous end-joining (NHEJ) or homologous recombination (HR) (Kass, E. M. & Jasin, M., *FEBS Letters* 584, 3703-3708 (2010)). Through the iterative cycle of break and NHEJ repair, insertions and/or deletions (INDELs) can be created at the site of the break. In contrast, genome editing by HR requires the delivery of a donor molecule to serve as an undamaged DNA molecule that the HR machinery uses to repair the break by a 'copy and paste' method (Porteus, MH, *Genome Biology* 16, 286 (2015)). For gene editing purposes, the HR pathway can be exploited to make precise nucleotide changes in the genome (Porteus, M. H. & Baltimore, D, *Science* 300, 763 (2003)). Using this strategy, disease-causing mutations can be replaced or entire open reading frames (ORFs) can be inserted at specific sites. One of the attractive features of precise genome editing rather than lentiviral gene transfer is that endogenous promoters, regulatory elements, and enhancers can be preserved to mediate precise spatiotemporal gene expression (Naldini, *Nature Reviews. Genetics* 12, 301-315 (2011); Woods et al., *Nature,* 440, 1123 (2006)).

Hematopoietic stem cells (HSCs) have the ability to repopulate an entire hematopoietic system (Baum et al., *Proceedings of the National Academy of Sciences USA* 89, 2804-2808 (1992)), and several genetic (Mukherjee, S. & Thrasher, A. J., *Gene* 525, 174-181 (2013); Cavazzana-Calvo et al., *Nature* 467, 318-322 (2010); Naldini, L., *Nature* 526, 351-360 (2015)) and acquired (Jenq, R. R. & van den Brink, M. R., *Nature Reviews Cancer* 10, 213-221 (2010)) diseases of the blood could potentially be cured by genome editing of HSCs. Recent studies have demonstrated efficient targeted integration in hematopoietic stem and progenitor cells (HSPCs) derived from mobilized peripheral blood, fetal liver, or cord blood by combining ZFN expression with exogenous HR donors delivered via single stranded oligonucleotides (ssODN) (Hoban, M. D. et al., *Blood* 125, 2597-2604 (2015)), integrase-defective lentiviral vectors (IDLV) (Genovese et al., *Nature* 510, 235-240 (2014)), or recombinant adeno-associated viral vectors serotype 6 (rAAV6) (Wang et al., *Nature Biotechnology* 33, 1256-1263 (2015)). However, the high editing frequencies in vitro did not result in high frequencies of edited cells following transplantation into immunodeficient mice. In this study, as high or higher in vitro HR-mediated targeted integration frequencies were achieved in mobilized peripheral blood and cord blood-derived CD34$^+$ HSPCs using CRISPR/Cas9 combined with rAAV6. In addition, by sorting with FACS, it was demonstrated that HR-modified cells could be purified and those purified cells demonstrated HSC properties by both cell surface phenotype and following transplantation into immunodeficient mice. Finally, targeted integration frequencies high enough to either simultaneously integrate into both alleles of the same gene or into one allele of two different genes were achieved, thus demonstrating that CRISPR/Cas9 and rAAV6 can be used to multiplex HR-mediated editing in CD34$^+$ HSPCs.

Figure 1B:
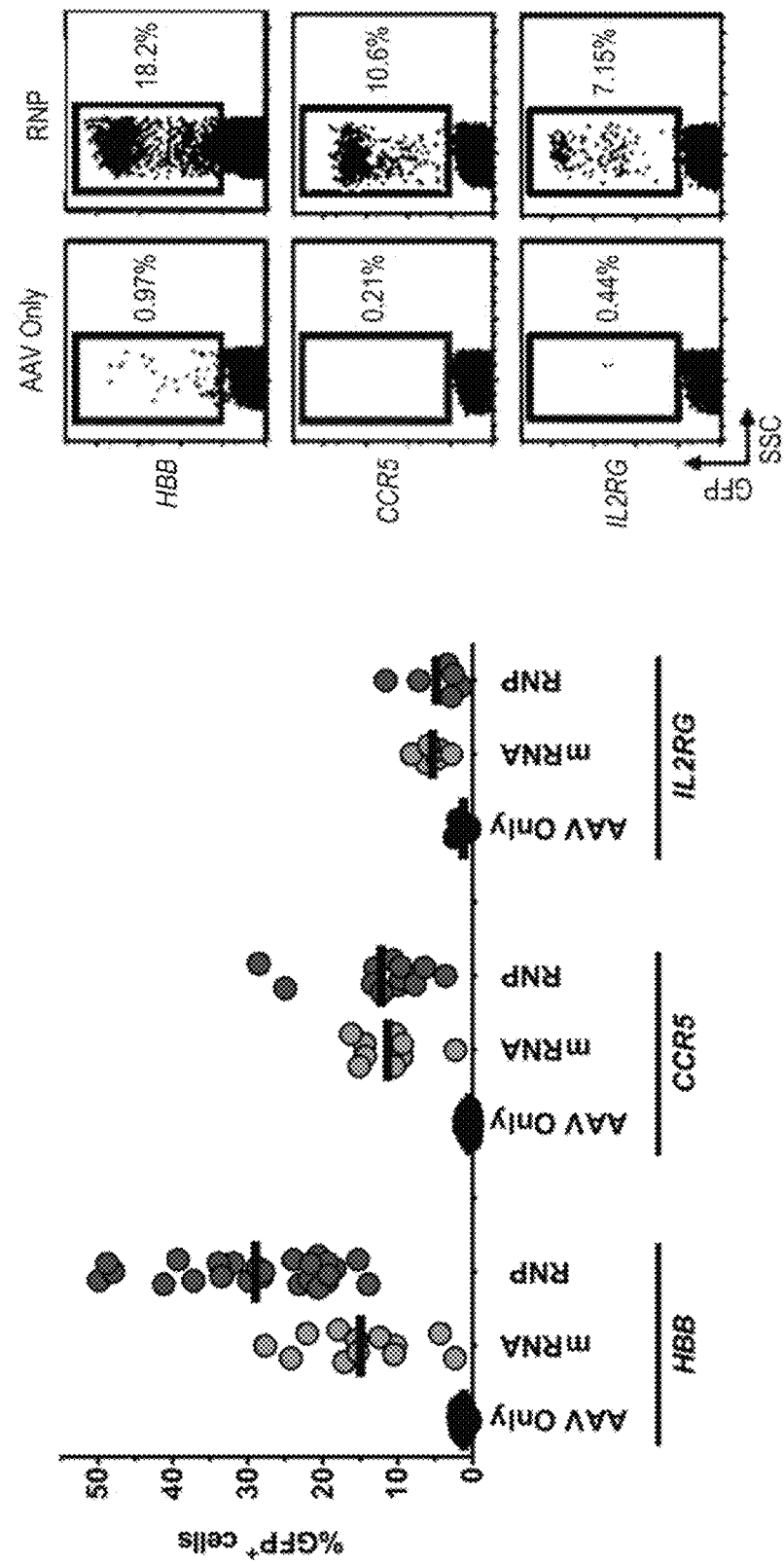
Figure 4:
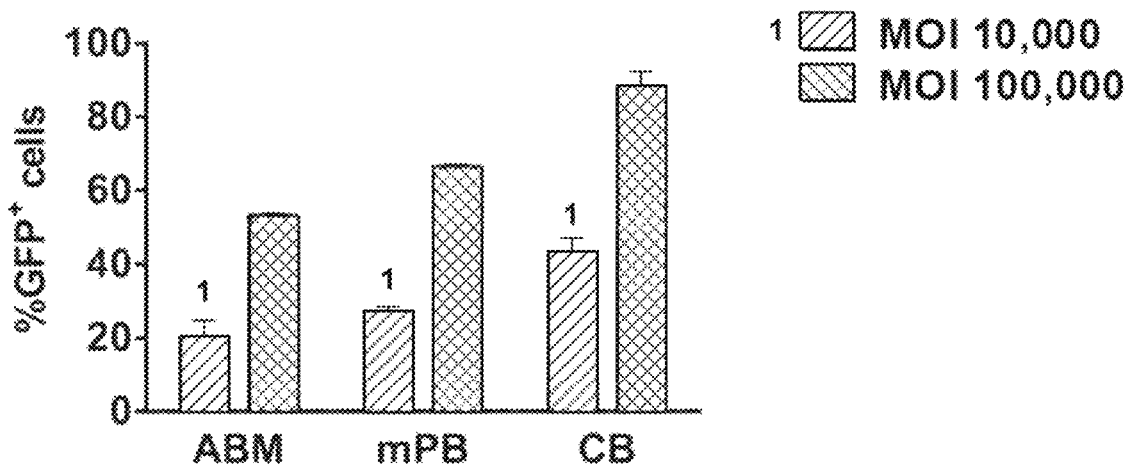
FIG. 4 shows high tropism of rAAV6 for CD34$^+$ HSPCs. CD34$^+$ HSPCs were transduced with a scAAV6 encoding GFP at multiplicities of infections (MOIs) of 10,000 or 100,000 for 48 hours and then analyzed for percent GFP expression by flow cytometry. scAAV was used because it eliminates second strand synthesis as a confounder of actual transduction. Results are from 2 independent experiments from at least two donors. ABM: Adult Bone Marrow; mPB: Mobilized Peripheral Blood; CB: Cord Blood.
Figure 5:
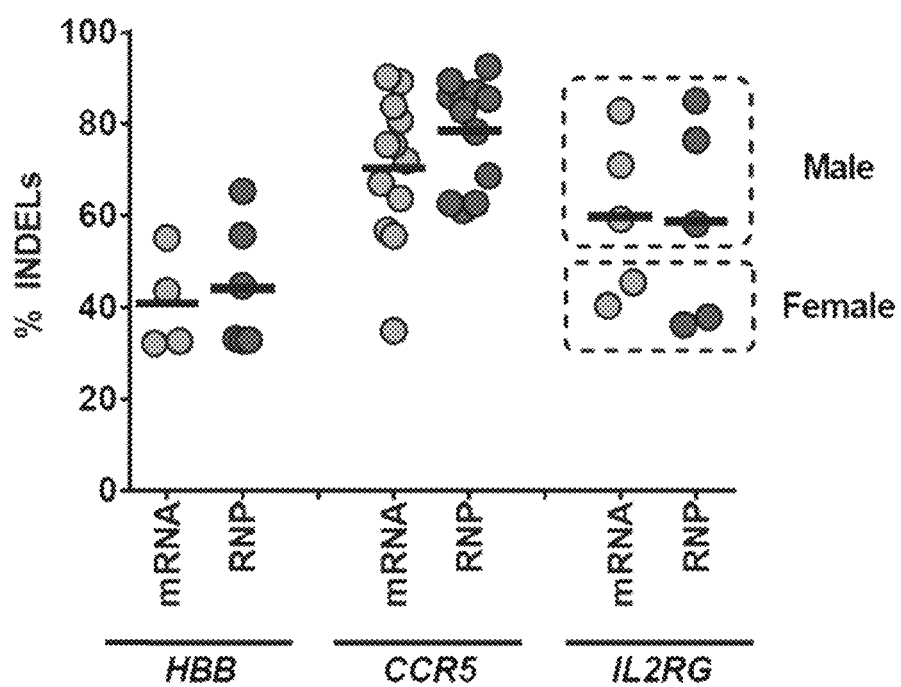
FIG. 5 shows high INDEL frequencies at the HBB, CCR5 and IL2RG loci created by Cas9 and chemically modified sgRNAs. CD34$^+$ HSPCs (derived from mPB or CB) were electroporated with 15 µg Cas9 mRNA/10 µg MS sgRNA (mRNA) or with 30 µg rCas9 protein/16 µg MS sgRNA via a ribonucleoprotein complex (RNP). Cells were allowed to grow for at least 4 days post-electroporation, after which gDNA was extracted, PCRs overlapping the target site were performed, and finally, extracted PCR bands were sequenced and analyzed for INDEL frequencies using TIDE. The IL2RG locus data is divided into male and female because of its location on the X chromosome. Each data point represents one CD34$^+$ donor with 5-12 donors from multiple independent experiments being compiled for each locus and treatment.
Figure 7A:
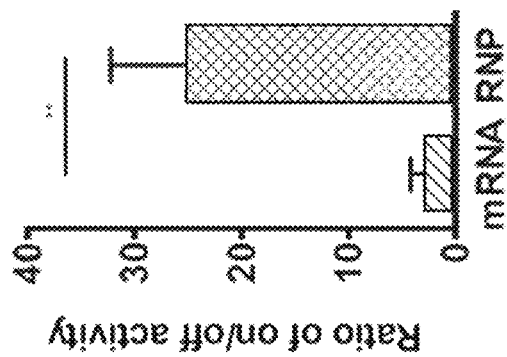
FIGS. 7A-7C display increased toxicity and off-target activity using the "All RNA" CRISPR system compared to RNP delivery. CD34+ HSPCs were electroporated with the CRISPR system (mRNA or RNP delivery) or without (AAV only), and then transduced with rAAV6 at an MOI of 100,000. Day 4 post-electroporation, cells were analyzed by flow cytometry and live cells were gated in high forward scatter (FSC) and low side scatter (SSC). Percent cells in FSC/SSC gate is shown relative to that of mock-electroporated (Mock) cells (FIG. 7A). sgRNA target sequences at the HBB on-target site and a highly complementary off-target site (Chr9:101833584-101833606) are shown in FIG. 7B (HBB on-target sgRNA sequence: SEQ ID NO:42, 5'-CTTGCCCCACAGGGCAGTAACGG; HBB off-target sgRNA sequence: SEQ ID NO:47, 5'-TCAGCCC-CACAGGGCAGTAACGG). PAM sequences are underlined and 5'-TCA sequence are the 3 mismatches of the off-target site. HSPCs were electroporated with either the "All RNA" or RNP-based CRISPR system, and 4 days post-electroporation gDNA was extracted and analyzed for INDEL frequencies using TIDE on the on-target HBB and the off-target site (FIG. 7B). Results from FIG. B were graphed as a ratio of on to off-target activity highlighting the increased specificity of the RNP system (FIG. 7C). Each dot in FIGS. 7A and 7B represents a separate CD34+ HSPC donor. Error bars represent S.E.M.
Figure 7B:
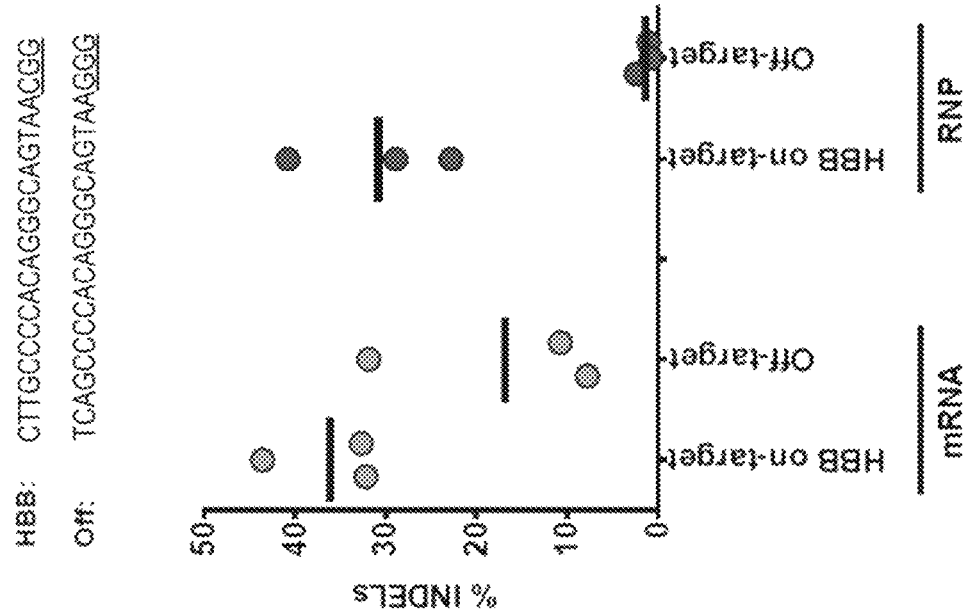
Figure 7C:
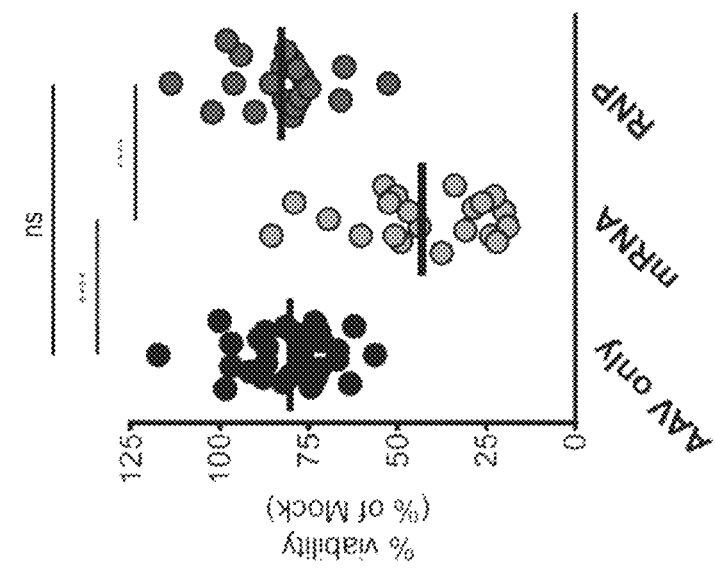

High transduction of HSPCs was confirmed using a self-complementary AAV6 (scAAV6) encoding GFP (Sather et al., *Science Translational Medicine* 7, 307ra156 (2015)) (FIG. 4). It has been previously shown increased CRISPR/Cas9 activity in primary HSPCs as measured by INDEL formation by using chemically modified sgRNAs at three disease-related genes beta-globin (HBB), interleukin-2 receptor gamma chain (IL2RG), and chemokine (C—C motif) receptor 5 (CCR5) (Hendel et al., *Nature Biotechnology* 33, 985-989 (2015)). To achieve gene editing at these three loci, cells were electroporated with sgRNAs chemically modified at both ends with 2'O-Methyl 3'phosphorothioate (MS sgRNA) in conjunction with either Cas9 mRNA or complexed directly to Cas9 protein, which both yielded high INDEL frequencies (FIG. 5). Gene-specific single-stranded AAV6 vectors (ssAAV6) were produced that contained a GFP expression cassette flanked by arms homologous to the targeted gene (FIG. 1A). Different parameters were optimized to achieve high targeting frequencies in HSPCs using Cas9 RNP-based delivery including 1) concentration of rCas9 protein (300 μg/ml), 2) sgRNA: rCas9 ribonucleoprotein complex molar ratio (2.5:1), 3) rAAV6 multiplicity of infection (100,000 MOI), and 4) timing of rAAV6 transduction relative to electroporation of RNPs (15 min post-electroporation) (FIGS. 6A-6D). By supplying homologous GFP-expressing donors via rAAV6 in combination with locus-specific DSBs created by RNP-based Cas9 delivery, stable GFP expression was achieved in about 30%, about 12%, and about 5% of cells, for HBB, CCR5, and IL2RG loci, respectively, in peripheral blood and cord blood-derived CD34$^+$ HSPCs (FIG. 1B). While high rAAV6-targeting efficiencies were also achieved using the "All RNA" CRISPR platform (FIG. 1B), cytotoxicity and off-target cleavage activity were significantly increased in comparison to RNP-based delivery (FIG. 7A-7C).

Figure 8A:
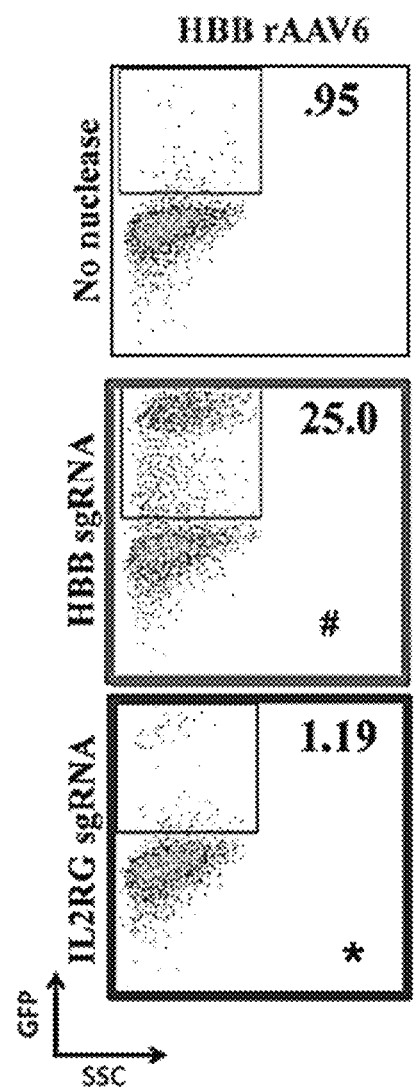
FIGS. 8A and 8B show the capture of rAAV6 by mismatching donor and nuclease. Mismatching nuclease and donor (boxes with asterisks) leads to infrequent end-capture events compared to on-target HR events observed with matched nuclease and homologous rAAV6 donor (boxes with hashtags). HSPCs were electroporated with 15 µg Cas9 mRNA and either HBB MS sgRNA or IL2RG MS sgRNA, then transduced with HBB-GFP rAAV6 and IL2RG-GFP rAAV6 followed by 18 days of culture (FIG. 8A). Experimental design as depicted in FIG. 8A is shown in FIG. 8B, but with mismatching IL2RG and CCR5 nuclease and rAAV6. FACS plots are representative images from 2-3 CD34+ HSPC donors.
Figure 8B:
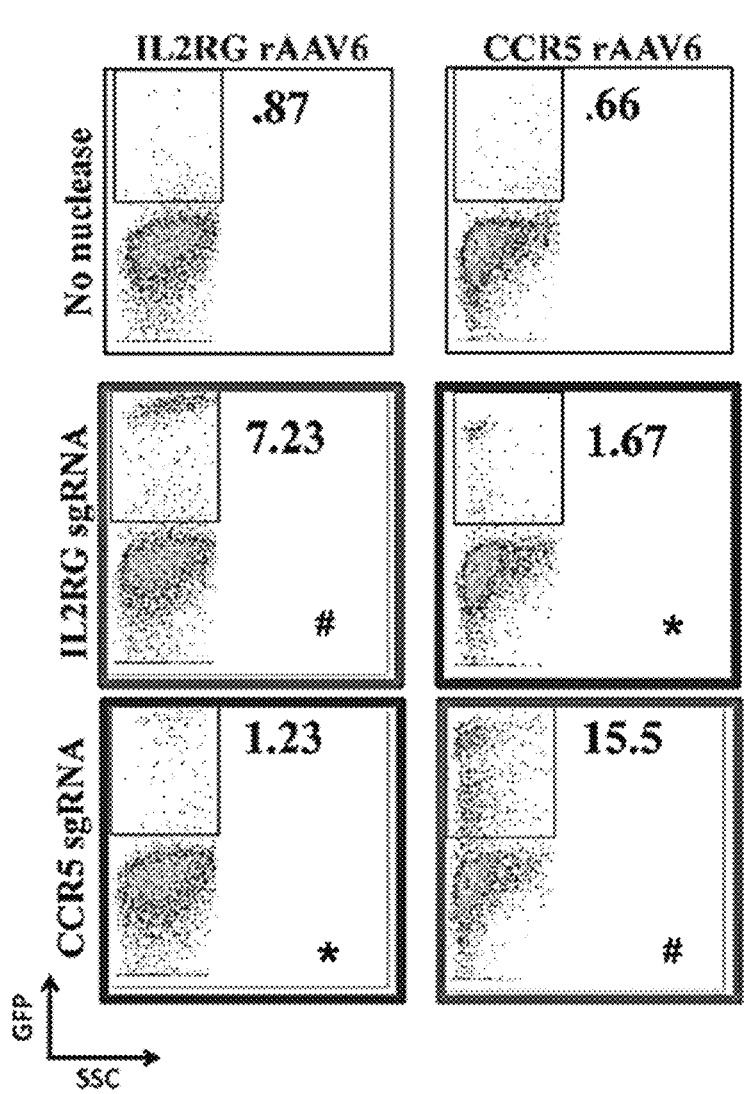

Because AAV genomes can be captured at the site of an off-target DSB via the NHEJ-mediated DSB repair pathway (Wang et al., *Nature Biotechnology* 33, 1256-1263 (2015); Wang et al., *Nucleic Acids Research* 44, e30 (2016); Miller et al., Nature Genetics 36, 767-773 (2004)), Experiments were performed wherein nucleases were mismatched with non-homologous donors to see if this occurs with the methods described herein. While about 20% cells that received matched HBB nuclease and HBB donor maintained GFP expression following 18 days in culture, IL2RG nuclease combined with HBB donor resulted in about 1% GFP$^+$ cells, which was slightly higher than background integration using AAV donor alone, suggesting that end-capture of the HBB donor is an infrequent event. These results were confirmed at the CCR5 and IL2RG loci using the same methodology (FIGS. 8A and 8B).

Figure 9A:
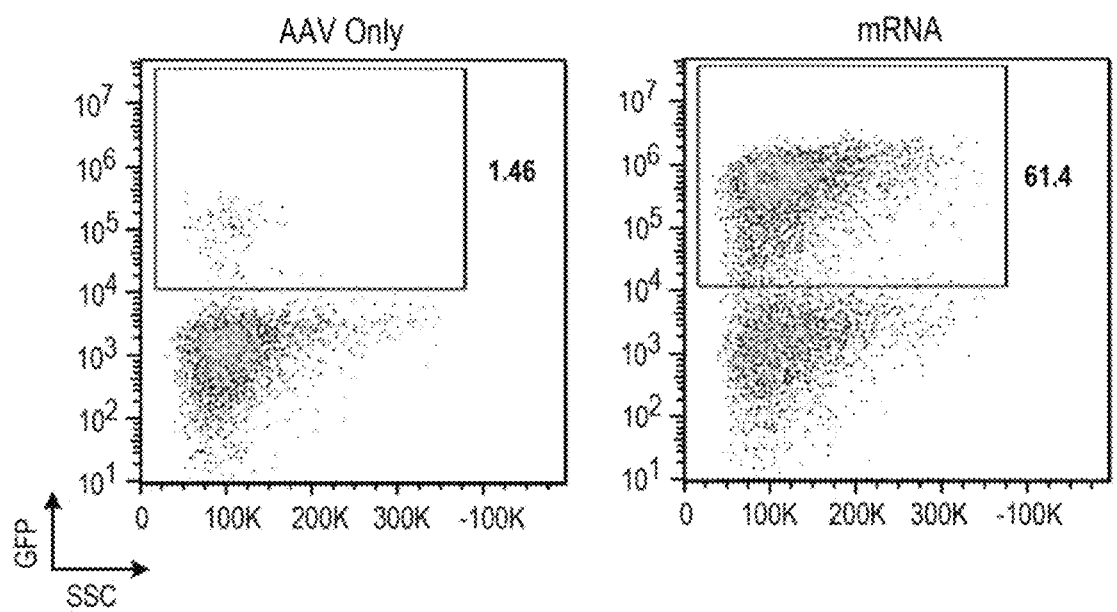
FIGS. 9A and 9B show that rAAV6 is an efficient HR donor template in primary human T cells. Primary T cells were isolated from buffy coats and activated for 3 days prior to HR experiment. T cells were electroporated with 15 µg Cas9 mRNA and 10 µg CCR5 MS sgRNA, and then transduced with CCR5-GFP rAAV6 at an MOI of 100,000. Cells were cultured for 15 and then analyzed by flow cytometry. Representative plots are shown to highlight stable integration of GFP cassette in activated T cells (FIG. 9A). Compiled frequencies of GFP+ T cells after 15 days in culture post-electroporation (FIG. 9B). Experiments were performed in T cells from three buffy coat donors and for the mRNA sample, each donor was done in duplicates. Error bars represent S.E.M.
Figure 9B:
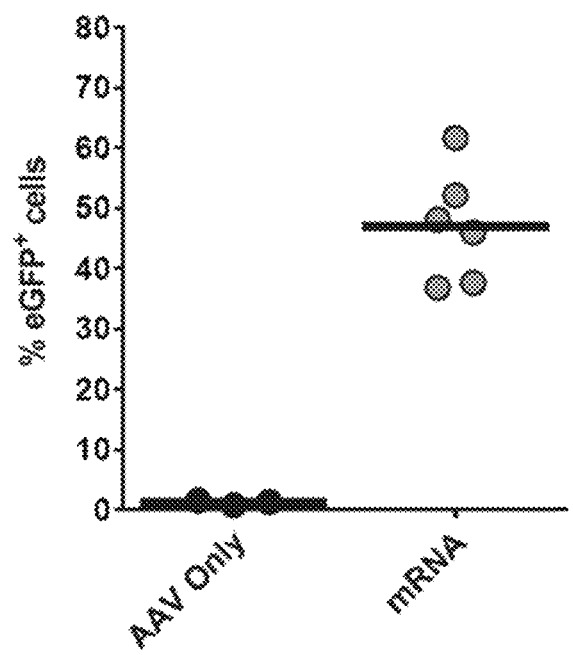

Next it was tested whether rAAV6 could serve as a suitable donor for HR in combination with CRISPR-induced DSBs in primary human T cells. Stimulated T cells were electroporated with Cas9 mRNA, CCR5-specific MS sgRNA, and then transduced with a CCR5 rAAV6 donor. Following two weeks in culture to dilute out episomal AAV6, about 50% T cells were GFP$^+$ confirming rAAV6 as an efficient donor in primary human T cells (FIGS. 9A and 9B), as has previously been shown (Hubbard et al., *Blood* (2016)).

Figure 1C:
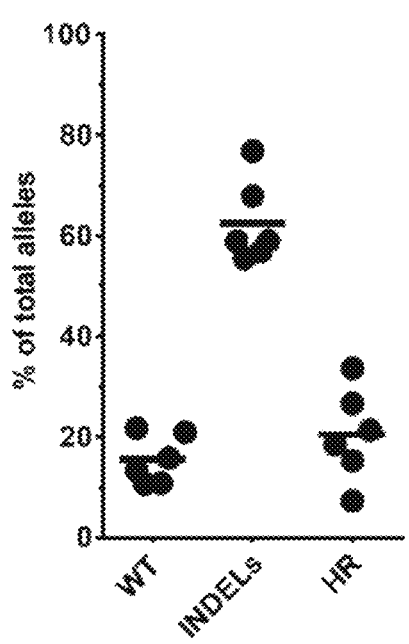
Figure 10:
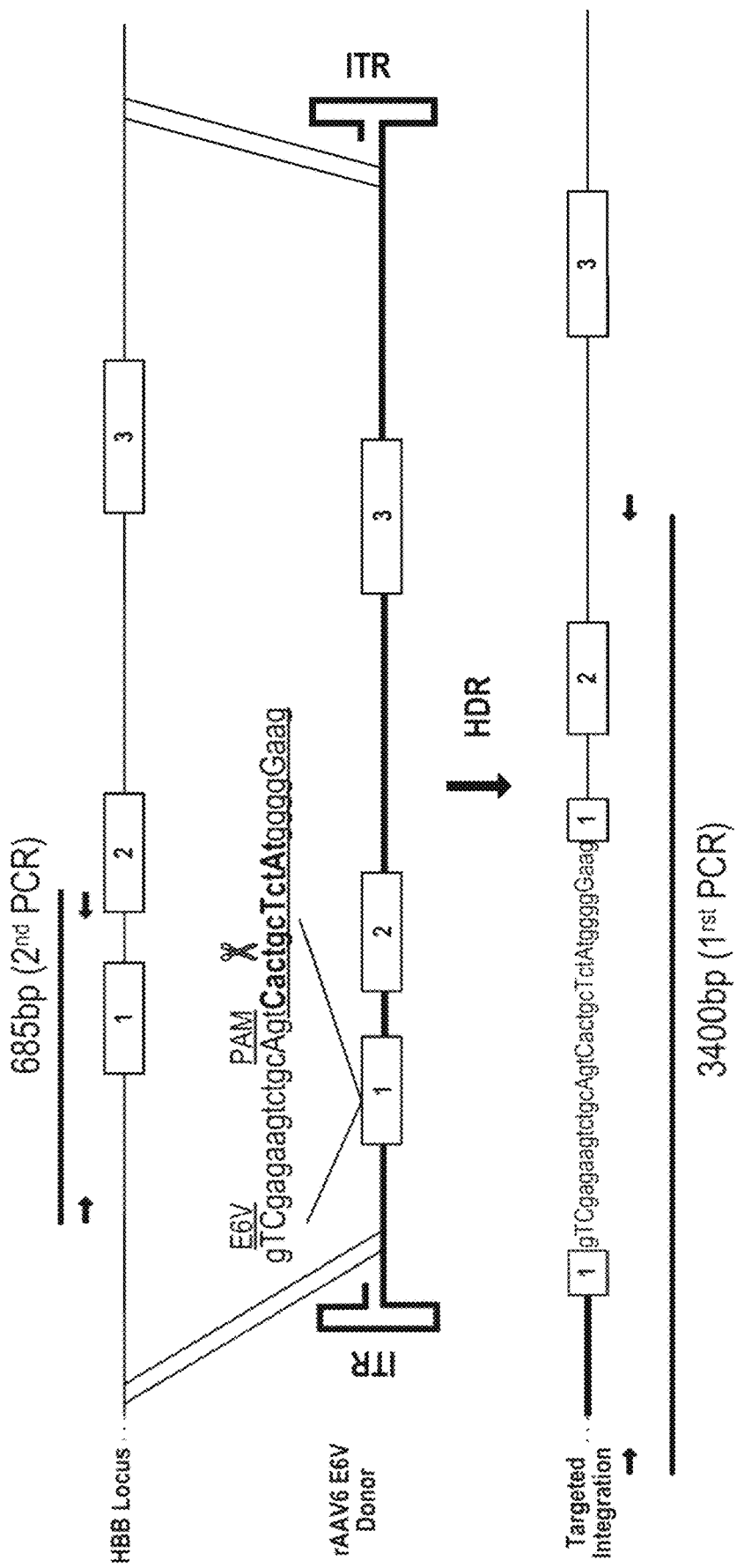
FIG. 10 depicts a schematic of targeting rAAV6 E6V homologous donor to the HBB locus. The human HBB locus on chromosome 11 is depicted at the top of the schematic and consists of 3 exons and 2 introns. The rAAV6 E6V donor includes the glutamine (E) to valine (V) mutation at codon 6, which is responsible for acquiring sickle cell anemia. Other SNPs (shown in bold) were introduced to PAM region and sgRNA binding site (black) to prevent recutting following HR in HSPCs (SEQ ID NO:4, 5'-GTCGAGAAGTCTGCAGTCACTGCTCTATGGGG-GAAG-3'). To analyze targeted integration frequencies in HSPCs, a 2-step PCR was performed. First, a 3.4 kb In-Out PCR was performed followed by a 2nd 685 bp PCR on the isolated first fragment. This 2nd PCR fragment was cloned into TOPO vectors, which were sequenced for type of HR event.
Figures 11A, 11B:
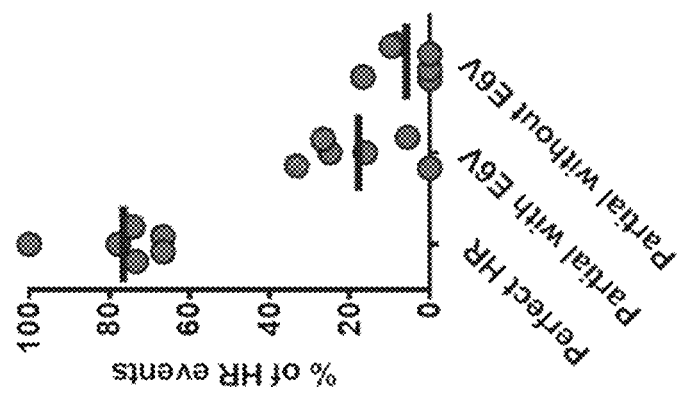
FIGS. 11A and 11B show different types of HR events at HBB using rAAV6 E6V homologous donor in CD34+ HSPCs. Representation of the different types of HR events at the HBB locus that were identified in sequenced TOPO clones (FIG. 11A) (WT HR event, SEQ ID NO:5, 5'-GAG-GAGAAGTCTGCCGTTACTGCCCTGTGGGGCAAG-3'; perfect HR, SEQ ID NO:48, 5'-GTCGAGAAGTCTGCAGTCACTGCTCTATGGGG-GAAA-3'; 5' end, SEQ ID NO:7, 5'-GTCGAGAAGTCTGCAGT-CACTGCCCTGTGGGGCAAG-3'; 3' end, SEQ ID NO:8, 5'-GAGGAGAAGTCTGCAGTCACTGCTCTATGGGG-GAAA-3'; and 5' and partial end, SEQ ID NO:9, 5'-GTCGAGAAGTCTGCAGTCACTGCTC-TATGGGGCAAG-3'). Alleles with perfect HR incorporated all intended nucleotide changes, including E6V, PAM, and all sgRNA SNPs. Changes in the 5' end incorporated E6V and PAM. Changes in the 3' end incorporated changes to the PAM and sgRNA, but not the E6V mutation. 5' and partial 3' events incorporated E6V, PAM, and half of sgRNA SNPs. Types of HR events were binned into 3 categories: 1) perfect HR, 2) partial HR events that included the E6V, and 3) partial HR events that did not include E6V (FIG. 11B). Notice that most of the HR events included the E6V mutation. Each dot represents a CD34+ HSPC donor from cord blood or adult bone marrow and 100 TOPO clones from each donor were sequenced.

This methodology was further tested to show that it could be used to make precise single nucleotide changes in HSPCs genomes. Sickle cell anemia is caused by a single nucleotide mutation, which changes an amino acid from glutamic acid (E) to valine (V) at codon 6 of the HBB gene (Hoban et al., *Blood* (2016)). Therefore, a 4.5 kb rAAV6 donor template was created that introduced the E6V mutation and also six other silent SNPs to interrupt the CRISPR PAM and sgRNA-binding site to prevent re-cutting and INDEL creation following HR (FIG. 10). Using an optimized protocol, an average integration frequency of 21% in six different HSPC donors (FIG. 1C) was measured, out of which 94% had the intended incorporation of the E6V mutation (FIGS. 11A and 11B). These results confirm that combining CRISPR with rAAV6 can mediate precise nucleotide changes to the HSPC genome.

Figure 1D:
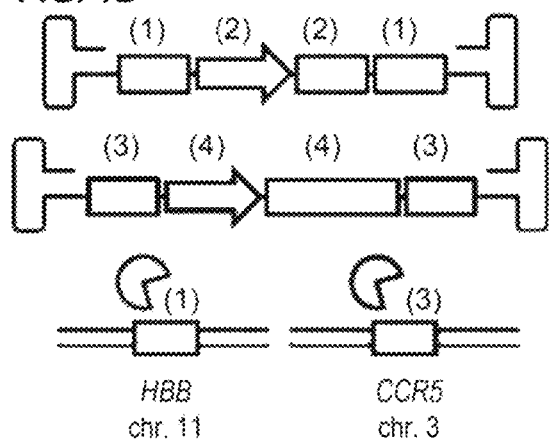
Figure 1E:
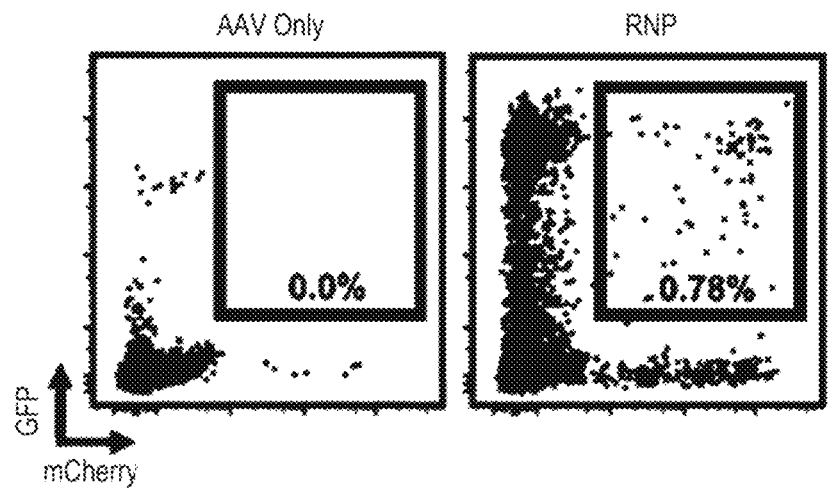
Figure 1F:
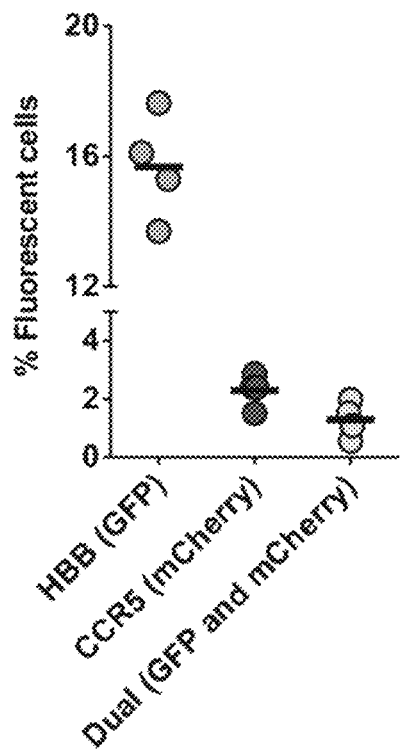

Given the relatively high frequencies of HR-mediated targeted integration at different loci, it was tested whether the process could be multiplexed. HBB-GFP and CCR5-mCherry rAAV6 donors were co-delivered with Cas9 RNP targeting both loci. This strategy resulted in single positive GFP or mCherry populations (as expected), but it also produced GFP/mCherry double positive cells (FIGS. 1D and 1E). This signifies that by combining the CRISPR system and rAAV6 donor delivery, multiplexed HR-mediated editing of HSPCs is possible, which now creates the experimental possibility of using this strategy to explore complex genetics in HSPC (Plomin, et al., *Genetics* 10, 872-878 (2009); Lvovs et al., *Acta Naturae* 4, 59-71 (2012)).

Figure 2A:
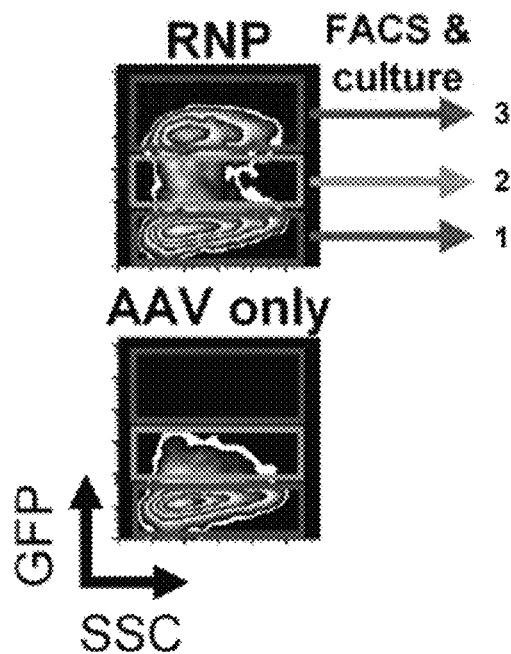
FIGS. 2A-2I provide FACS-based identification and enrichment of monogenic, dual-genic and dual-allelic genome-edited CD34+ hematopoietic stem and progenitor cells (HSPCs). 500,000 HSPCs were electroporated with HBB-RNP and then transduced with HBB-GFP rAAV6 at an MOI of 100,000. Representative FACS plots from day 4 post-electroporation highlight the HBB GFP$^{high}$ population (gate "3") generated by the addition of Cas9 RNP (FIG. 2A). At day 4 post-electroporation, HBB, CCR5 and IL2RG-targeted HSPCs from GFP$^{high}$ (gate "3"), GFP$^{low}$ (gate "2"), and GFP$^{neg}$ (gate "1") fractions were sorted and cultured for 15-20 days while monitoring GFP expression by flow cytometry (FIG. 2B). Error bars represent S.E.M. (N=11 (HBB), N=3 (CCR5 and IL2RG), all from different donors). HSPCs were targeted with CCR5-GFP, HBB-GFP, CCR5-tNGFR, and IL2RG-GFP (only female donors for IL2RG) as described above. At day 4 post-electroporation, GFP$^{high}$ (CCR5, HBB and IL2RG-targeted) and tNGFR$^{high}$ (CCR5-targeted) HSPC populations were single-cell sorted into 96-well plates containing methylcellulose to promote colony formation. After 14 days, gDNA was isolated from formed colonies and PCR was performed to detect targeted integrations (FIG. 2C). 95 (HBB), 115 (CCR5 GFP), 223 (CCR5 tNGFR), and 177 (IL2RG) colonies were screened from at least two different CD34$^+$ HSPC donors. 500,000 HSPCs were electroporated with HBB-RNP and transduced with HBB-GFP and HBB-tdTomato rAAV6 to assess biallelic-targeting efficiencies (FIG. 2D). A schematic diagram shows HBB-GFP (top AAV) and HBB-tdTomato (bottom AAV) targeting into HBB. (1): HBB homology arms; (2): GFP expression cassette; (3): tdTomato expression cassette. Representative FACS plot showing single positive (GFP$^{high}$ or tdTomato$^{high}$) and dual positive (GFP$^{high}$/tdTomato$^{high}$, boxed gate) populations at day 4 post-electroporation (FIG. 2E). HBB GFP$^{high}$/tdTomato$^{high}$ dual positive cells described above were sorted and cultured for 16 days while analyzing fluorescence expression by flow cytometry (FIG. 2F). Error bars represent S.E.M. (N=3 different HSPC donors) 500,000 HSPCs were electroporated and transduced as in FIG. 1D targeting GFP to HBB and mCherry to CCR5. Representative FACS plots at day 4 post-electroporation showing the GFP$^{high}$/mCherry$^{high}$ population (FIG. 2G; boxed gate). HBB GFP$^{high}$/CCR5 mCherry$^{high}$ HSPCs described above were sorted and cultured for 15 days while analyzing fluorescence by flow cytometry (FIG. 2H). Error bars represent S.E.M. (N=3 different HSPC donors). HBB GFP$^{high}$/CCR5 mCherry$^{high}$ HSPCs were single cell-sorted into 96-well plates containing methylcellulose. Representative images from fluorescence microscopy show lineage-restricted progenitors (BFU-E, CFU-E, CFU-GM) and multipotent progenitors (CFU-GEMM) with both GFP and mCherry expression (FIG. 2I).
Figure 2B:
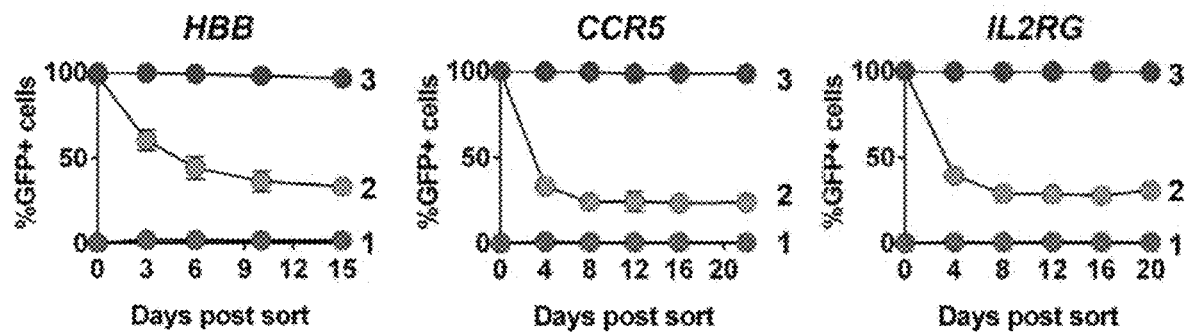
Figure 12:
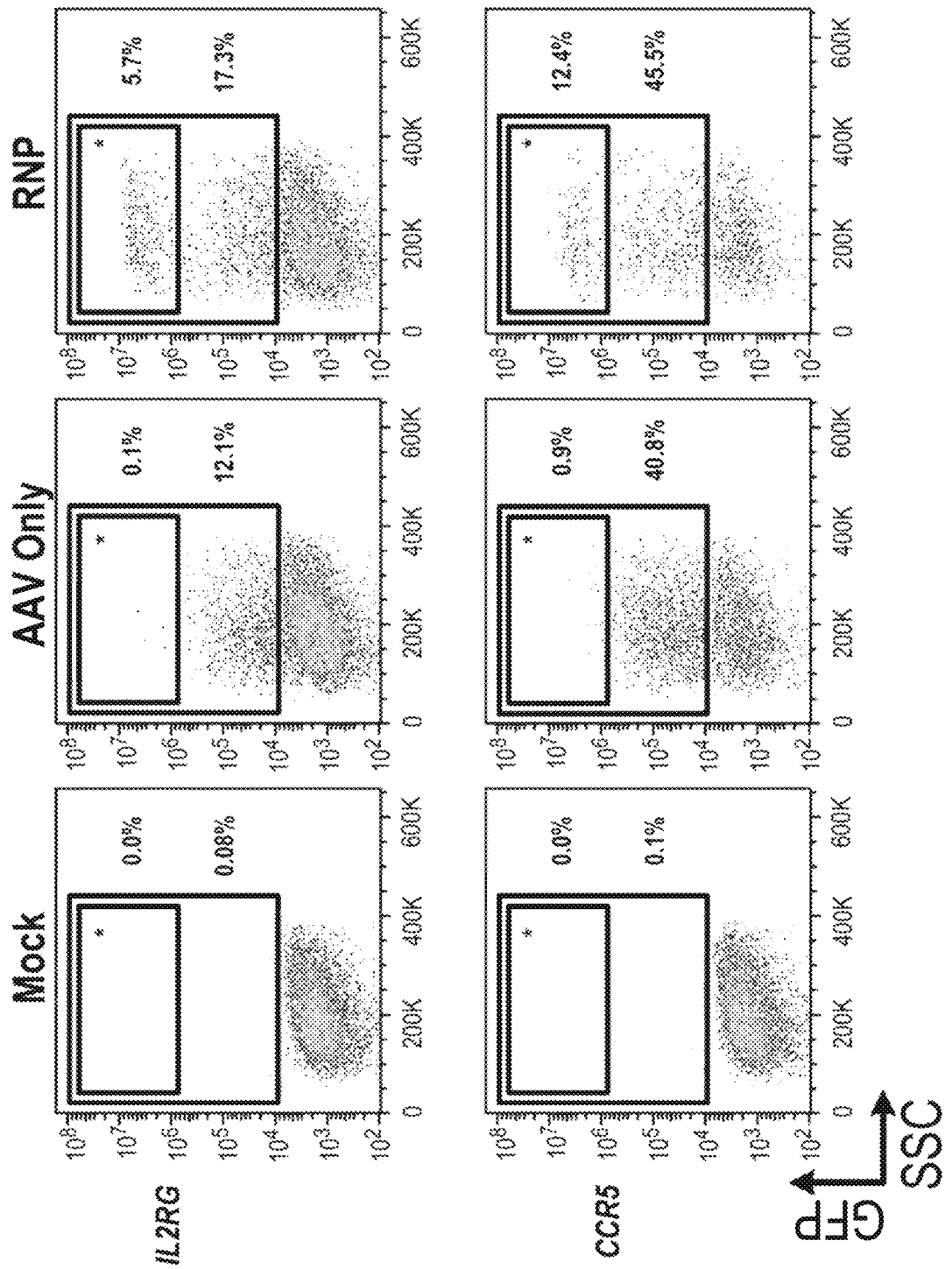
FIG. 12 shows a transgene expression shift following Cas9-mediated HR at the CCR5 and IL2RG loci. FACS plots showing difference in GFP expression with and without the presence of the CRISPR/Cas9 system (RNP-based delivery) at day 4 post-electroporation. CD34+ HSPCs were either 1) Mock-electroporated (Mock), 2) Mock and transduced with homologous rAAV6-GFP donor templates (AAV only) or 3) electroporated with locus-specific RNPs and transduced with rAAV6 (RNP). Block boxes represent total GFP positive cells and boxes with asterisks show percentage of GFP$^{high}$ cells. A ~57-fold and ~13-fold increase in percentage of cells in the GFP$^{high}$ population was observed following RNP treatment at the IL2RG and CCR5 locus, respectively.
Figure 14A:
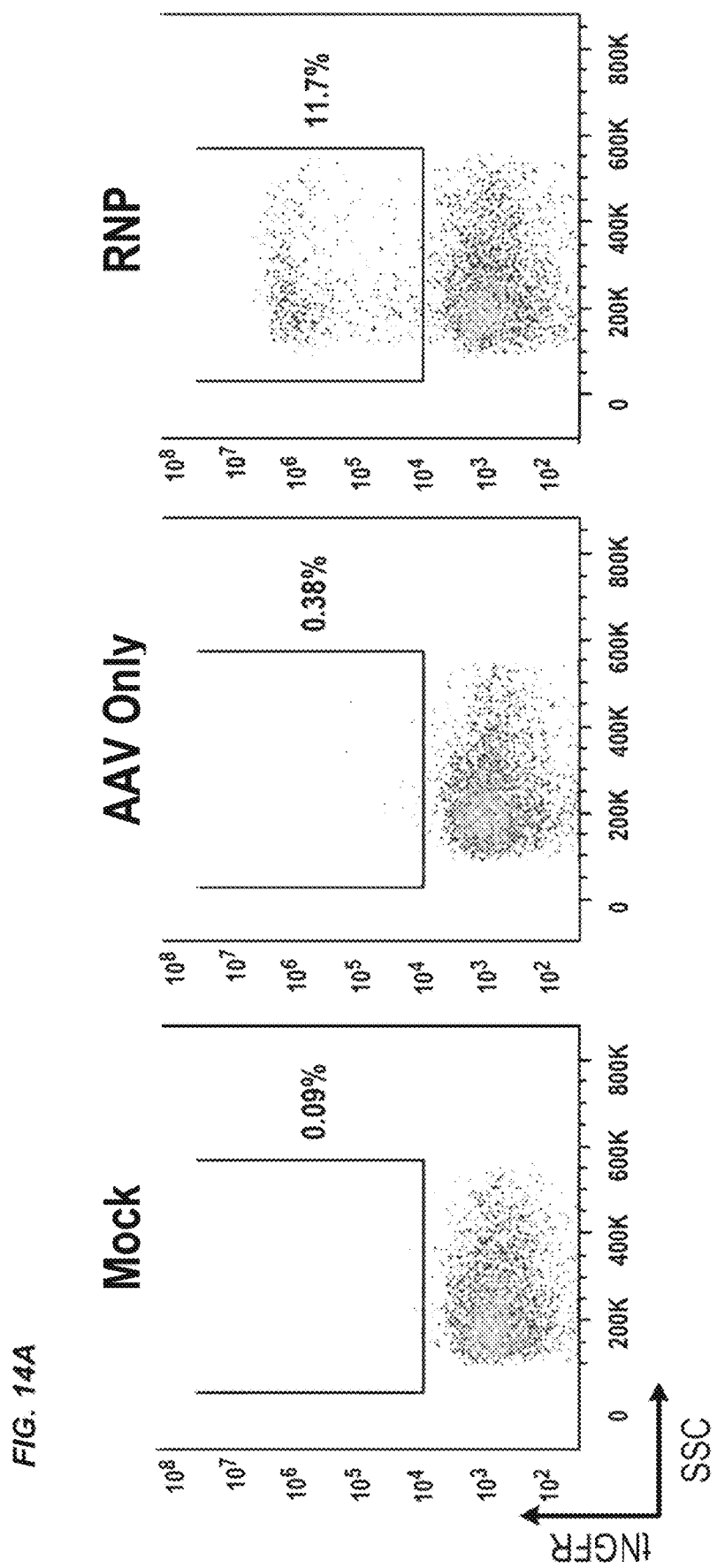
FIGS. 14A-14D show a Cas9-induced donor expression shift at CCR5 with a tNGFR reporter. HSPCs were electroporated with CCR5 RNPs, transduced with CCR5 tNGFR rAAV6 donors, and cultured for 18 days. Representative FACS plots are shown from each experimental group at day 18 post-electroporation.
Figure 14B:
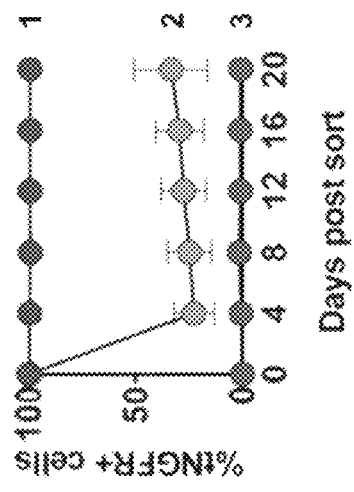
Figure 14D:
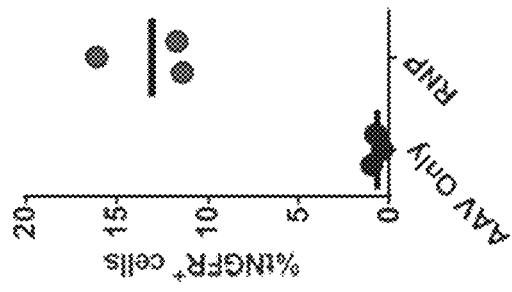
Figure 14C:
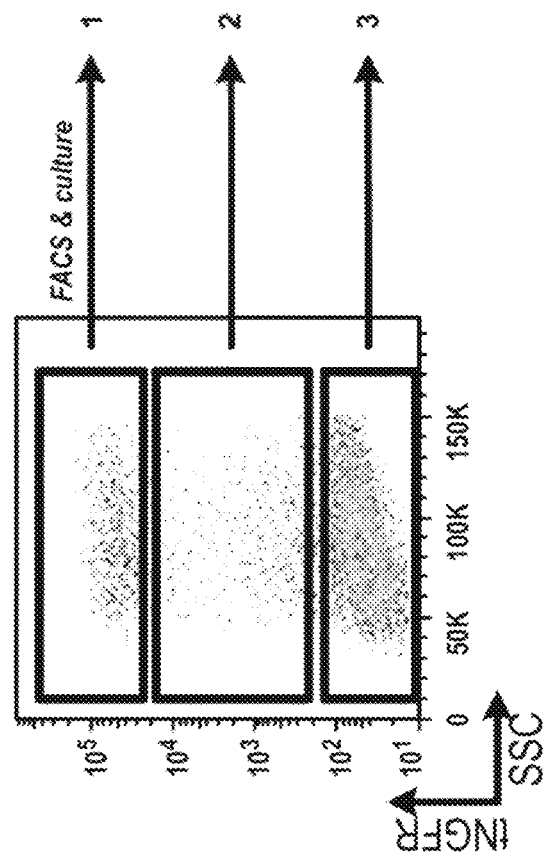

When analyzing fluorescence expression to monitor HR, it was observed at early time points following electroporation and transduction that while HSPCs receiving only rAAV6 donor and no nuclease expressed low levels of GFP, HSPCs that received both components generated a population with much higher GFP levels (mean fluorescence intensities or MFI). This GFP$^{high}$ population was observed at day 4 post-electroporation and was evident for all three targeted loci (HBB, IL2RG, and CCR5) (FIGS. 2A and 12). Since targeted cells at day 18 post-electroporation displayed the same high GFP expression it was hypothesized that this GFP$^{high}$ population was enriched for gene-targeted cells. GFP$^{high}$ populations were therefore sorted and cultured, as well as GFP$^{low}$ and GFP$^{neg}$ populations at day 4 post-electroporation. While sorted GFP$^{low}$ and GFP$^{neg}$ populations were respectively about 25% and about 1% GFP$^+$ after 15-20 days in culture, the GFP$^{high}$ population was greater than 95% GFP$^+$ in cells targeted at each of the three loci, strongly suggesting that this GFP$^{high}$ population was indeed gene-targeted (FIG. 2B). In fact, linear regression models show that the percent of GFP$^{high}$ expressing HSPCs at day 4 post-electroporation strongly correlates with the total percentage of GFP$^+$ cells at day 18 (FIGS. 13A and 13B).

Figure 15:
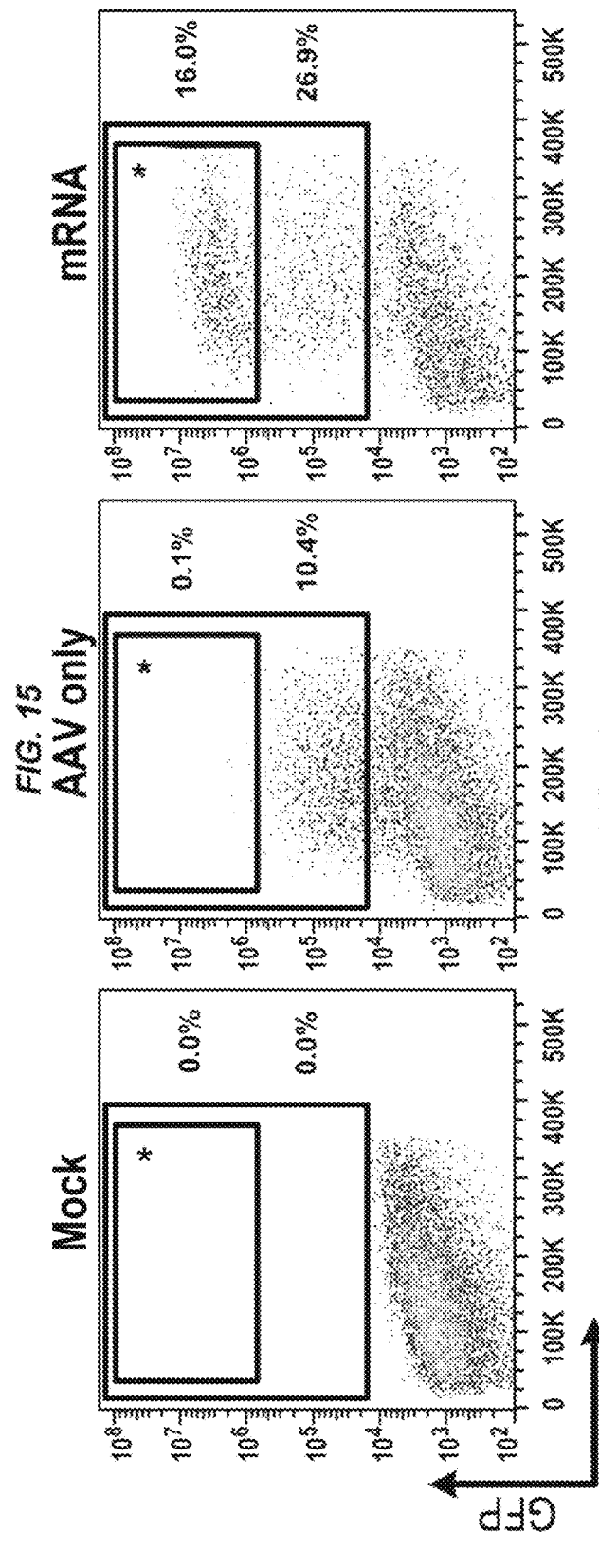
FIG. 15 shows a Cas9-induced shift in donor expression levels in primary human T cells. Human primary T cells were activated for 3 days prior to HR experiments in which cells were electroporated with 15 μg Cas9 mRNA and 10 μg CCR5 MS sgRNA, and then transduced with CCR5-GFP rAAV6 at an MOI of 100,000. Representative FACS plots are from day 4 post-electroporation. Black gates (black boxes) show total GFP+ cells while gates with asterisks show the GFP$^{high}$ population.
Figure 16:
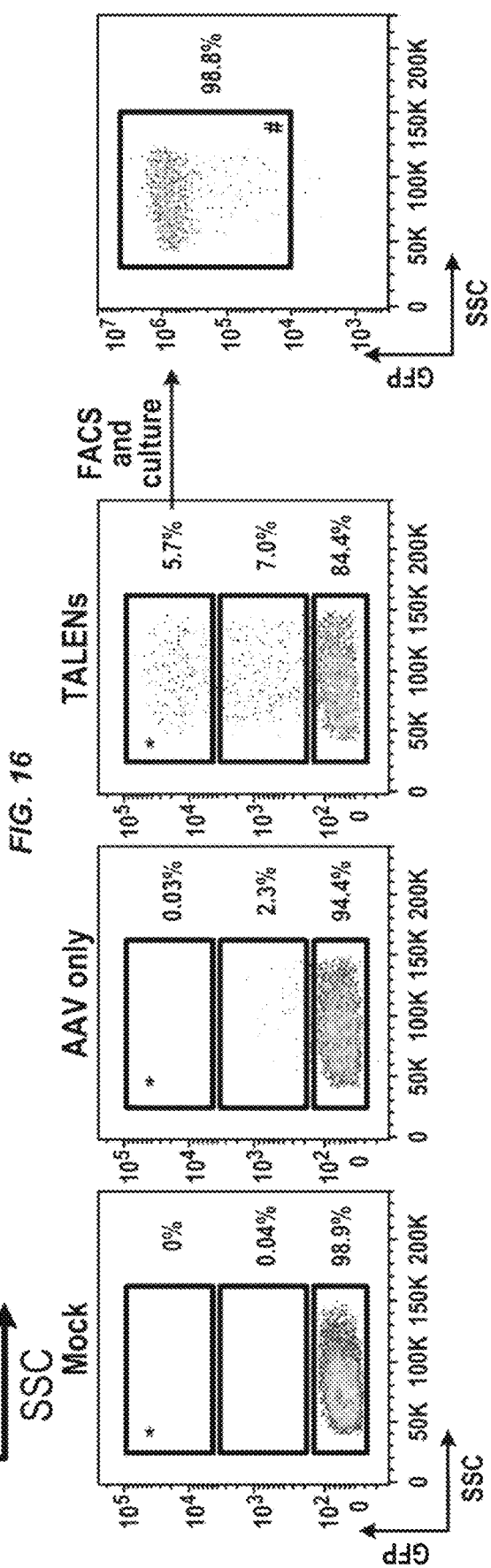
FIG. 16 shows the generation of the GFP$^{high}$ population with TALENs. CD34+ HSPCs were electroporated with a CCR5-specific TALEN pair (delivered as mRNA), and then were transduced with CCR5-GFP rAAV6 donor. The three left FACS plot are shown from analyses at day 4 post-electroporation with the gate with asterisk encompassing the GFP$^{high}$ population, which is only observed when TALENs are introduced. The GFP$^{high}$ population from the TALEN-treated sample was subsequently sorted and the right FACS plot shows GFP expression of this sorted population after 19 days in culture. The gate with hashtag defines all GFP+ cells. Note that this sample was analyzed on a different cytometer, hence the different gating.

Next it was tested whether this HR-mediated shift from episomal (low) to chromosomal (high) donor expression was a transgene-, cell-, or nuclease-dependent phenomenon. The truncated nerve growth factor receptor (tNGFR), in which the cytoplasmic intracellular signaling domain is removed, rendering it signaling incompetent, is an attractive candidate for enrichment of gene-targeted HSPCs. It is expressed on the cell surface, thereby allowing antibody-mediated detection of gene marking and it has already been used in human clinical trials (Bonini et al., *Science* 276, 1719-1724 (1997); Ciceri et al., *The Lancet. Oncology* 10, 489-500 (2009); Oliveira et al., *Science translational medicine* 7, 317ra198 (2015)). Using a CCR5 tNGFR rAAV6 donor, a tNGFR$^{high}$ population was observed by day 4 post-electroporation that was not evident without the presence of nuclease (FIGS. 14A-14D). After sorting and culturing, greater than 95% of tNGFR$^{high}$ cells maintained NGFR expression throughout 3 weeks in culture, confirming that the tNGFR expression in this population is from stable integration of the transgene. T cells were also targeted with a CCR5 GFP rAAV6 donor and observed the same GFP$^{high}$ population at day 4 post-electroporation, suggesting that this phenomenon applies to other primary blood cells as well (FIG. 15). To see if this expression shift was specific to the CRISPR/Cas9 system, HSPCs were targeted with a CCR5-GFP rAAV6 donor using TALENs. Again, a GFP$^{high}$ population was produced by the addition of TALENs with the rAAV6 donor, and FACS confirmed that this population maintained stable GFP expression over 3 weeks in culture (FIG. 16). These data imply that the log-fold higher expression is a conserved event when an ssAAV6 homologous donor is combined with site-specific nucleases to target primary blood cells, and importantly, it enables the early enrichment of HSPCs with targeted integrations. This increase in expression was the result of poor expression from an ssAAV extrachromosomal vector that is rescued after the transgene cassette is integrated into the genome. Of note, this increase in expression is seen even when the integration occurs into loci (HBB, CCR5, IL2RG) that are transcriptionally silent in HSPCs.

Figure 2C:
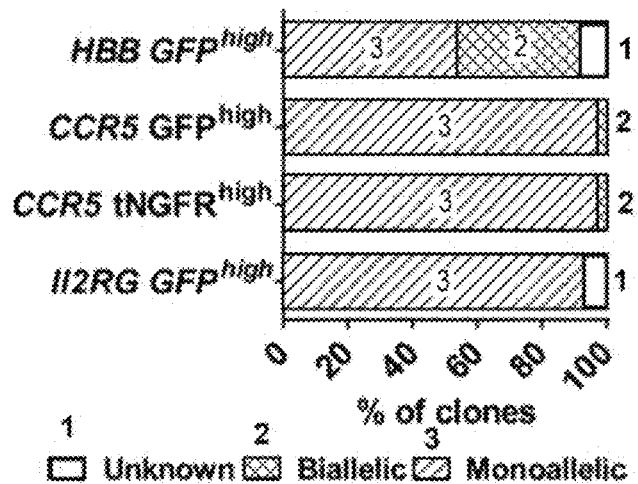
Figure 17B:
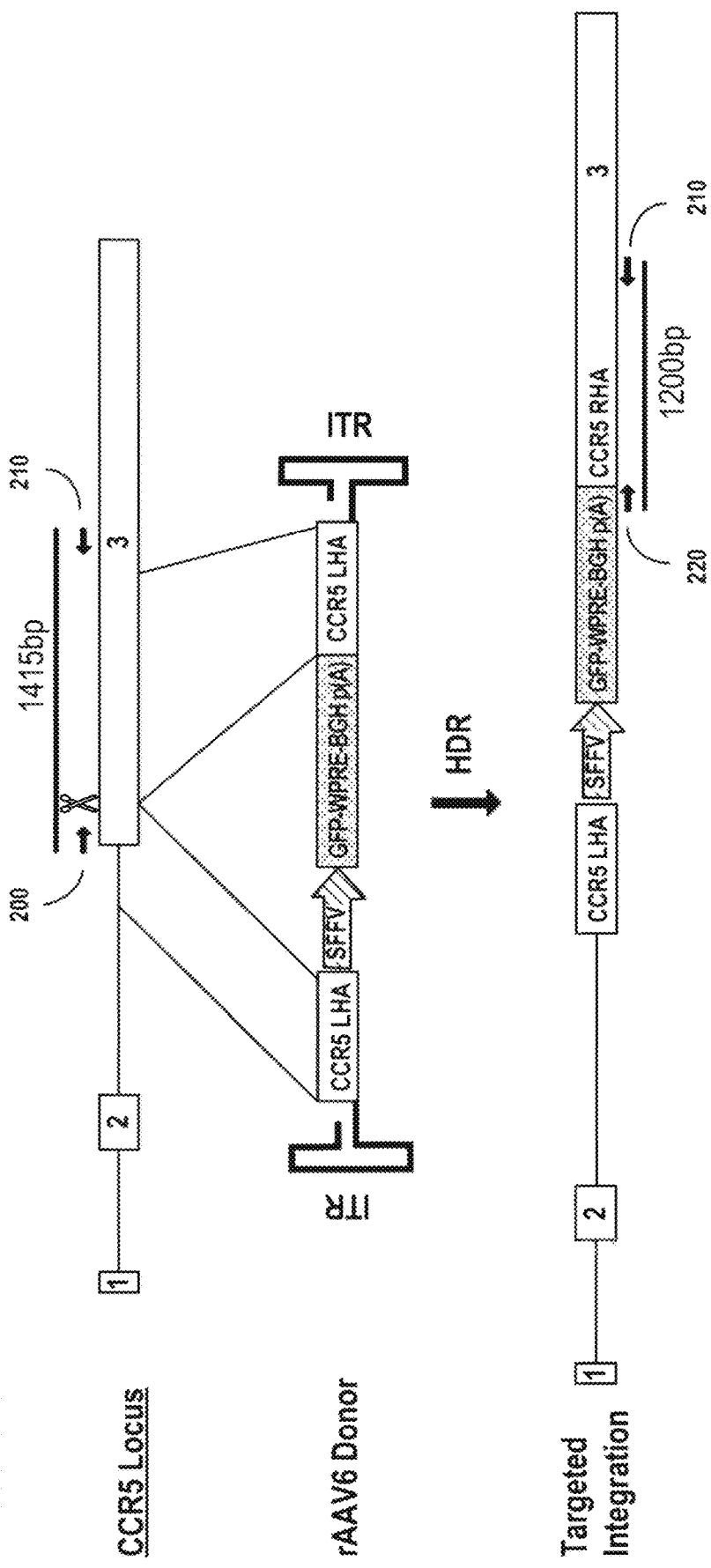
Figure 17C:
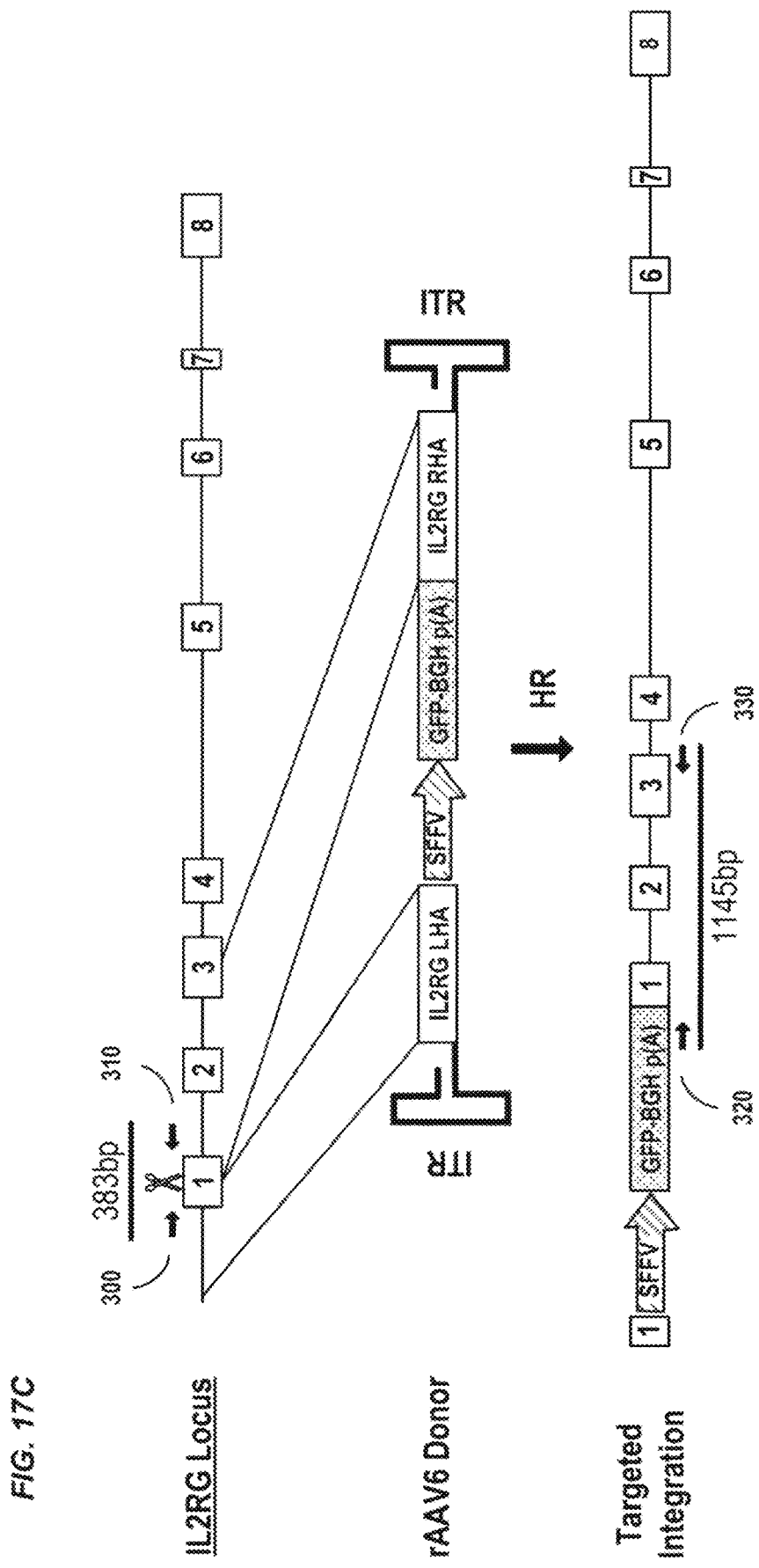
Figure 18A:
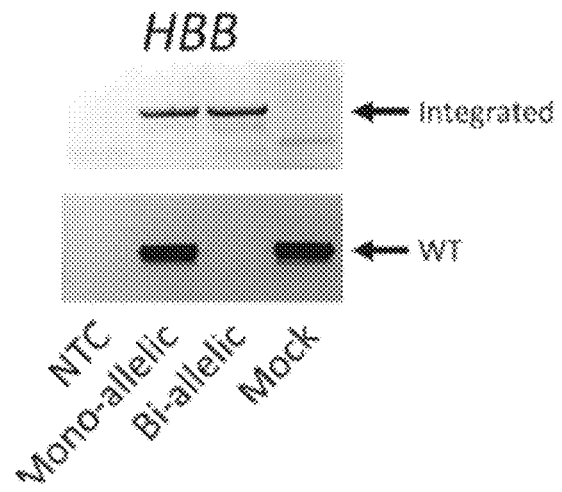
FIGS. 18A-18D provide genomic analyses of the HBB, CCR5, and IL2RG GFP$^{high}$ clones. The clones have seamless on-target integration. Representative agarose gels for genotyping methylcellulose clones derived from HBB, CCR5, and IL2RG GFP$^{high}$ populations (FIGS. 18A, 18B, and 18C, respectively. Note that for IL2RG experiments, HSPCs were derived from female donors allowing determination of mono versus biallelic integration since IL2RG is located on the X chromosome. Wildtype, monoallelic and biallelic integration events are shown for each locus, except for IL2RG for which we did not observe any biallelic integrations (see FIGS. 17A, 17B and 17C for PCR primer locations).
Figure 18B:
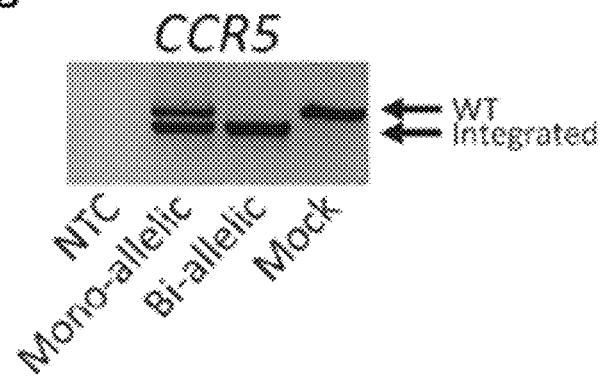
Figure 18C:
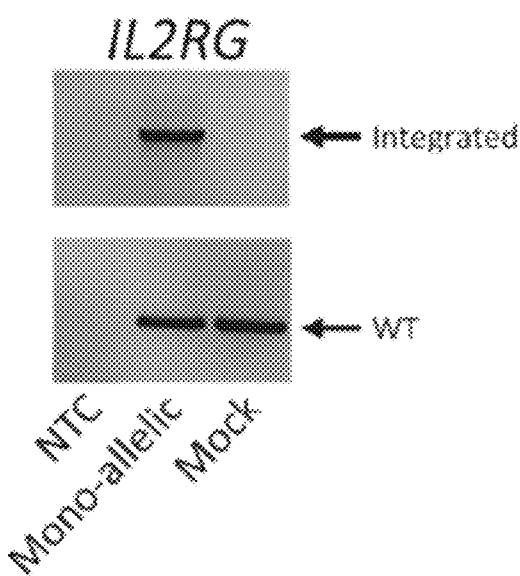
Figure 18D:
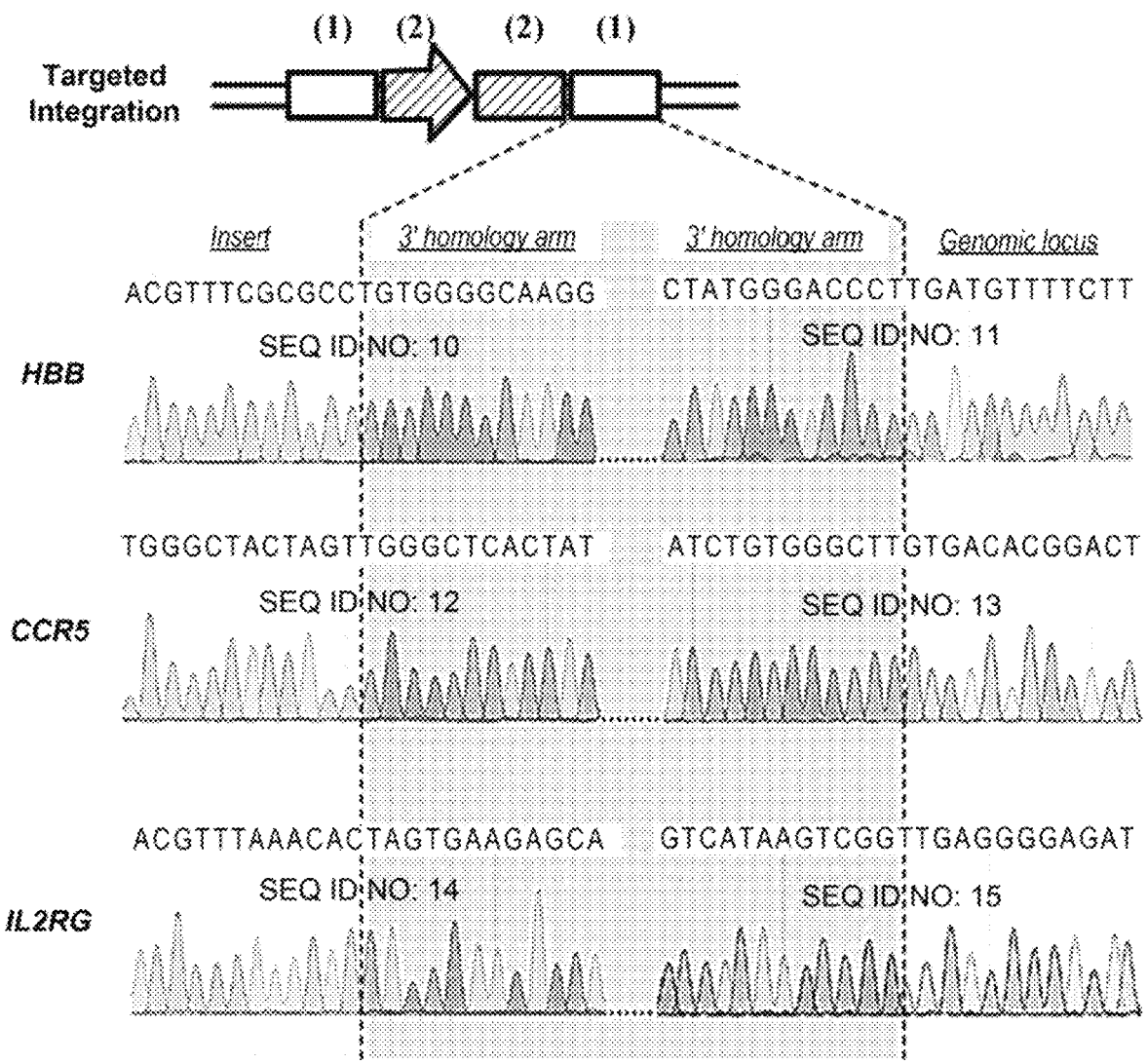

To molecularly confirm that the GFP$^{high}$ population was in fact a pure population of cells with on-target integration, 'In-Out PCR' was used to determine integration frequencies and allelic distribution in methylcellulose clones derived from the GFP$^{high}$ population from HSPCs targeted at HBB (95 clones), CCR5 (115 clones) and IL2RG (117 clones) (FIGS. 17A-17C). Collectively, 95% of clones (366 out of 387) from all three populations had targeted integration, with HBB displaying a significant number of biallelic integrations (about 30%) (FIGS. 2C and 18A-18D). Clones were also analyzed from the CCR5-targeted tNGFR$^{high}$ population (223 clones), which were confirmed to be a 99% targeted population (FIG. 2C). These data confirmed that the log-fold transgene expression shift following rAAV6 and RNP delivery is due to HR at the intended locus and can be used to enrich gene-targeted HSPCs.

Figure 2D:
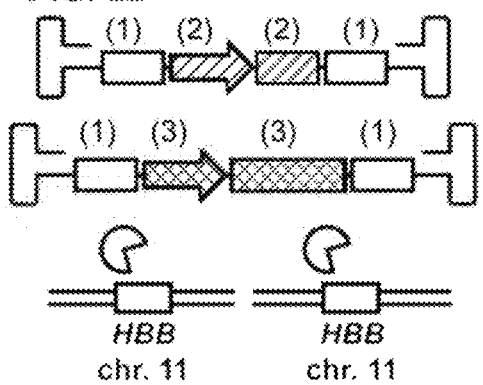
Figure 2F:
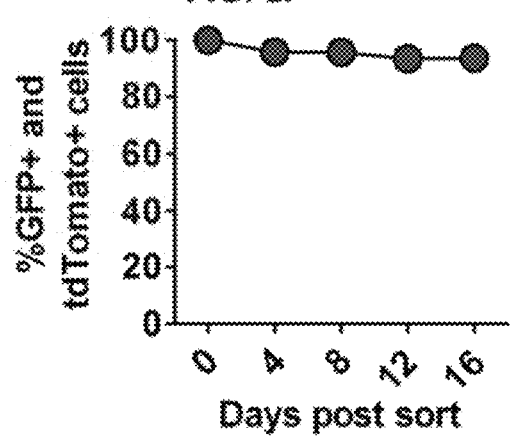
Figure 2E:
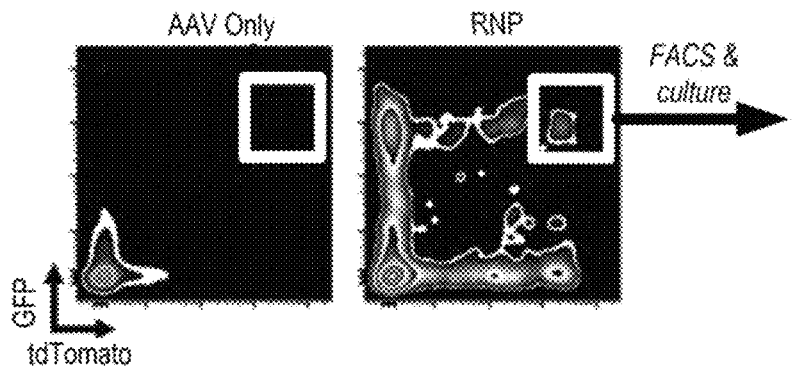
Figure 2G:
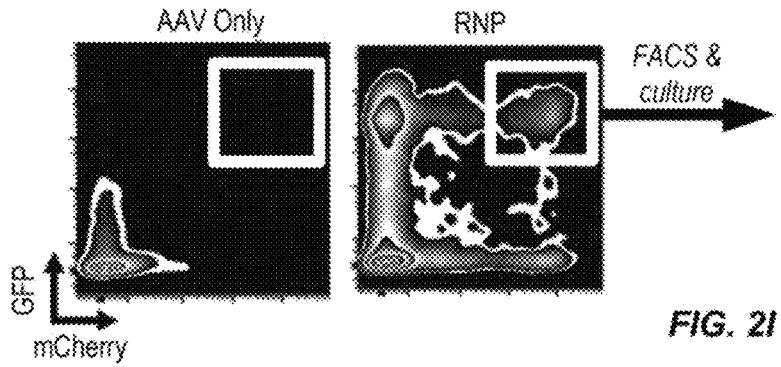
Figure 2H:
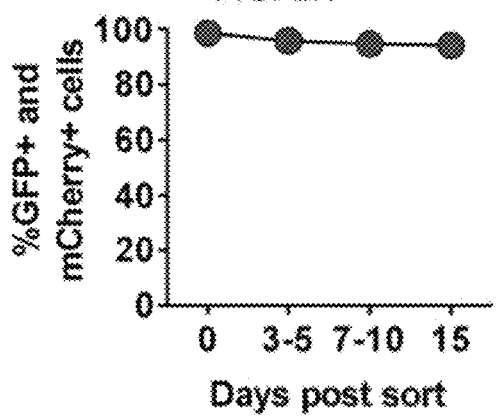
Figure 2I:
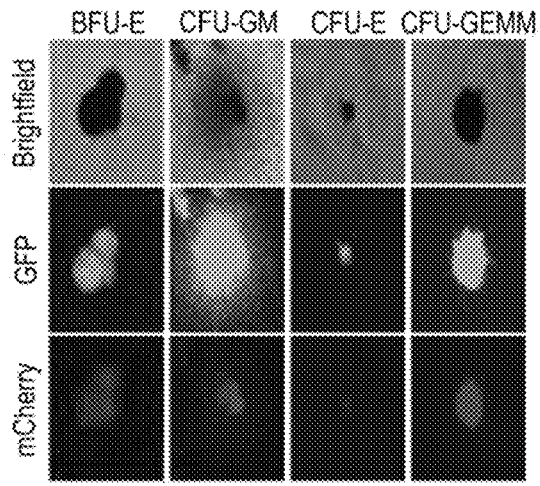

While mono-allelic integration was mainly observed at CCR5 and IL2RG, about 30% of GFP$^{high}$ HBB clones underwent biallelic integration. To confirm this observation, the HBB locus was targeted with both a GFP and a tdTomato rAAV6 donor and observed that the rates of double-positive cells correlated to a biallelic modification frequency of about 20% (FIGS. 19A-19C). Following sorting of the GFP$^{high}$/tdTomato$^{high}$ population, cells maintained double-positive for more than two weeks in culture (FIGS. 2D, 2E and 2F), and more importantly, it was confirmed in methylcellulose clones by 'In-Out PCR' that double positive clones had on-target integration of both genes into each allele (FIGS. 19A-19C). These results demonstrate the utility of using rAAV6 and Cas9 to induce biallelic homologous recombination in HSPCs, which may have implications for studying diseases that require gene modifications or gene knockout at both alleles.

Enrichment for multigenic HR in HSPCs would allow for the characterization of gene-gene interactions that could ultimately circumvent the bottleneck of functional annotation of disease-associated gene networks. The enrichment strategy was utilized to see if a pure population of cells could be generated with targeted integration at two different genes based on the experiment described in FIGS. 1D and 1E. To that end, double positive HBB GFP$^{high}$/CCR5 mCherry$^{high}$ HSPCs were sorted at day 4 post-electroporation and cultured for 15 days while being analyzed for fluorescence. As expected, about 90% of HBB GFP$^{high}$/CCR5 mCherry$^{high}$ cells maintained their dual fluorescence (FIGS. 2E-2H).

In-Out PCR on GFP/mCherry double positive methylcellulose clones showed on-target integration at both loci in 88% of clones (57 clones screened) (FIG. 20). These data strongly suggest that the present methods allow for early enrichment of multiplexed genome-edited HSPCs.

Figure 3A:
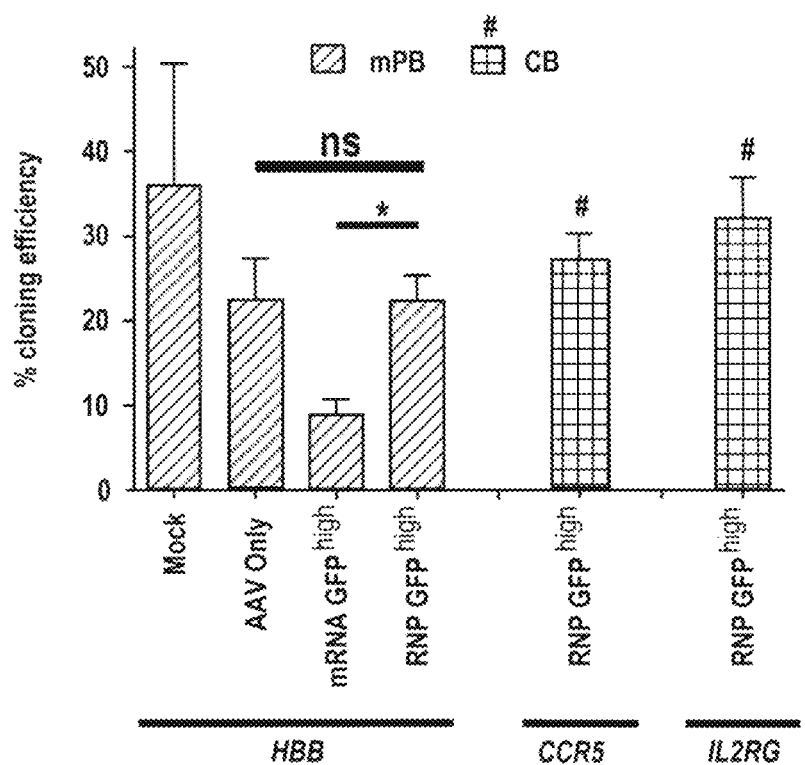
FIGS. 3A-3G illustrate that enriched genome-edited hematopoietic stem and progenitor cells (HSPCs) display long-term and multi-lineage reconstitution in NSG mice. At day 4 post-electroporation, CD34+ HSPCs from the indicated experimental groups were single-cell sorted into 96-well plates containing methylcellulose (FIG. 3A). The number of colony forming units (CFUs) were counted 14 days post-sort and shown relative to the total number of cells sorted (% cloning efficiency). Error bars represent S.E.M. (N=3 different HSPC donors), *p<0.05, ns=p≥0.05, unpaired Student's t-test. mPB: mobilized peripheral blood, CB: cord blood. Colonies shown in FIG. 3A were scored according to their morphology: 1) CFU-Erythroid (CFU-E), 2) Burst Forming Unit-Erythroid (BFU-E), 3) CFU-Granulocyte/Macrophage (CFU-GM), and 4) CFU-Granulocyte/Erythrocyte/Macrophage/Megakaryocyte (CFU-GEMM) (FIG. 3B). Error bars represent S.E.M. (N=3 different HSPC donors). 500,000 HSPCs isolated from mobilized peripheral blood (mPB), adult bone marrow (ABM), or cord blood (CB) were electroporated with HBB-RNP and transduced with HBB-GFP rAAV6. At day 4 post-electroporation, cells were phenotyped by flow cytometry for the cell surface markers CD34, CD38, CD90, and CD45RA (FIGS. 21A and 21B). Percent GFP$^{high}$ cells in the indicated subpopulations are shown (FIG. 3C). Error bars represent S.E.M. (N=3 from different HSPC donors). CD34+ or CD34$^+$/CD38$^-$/CD90$^+$ cells were sorted directly from freshly isolated cord blood CD34$^+$ HSPCs, cultured overnight, and then electroporated with HBB-RNP and transduced with HBB-GFP rAAV6. Bars show average percent GFP$^+$ cells at day 18 post-electroporation (FIG. 3D). Error bars represent S.E.M. (N=3 from different HSPC donors), p<0.01, paired Student's t-test. 500,000 HBB-targeted HSPCs were injected into the tail vein of sub lethally irradiated NSG mice except for the GFP$^{high}$ group, for which 100,000-500,000 cells were injected. 16 weeks post-transplantation, PBMCs were isolated by Ficoll density gradient centrifugation from the bone marrow, and human chimerism and GFP expression was analyzed by flow cytometry. Top panel, Representative FACS plot from a mouse transplanted with HBB RNP GFP$^{high}$ HSPCs showing engrafted human cells in the gate (shown in box) (huCD45+/HLA-ABC+). Bottom panel: Representative FACS plot showing GFP expression in human cells. CD19$^+$ B cells and CD33$^+$ myeloid cells were backgated and shown in (1) and (2), respectively (FIG. 3E). Human engraftment in NSG mice from all experimental groups determined as described above (FIG. 3F). Three different HSPC donors were used for engraftment studies (N=number of data points within group), **p<0.0001, ns=p≥0.05, one-way ANOVA and Tukey's multiple comparison test.
Figure 3B:
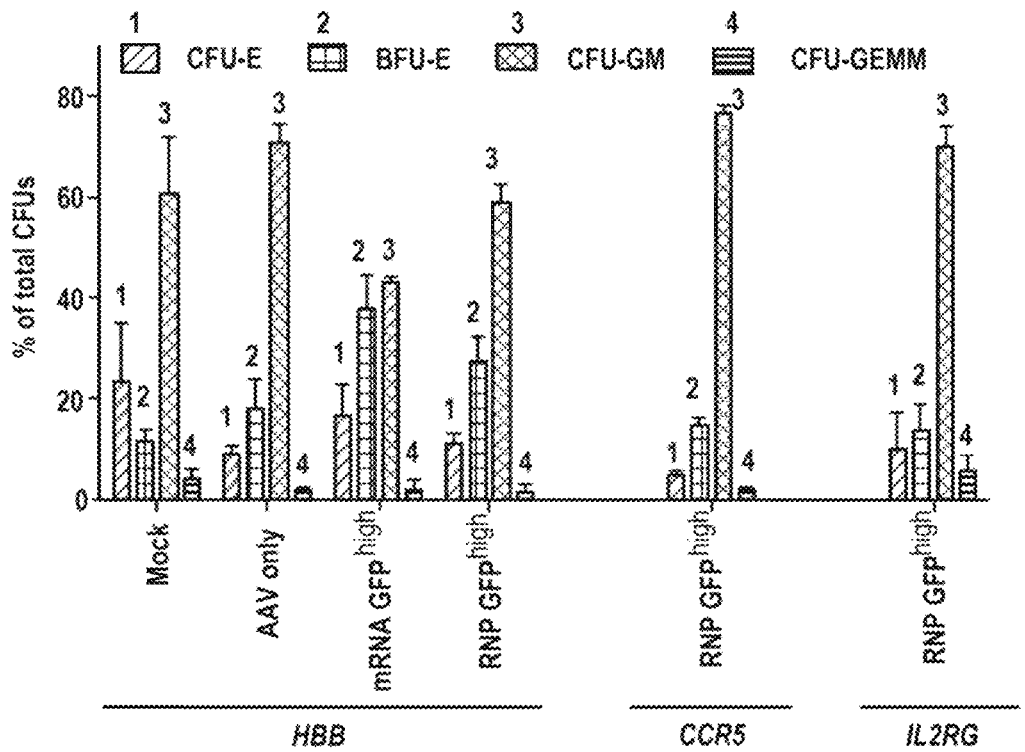

Because HSPCs are a heterogeneous population of cells with differential stem cell potential (Seita, J. & Weissman, I. L., *Wiley Interdisciplinary Reviews. Systems Biology and Medicine* 2, 640-653 (2010)), next evaluated was the stem and progenitor cell capacity of enriched targeted HSPCs in vitro and in vivo. The colony forming unit (CFU) assay was first used to characterize the functional potential of HBB $GFP^{high}$, CCR5 $GFP^{high}$ and IL2RG $GFP^{high}$ HSPCs to form erythroid (CFU-E and BFU-E), granulocyte/macrophage (CFU-GM), and multilineage (CFU-GEMM) clones in methylcellulose. Compared to mock-electroporated (Mock) HSPCs or HSPCs treated with rAAV6 only, no difference was observed in the colony formation potential of RNP-treated cells (FIG. 3A) or the distribution of colony types between experimental groups (FIG. 3B), confirming RNP-edited HSPCs have a similar progenitor potential as unedited cells. However, a significant decrease in cloning efficiency was observed for the mRNA-treated cells compared to the RNP (FIG. 3B).

Figure 3C:
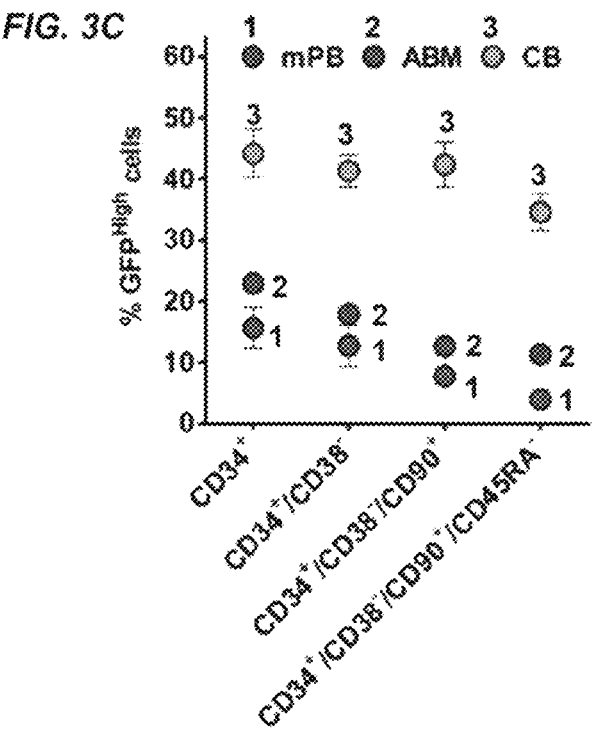
Figure 3D:
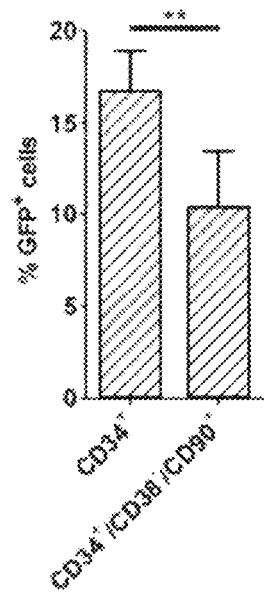
Figures 21A, 21B:
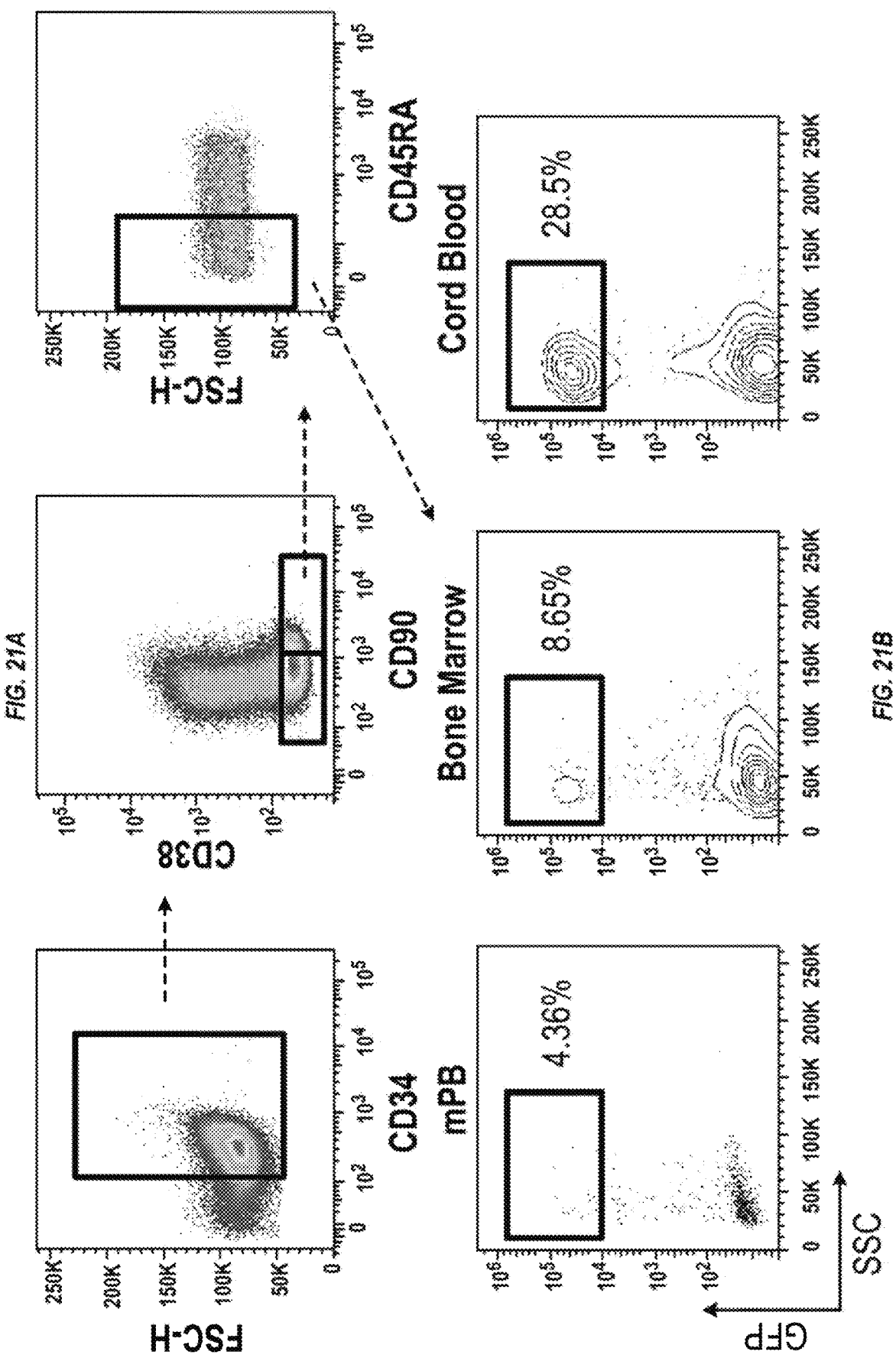
FIGS. 21A and 21B show representative FACS gating scheme for analyzing HBB and CCR5 targeting rates in different HSPC subpopulations. Representative FACS plots at day 4 post-electroporation of CD34+ HSPCs show the gating scheme for analyzing targeting frequencies in different subsets of HSPCs. Cells were immunophenotyped for CD34, CD38, CD90, and CD45RA expression and relevant FACS gates are indicated (FIG. 21A). Representative FACS plots showing GFP$^{high}$ cells in the CD34+/CD38-/CD90+/CD45RA- population of HSPCs derived from mobilized peripheral blood, bone marrow, or cord blood (FIG. 21B).
Figure 22:
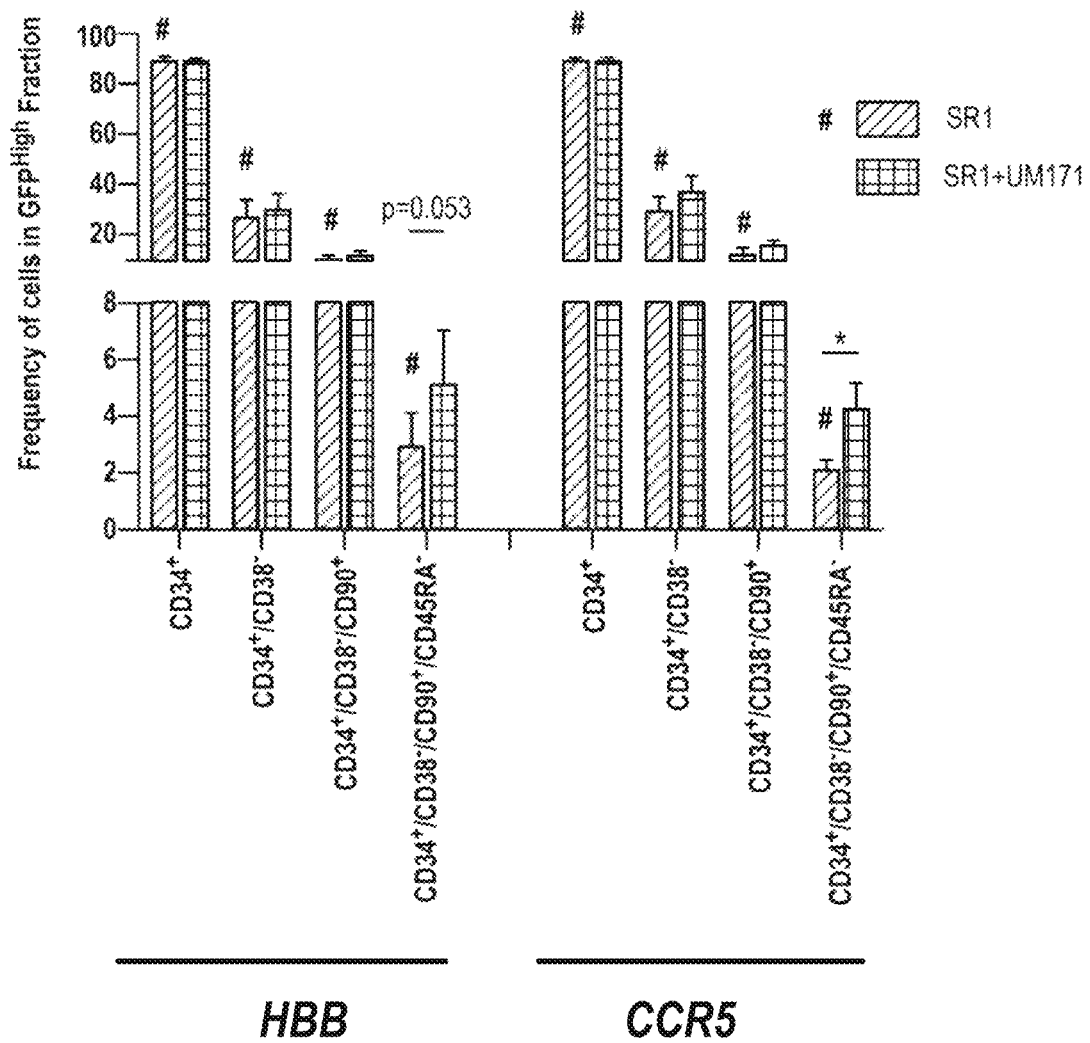
FIG. 22 illustrates that the small molecule UM171 increases percentage of HSCs in GFP$^{high}$ fraction by two fold. CD34+ HSPCs derived from cord blood were cultured in either standard HSPC media that includes SR1 or media with UM171 (35 nM final concentration) from isolation of HSPCs and for the entire duration of the experiment. Cells were subject to our standard rAAV6 and CRISPR/Cas9 targeting protocol at the HBB or CCR5 locus. Frequencies of cells in the GFP$^{high}$ population were analyzed at day 4 post-electroporation by flow cytometry (see FIGS. 21A and 21B for gating scheme). Error bars represent S.E.M. and experiments were performed in 5 HSPC donors in 2 independent experiments.

The classic model of human hematopoiesis is defined by a cell surface marker expression-based hierarchy initiated by HSCs that both self-renew and differentiate into multipotent progenitors, which in turn give rise to lineage-restricted progenitors, and finally terminally differentiated blood cells (Baum et al, supra; Majeti et al., *Cell Stem Cell* 1, 635-645 (2007); Doulatov et al., *Cell Stem Cell* 10, 120-136 (2012)). $CD34^+$ expression defines the heterogeneous HSPC population, which can be further classified as a multipotent progenitor ($CD34^+/CD38^-$), long-term repopulating cell in xenograft mice ($CD34^+/CD38^-/CD90^+$), and more recently, a population highly enriched for HSCs ($CD34^+/CD38^-/CD90^+/CD45RA^-$). Frequencies of $GFP^{high}$ cells were evaluated in the four different subpopulations by immunophenotypic analysis at day 4 post-electroporation. Generally, a negative correlation was observed between targeting frequencies and the immunophenotypic primitiveness of the analyzed population (FIGS. 3C, 21A and 21B), and combining all three sources of HSPCs (mobilized peripheral blood, adult bone marrow, and cord blood), a significant decrease of $GFP^{high}$ cells was found in the $CD34^+/CD38^-/CD90^+/CD45RA^-$ fraction compared to the total $CD34^+$ population (p=0.004) (FIG. 3C). Because concerns exist regarding the relationship between HSC potential and stem cell surface marker expression following in vitro culturing conditions (Weidner et al., *Scientific Reports* 3, 3372 (2013)), another strategy was employed to evaluate targeting rates in HSC populations. $CD34^+$ or $CD34^+/CD38^-/CD90^+$ (HSCs) cells were sorted from fresh HSPCs and used in HR experiments after 12-16 hours in culture. A 38% reduction was observed in targeting efficiencies in the long-term repopulating cells compared to the heterogeneous $CD34^+$ population (FIG. 3D), confirming previous immunophenotyping data. It was reasoned that the small molecule, UM171, which has been shown to expand HSCs in vitro (Fares et al., Science 345, 1509-1512 (2014)), could enhance targeting efficiencies and/or expand the targeted HSC population. Therefore, UM171 was added to HSPC media during targeting experiments in $CD34^+$ HSPCs and analyzed the subpopulations by immunophenotyping. UM171 selectively increased the fraction of $CD34^+/CD38^-/CD90^+/CD45RA^-$ in the $GFP^{high}$ population by about 2 fold (FIG. 22). Together, these results suggest that though it is more difficult to target HSCs than more committed progenitors and this decrease may be at least partially rescued by the addition of UM171.

Figure 3E:
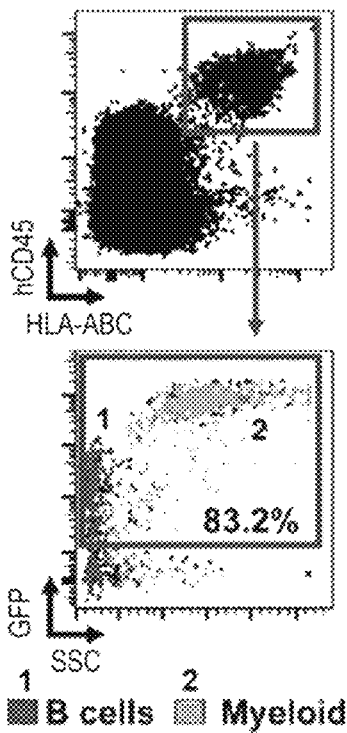
Figure 3F:
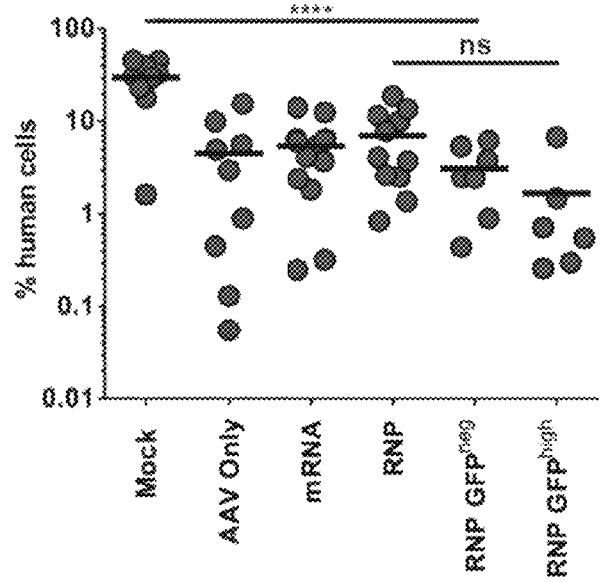
Figure 3G:
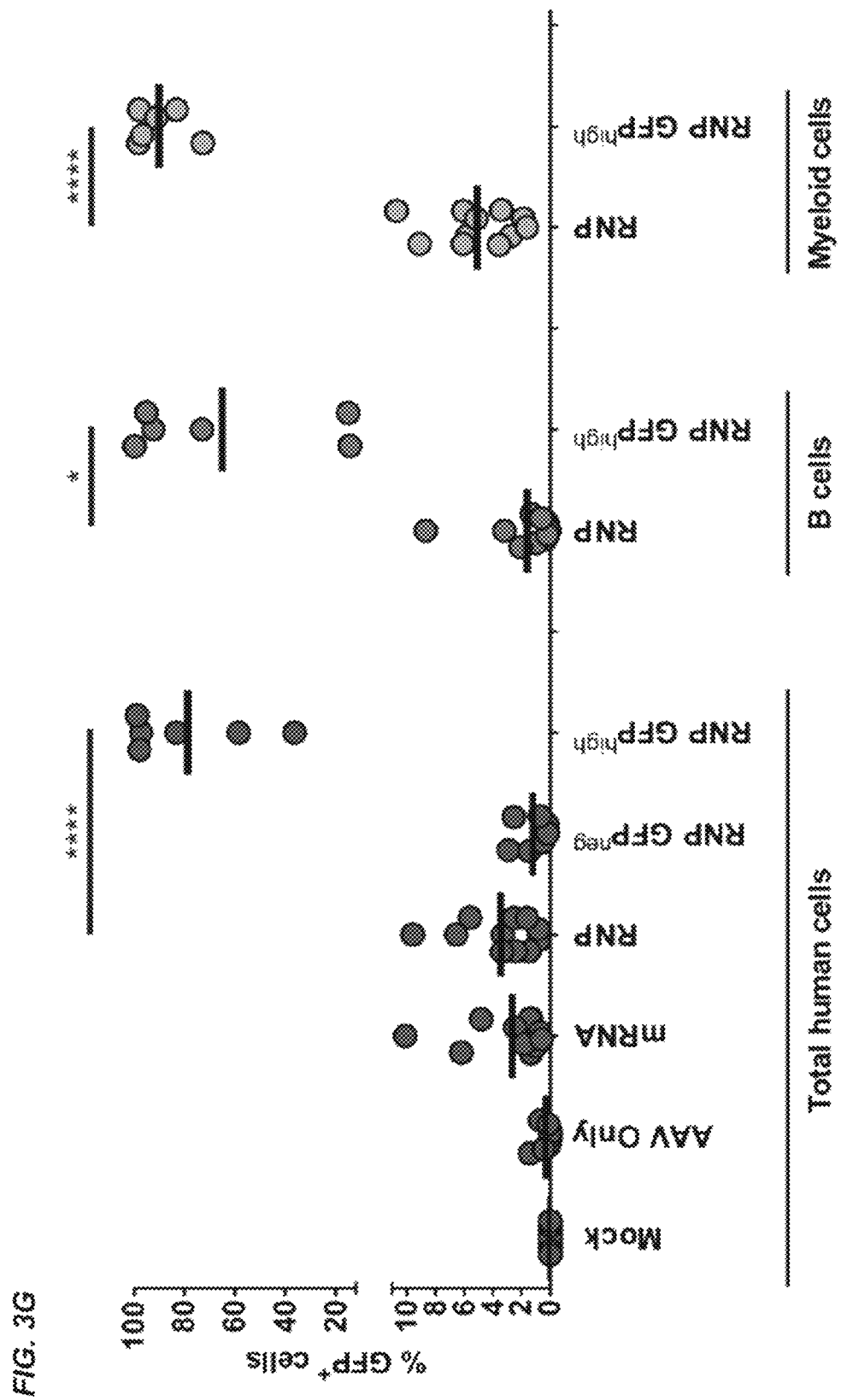
Figure 23:
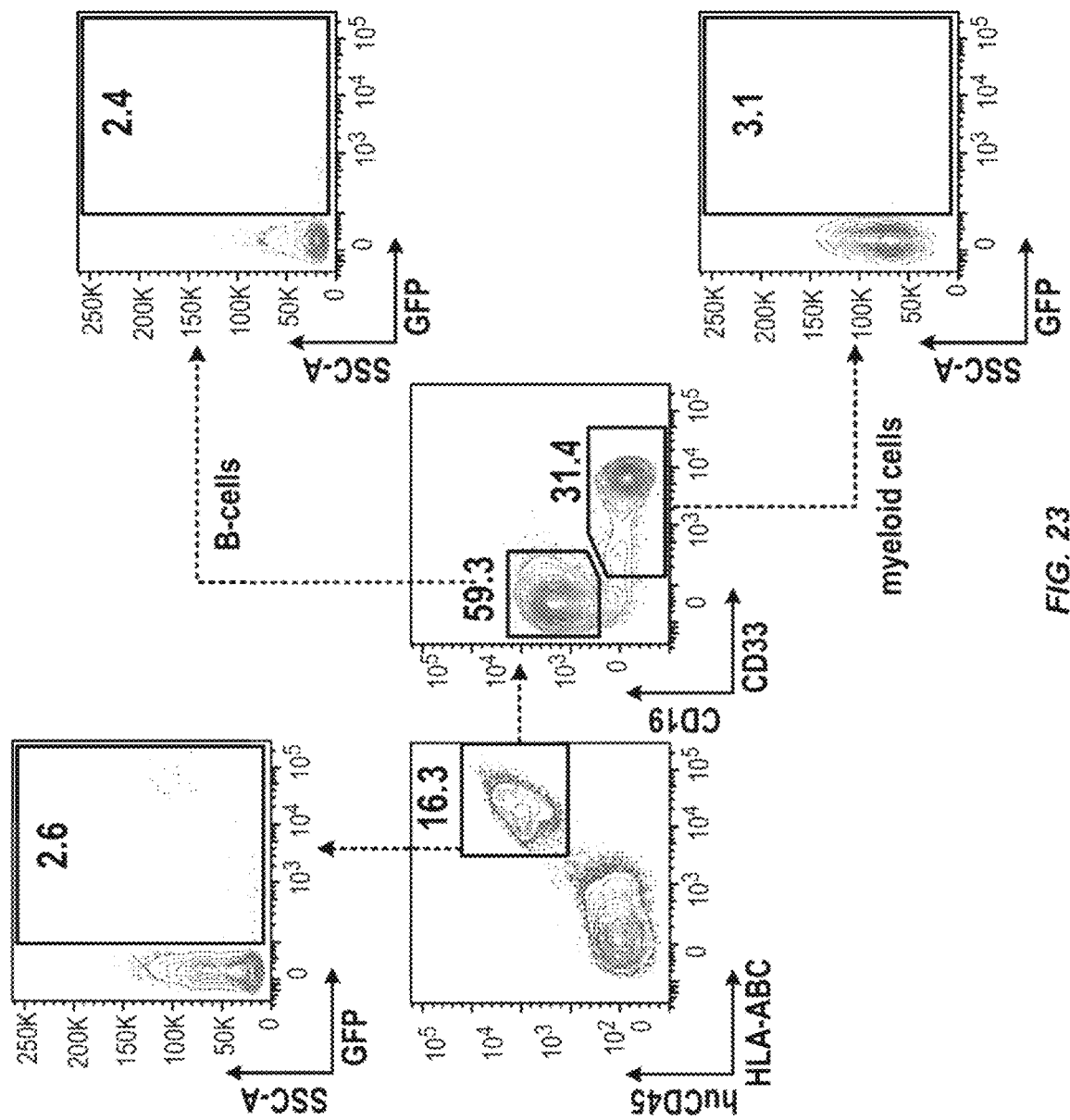
FIG. 23 provides a representative gating scheme for the analysis of human engraftment in FIG. 3G. At week 16 post-transplantation of genome-edited HSPCs, NSG mice were sacrificed, and bone marrow was harvested from femur, tibia, hips, humerus, sternum, and vertebrae. Cells were subject to Ficoll density gradient to isolate mononuclear cells, which were analyzed for human engraftment by flow cytometry. Human engraftment was delineated as huCD45/HLA-ABC double positive. B cells were marked by CD19 expression, and myeloid cells identified by CD33 expression. GFP expression was analyzed in total human cells (2.6%) B-cells (2.4%) and myeloid cells (3.1%). Representative FACS gating scheme is from one mouse from the RNP experimental group.
Figure 25A:
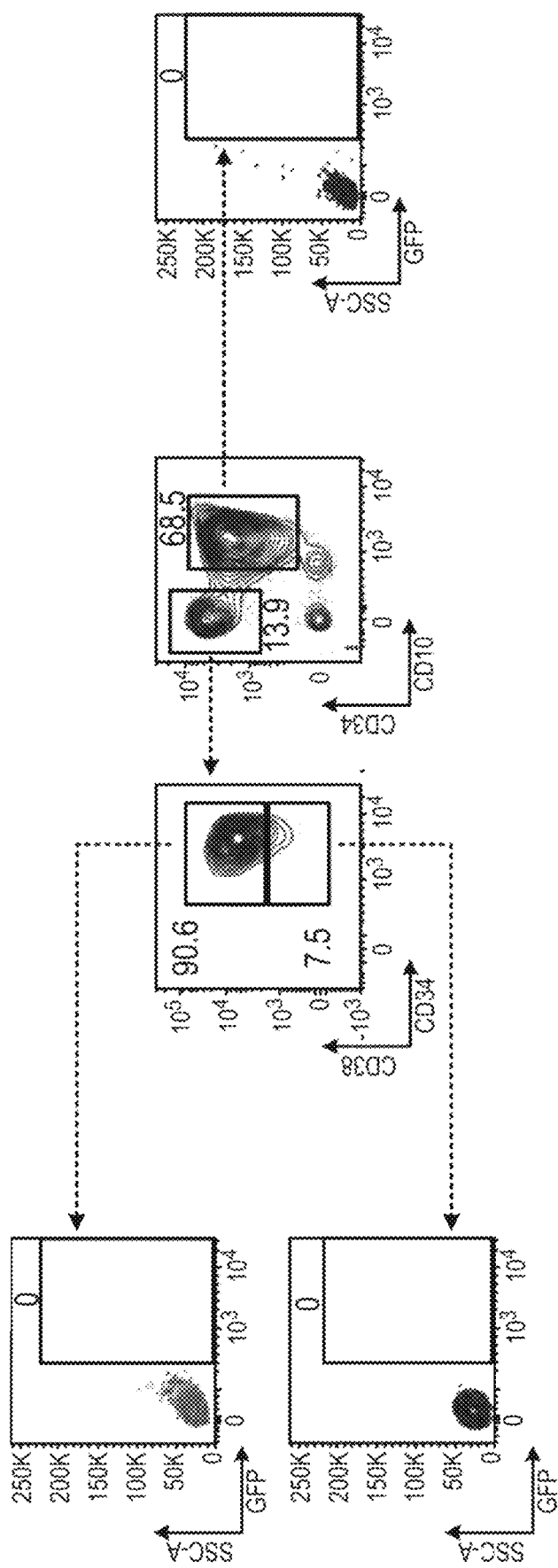
FIGS. 25A-25C show the presence of genome-edited human HSPCs in the bone marrow of NSG at week 16 post-transplantation. Representative FACS plots from the analysis of NSG mice from the Mock (FIG. 25A) or RNP experimental group at week 16 post-transplantation (FIG. 25B). Mice were sacrificed and bone marrow was harvested, PBMCs were isolated via Ficoll density gradient, after which human CD34+ cells were enriched by magnetic-activated cell sorting (MACS), and finally cells were stained with anti-CD34, anti-CD38, and anti-CD10 antibodies to identify human GFP$^+$ cells in the CD34+/CD10$^-$ and CD34+/CD10$^-$/CD38$^-$ populations (note that CD10 was included as a negative discriminator for immature B cells). Collective data from the analysis of GFP+ cells in the human CD34+/CD10$^-$ population from the RNP (N=11) and RNP GFP$^{high}$ (N=6) experimental groups (FIG. 25C). For the RNP GFP$^{high}$ group, cells from all six mice were pooled before analysis and thus, no error bar is available. Error bar on RNP group represents S.E.M.
Figure 25B:
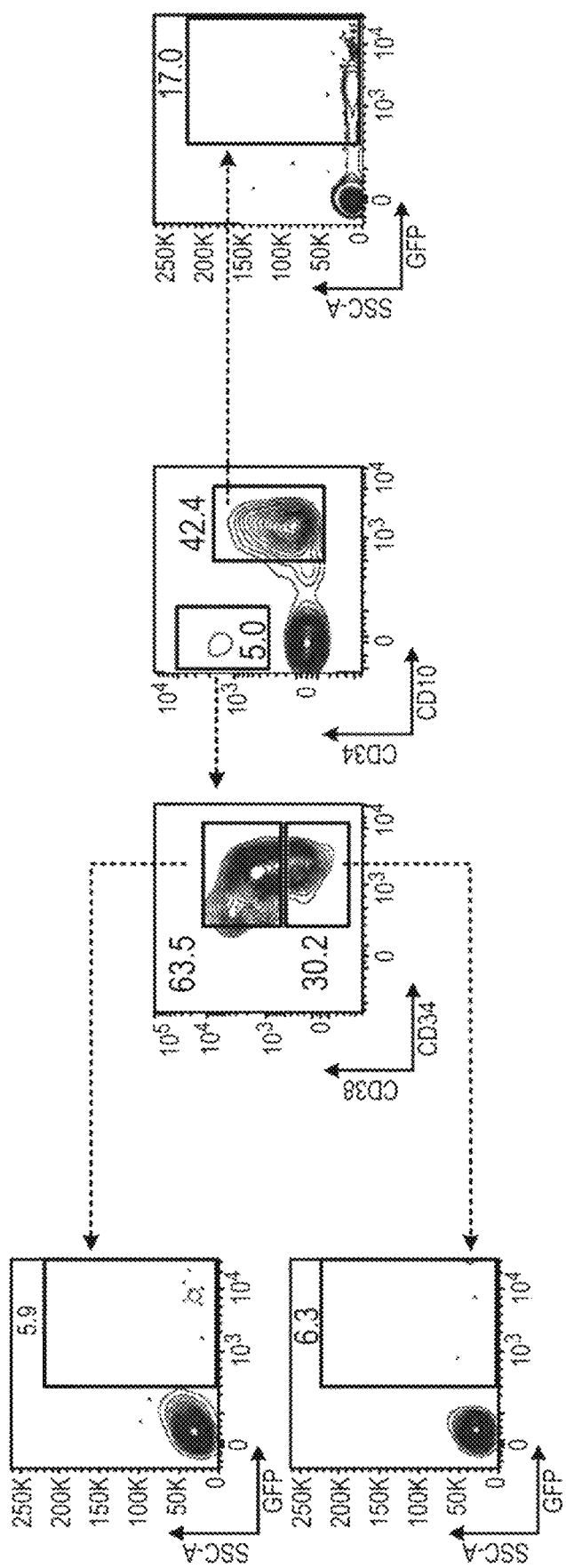
Figure 25C:
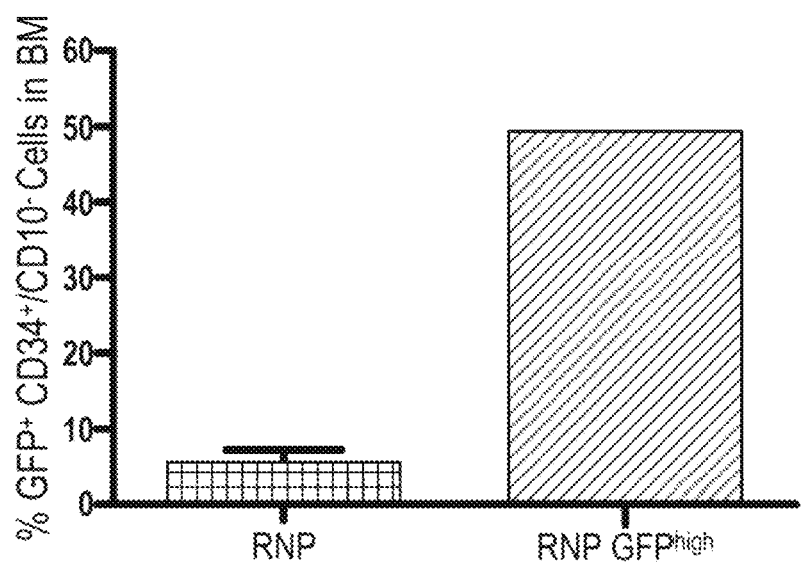

While immunophenotypic analyses of stem cell-associated surface markers can shed light on targeting efficiencies in primitive cells, the current gold standard for true HSC function, defined by the capacity to self-renew and form differentiated blood cells, is in vivo engraftment into immunocompromised non-obese diabetic (NOD)-SCID-gamma (NSG) mice. $CD34^+$ HSPCs derived from mobilized peripheral blood (mPB) were used for these studies because of their high clinical relevance, although these cells have been shown to have reduced engraftment capacity in NSG mice compared to HSPCs derived from fetal liver, cord blood, and bone marrow (Wang et al., supra; Gu et al., Human gene therapy methods 25, 221-231 (2014)). HSPCs from the following experimental groups targeting HBB were transplanted into each irradiated mouse by tail vein injection: (1) Mock electroporated, (2) rAAV6 only, (3) mRNA+rAAV6, (4) RNP+rAAV6, (5) RNP+rAAV6 $GFP^{neg}$ (to control for sorting), and (6) RNP+rAAV6 $GFP^{high}$. All mice displayed human engraftment in the bone marrow as measured by the presence of hCD45/HLA-ABC double positive cells 16 weeks post-transplant (FIGS. 3E and 23). While a decrease in chimerism was observed for all treatment groups compared to Mock, all groups with nuclease-treated cells displayed similar chimerism to the rAAV6 only group. A small, but not statistically significant, decrease was measured for the RNP $GFP^{high}$ group compared to RNP, which can be explained partially by transplantation of fewer total cells (FIG. 24), and partially by the presence of fewer HSCs in the enriched $GFP^+$ population compared to the bulk RNP-treated population (FIG. 24). There was a significant decrease from RNP input targeting frequencies (about 16% in the $CD34^+$ mPB HSPCs, FIG. 3C) compared to output rates in the bone marrow (BM) at week 16 (3.5%) (FIG. 3F). This decrease is consistent with previous publications and immunophenotyping of input cells that showed an average of 4% targeting in the $CD34^+/CD38^-/CD90^+/CD45RA^-$ population (FIG. 3C). In contrast, mice transplanted with RNP $GFP^{high}$ cells had an average of 79% $GFP^+$ human cells at week 16 after transplant, with three mice showing greater than 97% $GFP^+$ human cells (FIGS. 3E and 3G). Importantly, both myeloid ($CD33^+$) and lymphoid ($CD19^+$) reconstitution was observed with an average of 91% and 65% $GFP^+$ cells, respectively (FIG. 3G). 5% and 49% $GFP^+$ human HSPCs were also detected in the BM of mice transplanted with RNP and RNP $GFP^{high}$ cells, respectively (FIGS. 25A-25C). Collectively, these data show that the RNP $GFP^{high}$ fraction contains edited human HSCs that give rise to multipotent progenitors, and finally edited terminally differentiated blood cells.

By combining rAAV6 donor delivery with the CRISPR/Cas9 system and FACS, it has been demonstrated that it is feasible to generate and enrich a highly purified population of gene-targeted HSPCs that maintains long-term repopulation potential in NSG mice. The CRISPR/Cas9 system allows for simple engineering of simultaneous multigenic DSBs, and this feature was used to enrich cells that had undergone multigenic HR as well. More importantly, HSPCs progressively lose stemness as culture time increases, but the methods outlined above allow for robust enrichment of genome edited HSCs early in the culturing process (by day 4 post-electroporation). It is possible that the identification of targeted HSCs can be done at least a day earlier as well (data not shown).

While studies of human HSC biology have mainly been facilitated by the use of lentiviral-based transgene expression or shRNA expression for gene knockdown, these results show that genome editing using CRISPR/Cas9 RNP electroporation and rAAV6 transduction can now be added to the research toolbox for these cells. The presented approach has several advantages over lentiviral-based approaches for studying gene-function in HSPCs because it allows for 1) precise modifications to the gene-of-interest, 2) early enrichment of gene-targeted populations, 3) early purification of biallelic gene knock-in and/or knock-out populations, 4) fluorescent protein-based hematopoietic cell lineage tracing, and 5) enrichment of multigenic HR to study gene-gene-function relationships. Furthermore, this methodology has the potential to advance the biological understandings of gene function in quintessential HSC activities, like self-renewal and differentiation, which may improve HSC-based therapies.

The data presented here show that true HSCs are more resistant to targeted integration by HR than the bulk $CD34^+$ stem and progenitor population regardless of source, confirming previously published results (Hubbard et al., Blood 127:2513-2522 (2016)). Consequently, enrichment of targeted cells resulted in the removal of the majority of HSCs, leading to an overall 8-fold decrease in the total number of HSCs in the transplanted enriched population (FIG. 24). Even though 8-fold fewer total HSCs were transplanted from the enriched population compared to the non-enriched ($GFP^{high}$ vs. RNP), it was found that there was still an average of 5-fold more total edited cells in the mice from the enriched group 16 weeks post-transplant in the bone marrow of the mice (FIG. 24). Hence, the enrichment strategy described herein not only yields strikingly higher relative percentage of modified cells in the transplanted mice, but the absolute number of modified human cells in the mice was also higher, which suggests that the enrichment methods described herein have the potential to overcome the problem of inefficient HSC targeting. Moreover, recent advances in ex vivo HSC expansion protocols and identification of small molecule drugs, like UM171 (Fares et al., Science 345, 1509-1512 (2014)) that expands HSCs, might be combined with the methods described herein to generate a large and highly enriched population of genome-edited HSCs.

The methods described in this example require a reporter gene to be inserted into the genome. While GFP is unsuitable for enriching targeted HSPCs for gene therapy because of its immunogenicity in humans, enrichment of $tNGFR^{high}$ HSPCs (or other such similar signaling-inert cell surface marker), by either FACS or magnetic beads, represents an ideal putative enrichment strategy for the next generation of homologous recombination-based cell and gene therapies.

In summary, this example shows that by combining CRISPR/Cas9 RNP delivery with rAAV6 transduction in human HSPCs high frequencies of HR-mediated editing can be achieved, that the process is efficient enough to achieve high frequencies of multiplexed HR editing, that modified cells can be identified and enriched for early in the manufacturing process, and that the modified cells can reconstitute multi-lineage hematopoiesis after transplantation into immunodeficient mice. The methods described herein and these key features form the strong foundation for not only enabling sophisticated genetic studies of HSC biology but also comprise an approach to definitively curing patients, such as those who have sickle cell disease, using HSPCs that have been precisely edited by homologous recombination using the CRISPR/Cas9 system.

Materials and Methods
AAV Vector Production
AAV vector plasmids were cloned in the pAAV-MCS plasmid (Agilent Technologies, Santa Clara, Calif.) containing ITRs from AAV serotype 2. IL2RG (SEQ ID NO:40) and HBB (SEQ ID NO:38) vectors contained promoter, TurboGFP, and BGH polyA. CCR5 donors (SEQ ID NO:39) contained promoter, Citrine, and BGH polyA. For simplicity and because they were analyzed with same laser/filter during flow cytometry, TurboGFP and Citrine are referred to as GFP throughout. The CCR5 donor used with TALENs was identical to the donor used for CRISPR/Cas9, except the homology arms were changed to flank the TALEN cut site. AAV6 vectors were produced as described with a few modifications (Khan et al., Nature Protocols 6, 482-501 (2011)). Briefly, 293FT cells (Life Technologies, Carlsbad, Calif., USA) were seeded at $13 \times 10^6$ cells per dish in ten 15-cm dishes one day before transfection. One 15-cm dish was transfected using standard PEI transfection with 6 µg ITR-containing plasmid and 22 µg pDGM6 (a kind gift from David Russell, University of Washington, Seattle, Wash., USA), which contains the AAV6 cap genes, AAV2 rep genes, and adenovirus helper genes. Cells were incubated for 72 hours until harvest of AAV6 from cells by three freeze-thaw cycles followed by a 45 min incubation with TurboNuclease at 250 U/mL (Abnova, Heidelberg, Germany). AAV vectors were purified on an iodixanol density gradient by ultracentrifugation at 48,000 rpm for 2 h at 18° C. AAV vectors were extracted at the 60-40% iodixanol interface and dialyzed three times in PBS with 5% sorbitol in the last dialysis using a 10K MWCO Slide-A-Lyzer G2 Dialysis Cassette (Thermo Fisher Scientific, Santa Clara, Calif., USA). Vectors were added pluronic acid to a final concentration of 0.001%, aliquoted, and stored at −80° C. until use. AAV6 vectors were tittered using quantitative PCR to measure number of vector genomes as described here (Aurnhammer et al., Human gene therapy methods 23, 18-28 (2012)).

CD34+ Hematopoetic Stem and Progenitor Cells
Frozen CD34+ HSPCs derived from bone marrow or mobilized peripheral blood were purchased from AllCells (Alameda, Calif., USA) and thawed according to manufacturer's instructions. $CD34^+$ HSPCs from cord blood were either purchased frozen from AllCells or acquired from donors under informed consent via the Binns Program for Cord Blood Research at Stanford University and used without freezing. $CD34^+$ HSPCs were cultured in StemSpan SFEM II (Stemcell Technologies, Vancouver, Canada) supplemented with SCF (100 ng/ml), TPO (100 ng/ml), Flt3-Ligand (100 ng/ml), IL-6 (100 ng/ml), and StemRegenin1 (0.75 mM). When indicated, UM171 (Stemcell Technologies) was added to the media at a final concentration of 35 nM. Cells were cultured at 37° C., 5% $CO_2$, and 5% $O_2$.

T Cell Isolation and Culturing
Primary human $CD3^+$ T cells were isolated from buffy coats obtained from the Stanford School of Medicine Blood Center using a human T Cell Isolation Kit (Miltenyi Biotec, San Diego, Calif., USA) according to manufacturer's instructions. CD3+ T cells were cultured in X-VIVO 15 (Lonza, Walkersville, Md., USA) containing 5% human serum (Sigma-Aldrich, St. Louis, Mo., USA), 10 ng/ml human rIL-7 (BD Biosciences, San Jose, Calif., USA), and 100 IU/ml human rIL-2 (Peprotech, Rocky Hill, N.J., USA). T cells were activated directly after isolation with immobilized anti-CD3 antibody (clone: OKT3, Tonbo Biosciences, San Diego, Calif., USA) and soluble anti-CD28 antibody (clone: CD28.2, Tonbo Biosciences) for three days. Unstimulated T cells were cultured in X-VIVO 15 (Lonza, Walkersville, Md., USA) with 5% human serum and 10 ng/ml human rIL-7. T cells were cultured at 37° C., 5% $CO_2$, and ambient oxygen levels.

Electroporation and Transduction of Cells

All synthetic sgRNAs were purchased from TriLink Bio-Technologies (San Diego, Calif., USA). sgRNAs were chemically modified with three terminal nucleotides at both the 5' and 3' ends containing 2'O-Methyl 3'phosphorothioate and HPLC-purified. The genomic sgRNA target sequences with PAM in bold) were: HBB: 5'-CTTGCCC-CACAGGGCAGTAACGG-3', SEQ ID NO:42; CCR5: 5'-GCAGCATAGTGAGCCCAGAAGGG-3', SEQ ID NO:43; IL2RG: 5'-TGGTAATGATGGCTTCAACATGG-3', SEQ ID NO:44. An alternative for CCR5 is 5'-GGCAG-CATAGTGAGCCCAGAAGG-3', SEQ ID NO:35.

Cas9 mRNA containing 5-methylcytidine and pseudouridine was purchased from TriLink BioTechnologies. Cas9 protein was purchased from Life Technologies. Cas9 RNP was made by incubating protein with sgRNA at a molar ratio of 1:2.5 at 25° C. for 10 min immediately prior to electroporation.

CD34+ HSPCs were electroporated 1-2 days after thawing or isolation. T cells were electroporated either three days following activation or 2 hours after isolation (unstimulated T cells). Both CD34+ HSPCs and T cells were electroporated using the Lonza Nucleofector 2b (program U-014) and the Human T Cell Nucleofection Kit (VPA-1002, Lonza) with the following conditions: $5 \times 10^6$ cells/ml, 300 ug/ml Cas9 protein complexed with sgRNA at 1:2.5 molar ratio, or 100 μg/ml synthetic chemically modified sgRNA with 150 μg/ml Cas9 mRNA (TriLink BioTechnologies). Following electroporation, cells were incubated for 15 min at 37° C. after which they were added AAV6 donor vectors (generally at an MOI of 100,000 unless otherwise specified), incubated at 30° C. for 24 hours, then finally transferred back to 37° C. For experiment targeting both HBB and CCR5, half the amounts of RNP and AAV was used for each locus.

Measuring Targeted Integration of Fluorescent and tNGFR Donors

Rates of targeted integration of fluorescent and tNGFR donors was measured by flow cytometry at least 18 days after electroporation. Targeted integration of an tNGFR expression cassette was measured by flow cytometry of cells stained with APC-conjugated anti-human CD271 (NGFR) antibody (clone: ME20.4, BioLegend, San Diego, Calif.). For sorting of $GFP^{high}$, $GFP^{high}$/$mCherry^{high}$, $GFP^{high}$/$tdTomato^{high}$, or $tNGFR^{high}$ populations, cells were sorted on a FACS Aria II SORP using the LIVE/DEAD Fixable Blue Dead Cell Stain Kit (Life Technologies) to discriminate live and dead cells according to manufacturer's instructions.

Immunophenotyping of Targeted Cells

Harvested wells were stained with LIVE/DEAD Fixable Blue Dead Cell Stain (Life Technologies) and then with anti-human CD34 PE-Cy7 (581, BioLegend), CD38 Alexa Fluor 647 (AT1, Santa Cruz Biotechnologies, Santa Cruz, Calif., USA), CD45RA BV 421 (HI100, BD Biosciences), and CD90 BV605 (5E10, BioLegend) and analyzed by flow cytometry. For sorting of $CD34^+$ or $CD34^+/CD38^-/CD90^+$ cells, CB-derived CD34+ HSPCs were stained directly after isolation from blood with anti-human CD34 FITC (8G12, BD Biosciences), CD90 PE (5E10, BD Biosciences), CD38 APC (HIT2, BD Bioscience), and cells were sorted on a FACS Aria II (BD Bioscience), cultured overnight, and then electroporated with HBB RNP and transduced with HBB GFP rAAV6 using optimized parameters.

Measuring Targeted Integration of the E6V Donor

For assessing the allele modification frequencies and spectrum of HR events in samples with targeted integration of an RFLP donor, PCR amplicons spanning the targeted region were created using one primer outside the donor homology arm and one inside, for example, HBB_outside: 5'-GGTGACAATTTCTGCCAATCAGG-3', SEQ ID NO:45 and HBB_inside: 5'-GAATGGTAGCTGGAT-TGTAGCTGC-3', SEQ ID NO:46. The PCR product was gel-purified and re-amplified using a nested primer set (HBB_nested_fw: 5'-GAAGATATGCTTAGAACCGAGG-3', SEQ ID NO:16 and HBB_nested_rw: 5'-CCA-CATGCCCAGTTTCTATTGG-3', SEQ ID NO:17) to create a 685 bp PCR amplicon that was gel-purified and cloned into a TOPO plasmid using the Zero Blunt TOPO PCR Cloning Kit (Life Technologies) according to the manufacturer's protocol. TOPO reactions were transformed into XL-1 Blue competent cells, plated on kanamycin-containing agar plates, and single colonies were sequenced by McLab (South San Francisco, Calif., USA) by rolling circle amplification followed by sequencing using the following primer: 5'-GAAGATATGCTTAGAACCGAGG-3', SEQ ID NO:16.

Measuring INDEL Frequencies

INDEL frequencies were quantified using the TIDE software (Brinkman et al., Nucleic acids research 42, e168 (2014)) (Tracking of Indels by Decomposition) and sequenced PCR-products obtained by PCR of genomic DNA extracted at least four days following electroporation as previously described (Hendel et al., Nature biotechnology 33, 985-989 (2015)).

Methylcellulose Colony-Forming Unit (CFU) Assay

The CFU assay was performed by FACS sorting of single cells into 96-well plates containing MethoCult Optimum (Stemcell Technologies) four days after electroporation and transduction. After 12-16 days, colonies were counted and scored based on their morphological appearance in a blinded fashion.

Genotyping of Methylcellulose Colonies

DNA was extracted from colonies formed in methylcellulose from FACS sorting of single cells into 96-well plates. Briefly, PBS was added to wells with colonies, and the contents were mixed and transferred to a U-bottomed 96-well plate. Cells were pelleted by centrifugation at 300×g for five minutes followed by a wash with PBS. Finally, cells were resuspended in 25 μl QuickExtract DNA Extraction Solution (Epicentre, Madison, Wis., USA) and transferred to PCR plates, which were incubated at 65° C. for ten minutes followed by 100° C. for two minutes. Integrated or non-integrated alleles were detected by PCR.

For CCR5, a 3-primer PCR was set up with a forward primer binding in the left homology arm, a forward primer binding in the insert, and a reverse primer binding in CCR5 outside the right homology arm (FIG. 17B), for example, CCR5_inside_LHA: 5'-GCACAGGGTGGAACAA-GATGG-3', SEQ ID NO:19; CCR5_insert: 5'-AAGGGG-GAGGATTGGGAAGAC-3', SEQ ID NO:20; CCR5_outside_RHA: 5'-TCAAGAATCAGCAATTCTCT-GAGGC-3', SEQ ID NO:21.

For HBB and IL2RG, two different PCRs were set up to detect integrated (one primer in insert and one primer outside right homology arm) and non-integrated (primer in each homology arm) alleles, respectively (FIGS. 17A and 17C), for example, HBB_int_fw: 5'-GTACCAGCACGCCTTCAAGACC-3', SEQ ID NO:18; HBB_int_rv: 5'-GATCCTGAGACTTCCACACTGATGC-3', SEQ ID NO:23; HBB_no_int_fw: 5'-GAAGATATGCT-TAGAACCGAGG-3', SEQ ID NO:16; HBB_no_int_rv: 5'-CCACATGCCCAGTTTCTATTGG-3', SEQ ID NO:17;

IL2RG_int_fw: 5'-GTACCAGCACGCCTTCAAGACC-3', SEQ ID NO:18; IL2RG_int_rv: 5'-CAGATATCCAGAGCCTAGCCTCATC-3', SEQ ID NO:27; IL2RG_no_int_fw: 5'-TCACACAGCACATATTTGCCACACCCTCTG-3', SEQ ID NO:28; and IL2RG_no_int_rv: 5'-TGCCCACATGATTGTAATGGCCAGTGG-3', SEQ ID NO:29.

For detecting dual integration of GFP and tdTomato into two HBB alleles, a primer in HBB outside the right homology arm was used together with either a GFP or tdTomato-specific primer, for example, HBB_outside_RHA: 5'-GATCCTGAGACTTCCACACTGATGC-3', SEQ ID NO:23; GFP: 5'-GTACCAGCACGCCTTCAAGACC-3', SEQ ID NO:18; and tdTomato: 5'-CGG-CATGGACGAGCTGTACAAG-3', SEQ ID NO:32. Clones with dual GFP (HBB)/mCherry (CCR5) integrations were screened for integrations using the same primer sets as above.

Transplantation of CD34+ HSPCs into NSG Mice

For in vivo studies, 6 to 8 week-old NOD scid gamma (NSG) mice were purchased from the Jackson laboratory (Bar Harbor, Me. USA). The experimental protocol was approved by Stanford University's Administrative Panel on Lab Animal Care. Sample sizes were not chosen to ensure adequate power to detect a pre-specified effect size. Four days after electroporation/transduction or directly after sorting, 500,000 cells (or 100,000-500,000 cells for the GFP$^{high}$ group) were administered by tail-vein injection into the mice after sub-lethal irradiation (200 cGy) using an insulin Syringe with a 27 gauge×½" needle. Mice were randomly assigned to each experimental group and evaluated in a blinded fashion.

Assessment of Human Engraftment

At week 16 post-transplantation mice were sacrificed, total mouse bone marrow (BM) (2× femur, 2× tibia, 2× humerus, sternum, 2× pelvis, spine) was collected and crushed using mortar and pestle. Mononuclear cells (MNCs) were enriched using Ficoll gradient centrifugation (Ficoll-Paque Plus, GE Healthcare, Sunnyvale, Calif., USA) for 25 minutes at 2,000×g, room temperature. Cells were blocked for nonspecific antibody binding (10% vol/vol, TruStain FcX, BioLegend) and stained (30 minutes, 4° C., dark) with monoclonal anti-human CD45 V450 (HI30, BD Biosciences), CD19 APC (HIB19, BD Biosciences), CD33 PE (WM53, BD Biosciences), HLA-ABC APC-Cy7 (W6/32, BioLegend), anti-mouse CD45.1 PE-Cy7 (A20, eBioScience, San Diego, Calif., USA), anti-mouse PE-Cy5 mTer119 (TER-119, eBioscience) antibodies. Normal multi-lineage engraftment was defined by the presence of myeloid cells (CD33$^+$) and B-cells (CD19$^+$) within engrafted human CD45$^+$/HLA-ABC$^+$ cells. Parts of the mouse BM were used for CD34-enrichment (MACS CD34 MicroBead Kit Ultra-Pure, human, Miltenyi Biotec) and the presence of human hematopoietic stem and progenitor cells (HSPCs) was assessed by staining with anti-human CD34 APC (8G12, BD Biosciences), CD38 PE-Cy7 (HB7, BD Biosciences), CD10 APC-Cy7 (HI10a, BioLegend), and anti-mouse CD45.1 PE-Cy5 (A20, eBioScience) and analyzed by flow cytometry. The estimation of the total number of modified human cells in the bone marrow (BM) at week 16 post-transplant was calculated by multiplying percent engraftment with percent GFP+ cells among engrafted cells. This number was multiplied by the total number of MNCs in the BM of a NSG mouse (1.1×10$^8$ per mouse) to give the total number of GFP$^+$ human cells in the total BM of the transplanted mice. The total number of MNCs in the BM of a NSG mouse was calculated by counting the total number of MNCs in one femur in four NSG mice. The total number of MNCs in one mouse was then calculated assuming one femur is 6.1% of the total marrow as found in Boggs, D. R. *American Journal of Hematology* 16, 277-286 (1984).

Example 2. Beta-globin Gene Targeting in Human Hematopoietic Stem Cells Using Cas9 Ribonucleoprotein and rAAV6

The β-hemoglobinopathies including sickle cell disease (SCD) and β-thalassemia (β-thal) affect millions of people worldwide[1]. SCD and β-thal are caused by mutations in the β-globin gene (HBB) resulting in either abnormal sickling or severely reduced protein production, respectively. A curative strategy for the β-hemoglobinopathies would be ex vivo HBB gene correction in patient-derived hematopoietic stem and progenitor cells (HSPCs) followed by autologous hematopoietic stem cell transplantation (auto-HSCT). This example describes the first CRISPR/Cas9 gene-editing platform for achieving homologous recombination (HR) at the HBB gene in long-term repopulating HSCs (LT-HSCs) derived from mobilized peripheral blood. In this example, electroporation of Cas9 protein complexed with chemically modified sgRNAs was combined with delivery of a HR donor by recombinant adeno-associated viral vectors, serotype 6 (rAAV6). Notably, by including a reporter gene in the HR donor, it was possible to identify and purify a population of HSPCs with greater than 90% of the cells having targeted integration at the HBB gene. These cells could be identified because HR-mediated integration causes the reporter gene to be expressed at log-fold higher levels than the non-integrated reporter. When transplanted into immunodeficient mice, the purified population gave rise to engraftment of HBB-edited human cells in primary and secondary recipients, confirming the presence of LT-HSCs. Importantly, this example shows efficient correction of the SCD-causing E6V mutation in SCD patient-derived CD34$^+$ HSPCs by either editing the nucleotide mutation or knocking in an anti-sickling β-globin cDNA. Edited SCD CD34$^+$ cells were shown to express adult β-globin (HbA) mRNA after HSPCs were differentiated into erythrocytes in vitro, confirming intact transcriptional regulation of the edited HBB allele. Collectively, these preclinical studies outlined a CRISPR-based methodology for targeting HSCs by HR at the HBB locus to advance the development of next generation therapies for β-hemoglobinopathies.

The World Health Organization estimates that 300,000 children are born each year with a β-hemoglobinopathy. Allogeneic hematopoietic stem cell transplantation (allo-HSCT) is curative and highlights that transplantation of hematopoietic stem cells (HSCs) with only a single wild-type gene can cure both diseases[2]. Allo-HSCT is limited, however, because of toxicities associated with the procedure, including the risk of graft vs. host disease, and because of the inability to find immunologically matched donors. An alternative to using allogeneic HSCs to cure the β-hemoglobinopathies is to use homologous recombination (HR) to directly modify the HBB gene in the patient's own HSCs[3, 4].

The first step in potentially curing β-hemoglobinopathies using HR was described in 1985 when Smithies and colleagues were able to modify the human HBB gene by HR in a human embryonic carcinoma cell line, albeit at an extremely low frequency[5] (10$^{-6}$). The subsequent discoveries that a site-specific DNA double-strand break (DSB) could stimulate HR-mediated correction of a reporter gene and that engineered nucleases could be used to induce this DSB, formed the foundation of using HR-mediated genome editing using engineered nucleases to directly modify the HBB gene[6, 7]. More recently, TAL effector nucleases (TALENs) and zinc finger nucleases (ZFNs) have been utilized to modify the HBB gene by HR in both human cell lines and hematopoietic stem and progenitor cells (HSPCs)[8, 9]. The ease of engineering as well as the robust activity of the CRISPR/Cas9 RNA-guided endonuclease system makes it a promising tool to apply to the ongoing challenge of developing effective and safe HR-mediated genome editing to cure the β-hemoglobinopathies[10, 11]. In some embodiments, the CRISPR/Cas9 complex consists of the Cas9 endonuclease and a 100-nucleotide (nt) single guide RNA (sgRNA). For the Cas9 derived from *Streptococcus pyogenes*, target identification relies first on identification of a 3-base pair protospacer adjacent motif (PAM) and then RNA-DNA Watson-Crick hybridization between a 20-nucleotide stretch of the sgRNA and the DNA target site. After an allosteric change induced by sgRNA hybridization to the target DNA, Cas9 is triggered to cleave both DNA strands creating a blunt-end DSB[12]. DSB formation activates one of two highly conserved repair mechanisms, canonical non-homologous end-joining (NHEJ) and homologous recombination[13] (HR). Through iterative cycles of break and NHEJ repair, insertions and/or deletions (INDELs) can be created at the site of the break. In contrast, genome editing by HR requires the delivery of a DNA donor molecule to serve as a template, which the cellular HR machinery uses to repair the break by a 'copy and paste' method[14]. For gene editing purposes, the HR pathway can be exploited to make precise nucleotide changes in the genome. Using this strategy, disease-causing mutations can be replaced or entire open reading frames (ORFs) can be inserted at specific sites. One of the key features of precise genome editing, in contrast to viral vector-based gene transfer methods, is that endogenous promoters, regulatory elements, and enhancers can be preserved to mediate spatiotemporal gene expression[3, 8, 15, 16] While the CRISPR/Cas9 system is ineffective in stimulating genome editing when delivered as DNA expression plasmids in primary human blood cells, such as T cells and HSPCs, the system is highly effective when delivered as an all RNA or RNP system delivered by electroporation when the sgRNA is synthesized with chemical modifications to prevent exonuclease degradation".

Hematopoietic stem cells (HSCs) have the ability to repopulate an entire hematopoietic system[18], and several genetic[19-21] and acquired[22] diseases of the blood could potentially be cured by genome editing of HSCs. Recent studies have demonstrated efficient targeted integration in HSPCs by combining ZFN expression with exogenous HR donors delivered via single stranded oligonucleotides (ssODN)[9], integrase-defective lentiviral vectors (IDLV)[23], or recombinant adeno-associated viral vectors of serotype 6 (rAAV6)[24, 25]. In most of these studies, however, the high editing frequencies in vitro did not result in high frequencies of edited cells following transplantation into immunodeficient mice. Moreover, in some of these studies the HSPCs used were derived from fetal liver, which is a non-clinically relevant HSPC source compared to cells derived from bone marrow or mobilized peripheral blood. While De Ravin et al. (2016) showed 6-16% gene marking at the "safe harbor" AAVS1 site of human cells in the bone marrow of NSG mice transplanted with edited cells, secondary bone marrow transplants were not performed (the current standard to measure LT-HSC activity). Collectively, these studies suggest that targeting LT-HSCs by HR at disease-causing loci is difficult in clinically relevant HSPCs.

In this study, efficient in vitro HR-mediated editing frequencies was achieved at the HBB locus in CD34+ HSPCs derived from adult bone marrow (ABM), cord blood (CB), or mobilized peripheral blood (mPB) (the latter from both healthy donors and SCD patients (non-mobilized)) using Cas9 ribonucleoproteins (RNPs) combined with rAAV6 homologous donor delivery. In brief, this study demonstrated: 1) Cas9 and rAAV6-mediated HBB targeting in LT-HSCs characterized by the identification of modified human cells in secondary transplants of immunodeficient mice, 2) efficient correction of the SCD-causing E6V mutation in multiple SCD patient-derived HSPCs, and 3) development of a purification scheme using either FACS or magnetic bead enrichment to create HSPC populations in which greater than 85% of the cells have been modified by HR-mediated targeted integration. This purification can be performed early in the manufacturing process when LT-HSCs are still preserved, and may prove valuable in a clinical setting for removing untargeted HSPCs that will be in competition with HR-edited HSPCs for engraftment and re-population following transplantation.

Figure 26:
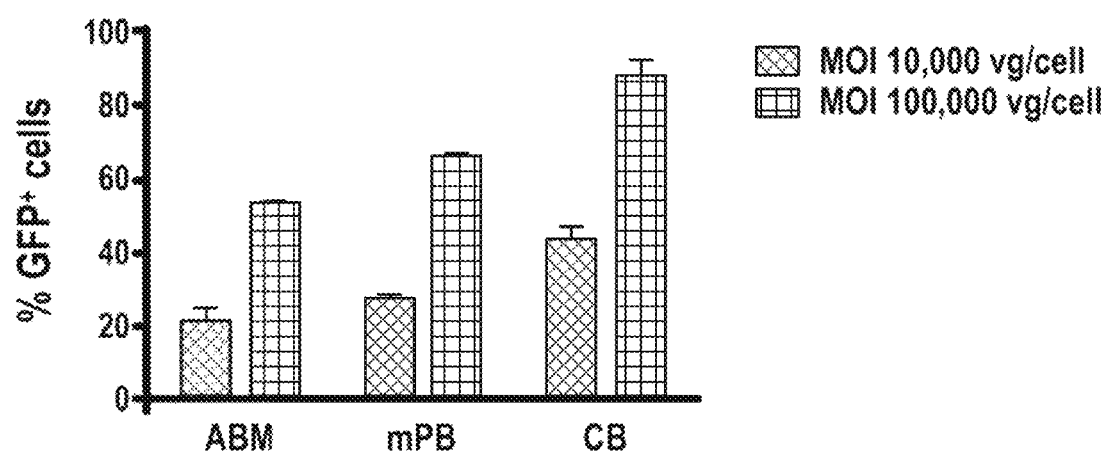
FIG. 26 shows high tropism of rAAV6 for CD34$^+$ HSPCs. CD34$^+$ HSPCs were transduced with a scAAV6 expressing GFP from an SFFV promoter at multiplicities of infections (MOIs) of 10,000 vg/cell or 100,000 vg/cell for 48 hrs and then analyzed for percent GFP expression by flow cytometry, using a non-transduced sample to set the GFP$^+$ gate at less than 0.1% GFP+ cells. scAAV was used because it eliminates second strand synthesis as a confounder of actual transduction. Results are from two independent experiments from at least two donors, and error bars represent S.D. ABM: Adult Bone Marrow; mPB: Mobilized Peripheral Blood; CB: Cord Blood.
Figure 27B:
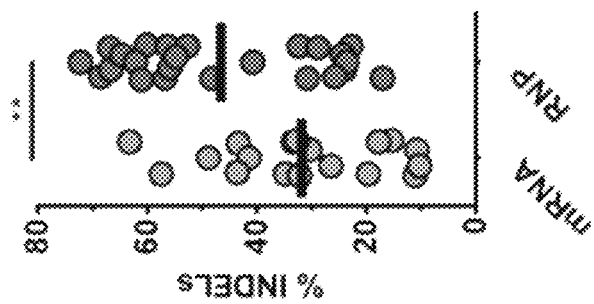
Figure 27A:
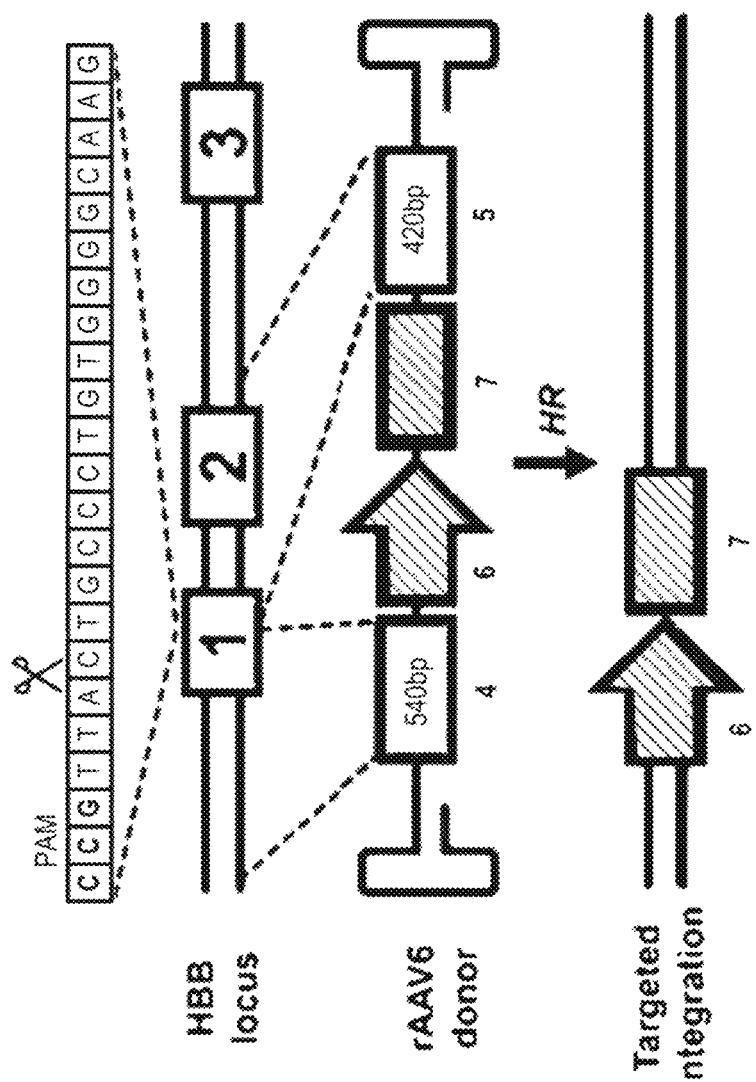
Figure 28A:
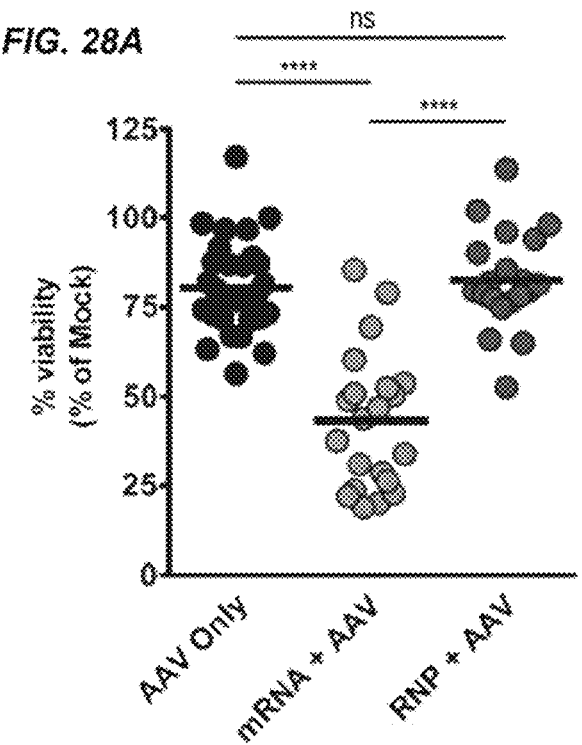
FIGS. 28A-28C show the increased toxicity and off-target activity using the "All RNA" CRISPR system compared to RNP delivery.
Figure 28B:
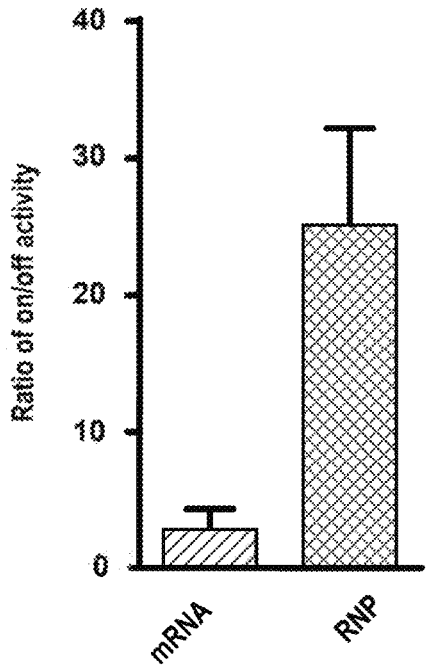
Figure 28C:
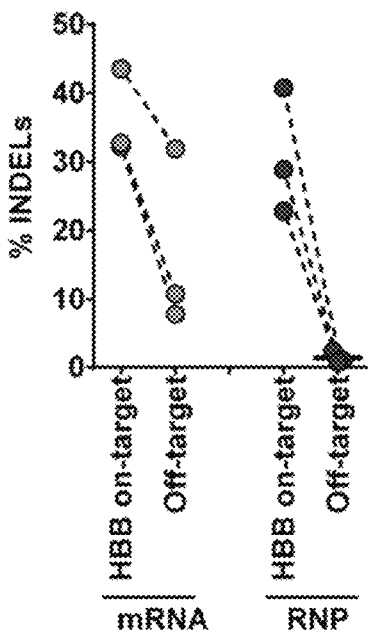

Transduction of HSPCs was confirmed using a self-complementary AAV6 (scAAV6) with an SFFV-GFP expression cassette[26] (FIG. 26). HBB-specific single-stranded AAV6 vectors (ssAAV6) were then produced that contained SFFV-GFP flanked by arms homologous to HBB (FIG. 27A). To achieve gene editing at HBB, two different CRISPR platforms were employed, which have previously been shown to be highly active in primary cells". Both platforms use sgRNAs chemically modified at both termini with 2' O-Methyl 3'phosphorothioate (MS sgRNA) and are either delivered in conjunction with Cas9 mRNA or as a ribonucleoprotein (RNP) complex, in which the sgRNA is complexed directly to Cas9 protein prior to delivery. Both platforms yielded high insertion/deletion (INDEL) frequencies when electroporated into HSPCs, with the RNP showing higher activity (FIG. 27B). By supplying the ssAAV6 HBB donor after electroporation of Cas9 RNP stable GFP expression was achieved in an average of 29% of HSPCs (FIG. 27C). Lower targeting efficiencies were observed using the mRNA CRISPR platform (15%) (FIG. 27C). Cytotoxicity and off-target cleavage activity (of a reported off-target site)[17] was significantly decreased using the RNP system (FIG. 28).

Figure 29A:
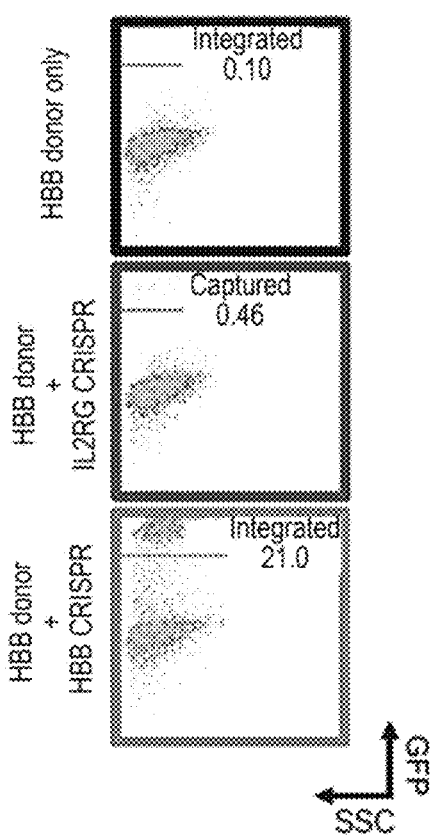
FIGS. 29A-29C show the capture of rAAV6 by mismatching donor and nuclease.
Figure 29B:
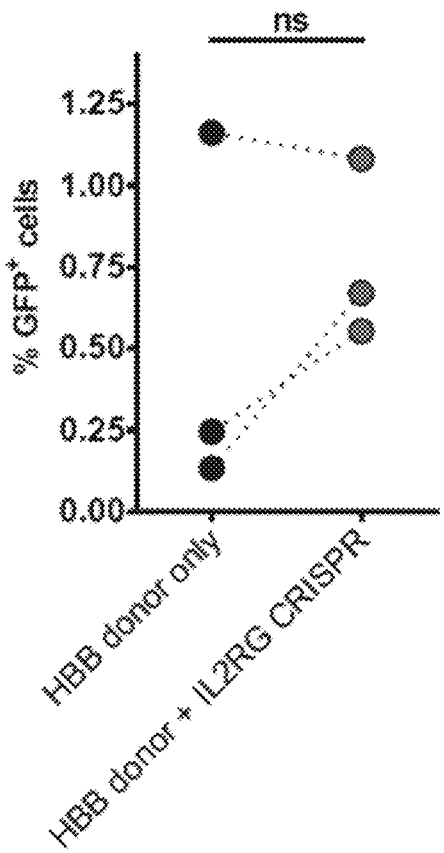
Figure 29C:
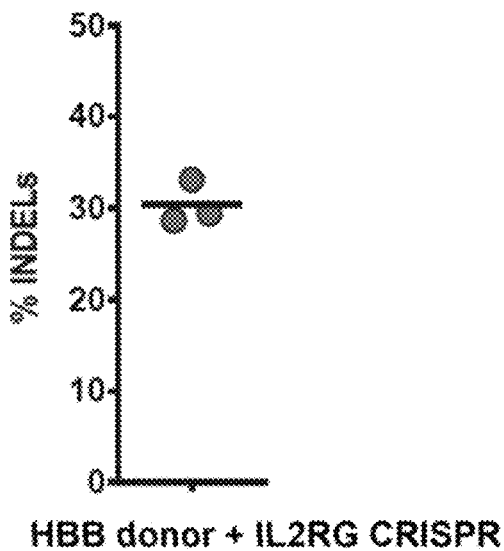

Because AAV genomes can be captured at the site of an off-target DSB via the NHEJ-mediated DSB repair pathway[24, 27, 28], experiments were performed wherein a nuclease was mismatched with a non-homologous donor to see if this occurs with the presently described methods. While about 20% of the cells that received matched HBB nuclease and HBB donor maintained GFP expression following 18 days in culture, IL2RG nuclease combined with HBB donor resulted in 0.8% GFP+ cells (FIG. 29), which was not significantly higher than the 0.5% GFP+ cells observed when using the HBB AAV donor alone. These results demonstrate that end-capture of the HBB donor is an infrequent event using this system in human HSPCs. Furthermore, the observed GFP expression in 0.5% of HSPCs with AAV donor alone suggests that random integration of rAAV6 is limited in human HSPCs. In fact, analysis of these GFP+ cells after AAV donor alone shows that they are the result of targeted integration without a double-strand break[29,30] and thus represent functional on-target events.

Figure 30C:
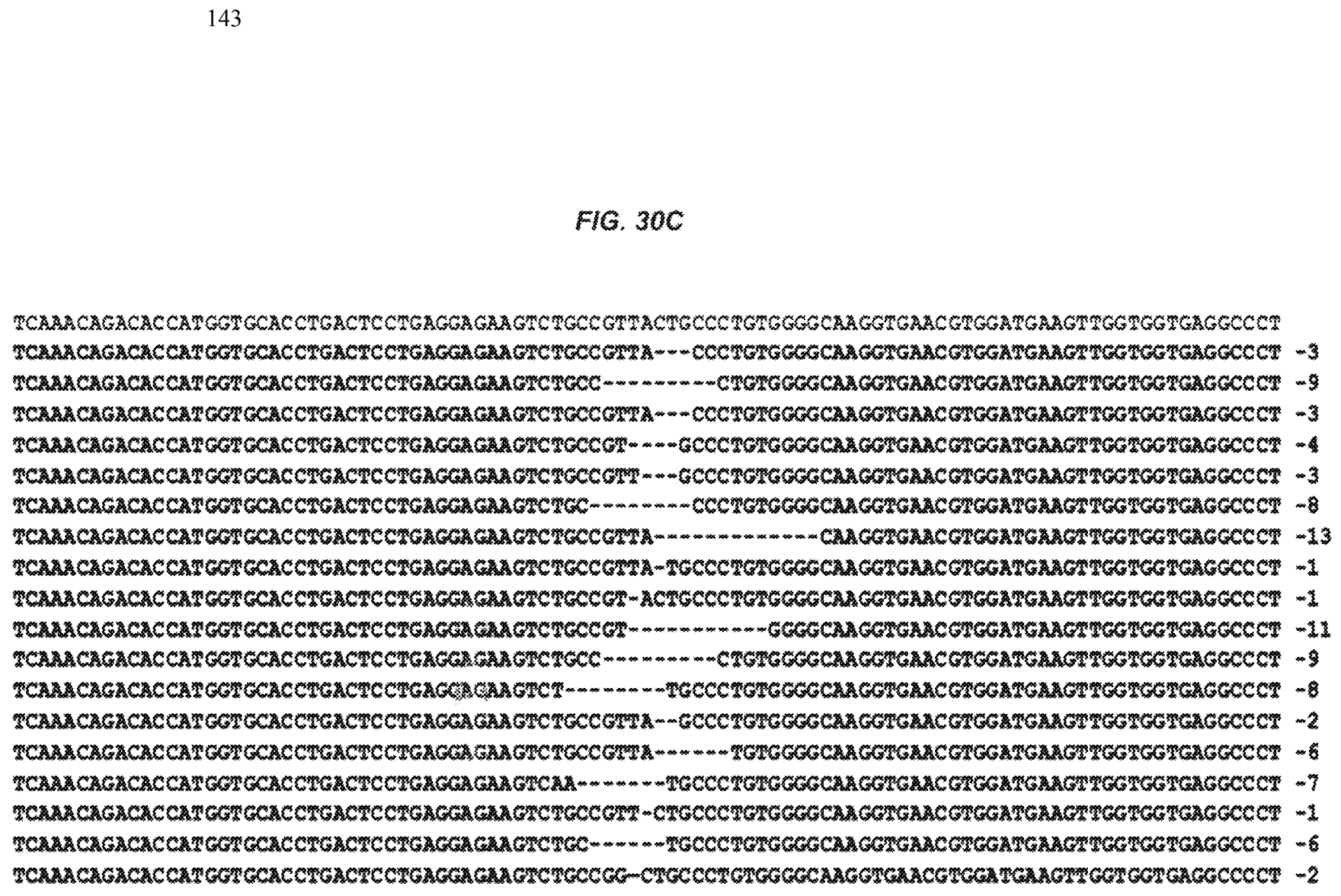

Sickle cell disease is caused by a single nucleotide mutation (adenine to thymine), which changes an amino acid from glutamic acid (E) to valine (V) at codon 6 of the HBB gene[31]. A 4.5 kb rAAV6 donor template was created that would introduce the E6V mutation along with six other silent SNPs. These additional SNPs, which change the CRISPR PAM site and the sgRNA target site, were introduced to prevent Cas9 from re-cutting the target site after HR and subsequently creating an HBB gene-disrupting INDEL that would inactivate the beneficial first HR event (FIG. 30). Using this rAAV6 donor with CRISPR RNP delivery an average allelic modification frequency of 19% was measured in six different HSPC donors (FIG. 27D). These results confirmed that the combined use of CRISPR with rAAV6 can precisely change the nucleotide at the position of the mutation that causes sickle cell disease. This frequency of HR-editing is clinically beneficial as chimerism studies in mouse and humans have shown that percentages of corrected HSPCs as low as 2% can lead to circulating RBCs being predominantly derived from this small percentage of wild-type HSPCs because of their survival advantage over sickle RBCs[32, 33].

Figure 31A:
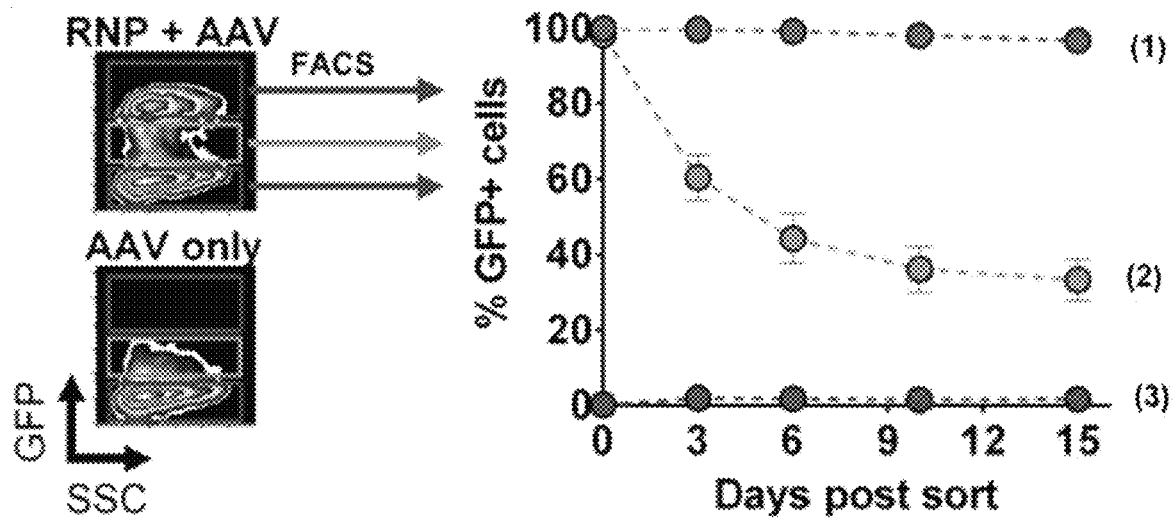
FIGS. 31A-31D show the enrichment of HBB-Targeted CD34+ HSPCs using FACS and magnetic bead-based technologies.
Figure 31B:
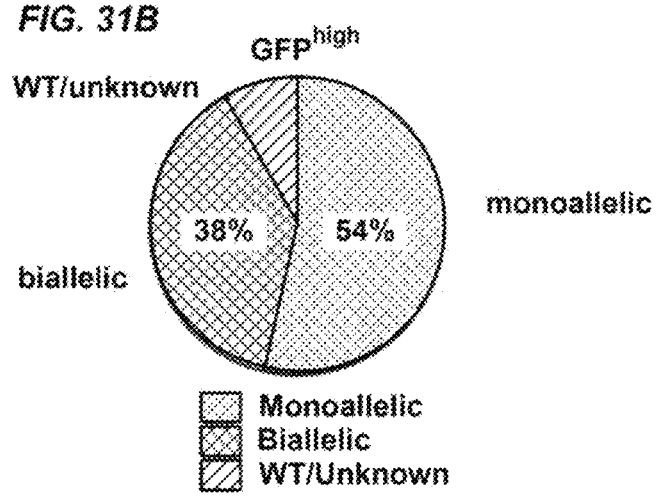
Figure 32:
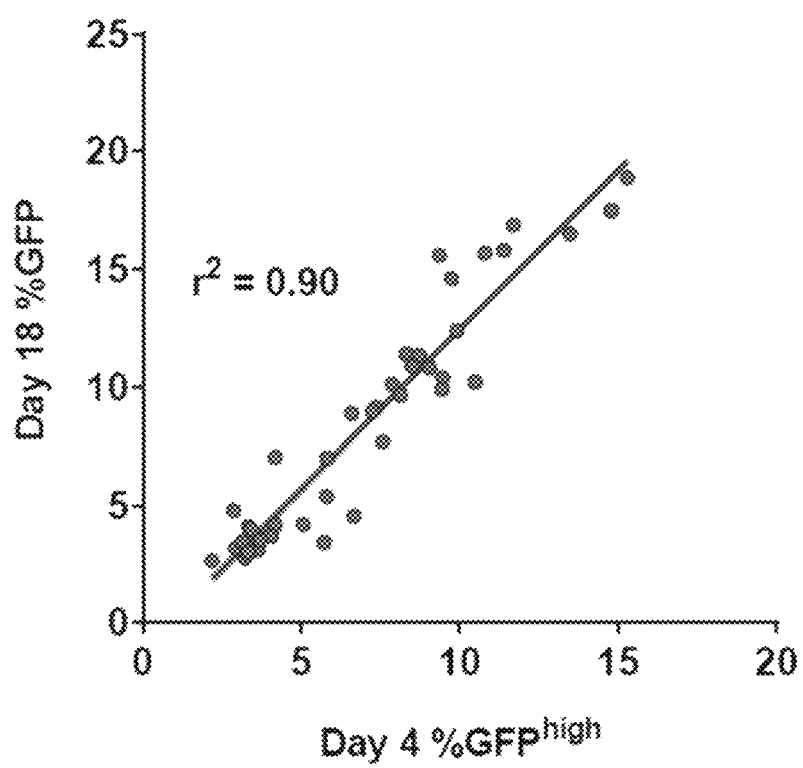
FIG. 32 shows a linear regression model illustrating that the day 4 GFP$^{high}$ population is a reliable predictor of targeting frequencies. Day 4 GFP$^{high}$ percentages (x-axis) were plotted against day 18 total GFP+ percentages (y-axis), and linear regression was performed. Data was generated from experiments including a total of 38 different CD34+ HSPC donors, treated with either 15 µg or 30 µg Cas9 RNP to generate data points with a wider distribution of targeting frequencies.

Since HSCs differentiate and progressively lose their long-term repopulating capacity upon culturing, the identification of gene-edited HSPCs early in the manufacturing process would be of great use to the HSC genome-editing field. Accordingly, in experiments using a GFP-expressing rAAV6 donor it was observed that while HSPCs receiving only rAAV6 donor expressed low levels of GFP, HSPCs that also received Cas9 RNP generated a population at day 4 post-electroporation that expressed much higher GFP levels (FIG. 31A, left panel). Since targeted cells at day 18 post-electroporation displayed the same high GFP expression it was hypothesized that this GFP$^{high}$ population was enriched for HBB-targeted cells. The GFP$^{high}$ population was therefore sorted and cultured, as well as the GFP$^{low}$ and GFP$^{neg}$ populations at day 4 post-electroporation. While sorted GFP$^{low}$ and GFP$^{neg}$ populations were respectively about 25% and about 1% GFP$^+$ after 15-20 days in culture, the GFP$^{high}$ population was greater than 95% GFP$^+$, strongly suggesting that this GFP$^{high}$ population was indeed HBB-targeted (FIG. 31B, right panel). In fact, linear regression showed that the percentage of GFP$^{high}$ expressing HSPCs at day 4 post-electroporation strongly correlates with the total percentage of GFP$^+$ cells at day 18 (FIG. 32).

Figure 33A:
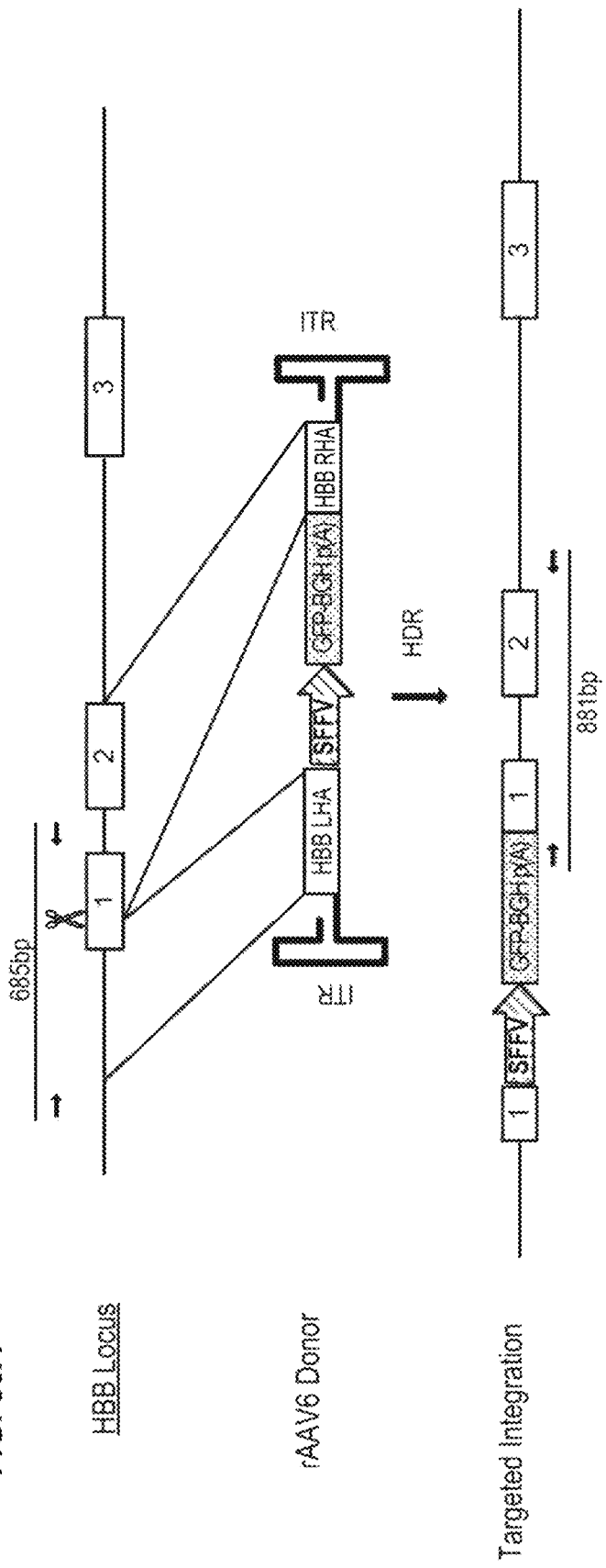
FIGS. 33A-33C provide an overview of PCR genotyping of methylcellulose colonies with HR of the GFP donor at the HBB locus.
Figure 33B:
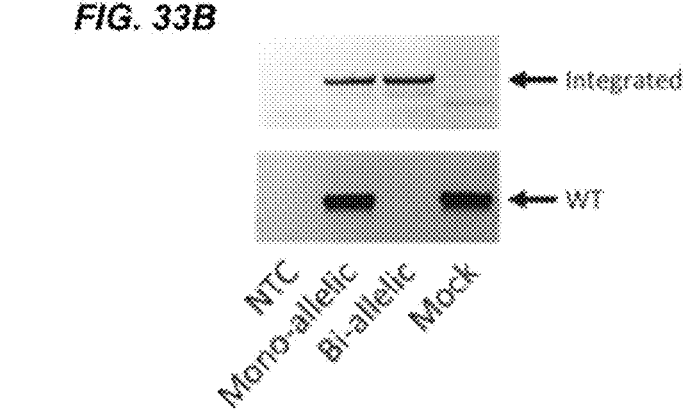
Figure 33C:
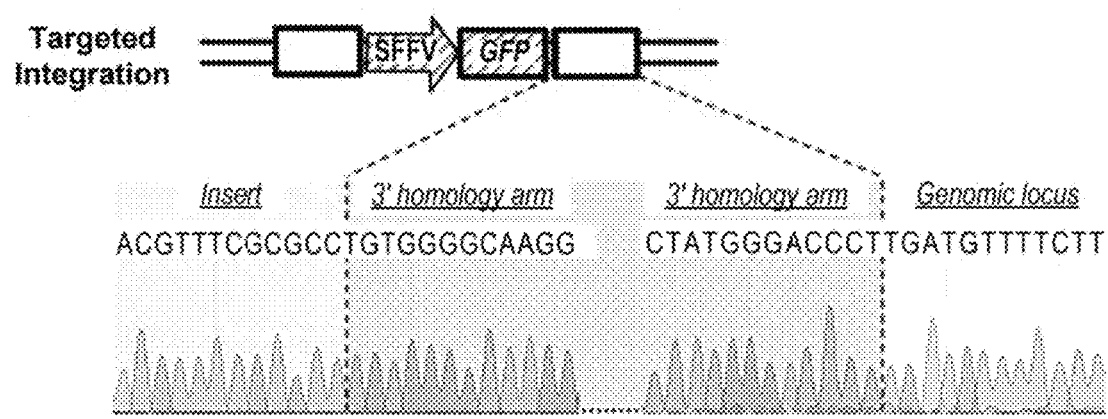

To confirm that the GFP$^{high}$ population was enriched for on-target integration, 'In-Out PCR' (i.e., one primer binding the HBB locus outside the region of the homology arm and the other binding the integrated insert) was used to determine integration frequencies and allelic distribution in methylcellulose clones derived from the GFP$^{high}$ population (95 clones). A total of 92% of clones had a targeted integration, with 38% harboring biallelic integrations (FIGS. 31B and 33). However, it should be noted that this assay generates colonies from progenitor cells and that the biallelic integration rates could be different in LT-HSCs. Nonetheless, these data highly suggest that the log-fold transgene expression shift following rAAV6 and RNP delivery is due to HR at the intended locus and that the shift can be used for FACS-based enrichment of HBB-targeted HSPCs.

Figure 31C:
Figure 31D:
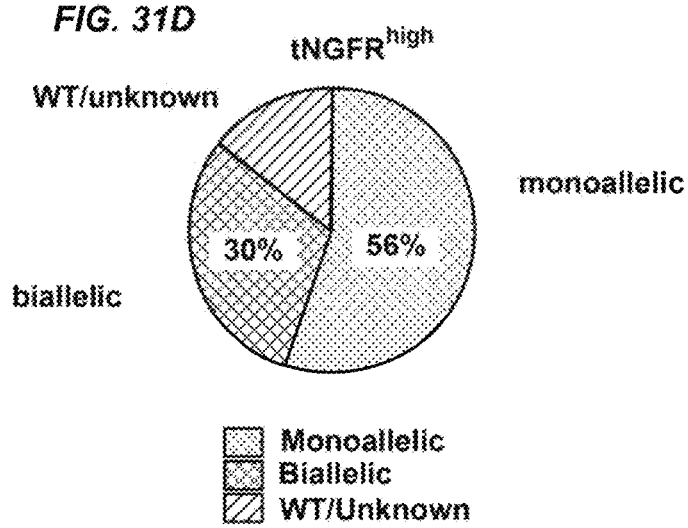
Figure 34A:
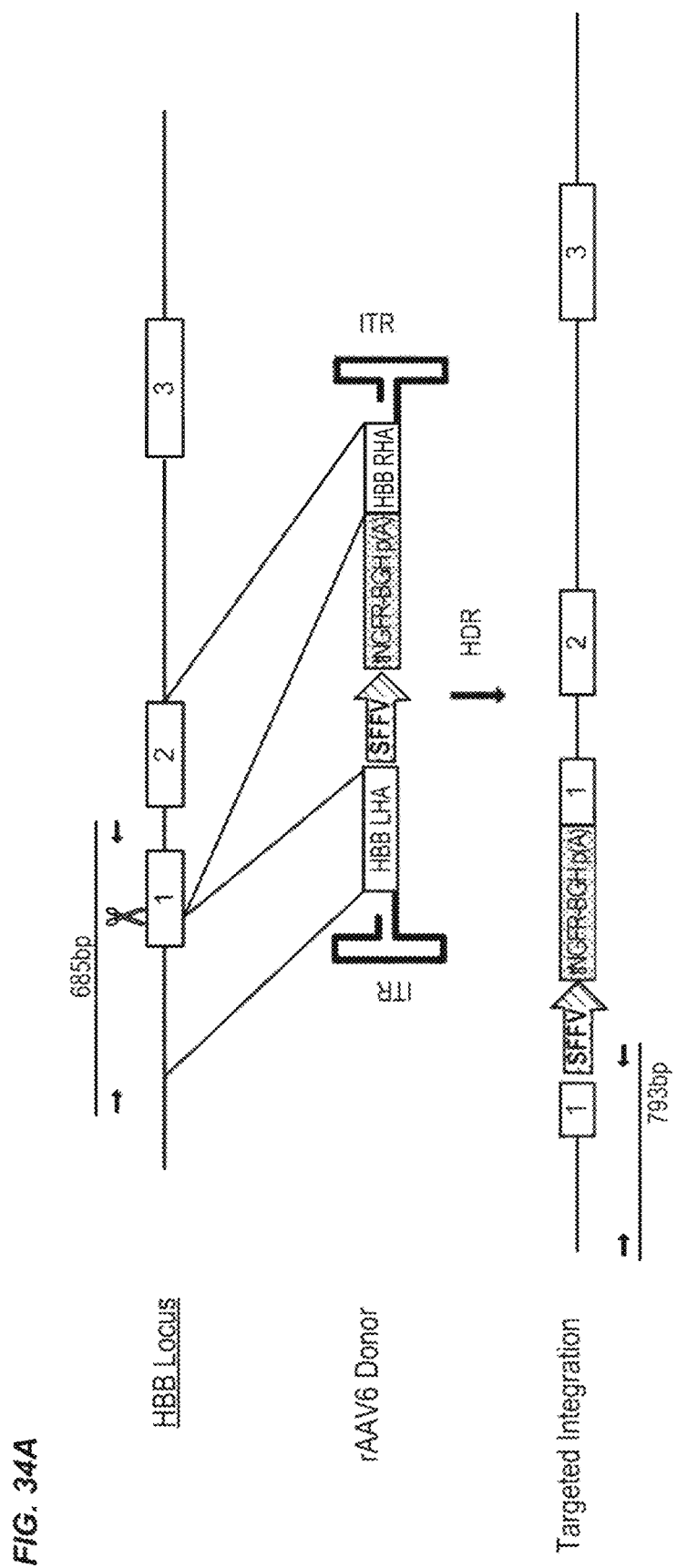
FIGS. 34A-34C provide an overview of PCR genotyping of methylcellulose colonies with HR of a tNGFR donor at the HBB locus.
Figure 34B:
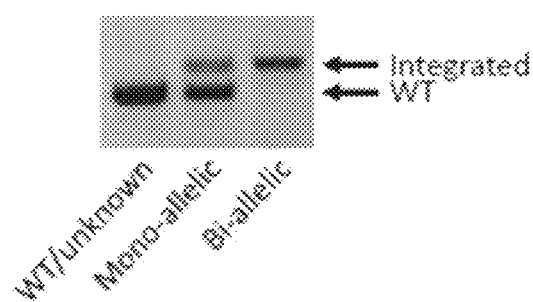
Figure 34C:
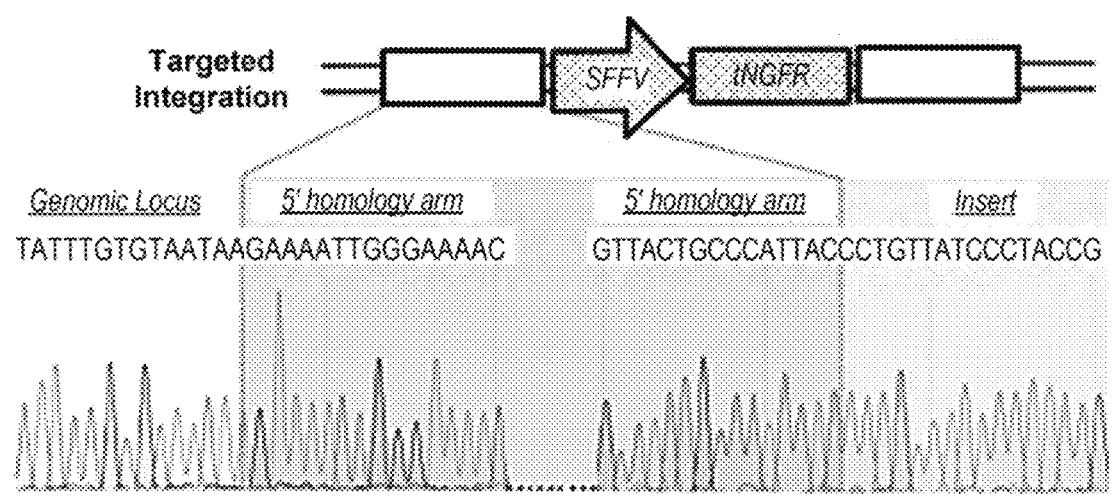

While GFP is not a clinically relevant reporter gene, the truncated nerve growth factor receptor (tNGFR), in which the cytoplasmic intracellular signaling domain is removed, rendering it signaling incompetent, can be used to identify and enrich for targeted HSPCs instead. tNGFR is expressed on the cell surface, thereby allowing antibody-mediated detection of gene marking and it has already been used in human clinical trials[34-37]. Therefore, it was tested whether it was possible to enrich HBB-targeted HSPCs using tNGFR magnetic bead-based separation technology. HSPCs that received RNP and rAAV6 donor (with a tNGFR expression cassette) produced a tNGFR$^{high}$ population that was not present in cells transduced with rAAV6 alone, consistent with findings with a GFP cassette (FIG. 31C, left panel). tNGFR$^{high}$ cells were then enriched using anti-NGFR magnetic microbeads and after 18 days in culture, an average of 84% of HSPCs were tNGFR$^+$ (FIG. 31C, right panel). 'In/Out PCR' was then performed on tNGFR$^{high}$ HSPC methylcellulose clones to determine on-target integration frequencies, and found that comparable to GFP$^{high}$ 86% of clones had a targeted integration with 30% having biallelic integrations (FIGS. 31D and 34). These results show that HR-edited cells can be identified and purified early in the cell manufacturing process using a clinically compatible cell surface marker. Using the CRISPR-Cas9 RNP system combined with rAAV6 donor delivery, a high percentage of these purified HSPCs (greater than 30%) have undergone HR-mediated editing at both HBB alleles.

Figure 35A:
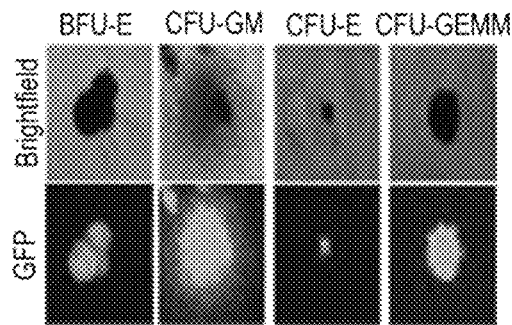
FIGS. 35A-35E show that the GFP$^{high}$ population maintains hematopoietic progenitor repertoire and contains immunophenotypic stem cells.
Figure 35B:
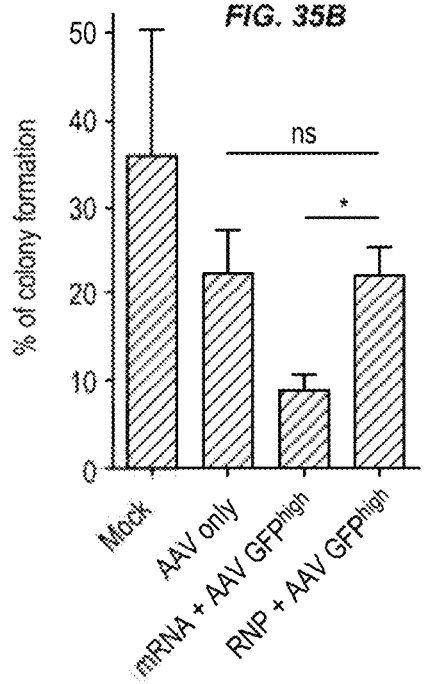
Figure 35C:
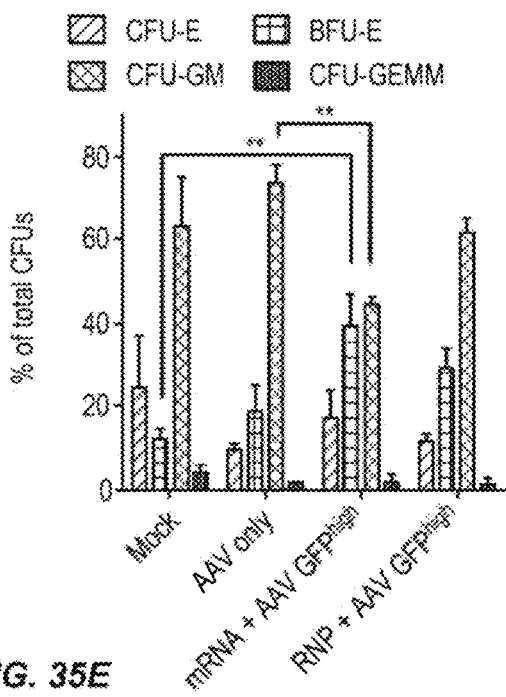

Because HSPCs are a heterogeneous population of cells with differential stem cell potential[38], the stem and progenitor cell capacity of enriched targeted HSPCs was evaluated in vitro and in vivo. The colony forming unit (CFU) assay was used to characterize the functional potential of HBB GFP$^{high}$ HSPCs to form erythroid (CFU-E and BFU-E), granulocyte/macrophage (CFU-GM), and multi-lineage (CFU-GEMM) colonies in methylcellulose. Compared to mock-electroporated HSPCs or HSPCs treated with rAAV6 only, no significant difference was observed in the colony formation potential of RNP-treated cells (FIGS. 35A and 35B) or in the distribution of colony types between these experimental groups (FIG. 35C). These results confirm that RNP-edited HSPCs have a similar progenitor potential as unedited cells. However, a significant decrease in cloning efficiency and a clonal skewing was observed for the mRNA-treated cells (FIGS. 35B and 35C), implying that mRNA delivery of Cas9 negatively influences progenitor biology. It is possible, however, that the formulation of the Cas9 mRNA can be adjusted to minimize or even eliminate this observed toxicity.

Figure 35D:
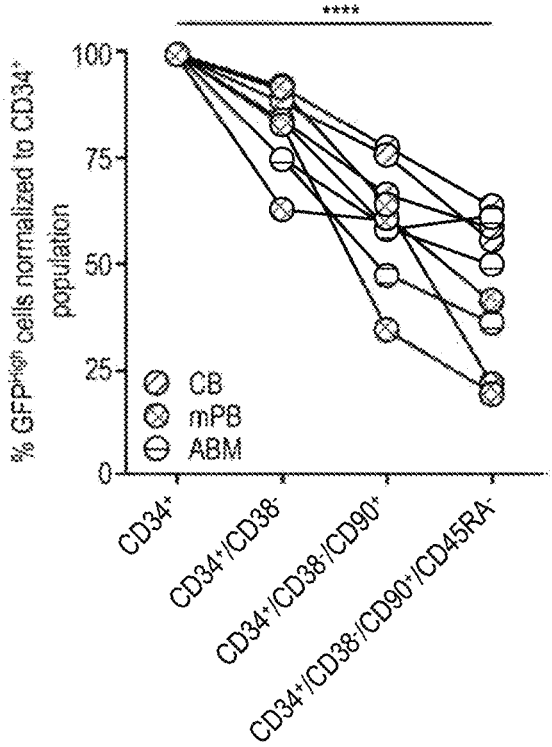
Figure 35E:
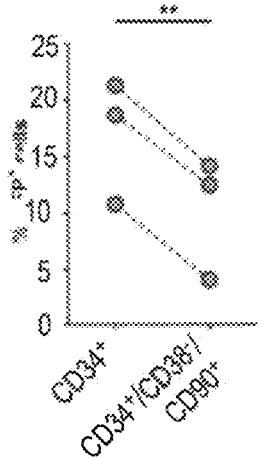
Figure 36A:
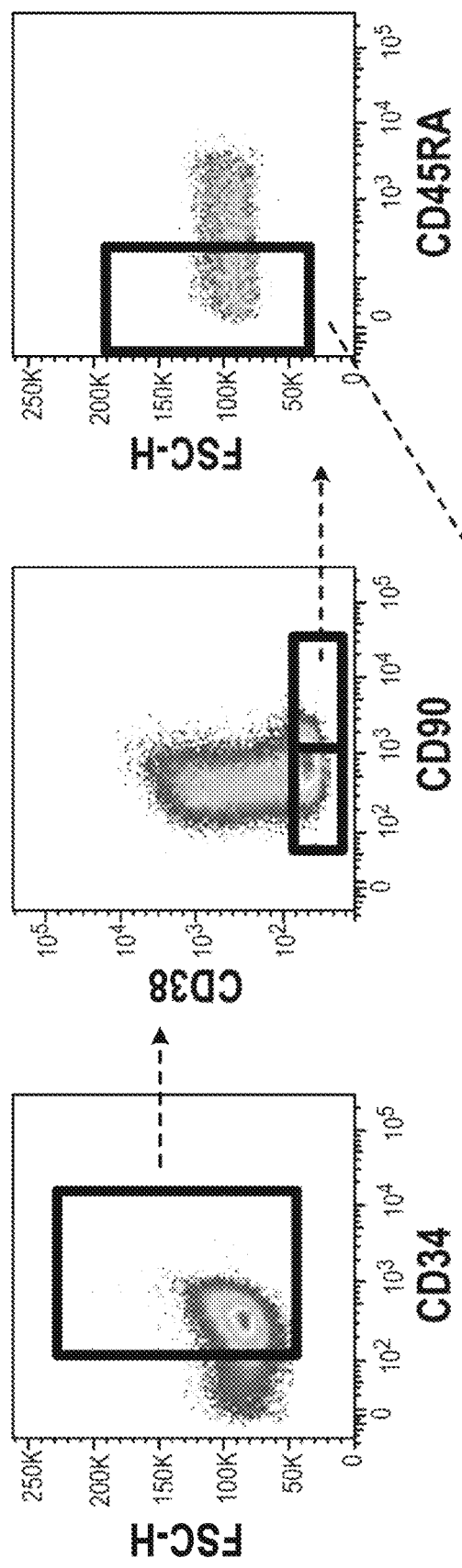
FIGS. 36A and 36B show a representative FACS gating scheme for analyzing HBB targeting rates in different HSPC subpopulations. Representative FACS plots at day 4 post-electroporation of CD34⁺ HSPCs showing the gating scheme for analyzing targeting frequencies in different subsets of HSPCs (FIG. 35D).
Figure 36B:
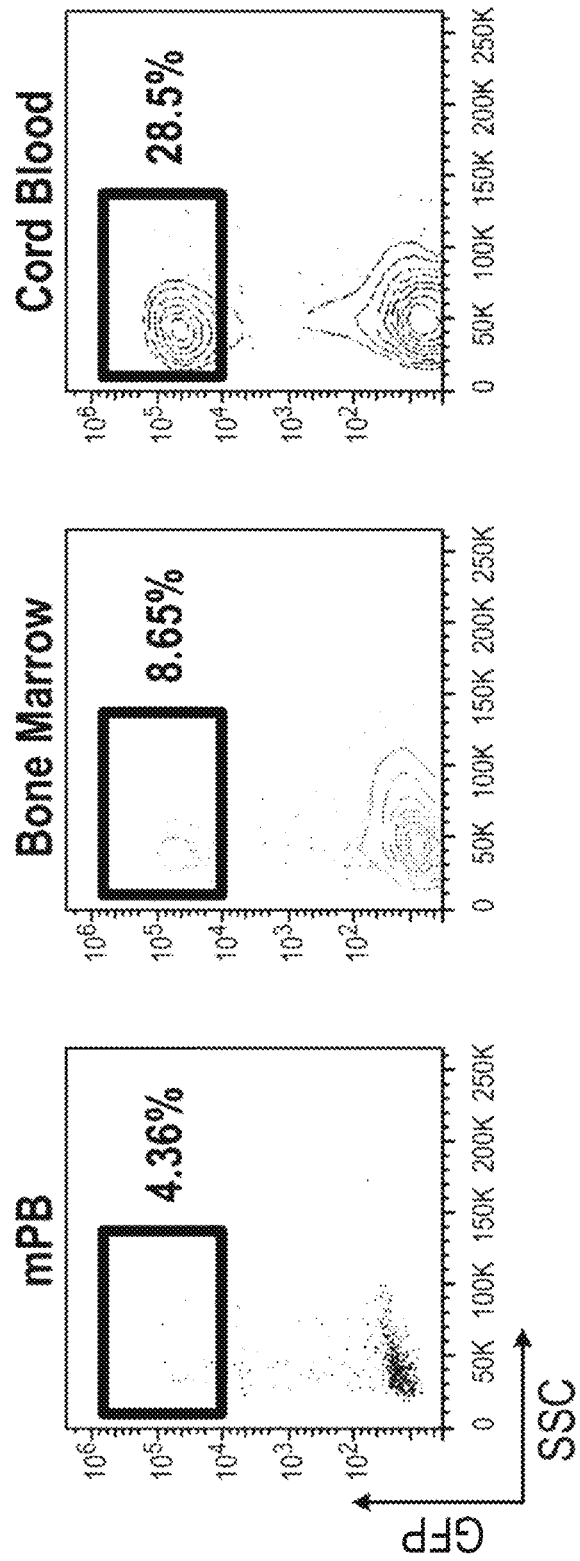
Figure 44:
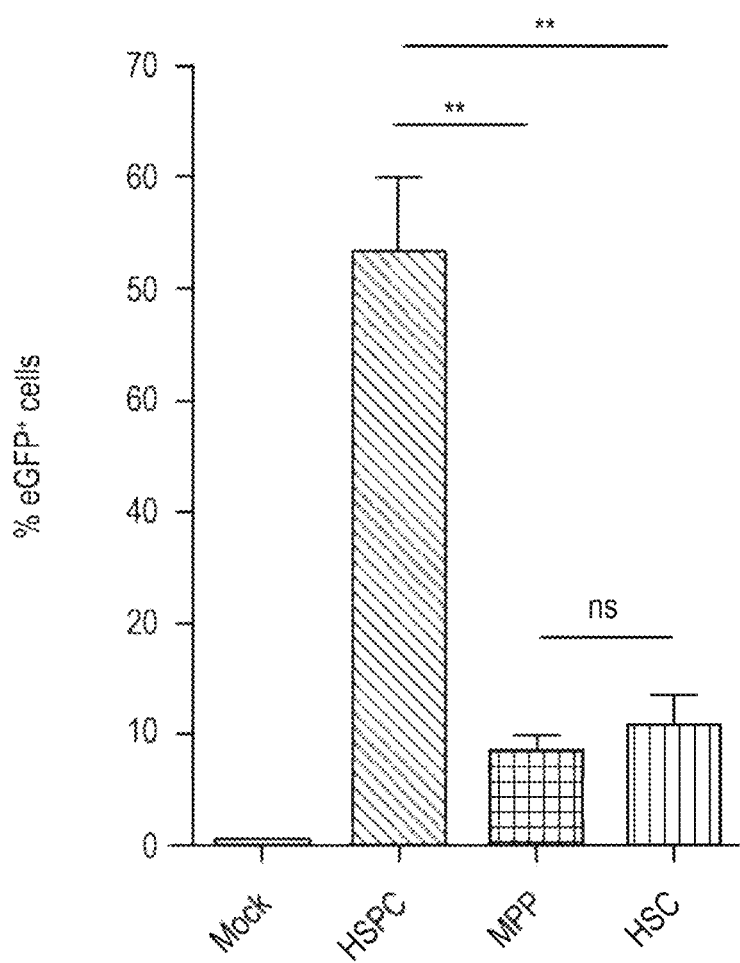
FIG. 44 shows low AAV6 tropism in MPPs and HSCs. MPP (CD34$^+$/CD38$^-$/CD90$^-$/CD45RA$^-$) and HSC (CD34+/CD38$^-$/CD90+/CD45RA$^-$) populations were sorted from fresh cord-blood-derived CD34+ HSPCs and immediately after sorting, cells were transduced with scAAV6-SFFV-eGFP at an MOI of 100,000 vg/cell along with the bulk HSPC population. scAAV6 was used because it eliminates second strand synthesis as a confounder of actual transduction. Two days later, transduction efficiencies were measured by flow cytometric analysis of eGFP expression using non-transduced cells (Mock) to set the GFP$^+$ gate. Error bars represent S.E.M., N=2 different HSPC donors, ns=p≥0.05, **p<0.01, unpaired t test with Welch's correction.

The classic model of human hematopoiesis is defined by a cell surface marker expression-based hierarchy initiated by HSCs that both self-renew and differentiate into multipotent progenitors, which in turn give rise to lineage-restricted progenitors, and finally terminally differentiated blood cells[18, 39, 40]. CD34$^+$ expression defines the heterogeneous HSPC population, which can be further classified as a multipotent progenitor (CD34$^+$/CD38$^-$), long-term repopulating cell in xenograft mice (CD34$^+$/CD38$^-$/CD90$^+$), and more recently, a population highly enriched for HSCs (CD34$^+$/CD38$^-$/CD90$^+$/CD45RA$^-$). Frequencies of GFP$^{high}$ cells in the four different subpopulations was evaluated by immunophenotypic analysis at day 4 post-electroporation, and a significant negative correlation between targeting frequencies and the immunophenotypic primitiveness of the analyzed population was observed (FIGS. 35D and 36). The relative decrease in HR-editing of immunophenotypically more primitive cells was less in cells derived from cord blood. Because concerns exist regarding the relationship between HSC potential and stem cell surface marker expression following in vitro culturing conditions[41], another strategy was employed to evaluate targeting rates in the primitive HSC population. CD34$^+$ or CD34$^+$/CD38$^-$/CD90$^+$ (HSCs) cells were sorted from fresh HSPCs and used in HR experiments after 12 to 16 hours in culture. A 38% reduction in targeting efficiencies in the HSCs was observed, compared to the heterogeneous CD34$^+$ population (FIG. 35E), supporting previous immunophenotyping data. To test if inefficient targeting of primitive cells was due to reduced rAAV6 donor availability, HSCs and multi potent progenitors (MPPs) from fresh cord blood were sorted and immediately transduced them with scAAV6-SFFV-GFP, followed by GFP expression analysis after 48 hours. Results showed a 5-fold reduction in the number of GFP+ HSCs and MPPs compared to the bulk CD34+ population (FIG. 44). Collectively, the data suggest that HSCs are more difficult to target than progenitor cells, which can be partially explained by reduced donor availability from decreased rAAV6 transduction. Nonetheless, even in the sorted HSC population, HR-editing frequencies above 4% and usually above 10% were achieved (FIG. 35E).

Figure 37A:
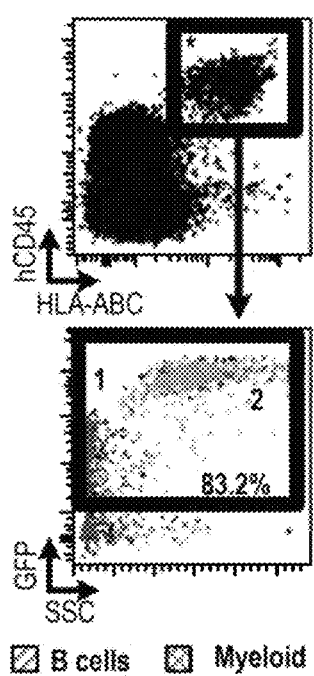
FIGS. 37A-37G show that HBB gene edited HSPCs display long-term and multi-lineage reconstitution in NSG mice.
Figure 37B:
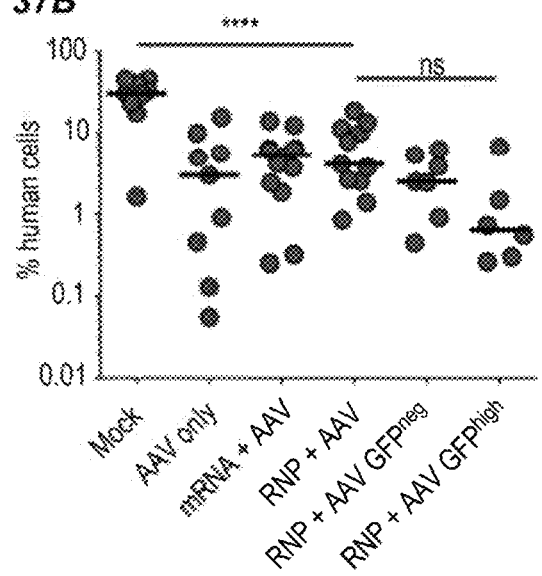
Figure 37C:
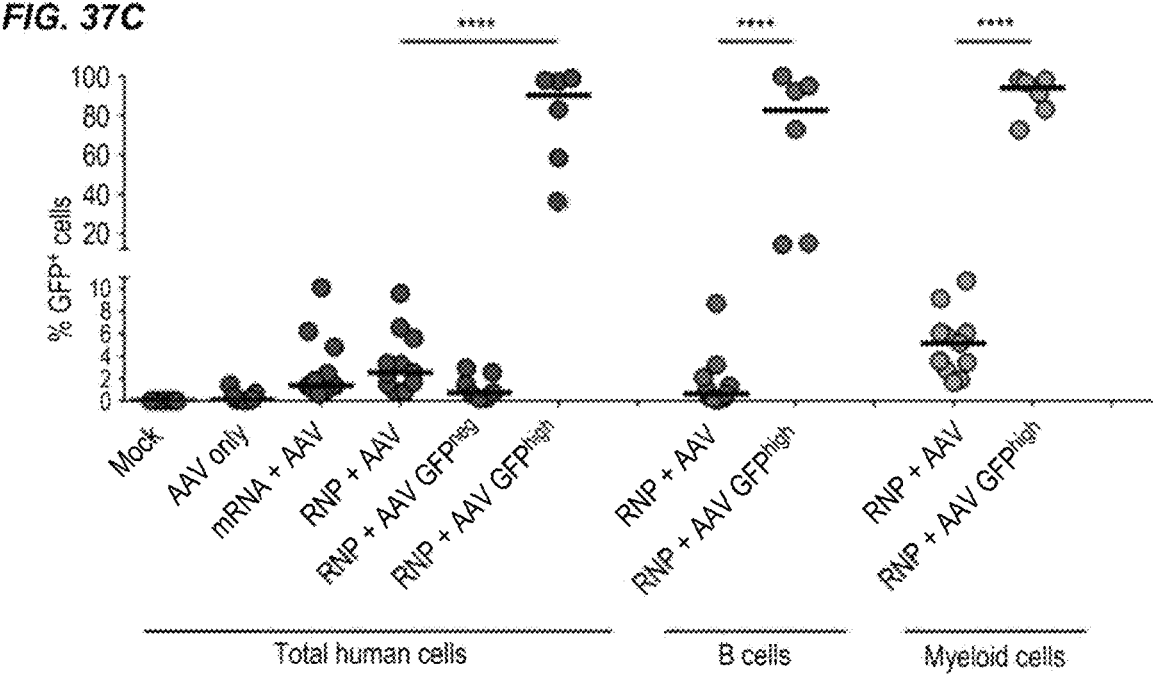
Figure 37D:
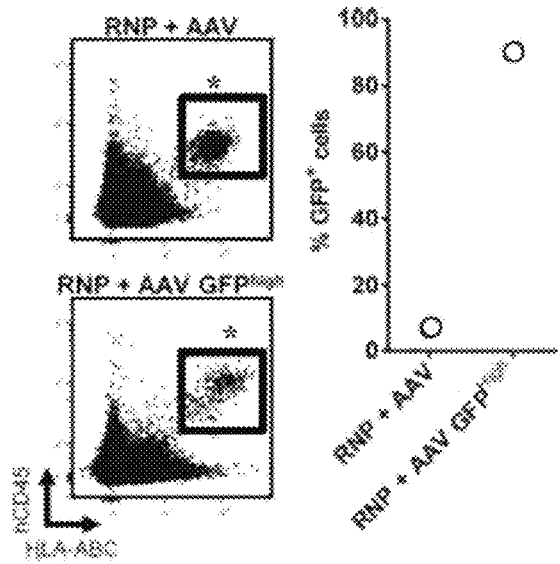
Figure 37E:
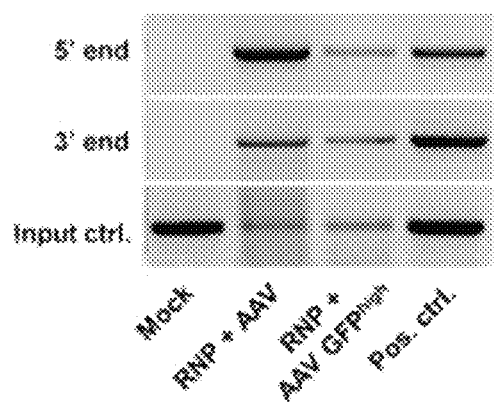
Figure 40A:
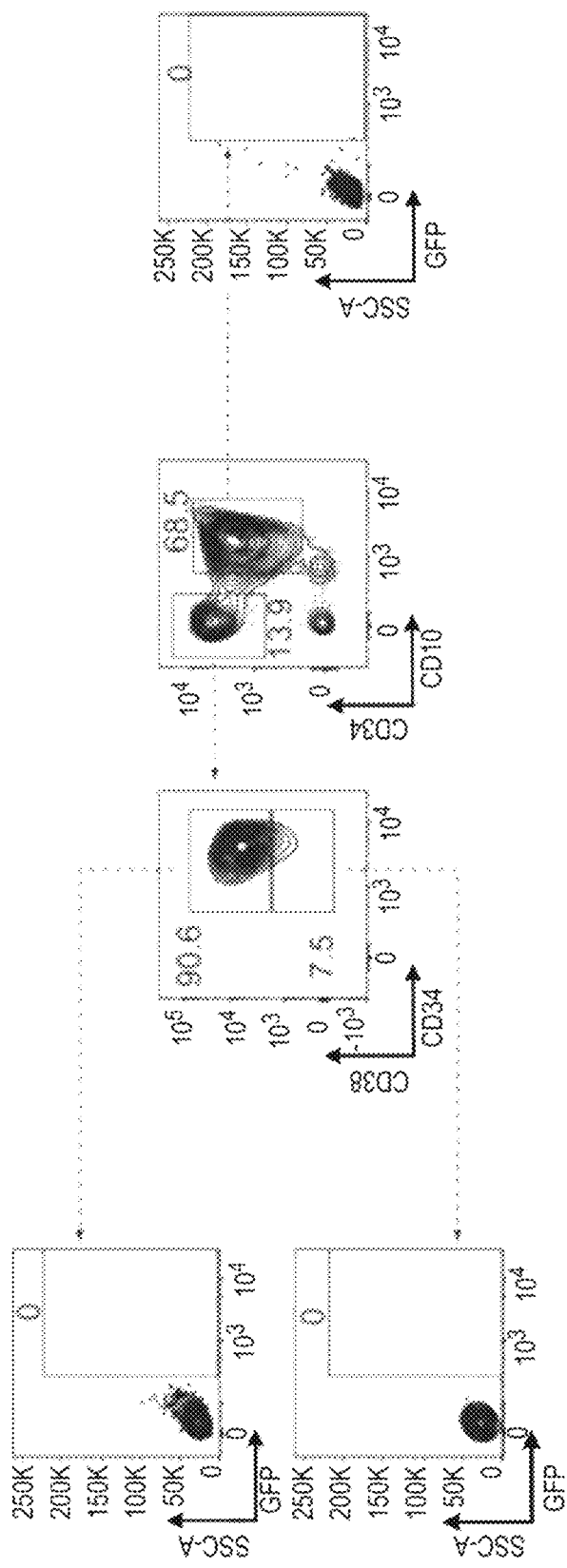
FIGS. 40A-40C show results in genome-edited human HSPCs in the bone marrow of NSG mice at week 16 post-transplantation. Representative FACS plots from the analysis of NSG mice from the Mock (FIG. 40A) or RNP (FIG. 40B) experimental group at week 16 post-transplantation. Mice were sacrificed and bone marrow was harvested, PBMCs were isolated via Ficoll density gradient, after which human CD34+ cells were enriched by magnetic-activated cell sorting (MACS), and finally cells were stained with anti-CD34, anti-CD38, and anti-CD10 antibodies to identify human GFP⁺ cells in the CD34+/CD10⁻ and CD34+/CD10⁻/CD38⁻ populations (note that CD10 was included as a negative discriminator for immature B cells).
Figure 40B:
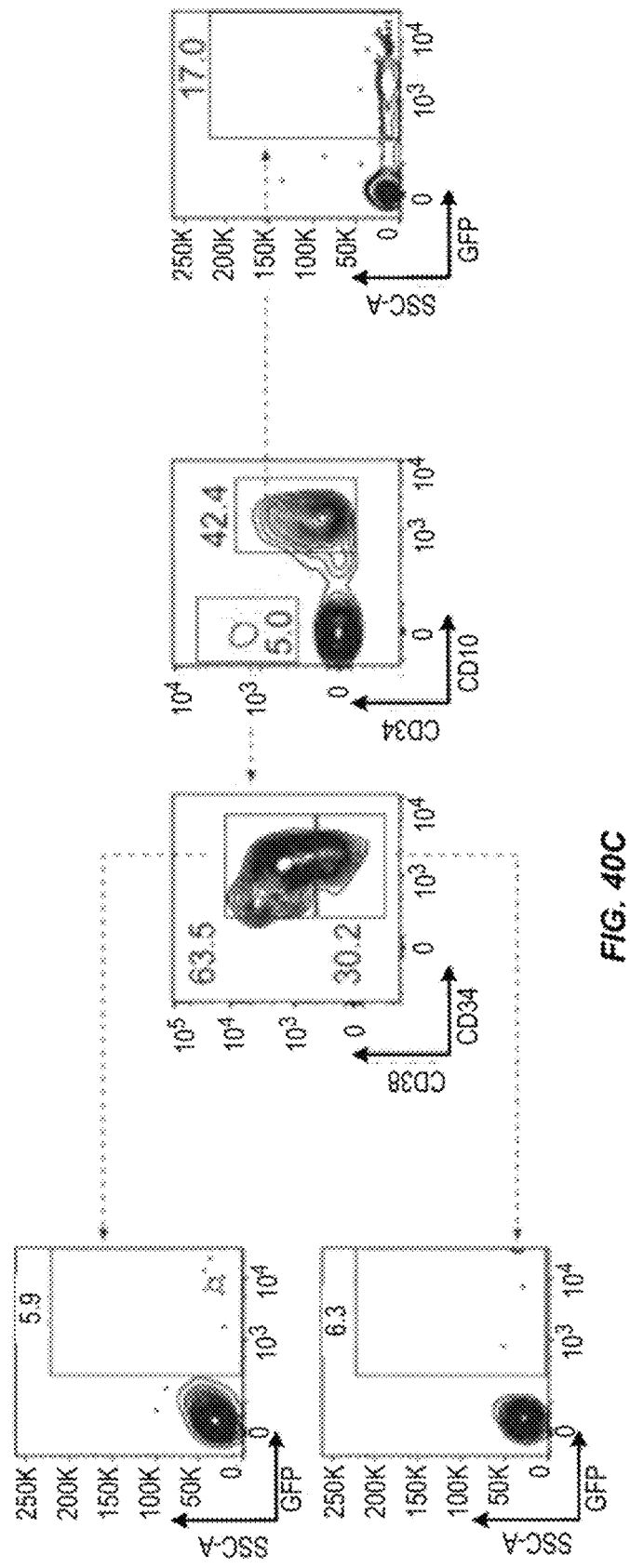
Figure 40C:
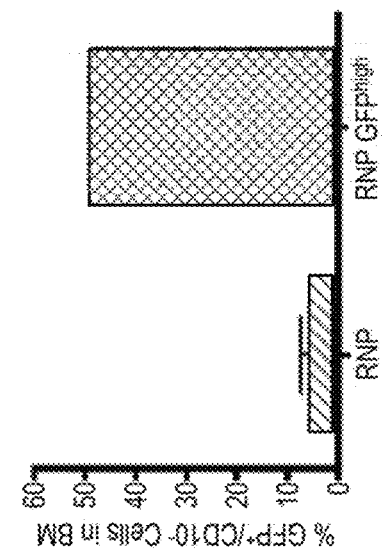

While immunophenotypic analyses of stem cell-associated surface markers can shed light on targeting efficiencies in primitive cells, the current gold standard for HSC function, defined by the capacity to self-renew and form differentiated blood cells, is in vivo engraftment into immunodeficient non-obese diabetic (NOD)-SCID-gamma (NSG) mice. CD34+ HSPCs derived from mobilized peripheral blood (mPB) were used for these studies because of their high clinical relevance, although these cells have been shown to have reduced engraftment capacity in NSG mice compared to HSPCs derived from fetal liver, cord blood, and bone marrow[24, 42]. HSPCs from the following experimental groups targeting HBB were transplanted into each irradiated mouse by tail vein injection: 1) mock-electroporated, 2) AAV6 only, 3) mRNA+AAV6, 4) RNP+AAV6, 5) RNP+AAV6 GFP$^{neg}$ (to control for sorting), and 6) RNP+AAV6 GFP$^{high}$. All mice displayed human engraftment in the bone marrow as measured by the presence of hCD45/HLA-ABC double positive cells 16 weeks post-transplant (FIGS. 37A (top) and 38). While a decrease in human cell chimerism was observed for all treatment groups compared to the Mock control, all groups with nuclease-treated cells displayed similar chimerism to the rAAV6 only group. A small, but not statistically significant, decrease for the RNP+AAV GFP$^{high}$ group compared to RNP+AAV was measured, which can be explained by transplantation of fewer total cells and fewer phenotypically identified LT-HSCs (FIG. 39). There was a significant decrease from RNP+AAV input targeting frequencies (16% in the CD34+ mPB HSPCs, FIG. 35D) compared to the percent GFP+ cells in the bone marrow at week 16 following transplantation (3.5%) (FIG. 37B). This decrease is consistent with previous publications, and immunophenotyping of input cells did in fact show an average of 4% targeting in the CD34+/CD38-/CD90+/CD45RA- population (FIG. 35D). Despite these observed reductions in vivo, the median rates of HBB gene targeting in human cells in the bone marrow (BM) (3.5%) appear to be higher than what was found in other studies, particularly Hoban et al., and Genovese et al., in which most mice appeared to have less than 1% gene-modification following transplant using ZFNs targeting HBB and IL2RG, respectively[9, 23]. In contrast, mice transplanted with RNP GFP$^{high}$ cells had a median of 90% GFP+ human cells at week 16 after transplant, with three mice showing greater than 97% GFP+ human cells (FIGS. 37A (bottom) and 37C). Both myeloid (CD33+) and lymphoid (CD19+) reconstitution was also observed, with a median of 94% and 83% GFP+ cells, respectively (FIG. 37C), implicating targeting of multipotent HSPCs. 5% and 49% GFP+ human HSPCs (CD34+/CD10−) were detected in the BM of mice transplanted with RNP+AAV and RNP+AAV GFP$^{high}$ cells, respectively (FIG. 40). Multi-parameter flow cytometric analysis showed no perturbations in lineage reconstitution and no evidence of abnormal hematopoiesis, a functional assessment of the safety of the editing procedure. To experimentally determine if HBB was targeted in LT-HSCs, secondary transplants were performed for the RNP+AAV and RNP+AAV GFP$^{high}$ groups. For both groups human cells were detected in the bone marrow of secondary recipients at 12 to 14 weeks after transplant (FIG. 37D, left) with 7% and 90% GFP+ cells for the RNP+AAV and RNP+AAV GFP$^{high}$ group, respectively (FIG. 37D, right). More importantly, HBB on-target integration events were confirmed in human cells sorted from the bone marrow of secondary recipients from GFP$^{high}$ and RNP+AAV experimental groups (FIG. 37E). Collectively, these data confirm that this strategy can edit the HBB gene in human LT-HSCs.

Figure 37F:
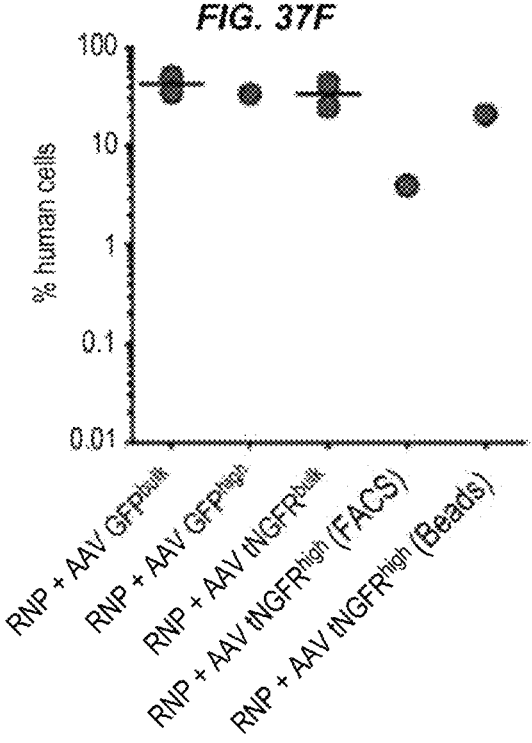
Figure 37G:
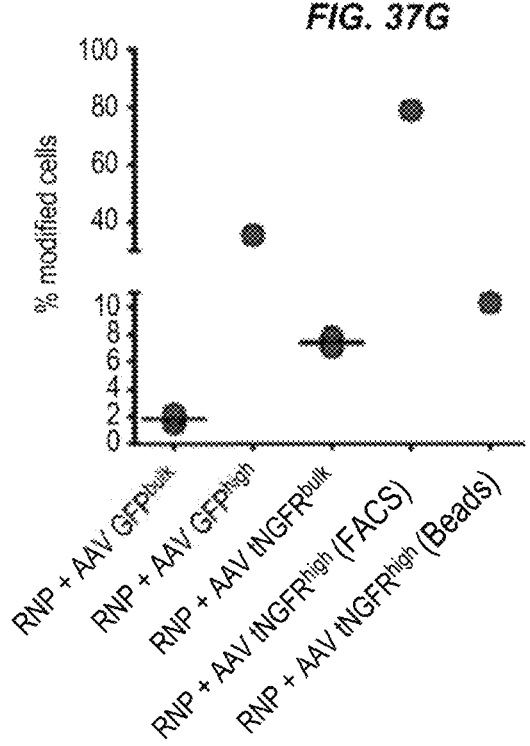
Figure 38A:
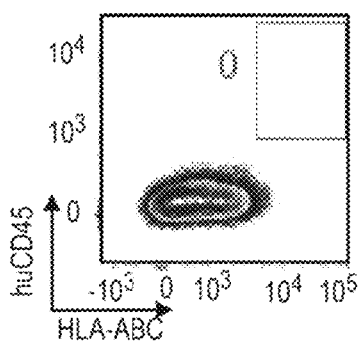
FIGS. 38A and 38B show a representative gating scheme for the analysis of human engraftment in FIGS. 37A-37E. NSG mice were sacrificed and bone marrow was harvested from femur, tibia, hips, humerus, sternum, and vertebrae. Cells were subject to Ficoll density gradient to isolate mononuclear cells, which were analyzed for human engraftment by flow cytometry.
Figure 38B:
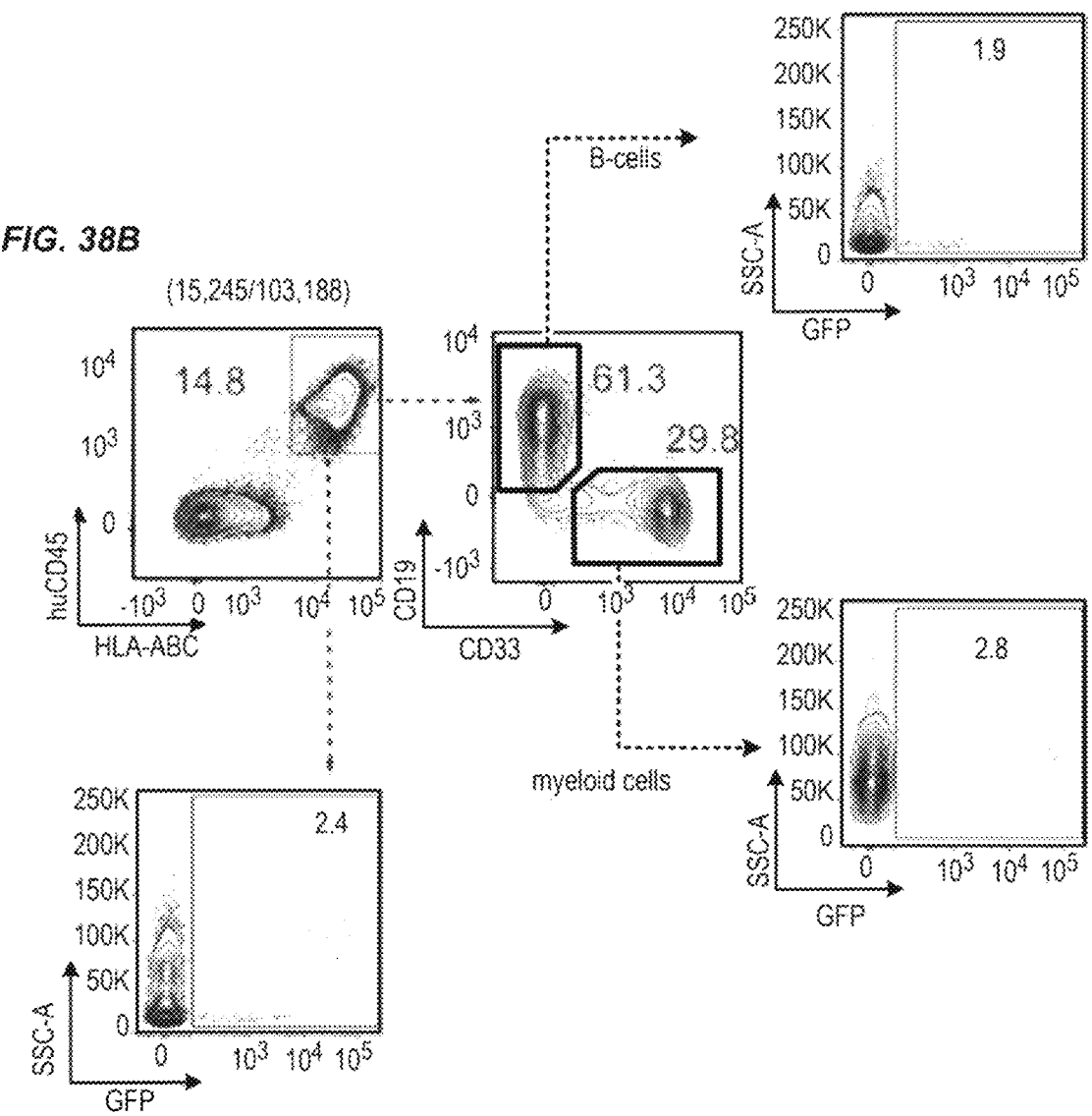

The genome editing process was scaled up to resemble a more clinically relevant CD34+ HSPC starting cell number. To that end, 80 million mPB-derived CD34+ HSPCs were electroporated with the HBB RNP CRISPR system, transduced with either SFFV-GFP or SFFV-tNGFR rAAV6, and then RNP+AAV, sorted GFP$^{high}$ and tNGFR$^{high}$ (enriched by FACS or magnetic microbeads) were bulk transplanted. At 16 weeks post-transplant, all mice displayed engraftment of edited human cells in the bone marrow (FIG. 37F). It should be noted that using this large scale procedure for the human cell engraftment was equivalent to "Mock" in the previously described experiment (FIG. 37B). While reductions were observed when comparing editing rates in the input cells to engrafted cells in vivo, the HBB-tNGFR mice showed a lower reduction (12% in vitro vs. 7.5% in vivo) than the HBB-GFP mice (10% in vitro vs. 1.9% in vivo), suggesting tNGFR could be a better transgene to evaluate editing of HSCs in vivo (FIG. 37G). Furthermore, mice transplanted with enriched targeted HSPCs displayed human cell editing frequencies of 10-75% (three mice) with human engraftment levels ranging from 4-30% (FIGS. 37F and 37G). These data show that the presently described methods are useful for performing large-scale genome editing in HSCs at the HBB locus.

Figure 46:
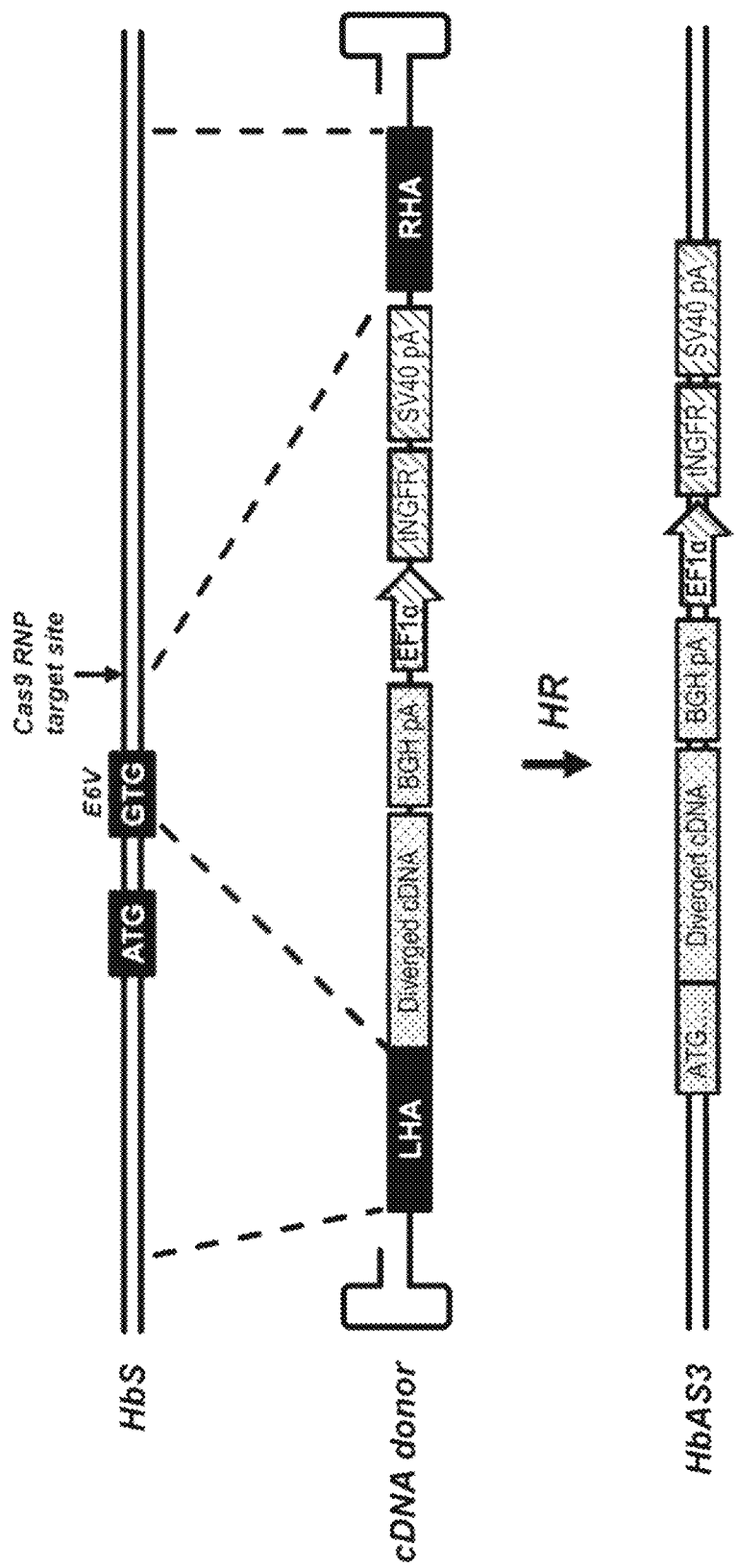
FIG. 46 shows an HBB cDNA donor with a tNGFR expression cassette. Provided is a schematic representation of the AAV6 donor encoding a functional HBB anti-sickling cDNA (G16D, E22A, T87Q) followed by an expression cassette for tNGFR. The left homology arm stops right before the sickle mutation (A→T) followed by the remaining HBB cDNA, which has been diverged from the endogenous sequence by introducing synonymous mutations at codon wobble positions. The HBB cDNA expression cassette is followed by an EF1α promoter driving tNGFR expression, which enables enrichment and tracking of modified cells.
Figure 47:
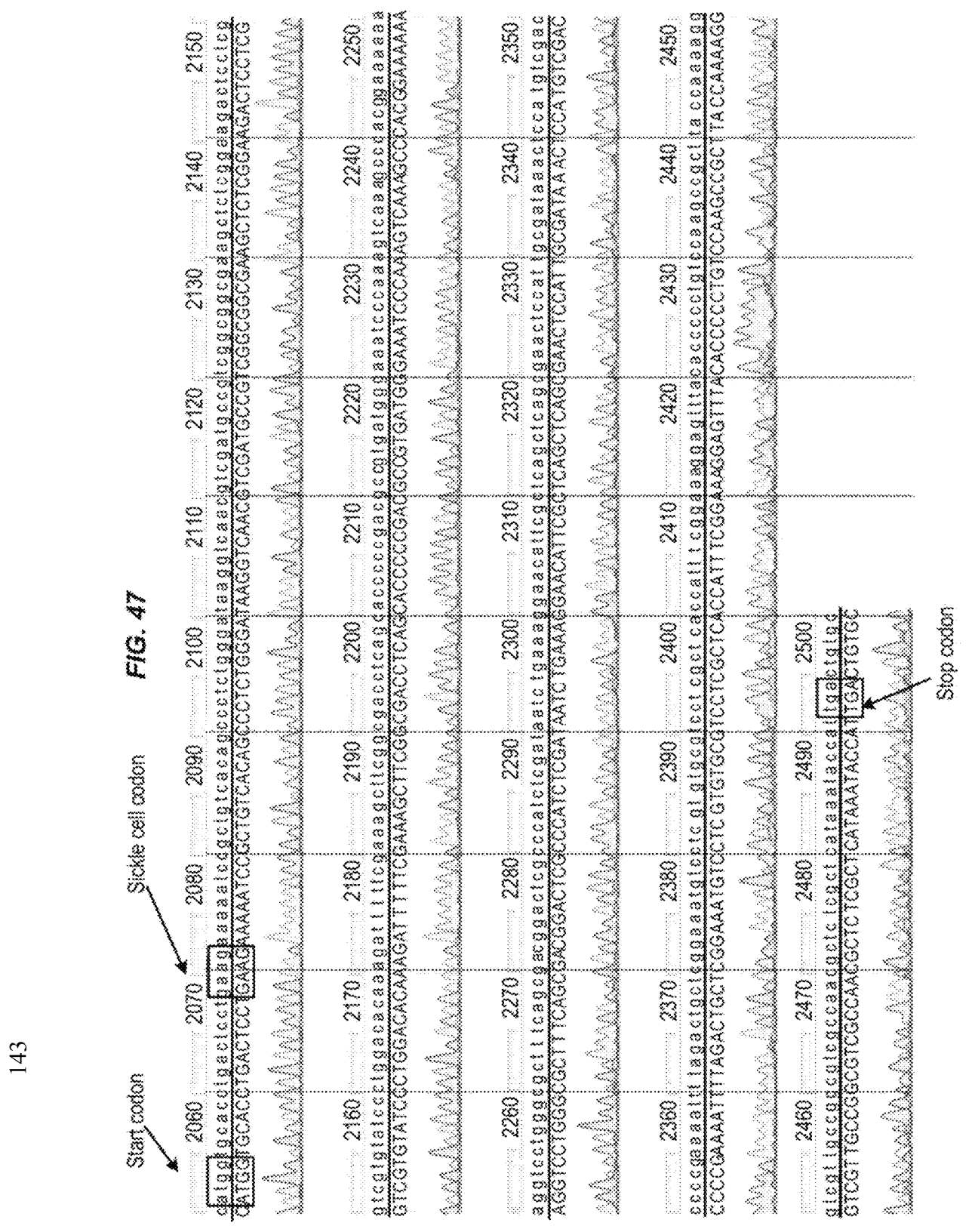

The ability of the methods described herein to correct the disease-causing E6V mutation in SCD patient-derived CD34+ HSPCs was tested. HSPCs were harvested from the peripheral blood of SCD patients, cultured for two days and then were subjected to the editing protocol. High frequencies of INDELs (FIG. 43A) and HR were first confirmed using an SFFV-GFP donor (FIG. 43B) at the HBB locus in SCD HSPCs. A therapeutic rAAV6 donor (corrective SNP donor) was then produced that was designed to revert the E6V mutation, while also introducing silent mutations to interrupt sgRNA binding and to prevent premature strand cross-over during HR (FIG. 45A). Targeting SCD HSPCs with the corrective SNP donor reverted an average of 50% of the E6V (HbS) alleles to WT (HbA) alleles (FIG. 43C). The HBB editing events were further analyzed in methylcellulose clones derived from HSPCs targeted with the corrective SNP donor and it was observed that an average of 45% of clones had at least one HbA allele (FIG. 45B). An anti-sickling HBB cDNA therapeutic donor (HbAS3[43]) was next created using previously reported strategies[8, 16] of knocking in divergent cDNAs into the gene start codon to preserve endogenous promoters/enhancer function, followed by a clinically relevant promoter (EF1α) driving tNGFR expression to allow for early enrichment and tracking of edited cells (SEQ ID NO:37) (FIG. 46). Using this donor, an average of 11% of SCD patient-derived HSPCs was targeted (FIGS. 43D and 47) and notably, a tNGFR$^{high}$ population was observed as described previously (FIG. 31C) at day 4 post-electroporation in the presence of RNPs, indicating the ability to enrich SCD-corrected HSPCs early in the culture process. Overall, these studies show that the methods of the present invention can correct the E6V mutation using two different donor designs.

Figure 43E:
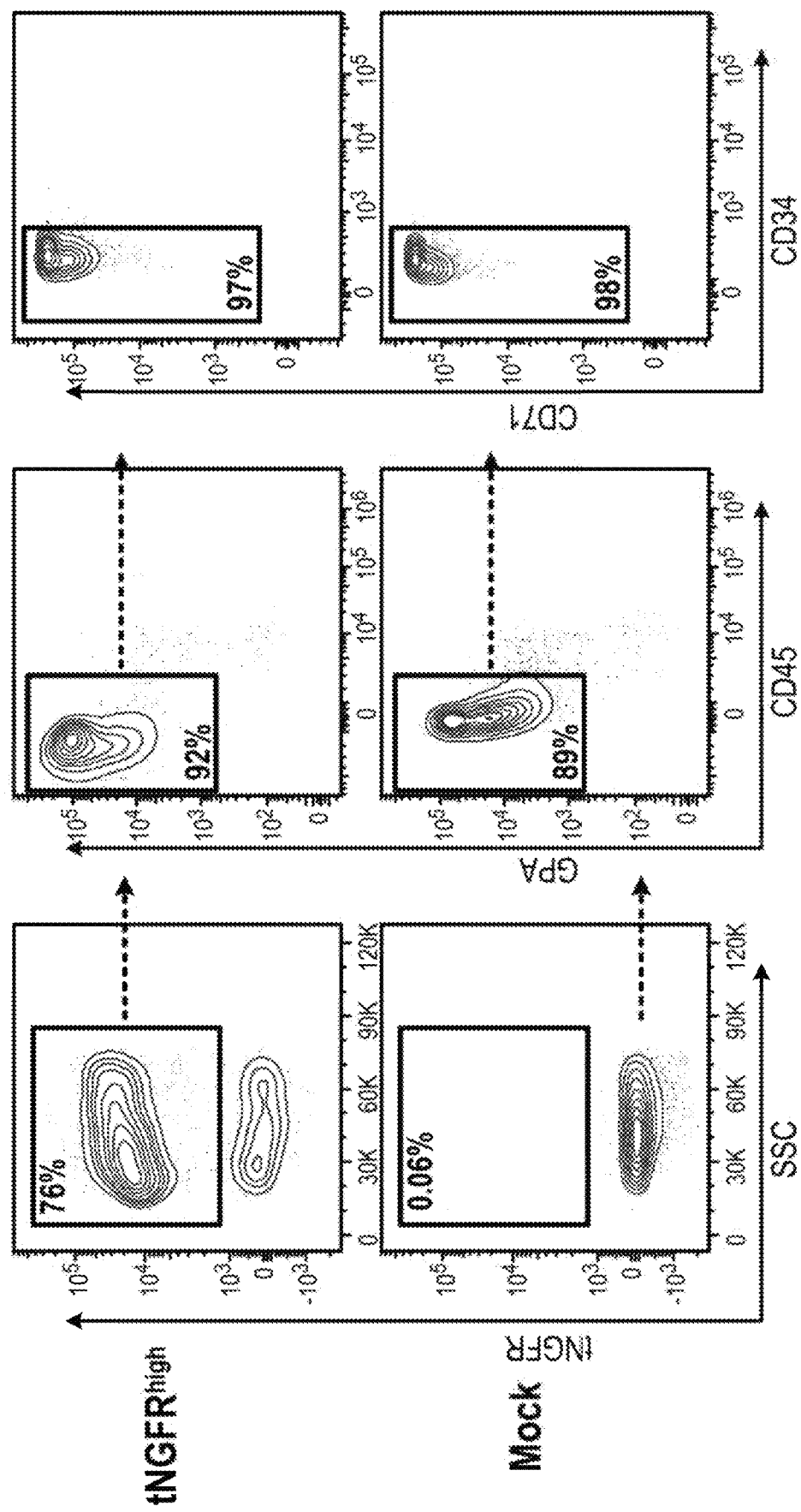
Figure 43F:
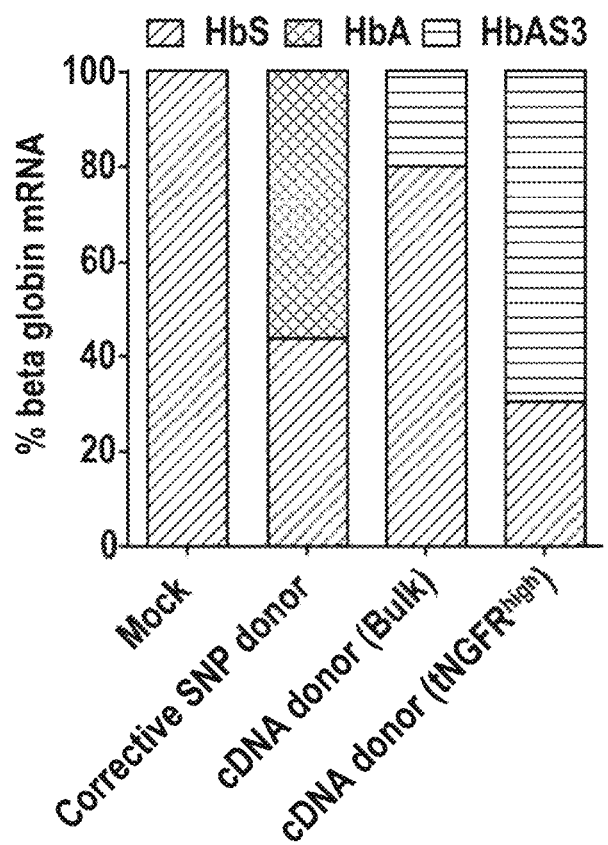
Figure 48:
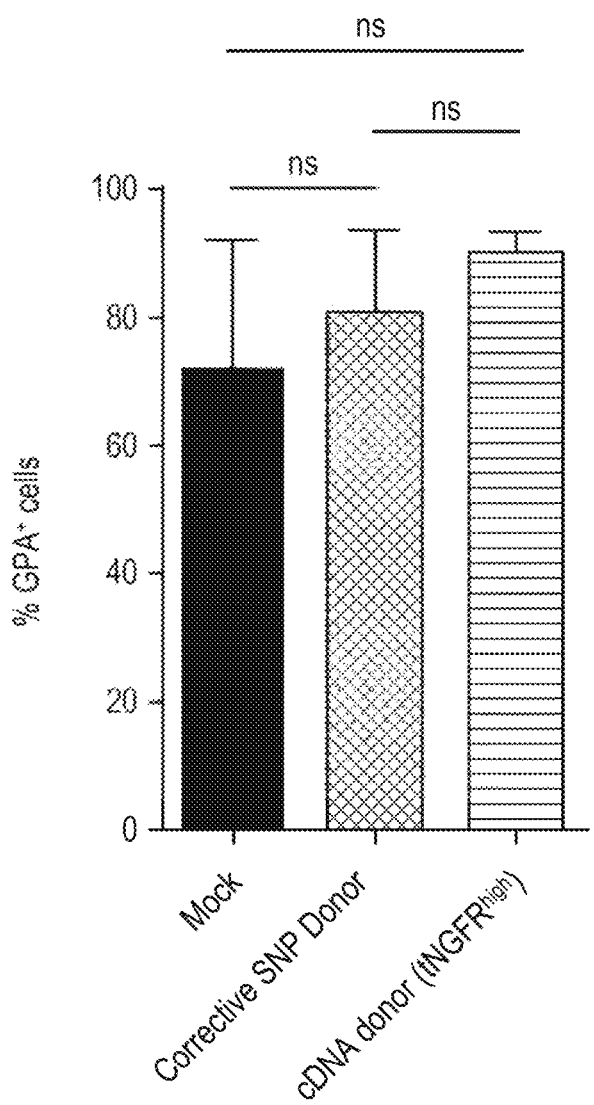
FIG. 48 shows that edited HSPCs from sickle cell patients differentiated into erythrocytes expressed Glycophorin A. CD34+ HSPCs derived from sickle cell patients were edited with Cas9 RNP and either the corrective SNP donor or the cDNA donor. Four days post-electroporation, cells edited with the cDNA donor were sorted for tNGFR$^+$ cells. This population as well as the populations edited with the corrective SNP donor and Mock cells were subjected to a 21-day erythrocyte differentiation protocol, followed by staining for Glycophorin A (GPA). Error bars represent S.E.M., N=2-3 different sickle cell patients, ns=p≥0.05, unpaired t test with Welch's correction.

Next it was tested whether the HBB-edited SCD HSPCs maintained their erythroid differentiation potential. To that end, tNGFR$^{high}$ and Mock HSPCs were subjected to a 21-day in vitro erythroid differentiation protocol at day 4 post-electroporation as previously described[44,45]. Flow cytometric analyses of tNGFR$^{high}$ and mock-electroporated cells post-erythroid differentiation showed a high proportion of GPA$^+$/CD45$^-$/CD71$^+$/CD34$^-$ cells, indicating the presence of mature differentiated erythrocytes that express hemoglobin[46] (FIGS. 43E and 48). Finally, to confirm that edited HBB alleles were transcribing adult β-globin (HbA) or HbAS3 mRNA, RT-qPCR was performed on erythrocytes differentiated from edited SCD HSPCs. Erythrocytes edited with the corrective SNP donor expressed 56% HbA mRNA out of total β-globin mRNA, while erythrocytes edited with the cDNA donor (bulk) expressed 20% HbAS3 mRNA. Thus the percentage of HbAS3 mRNA (20%) matched or exceeded the percentage of cells modified by the tNGFR cassette (11%) suggesting functional expression of the AS3 cDNA from the endogenous HBB promoter. Notably, enriched tNGFR$^{high}$ erythrocytes expressed 70% HbAS3 mRNA, confirming an enrichment of functionally corrected HSPCs (FIG. 43F).

These results show that LT-HSCs are more resistant to targeted integration by HR than lineage-committed progenitor cells regardless of source confirming previously published results[23]. It was also found, however, that cord blood-derived LT-HSCs are less resistant to editing than LT-HSCs derived from bone marrow or peripheral blood. Consequently, enrichment of targeted cells resulted in the removal of the majority of HSCs, leading to an overall 8-fold decrease in the total number of HSCs in the transplanted enriched population (FIG. 39). Even though 8-fold fewer total HSCs were transplanted in the enriched population compared to the non-enriched (GFP$^{high}$ vs. RNP+ AAV), it was observed that there was still an average of 5-fold more absolute number of edited cells in in the bone marrow of the mice from the enriched group 16 weeks post-transplant (FIG. 39). Hence, the enrichment strategy not only yields higher frequencies of modified cells in the transplanted mice, but the absolute number of modified human cells in the mice was also higher. Thus, the enrichment strategy can ameliorate the problem of inefficient HSC targeting. Recent advances in ex vivo HSC expansion protocols and identification of small molecule drugs, like UM171[47] that expand HSCs, can be combined with the methods described herein to generate a large and highly enriched population of genome-edited HSCs.

The methods described herein set the framework for CRISPR-mediated HBB targeting in LT-HSCs that has the power to be translated to the clinic. While GFP is unsuitable for enriching targeted HSPCs for gene therapy because of its immunogenicity in humans, the enrichment protocol using tNGFR (FIG. 31C) (or other such similar signaling-inert cell surface markers) is useful for the next generation of β-hemoglobinopathy therapies that are based on gene editing. These studies show that this methodology can enrich corrected SCD patient-derived HSPCs that can differentiate into erythrocytes that express HBB anti-sickling mRNA from the endogenous HBB promoter. This tNGFR selection strategy has the potential advantage over chemoselection strategies in that it avoids exposing the edited cells and the patients to potentially toxic chemotherapy[8]. The strategy of knocking-in a HBB cDNA along with a selectable marker to enrich for modified cells is applicable to both sickle cell disease and almost all forms of β-thalassemia. Furthermore, because the genome editing process can be efficiently scaled up to clinically relevant starting numbers, the methods described herein can be used to develop a GMP-compatible process for editing the HBB locus in HSPCs.

In conclusion, the methods described in this example lay the foundation for CRISPR/Cas9-mediated genome editing therapies not only for the β-hemoglobinopathies but also for a range of other hematological diseases and generally advances HSC-based cell and gene therapies.

Materials and Methods

AAV Vector Production

AAV vector plasmids were cloned in the pAAV-MCS plasmid (Agilent Technologies, Santa Clara, Calif.) containing ITRs from AAV serotype 2. The HBB rAAV6 GFP and tNGFR donor contained promoter, MaxGFP or tNGFR, and BGH polyA sequences. The left and right homology arms for the GFP and tNGFR HBB donors were 540 bp and 420 bp, respectively. The E6V rAAV6 donor contained 2.2 kb of sequence homologous to the sequence upstream of E6V. The nucleotide changes are depicted in FIG. 30. Immediately downstream of the last nucleotide change was 2.2 kb of homologous HBB sequence. HBB cDNA contained the same homology arms as GFP and tNGFR donors above, except that the left homology arm was shortened to end at the sickle mutation. A schematic overview of the sequence of the sickle allele aligned with the sequence of an allele that has undergone HR using the corrective SNP donor is depicted in FIG. 45A. The sickle corrective donor used in the SCD-derived HSPCs in FIG. 43C had a total of 2.4 kb sequence homology to HBB with the SNPs shown in FIG. 45A in the center (SEQ ID NO:36). Self complementary AAV6 (scAAV6) carrying the SFFV promoter driving GFP was kindly provided by Hans-Peter Kiem (Fred Hutchinson Cancer Research Center). AAV6 vectors were produced as described with a few modifications[48]. Briefly, 293FT cells (Life Technologies, Carlsbad, Calif., USA) were seeded at 13×10$^6$ cells per dish in ten 15-cm dishes one day before transfection. One 15-cm dish was transfected using standard PEI transfection with 6 μg ITR-containing plasmid and 22 μg pDGM6 (a kind gift from David Russell, University of Washington, Seattle, Wash., USA), which contained the AAV6 cap genes, AAV2 rep genes, and adenovirus helper genes. Cells were incubated for 72 hours until harvest of AAV6 from cells by three freeze-thaw cycles followed by a 45 min incubation with TurboNuclease at 250 U/mL (Abnova, Heidelberg, Germany). AAV vectors were purified on an iodixanol density gradient by ultracentrifugation at 48,000 rpm for two hours at 18° C. AAV vectors were extracted at the 60-40% iodixanol interface and dialyzed three times in PBS with 5% sorbitol in the last dialysis using a 10K MWCO Slide-A-Lyzer G2 Dialysis Cassette (Thermo Fisher Scientific, Santa Clara, Calif., USA). Vectors were added pluronic acid to a final concentration of 0.001%, aliquoted, and stored at −80° C. until use. AAV6 vectors were titered using quantitative PCR to measure number of vector genomes as described here[49].

CD34+ Hematopoietic Stem and Progenitor Cells

Frozen CD34$^+$ HSPCs derived from bone marrow or mobilized peripheral blood were purchased from AllCells (Alameda, Calif., USA) and thawed according to the manufacturer's instructions. CD34$^+$ HSPCs from cord blood were either purchased frozen from AllCells or acquired from donors under informed consent via the Binns Program for Cord Blood Research at Stanford University and used fresh without freezing. CD34+ HSPCs from SCD patients were purified within 24 hours of the scheduled apheresis. For volume reduction via induced rouleaux formation, whole blood was added 6% Hetastarch in 0.9% Sodium Chloride Injection (Hospira, Inc., Lake Forest, Ill., USA) in a proportion of 5:1 (v/v). Following a 60- to 90-minute incubation at room temperature, the top layer, enriched for HSPCs and mature leukocytes, was carefully isolated with minimal disruption of the underlying fraction. Cells were pelleted, combined, and resuspended in a volume of PBS with 2 mM EDTA and 0.5% BGS directly proportional to the fraction of residual erythrocytes (typically 200-400 mL). MNCs were obtained by density gradient separation using Ficoll and CD34$^+$ HSPCs were purified using the CD34$^+$ Microbead Kit Ultrapure (Miltenyi Biotec, San Diego, Calif., USA) according to the manufacturer's protocol. Cells were cultured overnight and then stained for CD34 and CD45 using APC anti-human CD34 (Clone 561; Biolegend, San Jose, Calif., USA) and BD Horizon V450 anti-human CD45 (Clone HI30; BD Biosciences, San Jose, Calif., USA), and a pure population of HSPCs defined as CD34$^{bright}$/CD45$^{dim}$ were obtained by cell sorting on a FACS Aria II cell sorter (BD Biosciences, San Jose, Calif., USA). All CD34$^+$ HSPCs were cultured in StemSpan SFEM II (Stemcell Technologies, Vancouver, Canada) supplemented with SCF (100 ng/ml), TPO (100 ng/ml), Flt3-Ligand (100 ng/ml), IL-6 (100 ng/ml), and StemRegenin1 (0.75 mM). Cells were cultured at 37° C., 5% CO$_2$, and 5% 02.

Electroporation and Transduction of Cells

The HBB and IL2RG synthetic sgRNAs used here were purchased from TriLink BioTechnologies (San Diego, Calif., USA) with chemically modified nucleotides at the three terminal positions at both the 5' and 3' ends. Modified nucleotides contained 2'O-Methyl 3'phosphorothioate and the sgRNA was HPLC-purified. The genomic sgRNA target sequences with PAM in bold were: HBB: 5'-CTTGCCC-CACAGGGCAGTAACGG-3' (SEQ ID NO:42)[50, 51]; IL2RG: 5'-TGGTAATGATGGCTTCAACATGG-3' (SEQ ID NO:44). Cas9 mRNA containing 5-methylcytidine and pseudouridine was purchased from TriLink BioTechnologies. Cas9 protein was purchased from Life Technologies. Cas9 RNP was made by incubating protein with sgRNA at a molar ratio of 1:2.5 at 25° C. for 10 min immediately prior to electroporation. CD34$^+$ HSPCs were electroporated 1-2 days after thawing or isolation. CD34$^+$ HSPCs were electroporated using the Lonza Nucleofector 2b (program U-014) and the Human T Cell Nucleofection Kit (VPA-1002, Lonza) as it has been found that this combination is superior in optimization studies. The following conditions were used: 5×10$^6$ cells/ml, 300 ug/ml Cas9 protein complexed with sgRNA at 1:2.5 molar ratio, or 100 μg/ml synthetic chemically modified sgRNA with 150 μg/ml Cas9 mRNA (TriLink BioTechnologies, non-HPLC purified). Following electroporation, cells were incubated for 15 minutes at 37° C., after which AAV6 donor vectors were added at an MOI (vector genomes/cell) of 50,000-100,000 and then incubated at 30° C. or 37° C. overnight (if incubated at 30° C., plates were then transferred to 37° C.). Alternatively, for targeting experiments of freshly sorted HSCs (FIG. 35E), cells were electroporated using the Lonza Nucleofector 4D (program EO-100) and the P3 Primary Cell Nucleofection Kit (V4XP-3024). For the electroporation of 80 million CD34$^+$ HSPCs, the Lonza 4D-Nucleofector LV unit (program DZ-100) and P3 Primary Cell Kit were used.

Measuring Targeted Integration of Fluorescent and tNGFR Donors

Rates of targeted integration of GFP and tNGFR donors was measured by flow cytometry at least 18 days after electroporation. Targeted integration of a tNGFR expression cassette was measured by flow cytometry of cells stained with APC-conjugated anti-human CD271 (NGFR) antibody (BioLegend, clone: ME20.4). For sorting of GFP$^{high}$ or tNGFR$^{high}$ populations, cells were sorted on a FACS Aria II SORP using the LIVE/DEAD Fixable Blue Dead Cell Stain Kit (Life Technologies) to discriminate live and dead cells according to manufacturer's instructions.

Positive Selection and Enrichment of tNGFR+ HSPCs

Positive selection of targeted HSPCs was performed using the CD271 (tNGFR) Microbead Kit (Miltenyi Biotech, Auburn, Calif. USA), according to the manufacturer's instructions 72 hours post-electroporation. Briefly, tNGFR$^+$ cells were magnetically labeled with CD271 Microbeads, after which the cell suspension was loaded onto an equilibrated MACS column inserted in the magnetic field of a MACS separator. The columns were washed three times, and enriched cells were eluted by removing the column from the magnetic field and eluting with PBS. Enrichment was determined by flow cytometry during culture for 2-3 weeks by FACS analysis every 3 days.

Immunophenotyping of Targeted HSPCs

Harvested wells were stained with LIVE/DEAD Fixable Blue Dead Cell Stain (Life Technologies) and then with anti-human CD34 PE-Cy7 (581, BioLegend), CD38 Alexa Fluor 647 (AT1, Santa Cruz Biotechnologies, Santa Cruz, Calif., USA), CD45RA BV 421 (HI100, BD Biosciences), and CD90 BV605 (5E10, BioLegend) and analyzed by flow cytometry. For sorting of CD34$^+$ or CD34$^+$/CD38$^-$/CD90$^+$ cells, CB-derived CD34$^+$ HSPCs were stained directly after isolation from blood with anti-human CD34 FITC (8G12, BD Biosciences), CD90 PE (5E10, BD Biosciences), CD38 APC (HIT2, BD Bioscience), and cells were sorted on a FACS Aria II (BD Bioscience), cultured overnight, and then electroporated with HBB RNP and transduced with HBB GFP rAAV6 using optimized parameters.

Measuring Targeted Integration of the E6V Donor

For assessing the allele modification frequencies in samples with targeted integration of the E6V rAAV6 donor, PCR amplicons spanning the targeted region (see, FIG. 30A) were created using one primer outside the donor homology arm and one inside: HBB_outside 5'-GGTGACAAT-TTCTGCCAATCAGG-3' (SEQ ID NO:45) and HBB_inside: 5'-GAATGGTAGCTGGATTGTAGCTGC-3' (SEQ ID NO:46). The PCR product was gel-purified and re-amplified using a nested primer set (HBB_nested_fw: 5'-GAAGA-TATGCTTAGAACCGAGG-3' (SEQ ID NO:16) and HBB-_nested_rw: 5'-CCACATGCCCAGTTTCTATTGG-3') (SEQ ID NO:17) to create a 685 bp PCR amplicon (see, FIG. 30A) that was gel-purified and cloned into a TOPO plasmid using the Zero Blunt TOPO PCR Cloning Kit (Life Technologies) according to the manufacturer's protocol. TOPO reactions were transformed into XL-1 Blue competent cells, plated on kanamycin-containing agar plates, and single colonies were sequenced by McLab (South San Francisco, Calif., USA) by rolling circle amplification followed by sequencing using the following primer: 5'-GAAGA-TATGCTTAGAACCGAGG-3' (SEQ ID NO:16). For each of the six unique CD34+ donors used in this experiment, 100 colonies were sequenced. Additionally, 100 colonies derived from an AAV-only samples were sequenced and no integration events were detected.

Measuring INDEL Frequencies

INDEL frequencies were quantified using the TIDE software[52] (Tracking of Indels by Decomposition) and sequenced PCR-products obtained by PCR amplification of genomic DNA extracted at least four days following electroporation as previously described".

Methylcellulose Colony-Forming Unit (CFU) Assay

The CFU assay was performed by FACS sorting of single cells into 96-well plates containing MethoCult Optimum (Stemcell Technologies) four days after electroporation and transduction. After 12 to 16 days, colonies were counted and scored based on their morphological appearance in a blinded fashion.

Genotyping of Methylcellulose Colonies

DNA was extracted from colonies formed in methylcellulose from FACS sorting of single cells into 96-well plates. Briefly, PBS was added to wells with colonies, and the contents were mixed and transferred to a U-bottomed 96-well plate. Cells were pelleted by centrifugation at 300×g for 5 min followed by a wash with PBS. Finally, cells were resuspended in 25 µl QuickExtract DNA Extraction Solution (Epicentre, Madison, Wis., USA) and transferred to PCR plates, which were incubated at 65° C. for 10 min followed by 100° C. for 2 minutes. Integrated or non-integrated alleles were detected by PCR. For detecting HBB GFP integrations at the 3' end, two different PCRs were set up to detect integrated (one primer in insert and one primer outside right homology arm) and non-integrated alleles (primer in each homology arm), respectively (see, FIGS. 33A-C). HBB_int_fw: 5'-GTACCAGCACGCCTTCAAGACC-3' (SEQ ID NO:18), HBB_int_rv: 5'-GATCCTGAGACTTC-CACACTGATGC-3' (SEQ ID NO:23), HBB_no_int_fw: 5'-GAAGATATGCTTAGAACCGAGG-3' (SEQ ID NO:16), HBB_no_int_rv: 5'-CCACATGCCCAGTTTCT-ATTGG-3' (SEQ ID NO:17). For detecting HBB tNGFR integrations at the 5' end, a 3-primer PCR methodology was used to detect the integrated and non-integrated allele simultaneously (see, FIGS. 34A-34C). HBB_outside_5'Arm fw: GAAGATATGCTTAGAACCGAGG (SEQ ID NO:16), SFFV rev: ACCGCAGATATCCTGTTTGG (SEQ ID NO:22), HBB_inside_3'Arm_rev: CCA-CATGCCCAGTTTCTATTGG (SEQ ID NO:17). Note that for the primers assessing non-integrated alleles, the Cas9 cut site is at least 90 bp away from the primer binding sites (PBSs) and since CRISPR/Cas9 generally introduces INDELs of small sizes, the PBSs should only very rarely be disrupted by an INDEL.

Transplantation of CD34+ HSPCs into NSG Mice

For in vivo studies, 6 to 8 week-old NOD scid gamma (NSG) mice were purchased from the Jackson laboratory (Bar Harbor, Me. USA). The experimental protocol was approved by Stanford University's Administrative Panel on Lab Animal Care. Sample sizes were not chosen to ensure adequate power to detect a pre-specified effect size. Four days after electroporation/transduction or directly after sorting, 500,000 cells (or 100,000-500,000 cells for the GFP$^{high}$ group) were administered by tail-vein injection into the mice after sub-lethal irradiation (200 cGy) using an insulin syringe with a 27 gauge×½" needle. Mice were randomly assigned to each experimental group and evaluated in a blinded fashion. For secondary transplants, human cells from the RNP+AAV group were pooled and CD34+ cells were selected using a CD34 bead enrichment kit (MACS CD34 MicroBead Kit UltraPure, human, Miltenyi Biotec), and finally cells were injected into the femurs of female secondary recipients (3 mice total). Because GFP$^{high}$ mice had low engraftment, they were not CD34+-selected, but total mononuclear cells were filtered, pooled, and finally injected into the femur of two secondary recipients.

Assessment of Human Engraftment

At week 16 post-transplantation, mice were sacrificed, total mouse bone marrow (BM) (2× femur, 2× tibia, 2× humerus, sternum, 2× pelvis, and spine) was collected and crushed using mortar and pestle. Mononuclear cells (MNCs) were enriched using Ficoll gradient centrifugation (Ficoll-Paque Plus, GE Healthcare, Sunnyvale, Calif., USA) for 25 min at 2,000×g, room temperature. Cells were blocked for nonspecific antibody binding (10% vol/vol, TruStain FcX, BioLegend) and stained (30 min, 4° C., dark) with monoclonal anti-human CD45 V450 (HI30, BD Biosciences), CD19 APC (HIB19, BD Biosciences), CD33 PE (WM53, BD Biosciences), HLA-ABC APC-Cy7 (W6/32, BioLegend), anti-mouse CD45.1 PE-Cy7 (A20, eBioScience, San Diego, Calif., USA), and anti-mouse PE-Cy5 mTer119 (TER-119, eBioscience) antibodies. Normal multi-lineage engraftment was defined by the presence of myeloid cells (CD33+) and B-cells (CD19+) within engrafted human CD45+/HLA-ABC+ cells. Parts of the mouse BM were used for CD34-enrichment (MACS CD34 MicroBead Kit Ultra-Pure, human, Miltenyi Biotec) and the presence of human hematopoietic stem and progenitor cells (HSPCs) was assessed by staining with anti-human CD34 APC (8G12, BD Biosciences), CD38 PE-Cy7 (HB7, BD Biosciences), CD10 APC-Cy7 (HI10a, BioLegend), and anti-mouse CD45.1 PE-Cy5 (A20, eBioScience) and analyzed by flow cytometry. The estimation of the total number of modified human cells in the bone marrow (BM) at week 16 post-transplant was calculated by multiplying percent engraftment with percent GFP+ cells among engrafted cells. This number was multiplied by the total number of MNCs in the BM of a NSG mouse (1.1×10$^8$ per mouse) to give the total number of GFP+ human cells in the total BM of the transplanted mice. The total number of MNCs in the BM of a NSG mouse was calculated by counting the total number of MNCs in one femur in four NSG mice. The total number of MNCs in one mouse was then calculated assuming that one femur is 6.1% of the total marrow, as previously observed[53].

Differentiation of CD34+ HSPCs into Erythrocytes In Vitro

SCD patient-derived HSPCs were cultured in three phases following targeting at 37° C. and 5% CO$_2$ in SFEM II media according to previously established protocols[44, 45]. Media was supplemented with 100 U/mL penicillin/streptomycin, 2 mM L glutamine, 40 µg/mL lipids, 100 ng/mL SCF, 10 ng/mL IL-3 (PeproTech), 0.5 U/mL erythropoietin (eBiosciences), and 200 µg/mL transferrin (Sigma Aldrich). In the first phase, corresponding to days 0-7 (day 0 being day 4 post-electroporation), cells were cultured at 10$^5$ cells/mL. In the second phase, corresponding to days 7-11, cells were maintained at 10$^5$ cells/mL and erythropoietin was increased to 3 U/mL. In the third and final phase (days 11-21) cells were cultured at 10$^6$ cells/mL with 3 U/mL of erythropoietin and 1 mg/mL of transferrin. Erythrocyte differentiation of edited and non-edited HSPCs was assessed by flow cytometry using the following antibodies: hCD45 V450 (HI30, BD Biosciences), CD34 FITC (8G12, BD Biosciences), CD71 PE-Cy7 (OKT9, Affymetrix), and CD235a PE (GPA) (GA-R2, BD Biosciences).

Assessment of mRNA Levels in Differentiated Erythrocytes

RNA was extracted from 100,000-250,000 differentiated erythrocytes between days 16 and 21 of erythroid differentiation using the RNeasy Mini Kit (Qiagen, Hilden, Germany) and was DNase-treated with RNase-Free DNase Set (Qiagen). cDNA was made from 100 ng RNA using the iScript Reverse Transcription Supermix for RT-qPCR (Bio-Rad, Hercules, Calif.). Levels of HbS, HbA (from corrective SNP donor), and HbA-AA (anti-sickling HBB cDNA donor) were quantified by qPCR using the following primers and FAM/ZEN/IBFQ-labeled hydrolysis probes purchased as custom-designed PrimeTime qPCR Assays from IDT (San Jose, Calif.): HbS primer (fw): 5' TCACTAGCAACCT- CAAACAGAC 3' (SEQ ID NO:24), HbS primer (rv): 5' ATCCACGTTCACCTTGCC 3' (SEQ ID NO:25), HbS probe: 5' TAACGGCAGACTTCTCCACAGGAGTCA 3' (SEQ ID NO:26), HbA primer (fw): 5' TCACTAGCAACCTCAAACAGAC 3' (SEQ ID NO:24), HbA primer (rv): 5' ATCCACGTTCACCTTGCC 3' (SEQ ID NO:25), HbA probe: 5' TGACTGCGGAT-TTTTCCTCAGGAGTCA 3' (SEQ ID NO:33), HbAS3 primer fw: 5' GTGTATCCCTGGACACAAAGAT 3' (SEQ ID NO:34), HbAS3 primer (rv): 5' GGGCTTTGACTTTGGGATTTC 3' (SEQ ID NO:30), and HbAS3 probe: 5' TTCGAAAGCTTCGGCGACCTCA 3' (SEQ ID NO:31). Primers for HbA and HbS were identical, but probes differed by six nucleotides, and therefore it was experimentally confirmed that these two assays did not cross-react with targets. To normalize for RNA input, levels of the reference gene RPLP0 were determined in each sample using IDT's predesigned RPLP0 assay (Hs.PT.58.20222060). qPCR reactions were carried out on a LightCycler 480 II (Roche, Basel, Schwitzerland) using the SsoAdvanced Universal Probes Supermix (BioRad) following manufacturer's protocol and PCR conditions of 10 minutes at 95° C., 50 cycles of 15 seconds at 95° C. and 60 seconds at 58° C. Relative mRNA levels were determined using the relative standard curve method, in which a standard curve for each gene was made from serial dilutions of the cDNA. The standard curve was used to calculate relative amounts of target mRNA in the samples relative to levels of RPLP0.

REFERENCES

1. Lucarelli, G. et al. Allogeneic cellular gene therapy in hemoglobinopathies—evaluation of hematopoietic SCT in sickle cell anemia. *Bone marrow transplantation* 47, 227-230 (2012).
2. Gaziev, J. & Lucarelli, G. Allogeneic cellular gene therapy for hemoglobinopathies. *Hematology/oncology clinics of North America* 24, 1145-1163 (2010).
3. Naldini, L. Ex vivo gene transfer and correction for cell-based therapies. *Nature reviews. Genetics* 12, 301-315 (2011).
4. Porteus, M. Genome Editing: A New Approach to Human Therapeutics. *Annual review of pharmacology and toxicology* 56, 163-190 (2016).
5. Smithies, O., Gregg, R. G., Boggs, S. S., Koralewski, M. A. & Kucherlapati, R. S. Insertion of DNA sequences into the human chromosomal beta-globin locus by homologous recombination. *Nature* 317, 230-234 (1985).
6. Porteus, M. H. & Baltimore, D. Chimeric nucleases stimulate gene targeting in human cells. *Science* 300, 763 (2003).
7. Rouet, P., Smih, F. & Jasin, M. Expression of a site-specific endonuclease stimulates homologous recombination in mammalian cells. *Proceedings of the National Academy of Sciences of the United States of America* 91, 6064-6068 (1994).
8. Voit, R. A., Hendel, A., Pruett-Miller, S. M. & Porteus, M. H. Nuclease-mediated gene editing by homologous recombination of the human globin locus. *Nucleic acids research* 42, 1365-1378 (2014).
9. Hoban, M. D. et al. Correction of the sickle cell disease mutation in human hematopoietic stem/progenitor cells. *Blood* 125, 2597-2604 (2015).
10. Hsu, P. D., Lander, E. S. & Zhang, F. Development and applications of CRISPR-Cas9 for genome engineering. *Cell* 157, 1262-1278 (2014).
11. Doudna, J. A. & Charpentier, E. Genome editing. The new frontier of genome engineering with CRISPR-Cas9. *Science* 346, 1258096 (2014).
12. Jinek, M. et al. A programmable dual-RNA-guided DNA endonuclease in adaptive bacterial immunity. *Science* 337, 816-821 (2012).
13. Kass, E. M. & Jasin, M. Collaboration and competition between DNA double-strand break repair pathways. *FEBS letters* 584, 3703-3708 (2010).
14. Porteus, M. H. Towards a new era in medicine: therapeutic genome editing. *Genome biology* 16, 286 (2015).
15. Woods, N. B., Bottero, V., Schmidt, M., von Kalle, C. & Verma, I. M. Gene therapy: therapeutic gene causing lymphoma. *Nature* 440, 1123 (2006).
16. Hubbard, N. et al. Targeted gene editing restores regulated CD40L expression and function in X-HIGM T cells. *Blood* (2016).
17. Hendel, A. et al. Chemically modified guide RNAs enhance CRISPR-Cas genome editing in human primary cells. *Nature biotechnology* 33, 985-989 (2015).
18. Baum, C. M., Weissman, I. L., Tsukamoto, A. S., Buckle, A. M. & Peault, B. Isolation of a candidate human hematopoietic stem-cell population. *Proceedings of the National Academy of Sciences of the United States of America* 89, 2804-2808 (1992).
19. Mukherjee, S. & Thrasher, A. J. Gene therapy for PIDs: progress, pitfalls and prospects. *Gene* 525, 174-181 (2013).
20. Cavazzana-Calvo, M. et al. Transfusion independence and HMGA2 activation after gene therapy of human beta-thalassaemia. *Nature* 467, 318-322 (2010).
21. Naldini, L. Gene therapy returns to centre stage. *Nature* 526, 351-360 (2015).
22. Jenq, R. R. & van den Brink, M. R. Allogeneic haematopoietic stem cell transplantation: individualized stem cell and immune therapy of cancer. *Nature reviews. Cancer* 10, 213-221 (2010).
23. Genovese, P. et al. Targeted genome editing in human repopulating haematopoietic stem cells. *Nature* 510, 235-240 (2014).
24. Wang, J. et al. Homology-driven genome editing in hematopoietic stem and progenitor cells using ZFN mRNA and AAV6 donors. *Nature biotechnology* 33, 1256-1263 (2015).
25. De Ravin, S. S. et al. Targeted gene addition in human CD34(+) hematopoietic cells for correction of X-linked chronic granulomatous disease. *Nature biotechnology* 34, 424-429 (2016).
26. Sather, B. D. et al. Efficient modification of CCR5 in primary human hematopoietic cells using a megaTAL nuclease and AAV donor template. *Science translational medicine* 7, 307ra156 (2015).
27. Wang, J. et al. Highly efficient homology-driven genome editing in human T cells by combining zinc-finger nuclease mRNA and AAV6 donor delivery. *Nucleic acids research* 44, e30 (2016).
28. Miller, D. G., Petek, L. M. & Russell, D. W. Adeno-associated virus vectors integrate at chromosome breakage sites. *Nature genetics* 36, 767-773 (2004).
29. Russell, D. W. & Hirata, R. K. Human gene targeting by viral vectors. *Nature genetics* 18, 325-330 (1998).
30. Barzel, A. et al. Promoterless gene targeting without nucleases ameliorates haemophilia B in mice. *Nature* 517, 360-364 (2015).
31. Hoban, M. D., Orkin, S. H. & Bauer, D. E. Genetic treatment of a molecular disorder:

gene therapy approaches to sickle cell disease. *Blood* (2016).
32. Locatelli, F. et al. Related umbilical cord blood transplantation in patients with thalassemia and sickle cell disease. *Blood* 101, 2137-2143 (2003).
33. Kean, L. S. et al. Chimerism and cure: hematologic and pathologic correction of murine sickle cell disease. *Blood* 102, 4582-4593 (2003).
34. Bonini, C. et al. HSV-TK gene transfer into donor lymphocytes for control of allogeneic graft-versus-leukemia. *Science* 276, 1719-1724 (1997).
35. Ciceri, F. et al. Infusion of suicide-gene-engineered donor lymphocytes after family haploidentical haemopoietic stem-cell transplantation for leukaemia (the TK007 trial): a non-randomised phase I-II study. *The Lancet. Oncology* 10, 489-500 (2009).
36. Oliveira, G. et al. Tracking genetically engineered lymphocytes long-term reveals the dynamics of T cell immunological memory. *Science translational medicine* 7, 317ra198 (2015).
37. Bonini, C. et al. Safety of retroviral gene marking with a truncated NGF receptor. *Nature medicine* 9, 367-369 (2003).
38. Seita, J. & Weissman, I. L. Hematopoietic stem cell: self-renewal versus differentiation. *Wiley interdisciplinary reviews. Systems biology and medicine* 2, 640-653 (2010).
39. Majeti, R., Park, C. Y. & Weissman, I. L. Identification of a hierarchy of multipotent hematopoietic progenitors in human cord blood. *Cell stem cell* 1, 635-645 (2007).
40. Doulatov, S., Notta, F., *Laurenti*, E. & Dick, J. E. Hematopoiesis: a human perspective. *Cell stem cell* 10, 120-136 (2012).
41. Weidner, C. I. et al. Hematopoietic stem and progenitor cells acquire distinct DNA-hypermethylation during in vitro culture. *Scientific reports* 3, 3372 (2013).
42. Gu, A. et al. Engraftment and lineage potential of adult hematopoietic stem and progenitor cells is compromised following short-term culture in the presence of an aryl hydrocarbon receptor antagonist. *Human gene therapy methods* 25, 221-231 (2014).
43. Levasseur, D. N. et al. A recombinant human hemoglobin with anti-sickling properties greater than fetal hemoglobin. *The Journal of biological chemistry* 279, 27518-27524 (2004).
44. Dulmovits, B. M. et al. Pomalidomide reverses gamma-globin silencing through the transcriptional reprogramming of adult hematopoietic progenitors. *Blood* 127, 1481-1492 (2016).
45. Hu, J. et al. Isolation and functional characterization of human erythroblasts at distinct stages: implications for understanding of normal and disordered erythropoiesis in vivo. *Blood* 121, 3246-3253 (2013).
46. Romero, Z. et al. beta-globin gene transfer to human bone marrow for sickle cell disease. *The Journal of clinical investigation* (2013).
47. Fares, I. et al. Cord blood expansion. Pyrimidoindole derivatives are agonists of human hematopoietic stem cell self-renewal. *Science* 345, 1509-1512 (2014).
48. Khan, I. F., Hirata, R. K. & Russell, D. W. AAV-mediated gene targeting methods for human cells. *Nature protocols* 6, 482-501 (2011).
49. Aurnhammer, C. et al. Universal real-time PCR for the detection and quantification of adeno-associated virus serotype 2-derived inverted terminal repeat sequences. *Human gene therapy methods* 23, 18-28 (2012).
50. Hendel, A. et al. Quantifying genome-editing outcomes at endogenous loci with SMRT sequencing. *Cell reports* 7, 293-305 (2014).
51. Cradick, T. J., Fine, E. J., Antico, C. J. & Bao, G. CRISPR/Cas9 systems targeting beta-globin and CCR5 genes have substantial off-target activity. *Nucleic acids research* 41, 9584-9592 (2013).
52. Brinkman, E. K., Chen, T., Amendola, M. & van Steensel, B. Easy quantitative assessment of genome editing by sequence trace decomposition. *Nucleic acids research* 42, e168 (2014).
53. Boggs, D. R. The total marrow mass of the mouse: a simplified method of measurement. *American journal of hematology* 16, 277-286 (1984).

Figure 41C:
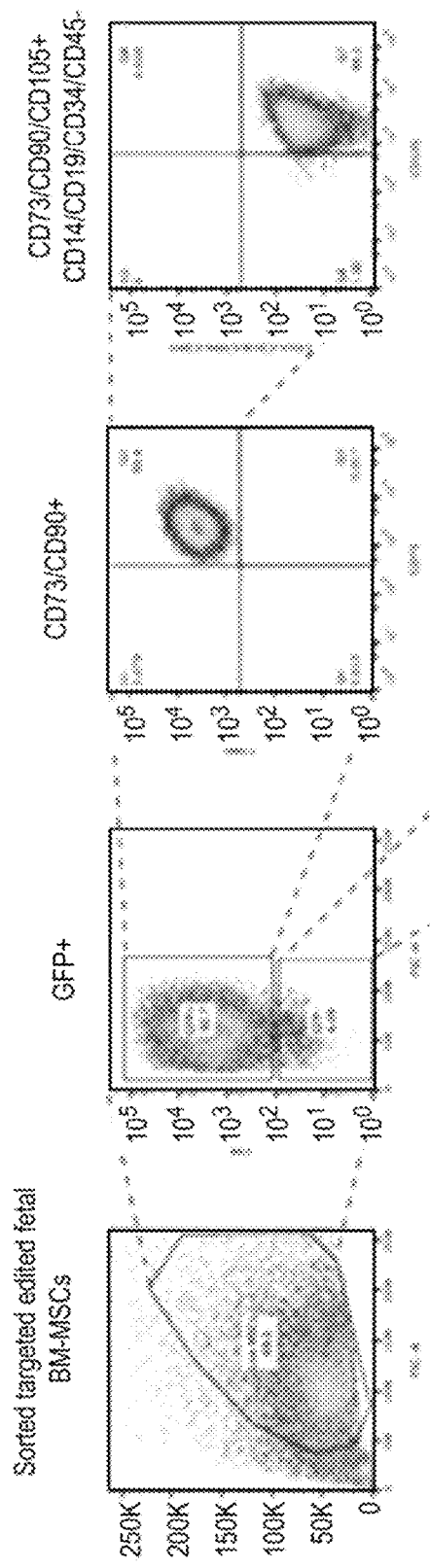
Figure 41D:
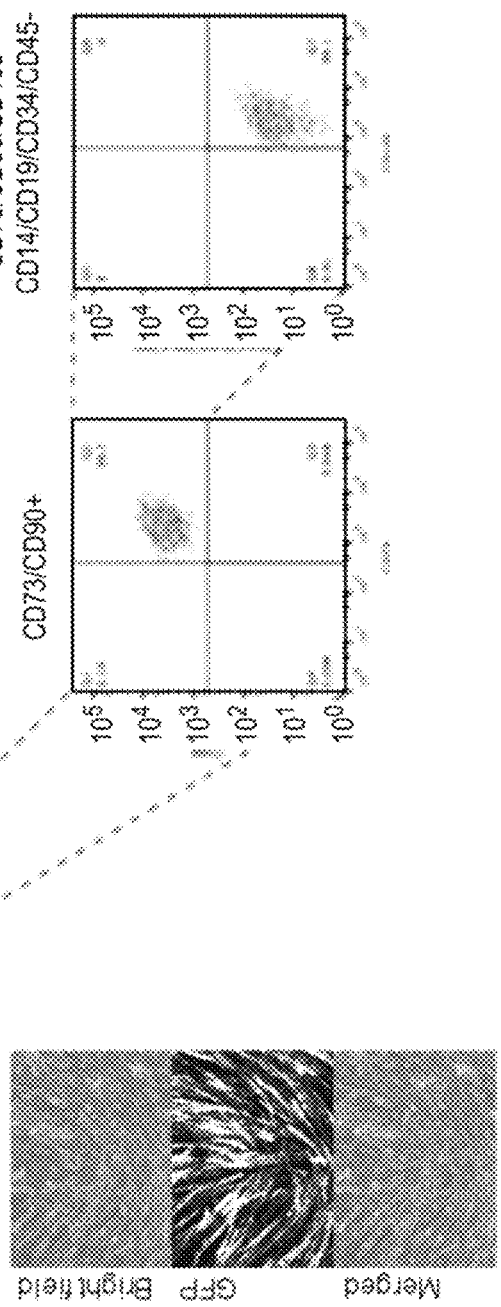

Example 3. Genome Editing by Homologous Recombination in Human Mesenchymal Stromal Cells (MSCs) Using rAAV6 and Chemically Modified sgRNAs This example demonstrates that the HR-mediated gene targeting and enrichment methods described in Examples 1 and 2 can be used to target MSCs and enrich for a population of targeted MSCs. In particular, FIG. 41A shows primary MSCs from two different sources were targeted at the HBB safe harbor locus with median efficiencies of 18.05% in fetal bone marrow (BM)-MSCs and 19.40% in umbilical cord blood (UCB)-MSCs. Both values were significantly higher than those of controls which were only transduced with donor AAV6. FIG. 41B shows that insertions and deletions can be created in MSCs at two different safe harbor loci, HBB and CCR5, using MS-modified guide RNA and Cas9 mRNA. FIGS. 41C and 41D show that targeted MSCs still maintain surface marker expression and morphology of MSCs, indicating that the gene targeting and enrichment methods described herein did not alter the phenotypes of MSCs beyond GFP expression.

MSCs have many potential applications in cell therapy due to their ability to facilitate angiogenesis, tissue regeneration, and immunomodulation. MSCs from various tissue sources are now being studied in clinical trials for putative therapy for a wide range of diseases and conditions including myocardial infarction, osteoarthritis, and graft-versus-host disease. Some therapies such as cancer therapy and tissue regeneration can be enhanced using engineered MSCs. However, current methods for engineering MSCs rely on retroviral and lentiviral vectors which have potential risks of insertional mutagenesis that may lead to cancer or other complications. The methods described herein advantageously provide a way to engineer MSCs in a controlled manner by inserting a gene expression cassette into known safe harbor loci to avoid the problems created by random insertion while at the same time allow the engineered trait to be passed onto subsequent generations of cells.

Materials and Methods

Cell Culture

Mesenchymal stromal cells (MSCs) were expanded as monolayers in complete medium consisting of MEM-α supplemented with 16.7% fetal bovine serum (FBS), 100 mg/ml streptomycin, 100 units/ml penicillin, and 2 mM L-glutamine. Cells were cultured at 37° C., 5% $CO_2$, and normoxic oxygen level until 80% to 90% confluency was reached. Medium was replaced twice weekly.

Nucleofection and Transduction

Cells at 80-90% confluency were rinsed with phosphate-buffered saline (PBS), trypsinized with TrypLE™ Express (Thermo Fisher Scientific Inc., MA, USA). Trypsinization reaction was stopped using 1 volume of complete medium per 1 volume of TrypLE™ Express, and cells were pelleted by centrifugation at 300×g for 3-5 minutes. For one nucleofection reaction, $5.0×10^5$ cells were resuspended in 100 µl of Opti-MEM® Reduced Serum Medium (Thermo Fisher Scientific Inc., MA, USA) with 10 µg modified guide RNA and 15 µg Cas9 mRNA (SmeC, TriLink BioTechnologies, San Diego, Calif., USA). The cells were nucleofected using the Lonza 4D-Nucleofector® System, Unit X, program CM-119. Immediately after nucleofection, cells were resuspended in an additional 500 µl of OptiMEM® containing $1.0×10^5$ MOI worth of AAV6 donor vector and incubated at 37° C. for 15 minutes. Cells were then seeded at $2.0×10^3$ to $1.0×10^4$ cells per $cm^2$ in complete medium and maintained at 37° C., 5% $CO_2$, and normoxic oxygen level for 48 hours before medium is replaced. Cells were subcultured and analyzed for GFP expression once 80% confluency is reached.

Flow Cytometry and FACS Enrichment

Efficiency of targeting was measured from the fraction of nucleofected and transduced cells with GFP expression. GFP expression was analyzed by flow cytometry for cells with MFI above that of episomal expression from donor cassette on an Accuri C6 flow cytometer (BD Biosciences, San Jose, Calif., USA).

For enrichment, starting at 5 days post-nucleofection, GFP-expressing targeted cells were enriched by fluorescent-activated cell sorting (FACS). Prior to sorting, cells were rinsed, trypsinized, and pelleted. The pelleted cells were washed twice with and resuspended in FACS buffer (2% FBS, 2 mM EDTA in PBS) at a density of $0.5-1.0×10^6$ cells per ml and kept on ice until sorting. GFP-expressing cells were sorted using a BD FACSARIA II cytometer (BD Biosciences, San Jose, Calif., USA) into sort buffer (30% FBS in PBS). Sorted cells were pelleted and resuspended in complete medium and expanded as described above.

Example 4. Enrichment Scheme Protocol for Hematopoietic Stem and Progenitor Cells (HSPCs)

This example provides an exemplary protocol that enables the enrichment of a population of genetically modified primary cells having targeted integration at a target nucleic acid. Although the following protocol relates to the enrichment of a population of gene-targeted hematopoietic stem and progenitor cells (HSPCs) using the CRISPR/Cas9 system and recombinant adeno-associated viral vector, serotype 6 (rAAV6), this enrichment scheme is applicable to any primary cell of interest, including other types of primary blood cells (e.g., immune cells such as T cells, B cells, dendritic cells, natural killer cells, macrophages, neutrophils, eosinophils, basophils, and mast cells) and primary mesenchymal cells (e.g., mesenchymal stem cells (MSCs), mesenchymal progenitor cells, mesenchymal precursor cells, and differentiated mesenchymal cells), as well as any nuclease-mediated gene-editing platform (e.g., zinc finger nucleases (ZFNs), transcription activator-like effector nucleases (TALENs), meganucleases) and any rAAV serotype or a variant thereof.

Day -2: Following CD34+ HSPC harvest from either mobilized peripheral blood, adult bone marrow, or cord blood, resuspend cells in cytokine cocktail and incubate at 37° C. for 24-48 hours to stimulate cell cycling.

Day 0: Nucleofect HSPCs with a gene-specific Cas9-MS sgRNA (either as "All RNA" or RNP delivery) and then resuspend cells in cytokine media and incubate at 15 min at 37° C. Also "Mock" nucleofect cells for the "AAV only" sample for the enrichment gating scheme.

15 min: Add gene-specific rAAV6 (MOIs ranging from 1000-100,000) containing a gene reporter cassette comprising a selectable marker such as GFP, mCherry, or tNGFR to be inserted between gene-homologous sequences such as a target nucleic acid sequence and then incubate at 30° C. or 37° C. overnight. Cell concentration is 1,000,000 cells/ml.

Day 1: Move cells to 37° C. if incubated at 30° C. after electroporation.

Day 2: Dilute cells to 400,000 cells/ml to promote viability.

Day 2-4: Enrichment can be performed at day 2, day 3, or day 4 depending on locus. 3 samples are prepared for the gating scheme: (1) non-transduced sample; (2) rAAV6 only sample; and (3) nuclease+rAAV6 sample. First run the non-transduced sample on a fluorescence-activated cell sorting (FACS) machine to get background fluorescent intensities. Then run the AAV only sample and make the "high" gate above the highest fluorescent positive cell. Specifically, the "high" population should have less than 1% positive cells in the rAAV6 only sample. Then run the nuclease+rAAV6 and there should be a "high" population generated if homologous recombination (HR) occurred. Sort this "high" population and greater than 90% of cells should have on-target integration event at one (monoallelic) or two alleles (biallelic). Alternatively, perform bead enrichment according to the manufacturer's protocol for the specific expressed cell surface marker. For example, magnetic bead separation such as magnetic-activated cell sorting (MACS) can be performed to enrich for the population of gene-targeted primary cells.

Figure 42:
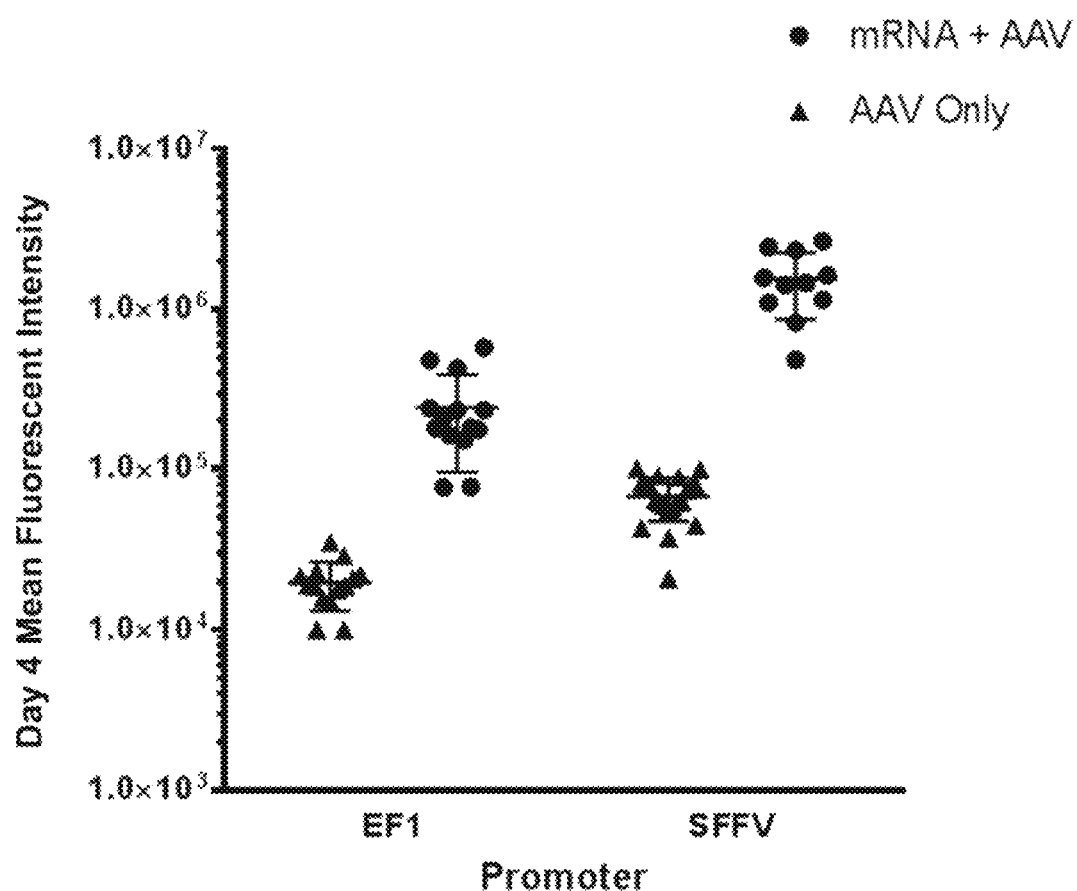
FIG. 42 shows the results of HSPCs that were nucleofected with Cas9 mRNA and MS sgRNA, precomplexed rCas9 with MS sgRNA, or Mock, and then rAAV6s (EF1-GFP or SFFV-GFP) were added to the cells. Four days later, cells were analyzed via FACS for percentage of GFP positive cells and mean fluorescent intensity (MFI) of the GFP+ cells.

FIG. 42 shows the results of HSPCs that were nucleofected with Cas9 mRNA and MS sgRNA ("All RNA"), precomplexed rCas9 protein with MS sgRNA (RNP), or Mock, and then rAAV6s (EF1-GFP or SFFV-GFP) were added to the cells. Four days later, cells were analyzed via FACS for percentage of GFP positive cells and mean fluorescent intensity (MFI) of the GFP+ cells. This data quantifies the log-fold GFP MFI increase observed when adding HBB-specific CRISPR and rAAV6 components ("mRNA+AAV") compared to just rAAV6 alone ("AAV Only") for two different promoters. The increase in expression of the selectable marker GFP upon HR was 12-fold for the EF1 promoter and 22-fold for the SFFV promoter compared to their respective "AAV Only" samples. This data also shows that this MFI shift was not dependent on promoters (log-fold increase in selectable marker expression was observed with both EF1 and SFFV promoters) in human HSPCs. Without being bound by any particular theory, the MFI shift was due to higher transgene expression from transcription in intact chromosomes (with histones) compared to episomes and thus confirmed targeted HR and demonstrates that the MFI shift is a ubiquitous event upon on-target HR.

Example 5. Multiplexing of Genome Editing in HSPCs and Human T Cells

This example illustrates the multiplexing of genome editing. In one instance, three separate genetic loci were edited in hematopoietic stem and progenitor cells (HSPCs). In the other instance, two separate genetic loci were edited in human T cells. Although the following example relates to multiplexed genome editing in HSPCs and T cells using the CRISPR/Cas9 system and recombinant adeno-associated viral vector, serotype 6 (rAAV6), the multiplexing approach described herein is applicable to any primary cell of interest, including other types of primary blood cells (e.g., other immune cells such as B cells, dendritic cells, natural killer cells, macrophages, neutrophils, eosinophils, basophils, and mast cells) and primary mesenchymal cells (e.g., mesenchymal stem cells (MSCs), mesenchymal progenitor cells, mesenchymal precursor cells, and differentiated mesenchymal cells), as well as any nuclease-mediated gene-editing platform (e.g., zinc finger nucleases (ZFNs), transcription activator-like effector nucleases (TALENs), meganucleases) and any rAAV serotype or a variant thereof.

Trigenic Targeting of CD34+ HSPCs

Figure 49A:
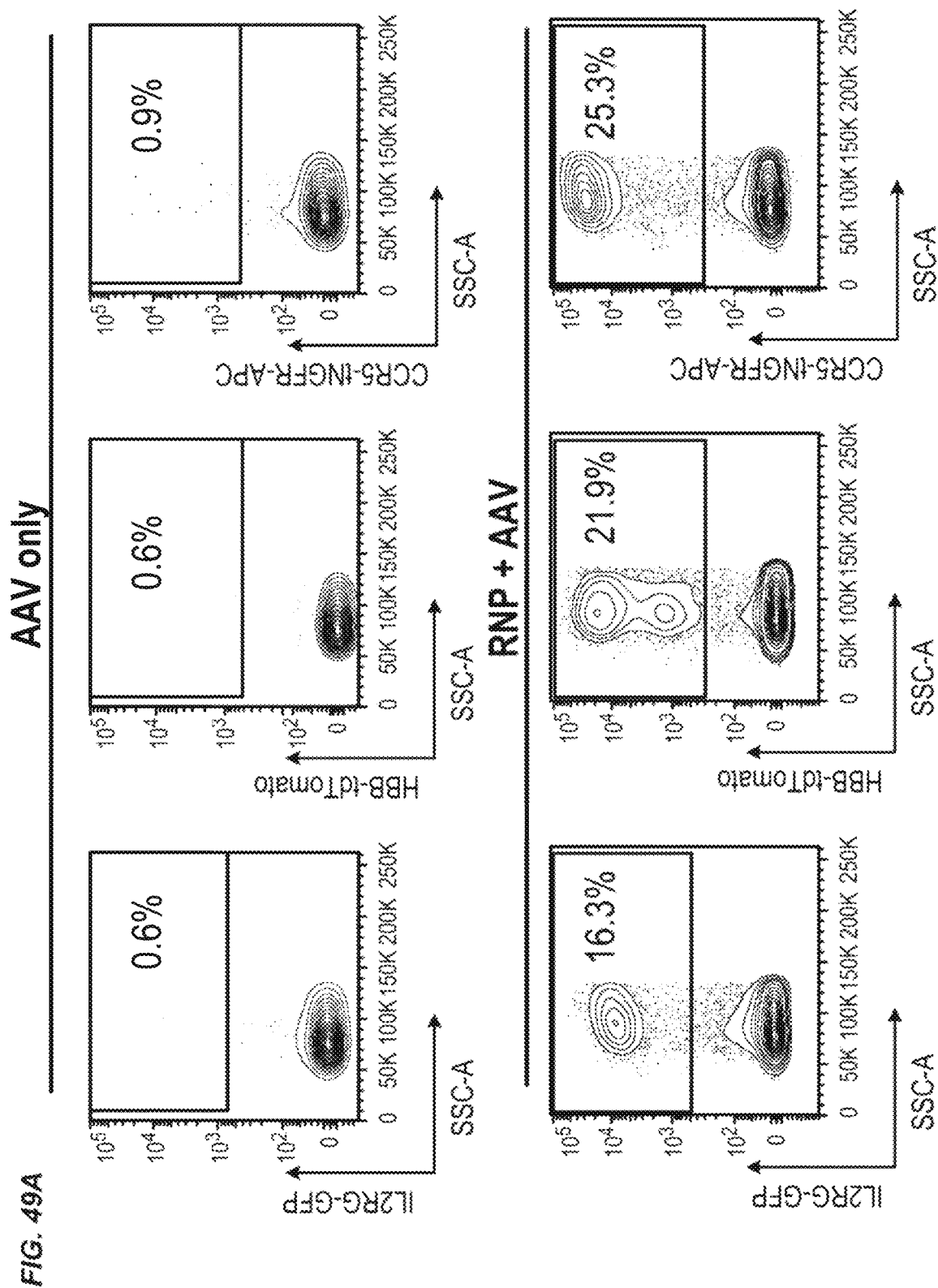
FIGS. 49A-49C show multiplexing recombination at three genes simultaneously in HSPCs.

For the trigenic targeting of CD34+ HSPCs, cells were electroporated with Cas9 RNP targeting IL2RG, HBB, and CCR5 (i.e., ribonucleoprotein (RNP) complexes comprising the Cas9 polypeptide and sgRNAs targeting IL2RG, HBB, and CCR5), followed by transduction of three rAAV6 donors that were homologous to each of the three genes (IL2RG-GFP (SEQ ID NO:41), HBB-tdTomato, and CCR5-tNGFR, respectively). FIG. 49A illustrates FACS plots of cells from day 4 post-electroporation, showing targeting at each of the three genes as well as a control sample that did not receive RNP (AAV only).

Figure 49B:
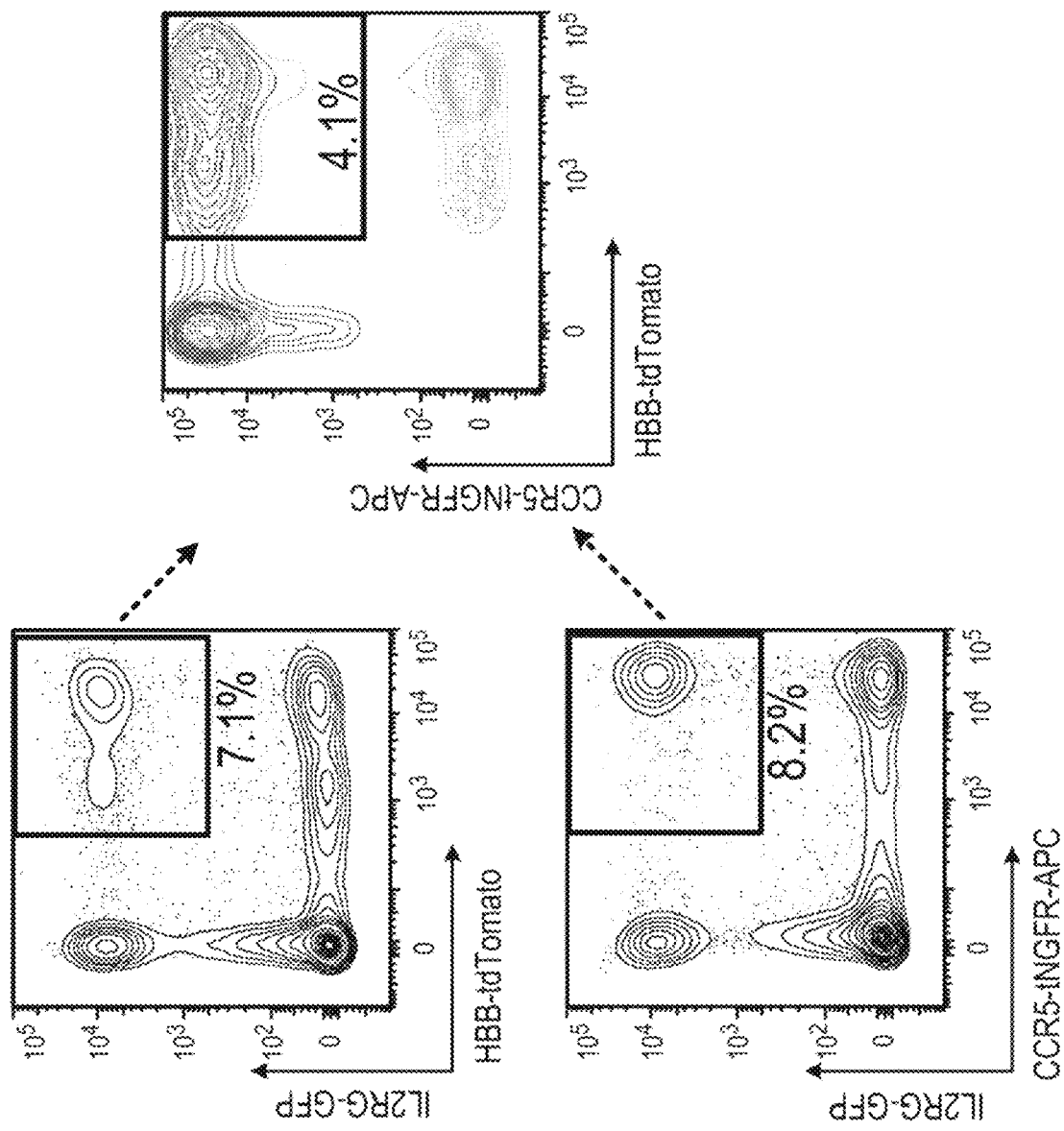
Figure 49C:
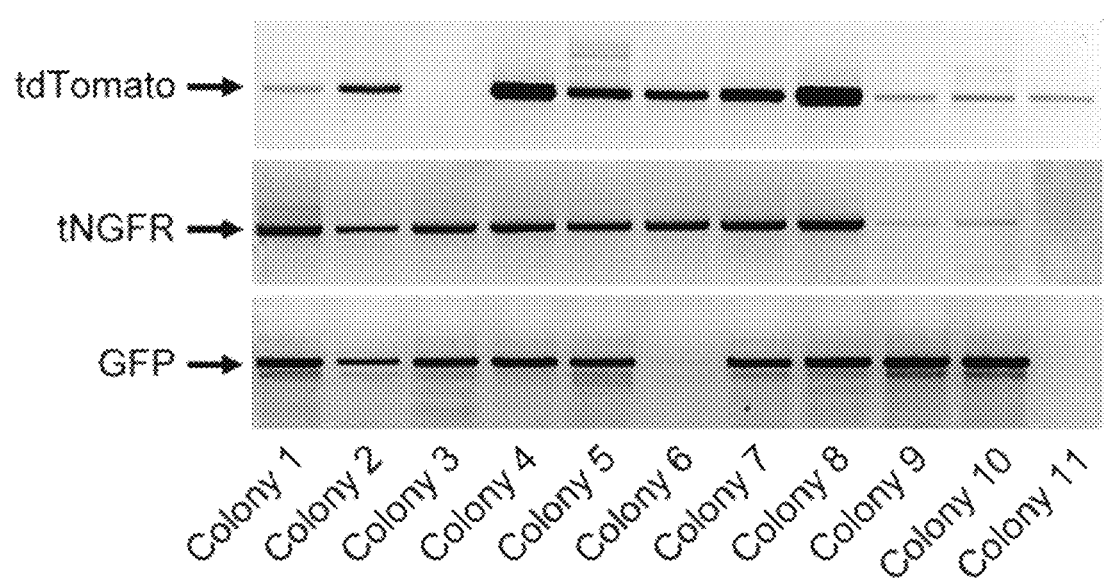

The FACS plots in FIG. 49B illustrate the identification of trigenic-targeted cells that were reporter$^{high}$ for all three reporters (i.e., GFP, tdTomato, and tNGFR). Methylcellulose clones that were derived from the triple-positive cells identified in FIG. 49B were subjected to In-Out genotyping PCR, and gel images (FIG. 49C) show colonies with targeted integration at all three genes in nine of elven colonies (note that GFP shows a faint band in colony #6).

These results show that enrichment of multiplexed genome editing is possible in CD34+ HSPCs (although multiplexed genome editing in any number of cell types is possible) by combining a nuclease-mediated genome editing platform such as the CRISPR/Cas9 system and rAAV homologous donor templates (e.g., rAAV6 homologous donor templates). Specifically, these results show that three different transgenes (e.g., GFP, tdTomato, and tNGFR) can be integrated into each of three different endogenous genes (e.g., IL2RG, HBB, and CCR5). Thus, the present invention is useful for the correction of any number of polygenic diseases and is also useful for the engineering of immune and blood cells that express multiple transgenes from multiple loci.

Dual-Allelic Integration in Primary Human T Cells

For this experiment, human primary T cells were isolated from buffy coats and stimulated for three days using anti-CD3 and anti-CD28 antibodies. Cells were then electroporated with CCR5-targeting Cas9 RNP (i.e., a ribonucleoprotein (RNP) complex comprising the Cas9 polypeptide and an sgRNA targeting CCR5), followed by transduction of two CCR5-specific rAAV6 donors that encoded the reporters GFP and mCherry. The FACS plots in FIG. 50A show the GFP$^{high}$/mCherry$^{high}$ dual-allelic targeting frequencies at day 4 post-electroporation.

FIG. 50B shows the cell viabilities of T cells that were treated as described above, measured at day 2 post-electroporation using a Trypan Blue exclusion assay.

These results show that genome editing in primary human T cells can be dualplexed by combining a nuclease-mediated genome editing platform such as the CRISPR/Cas9 system and rAAV homologous donor templates (e.g., rAAV6 homologous donor templates). Specifically, these results show that two different transgenes (e.g., GFP and mCherry) can be integrated into each of the two CCR5 alleles. Thus, the present invention is useful for any number of cell engineering uses, including T cell engineering. For example, the present invention is useful for engineering T cells that are resistant to HIV (e.g., performing dual-allelic knockout of CCR5 with simultaneous expression of factors that restrict HIV) or for multiplexed Chimeric Antigen Receptor (CAR) T cell engineering (e.g., performing CAR knock-in at genes that are desirable to knock out in CAR T cells (e.g., CD52 or TCRa) or performing multi-CAR expression or expression of CAR and potentiating factors).

Example 6. Enrichment Scheme Protocol for Human Primary T Cells

This example provides an exemplary protocol that enables the enrichment of a population of genetically modified primary cells having targeted integration at a target nucleic acid. Although this example relates to the enrichment of a population of gene-targeted human primary T cells using the CRISPR/Cas9 system and recombinant adeno-associated viral vector, serotype 6 (rAAV6), the enrichment scheme is applicable to any primary cell of interest, including other types of primary blood cells (e.g., other immune cells such as B cells, dendritic cells, natural killer cells, macrophages, neutrophils, eosinophils, basophils, and mast cells) and primary mesenchymal cells (e.g., mesenchymal stem cells (MSCs), mesenchymal progenitor cells, mesenchymal precursor cells, and differentiated mesenchymal cells), as well as any nuclease-mediated gene-editing platform (e.g., zinc finger nucleases (ZFNs), transcription activator-like effector nucleases (TALENs), meganucleases) and any rAAV serotype or a variant thereof.

Day −3: Following T cell isolation from peripheral blood mononuclear cells derived from buffy coats, resuspend cells in IL-2 and IL-7 containing media and stimulate with anti-CD3 and anti-CD28 antibodies. Incubate at 37° C. for 48-72 hours.

Day 0: Nucleofect human primary T cells with a gene-specific Cas9-MS sgRNA (either as "All RNA" or RNP delivery) and then resuspend cells in IL-2 and IL-7 media and incubate at 15 min at 37° C. Also "Mock" nucleofect cells for the "AAV only" sample for the enrichment gating scheme.

15 min: Add gene-specific rAAV6 (MOIs ranging from 1,000-500,000) containing a gene reporter cassette comprising a selectable marker such as GFP, mCherry, or tNGFR to be inserted between gene-homologous sequences such as a target nucleic acid sequence and then incubate at 30° C. or 37° C. overnight. Cell concentration is 500,000-1,000,000 cells/ml.

Day 1: Move cells to 37° C. if incubated at 30° C. after electroporation.

Day 2: Dilute cells to 500,000 cells/ml to promote viability.

Day 2-4: Enrichment can be performed at day 2, day 3, or day 4 depending on locus. 3 samples are prepared for the gating scheme: (1) non-transduced sample; (2) rAAV6 only sample; and (3) nuclease+rAAV6 sample. First run the non-transduced sample on a fluorescence-activated cell sorting (FACS) machine to get background fluorescent intensities. Then run the AAV only sample and make the "high" gate above the highest fluorescent positive cell. Specifically, the "high" population should have less than 1% positive cells in the rAAV6 only sample. Then run the nuclease+rAAV6 and there should be a "high" population generated if homologous recombination (HR) occurred. Sort this "high" population and greater than 90% of cells should have on-target integration event at one (monoallelic) or two alleles (biallelic).

Figure 51:
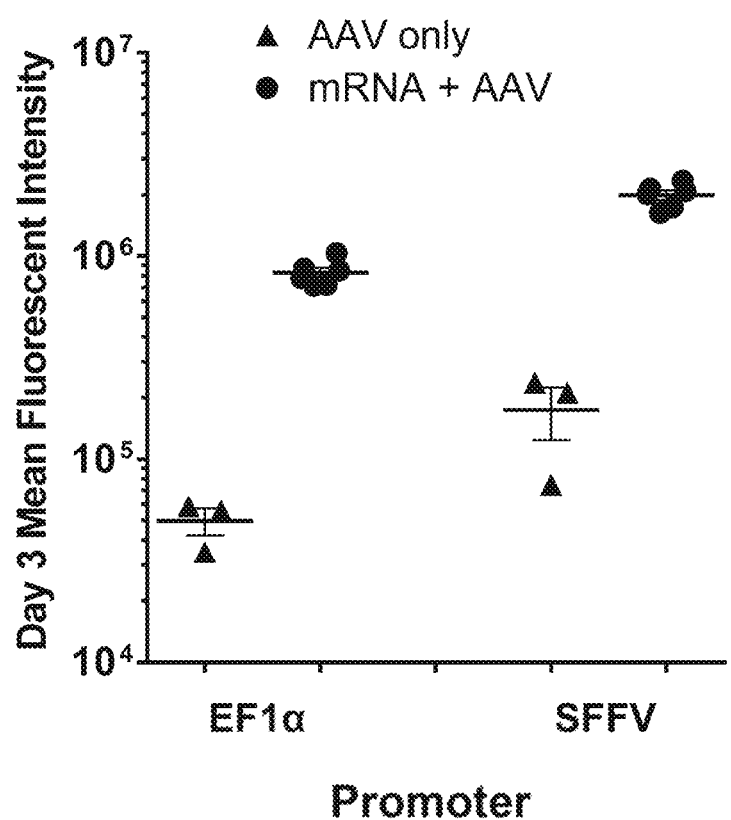
FIG. 51 shows the expression intensity shift of a GFP reporter upon targeted integration in T cells. Fluorescent intensity was measured day 3 post-electroporation in cells that were electroporated with Cas9 mRNA and MS-modified sgRNAs targeting CCR5, followed by transduction with rAAV6 vectors expressing GFP under the control of either an EF1α or SFFV (SEQ ID NO:39) promoter. An "AAV" group was included as a control.

FIG. 51 shows the results of human primary T cells that were electroporated with Cas9 mRNA and MS-modified sgRNAs targeting CCR5 three days after isolation and activation. Following electroporation, cells were transduced with rAAV6 vectors homologous to CCR5 and expressing GFP from either the EF1a or SFFV (SEQ ID NO:39) promoter. Three days later, cells were analyzed via FACS for percentage of GFP positive cells and mean fluorescent intensity (MFI) of the GFP+ cells. MFI+/−SEM is plotted from experiments in T cells from three different buffy coat donors. For the "mRNA+AAV" group, two electroporations were done for each buffy coat with two different CCR5 sgRNAs and results from both sgRNAs were pooled (N=6). This data quantifies the log-fold GFP MFI increase that was observed when adding CCR5-specific CRISPR and rAAV6 components ("mRNA+AAV") compared to just rAAV6 alone ("AAV Only") for two different promoters. The increase in expression of the selectable marker GFP upon HR was 17-fold for the EF1 promoter and 11-fold for the SFFV promoter compared to their respective "AAV Only" samples. This data also shows that the expression shift was only observed in the presence of CRISPR/Cas9 and not with the AAV donor alone. This data also shows that this MFI shift is not dependent on promoters (i.e., log-fold increase in selectable marker expression was observed with both EF1 and SFFV promoters) in human T cells. Without being bound by any particular theory, the MFI shift was due to higher transgene expression from transcription in intact chromosomes (with histones) compared to episomes and thus confirmed targeted HR and demonstrates that the MFI shift is a ubiquitous event upon on-target HR. The shift was observed at day 3 post electroporation and transduction, and thus allowed for early identification and enrichment of cells with targeted integration.

Figure 52:
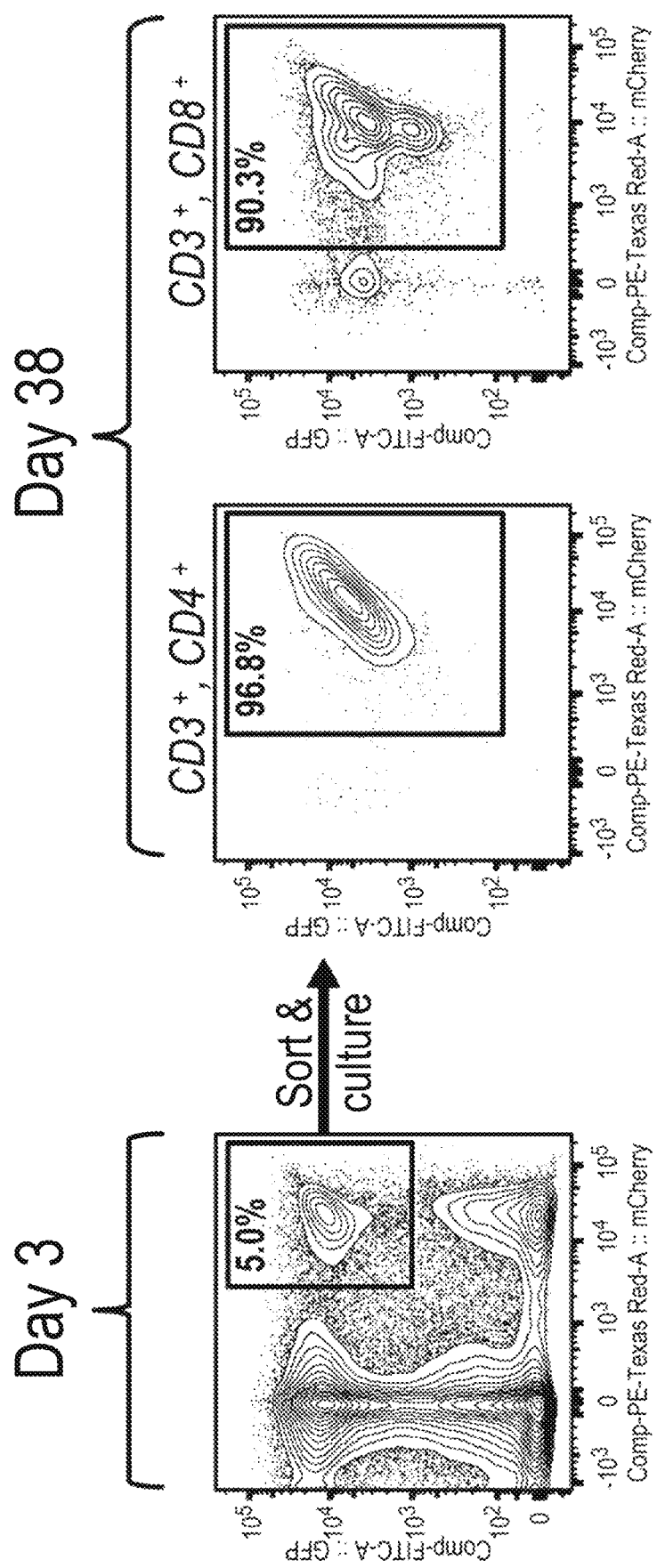
FIG. 52 shows early enrichment of T cells in which both alleles of CCR5 were targeted. The left panel shows FACS sorting of CD3$^+$ cells at day 3 post-electroporation that were GFP$^{high}$/mCherry$^{high}$. The sorted cells were cultured for an additional 35 days, at which point they were analyzed by flow cytometry. The FACS plots on the right show that 35 days after enrichment, 96.8% of CD4$^+$ T cells and 90.3% of CD8$^+$ T cells were still positive for both GFP and mCherry.

FIG. 52 shows the results of another experiment that similarly demonstrated that early enrichment of T cells with targeted integration of a transgene is possible. Three days after isolation and activation, human primary T cells were electroporated with RNP containing MS-modified sgRNAs targeting CCR5, followed by transduction with two different rAAV6 vectors homologous to CCR5 encoding GFP or mCherry. At day 3 post-electroporation, CD3+ cells that had been successfully targeted at both alleles (i.e., cells that were GFP$^{high}$/mCherry$^{high}$) were sorted by FACS (left panel) and cultured for an additional 35 days, after which they were analyzed by flow cytometry. FACS plots (two right panels) show that 96.8% of CD4$^+$ T cells and 90.3% of CD8$^+$ T cells were still positive for both GFP and mCherry 35 days after enrichment. The fact that greater than 90% of the cells still expressed both transgenes after this period of time showed stable expression in the sorted cells.

The data presented in this example show that the present methods are useful for applications in cell engineering, given that stably targeted cells can be enriched and that the enrichment can be done early in the manufacturing process, which can significantly reduce costs associated with unnecessary culturing of unedited cells.

V. Exemplary Embodiments

Exemplary embodiments provided in accordance with the presently disclosed subject matter include, but are not limited to, the claims and the following embodiments:

1. A method for inducing a stable gene modification of a target nucleic acid via homologous recombination in a primary cell, the method comprising:
   introducing into the primary cell:
   (a) a modified single guide RNA (sgRNA) comprising a first nucleotide sequence that is complementary to the target nucleic acid and a second nucleotide sequence that interacts with a CRISPR-associated protein (Cas) polypeptide, wherein one or more of the nucleotides in the first nucleotide sequence and/or the second nucleotide sequence are modified nucleotides;
   (b) a Cas polypeptide, an mRNA encoding a Cas polypeptide, and/or a recombinant expression vector comprising a nucleotide sequence encoding a Cas polypeptide, wherein the modified sgRNA guides the Cas polypeptide to the target nucleic acid; and
   (c) a homologous donor adeno-associated viral (AAV) vector comprising a recombinant donor template comprising two nucleotide sequences comprising two non-overlapping, homologous portions of the target nucleic acid, wherein the nucleotide sequences are located at the 5' and 3' ends of a nucleotide sequence corresponding to the target nucleic acid to undergo homologous recombination.
2. The method of embodiment 1, wherein the primary cell is selected from the group consisting of a primary blood cell, a primary mesenchymal cell, and a combination thereof
3. The method of embodiment 2, wherein the primary blood cell is selected from the group consisting of an immune cell, a red blood cell, a progenitor or stem cell thereof, and a combination thereof
4. The method of embodiment 3, wherein the immune cell is selected from the group consisting of a T cell, a B cell, a dendritic cell, a natural killer cell, a macrophage, a neutrophil, an eosinophil, a basophil, a mast cell, a precursor thereof, and a combination thereof
5. The method of embodiment 3, wherein the progenitor or stem cell is selected from the group consisting of a hematopoietic progenitor cell, a hematopoietic stem cell, and a combination thereof
6. The method of embodiment 3, wherein the red blood cell is a blood stem cell.
7. The method of embodiment 2, wherein the primary mesenchymal cell is selected from the group consisting of a mesenchymal stem cell, a mesenchymal progenitor cell, a mesenchymal precursor cell, a differentiated mesenchymal cell, and a combination thereof
8. The method of embodiment 7, wherein the differentiated mesenchymal cell is selected from the group consisting of a bone cell, a cartilage cell, a muscle cell, an adipose cell, a stromal cell, a fibroblast, a dermal cell, and a combination thereof
9. The method of any one of embodiments 1 to 8, wherein the primary cell is isolated from a mammal prior to introducing the modified sgRNA, the Cas polypeptide, and the homologous donor AAV vector into the primary cell.
10. The method of embodiment 9, wherein the primary cell or a progeny thereof is returned to the mammal after introducing the modified sgRNA, the Cas polypeptide, and the homologous donor AAV vector into the primary cell.
11. The method of any one of embodiments 1 to 10, wherein the primary cell comprises a population of primary cells.
12. The method of embodiment 11, wherein the population of primary cells comprises a heterogeneous population of primary cells.

13. The method of embodiment 11, wherein the population of primary cells comprises a homogeneous population of primary cells.
14. The method of any one of embodiments 1 to 13, wherein the homologous donor AAV vector is selected from a wild-type AAV serotype 1 (AAV1), wild-type AAV serotype 2 (AAV2), wild-type AAV serotype 3 (AAV3), wild-type AAV serotype 4 (AAV4), wild-type AAV serotype 5 (AAV5), wild-type AAV serotype 6 (AAV6), wild-type AAV serotype 7 (AAV7), wild-type AAV serotype 8 (AAV8), wild-type AAV serotype 9 (AAV9), wild-type AAV serotype 10 (AAV10), wild-type AAV serotype 11 (AAV11), wild-type AAV serotype 12 (AAV12), a variant thereof, and any shuffled chimera thereof
15. The method of embodiment 14, wherein the homologous donor AAV vector has at least about 90% sequence identity to any one selected from the group consisting of an AAV1, AAV2, AAV3, AAV4, AAV3, AAV5, AAV6, AAV7, AAV8, AAV9, AAV10, AAV11 and AAV12.
16. The method of any one of embodiments 1 to 15, wherein the homologous donor AAV vector is a wild-type AAV6 or an AAV6 variant having at least 95% sequence identity to wild-type AAV6.
17. The method of any one of embodiments 11 to 16, wherein the stable gene modification of the target nucleic acid is induced in greater than about 70% of the population of primary cells.
18. The method of any one of embodiments 11 to 16, wherein the stable gene modification of the target nucleic acid is induced in greater than about 80% of the population of primary cells.
19. The method of any one of embodiments 11 to 16, wherein the stable gene modification of the target nucleic acid is induced in greater than about 90% of the population of primary cells.
20. The method of any one of embodiments 1 to 19, wherein the modified nucleotides comprise a modification in a ribose group, a phosphate group, a nucleobase, or a combination thereof
21. The method of embodiment 20, wherein the modification in the ribose group comprises a modification at the 2' position of the ribose group.
22. The method of embodiment 21, wherein the modification at the 2' position of the ribose group is selected from the group consisting of 2'-O-methyl, 2'-fluoro, 2'-deoxy, 2'-O-(2-methoxyethyl), and a combination thereof
23. The method of embodiment 20, wherein the modification in the phosphate group comprises a phosphorothioate modification.
24. The method of any one of embodiments 1 to 23, wherein the modified nucleotides are selected from the group consisting of a 2'-O-methyl (M) nucleotide, a 2'-O-methyl 3'-phosphorothioate (MS) nucleotide, a 2'-O-methyl 3'-thioPACE (MSP) nucleotide, and a combination thereof
25. The method of any one of embodiments 1 to 24, wherein the modified sgRNA comprises one, two, or three consecutive or non-consecutive modified nucleotides at or near the 5'-end of the first nucleotide sequence and/or one, two, or three consecutive or non-consecutive modified nucleotides at or near the 3'-end of the second nucleotide sequence.
26. The method of embodiment 25, wherein the modified sgRNA comprises three consecutive modified nucleotides at the 5'-end of the first nucleotide sequence and three consecutive modified nucleotides at the 3'-end of the second nucleotide sequence.
27. The method of any one of embodiments 1 to 26, wherein the modified sgRNA is chemically synthesized.
28. The method of any one of embodiments 1 to 27, wherein the modified sgRNA comprises at least two different modified sgRNAs, wherein each modified sgRNA is directed to a different target nucleic acid.
29. The method of any one of embodiments 1 to 27, wherein the modified sgRNA comprises at least ten different modified sgRNAs, wherein each modified sgRNA is directed to a different target nucleic acid.
30. The method of embodiment 28 or 29, wherein all of the modified sgRNAs are introduced into the primary cell sequentially.
31. The method of embodiment 28 or 29, wherein at least some of the modified sgRNAs are introduced into the primary cell concomitantly.
32. The method of any one of embodiments 1 to 31, wherein the donor AAV vector comprises at least two different donor AAV vectors.
33. The method of any one of embodiments 1 to 31, wherein the donor AAV vector comprises at least ten different donor AAV vectors.
34. The method of embodiment 32 or 33, wherein each different donor AAV vector is directed to a different target nucleic acid.
35. The method of embodiment 32 or 33, wherein at least two of the different donor AAV vectors are directed to the same target nucleic acid.
36. The method of any one of embodiments 32 to 35, wherein all of the donor AAV vectors are introduced into the cell sequentially.
37. The method of any one of embodiments 32 to 35, where at least some of the donor AAV vectors are introduced into the cell concomitantly.
38. The method of any one of embodiments 1 to 37, wherein the Cas polypeptide is a Cas9 polypeptide, a variant thereof, or a fragment thereof
39. The method of any one of embodiments 1 to 38, wherein the modified sgRNA and the Cas polypeptide are incubated together to form a ribonucleoprotein (RNP) complex prior to introducing into the primary cell.
40. The method of embodiment 39, wherein the RNP complex and the homologous donor AAV vector are concomitantly introduced into the primary cell.
41. The method of embodiment 39, wherein the RNP complex and the homologous donor AAV vector are sequentially introduced into the primary cell.
42. The method of embodiment 41, wherein the RNP complex is introduced into the primary cell before the homologous donor AAV vector.
43. The method of any one of embodiments 39 to 42, wherein the RNP complex comprises two or more different RNP complexes, wherein each different RNP complex comprises a different modified sgRNA.
44. The method of any one of embodiments 1 to 38 wherein the Cas polypeptide is an mRNA encoding the Cas polypeptide.
45. The method of any one of embodiments 1 to 44, wherein the recombinant donor template comprises a plurality of different recombinant donor templates.
46. The method of any one of embodiments 1 to 45, wherein the recombinant donor template or plurality of different recombinant donor templates further comprises a nucleotide sequence encoding a marker selected from the group consisting of a selectable marker, a detectable marker, a cell surface marker, or a combination thereof 47. The method of embodiment 46, wherein each of the different recombinant donor templates in the plurality thereof further comprises a different nucleotide sequence encoding a marker selected from the group consisting of a selectable marker, a detectable marker, a cell surface marker, or combination thereof 48. The method of embodiment 46, wherein at least two of the different recombinant donor templates in the plurality thereof further comprises the same nucleotide sequence encoding a marker selected from the group consisting of a selectable marker, a detectable marker, a cell surface marker, or combination thereof 49. The method of any of embodiments 46 to 48, further comprising purifying the primary cell having the stable gene modification of the target nucleic acid using the marker.

50. The method of any one of embodiments 1 to 49, wherein introducing the modified sgRNA and the Cas polypeptide into the primary cell comprises electroporating the primary cell.

51. The method of any one of embodiments 1 to 50, wherein introducing the homologous donor AAV vector into the primary cell comprises transducing the primary cell.

52. The method of any one of embodiments 1 to 51, further comprising culturing the primary cell in a culture medium comprising a small molecule that increases targeting efficiency of gene modification via homologous recombination.

53. The method of embodiment 52, wherein the small molecule comprises UM171, any other pyrimidoindole derivative, a variant thereof, or a derivative thereof 54. A genetically modified primary cell produced by the method of any one of embodiments 1 to 53.

55. A pharmaceutical composition comprising the genetically modified primary cell of embodiment 54, and a pharmaceutically acceptable carrier.

56. A kit comprising:
(a) a modified single guide RNA (sgRNA) comprising a first nucleotide sequence that is complementary to the target nucleic acid and a second nucleotide sequence that interacts with a CRISPR-associated protein (Cas) polypeptide, wherein one or more of the nucleotides in the first nucleotide sequence and/or the second nucleotide sequence are modified nucleotides;
(b) a Cas polypeptide, an mRNA encoding a Cas polypeptide, and/or a recombinant expression vector comprising a nucleotide sequence encoding a Cas polypeptide, wherein the modified sgRNA guides the Cas polypeptide to the target nucleic acid;
(c) a homologous donor adeno-associated viral (AAV) vector comprising a recombinant donor template comprising two nucleotide sequences comprising two non-overlapping, homologous portions of the target nucleic acid, wherein the nucleotide sequences are located at the 5' and 3' ends of a nucleotide sequence corresponding to the target nucleic acid to undergo homologous recombination, and an instruction manual.

57. The kit of embodiment 56, further comprising a primary cell.

58. The kit of embodiment 56, further comprising a reagent for harvesting or isolating a primary cell from a subject.

59. The kit of embodiment 57 or 58, wherein the primary cell is selected from the group consisting of a primary blood cell, a primary mesenchymal cell, and a combination thereof 60. A method for preventing or treating a disease in a subject in need thereof, the method comprising administering to the subject the genetically modified primary cell of embodiment 54 or the pharmaceutical composition of embodiment 55 to prevent the disease or ameliorate one or more symptoms of the disease.

61. The method of embodiment 60, wherein administering comprises a delivery route selected from the group consisting of intravenous, intraperitoneal, intramuscular, intradermal, subcutaneous, intrathecal, intraosseous, and a combination thereof 62. The method of embodiment 60 or 61, wherein the disease is selected from the group consisting of a hemoglobinopathy, a viral infection, X-linked severe combined immune deficiency, Fanconi anemia, hemophilia, neoplasia, cancer, amyotrophic lateral sclerosis, Alzheimer's disease, Parkinson's disease, cystic fibrosis, blood diseases and disorders, inflammation, immune system diseases or disorders, metabolic diseases, liver diseases and disorders, kidney diseases and disorders, muscular diseases and disorders, bone or cartilage diseases and disorders, neurological and neuronal diseases and disorders, cardiovascular diseases and disorders, pulmonary diseases and disorders, and lysosomal storage disorders.

63. The method of embodiment 62, wherein the hemoglobinopathy is sickle cell disease, α-thalassemia, β-thalassemia, or δ-thalassemia.

64. The method of embodiment 62, wherein the viral infection is selected from the group consisting of a hepatitis B virus infection, hepatitis C virus infection, human papilloma virus infection, human immunodeficiency virus (HIV) infection, human T-lymphotrophic virus (HTLV) infection, Epstein-Barr virus infection, herpes virus infection, cytomegalovirus infection, and any other chronic viral infection.

65. The method of embodiment 62, wherein the muscular diseases and disorders are selected from the group consisting of Becker muscular dystrophy, Duchenne muscular dystrophy, Emery-Dreifuss muscular dystrophy, facioscapulohumeral muscular dystrophy, any other muscular dystrophy, and muscular atrophy.

66. A method for enriching a population of genetically modified primary cells having targeted integration at a target nucleic acid, the method comprising:
(a) introducing a DNA nuclease and a homologous donor adeno-associated viral (AAV) vector comprising a recombinant donor template into a population of primary cells, wherein the recombinant donor template comprises a nucleotide sequence encoding a selectable marker;
(b) culturing the population of primary cells for a period of time sufficient to produce a population of genetically modified primary cells and a population of unmodified primary cells; and
(c) separating the population of genetically modified primary cells from the population of unmodified primary cells based upon a higher expression of the selectable marker in the population of genetically modified primary cells compared to a population of primary cells to which only the homologous donor AAV vector has been introduced, thereby generating an enriched population of genetically modified primary cells.

67. The method of embodiment 66, wherein the population of primary cells is selected from the group consisting of primary blood cells, primary mesenchymal cells, and a combination thereof 68. The method of embodiment 67, wherein the primary blood cells are selected from the group consisting of immune cells, red blood cells, progenitors or stem cells thereof, and a combination thereof 69. The method of embodiment 68, wherein the immune cells are selected from the group consisting of T cells, B cells, dendritic cells, natural killer cells, macrophages, neutrophils, eosinophils, basophils, mast cells, precursors thereof, and a combination thereof 70. The method of embodiment 68, wherein the progenitors or stem cells are selected from the group consisting of hematopoietic progenitor cells, hematopoietic stem cells (HSCs), and a combination thereof 71. The method of embodiment 68, wherein the red blood cells are a blood stem cells.

72. The method of embodiment 67, wherein the primary mesenchymal cells are selected from the group consisting of mesenchymal stem cells (MSCs), mesenchymal progenitor cells, mesenchymal precursor cells, differentiated mesenchymal cells, and a combination thereof 73. The method of embodiment 72, wherein the differentiated mesenchymal cells are selected from the group consisting of bone cells, cartilage cells, muscle cells, adipose cells, stromal cells, fibroblasts, dermal cells, and a combination thereof 74. The method of any one of embodiments 66 to 73, wherein the DNA nuclease is selected from the group consisting of a CRISPR-associated protein (Cas) polypeptide, a zinc finger nuclease (ZFN), a transcription activator-like effector nuclease (TALEN), a meganuclease, a variant thereof, a fragment thereof, and a combination thereof 75. The method of any one of embodiments 66 to 74, wherein the DNA nuclease is a polypeptide, an mRNA encoding the polypeptide, and/or a recombinant expression vector comprising a nucleotide sequence encoding the polypeptide.

76. The method of any one of embodiments 66 to 75, wherein step (a) further comprises introducing into the population of primary cells a DNA-targeting RNA, a truncated DNA-targeting RNA, or a nucleotide sequence encoding the DNA-targeting RNA or truncated DNA-targeting RNA.

77. The method of embodiment 76, wherein the DNA-targeting RNA comprises a single guide RNA (sgRNA) or a truncated sgRNA.

78. The method of embodiment 77, wherein the sgRNA or truncated sgRNA comprises a first nucleotide sequence that is complementary to the target nucleic acid and a second nucleotide sequence that interacts with a Cas polypeptide.

79. The method of embodiment 78, wherein the Cas polypeptide comprises a Cas9 polypeptide, a variant thereof, or a fragment thereof 80. The method of embodiment 79, wherein the Cas polypeptide variant comprises a high-fidelity or enhanced specificity Cas9 polypeptide variant.

81. The method of any one of embodiments 77 to 80, wherein the sgRNA or truncated sgRNA comprises one or more modified nucleotides.

82. The method of embodiment 81, wherein one or more of the nucleotides in the first nucleotide sequence and/or the second nucleotide sequence are modified nucleotides.

83. The method of any one of embodiments 78 to 82, wherein the sgRNA or truncated sgRNA and the Cas polypeptide are incubated together to form a ribonucleoprotein (RNP) complex prior to introducing into the population of primary cells.

84. The method of embodiment 83, wherein the RNP complex and the homologous donor AAV vector are concomitantly introduced into the population of primary cells.

85. The method of embodiment 83, wherein the RNP complex and the homologous donor AAV vector are sequentially introduced into the population of primary cells.

86. The method of embodiment 85, wherein the RNP complex is introduced into the population of primary cells before the homologous donor AAV vector.

87. The method of embodiment 86, wherein the RNP complex is introduced into the population of primary cells about 15 minutes before the homologous donor AAV vector.

88. The method of any one of embodiments 66 to 87, wherein introducing the DNA nuclease into the population of primary cells comprises electroporating the population of primary cells.

89. The method of any one of embodiments 66 to 88, wherein introducing the homologous donor AAV vector into the population of primary cells comprises transducing the population of primary cells.

90. The method of any one of embodiments 66 to 89, wherein the recombinant donor template comprises two nucleotide sequences comprising two non-overlapping, homologous portions of the target nucleic acid, wherein the nucleotide sequences are located at the 5' and 3' ends of a nucleotide sequence corresponding to the target nucleic acid.

91. The method of any one of embodiments 66 to 90, wherein the homologous donor AAV vector is selected from a wild-type AAV serotype 1 (AAV1), wild-type AAV serotype 2 (AAV2), wild-type AAV serotype 3 (AAV3), wild-type AAV serotype 4 (AAV4), wild-type AAV serotype 5 (AAV5), wild-type AAV serotype 6 (AAV6), wild-type AAV serotype 7 (AAV7), wild-type AAV serotype 8 (AAV8), wild-type AAV serotype 9 (AAV9), wild-type AAV serotype 10 (AAV10), wild-type AAV serotype 11 (AAV11), wild-type AAV serotype 12 (AAV12), a variant thereof, and any shuffled chimera thereof 92. The method of embodiment 91, wherein the homologous donor AAV vector has at least about 90% sequence identity to any one selected from the group consisting of an AAV1, AAV2, AAV3, AAV4, AAV3, AAV5, AAV6, AAV7, AAV8, AAV9, AAV10, AAV11, and AAV12.

93. The method of any one of embodiments 66 to 92, wherein the homologous donor AAV vector is a wild-type AAV6 or an AAV6 variant having at least 95% sequence identity to wild-type AAV6.

94. The method of any one of embodiments 66 to 93, wherein greater than about 80% of the primary cells in the enriched population are genetically modified.

95. The method of any one of embodiments 66 to 93, wherein greater than about 85% of the primary cells in the enriched population are genetically modified.
96. The method of any one of embodiments 66 to 93, wherein greater than about 90% of the primary cells in the enriched population are genetically modified.
97. The method of any one of embodiments 66 to 93, wherein greater than about 95% of the primary cells in the enriched population are genetically modified.
98. The method of any one of embodiments 66 to 97, wherein the population of primary cells is cultured for a period of 2 to 4 days.
99. The method of embodiment 98, wherein the population of primary cells is cultured for a period of 2, 3, or 4 days.
100. The method of any one of embodiments 66 to 99, wherein step (b) further comprises culturing the population of primary cells in a culture medium comprising a small molecule that increases targeting efficiency of gene modification via homologous recombination.
101. The method of embodiment 100, wherein the small molecule comprises UM171, any other pyrimidoindole derivative, a variant thereof, or a derivative thereof
102. The method of any one of embodiments 66 to 101, wherein the selectable marker is a detectable marker or a cell surface marker.
103. The method of embodiment 102, wherein the detectable marker is a fluorescent protein.
104. The method of embodiment 102, wherein the cell surface marker is a truncated nerve growth factor receptor (tNGFR), a truncated epidermal growth factor receptor (tEGFR), a variant thereof, a fragment thereof, or a derivative thereof
105. The method of any one of embodiments 66 to 104, wherein the genetically modified primary cells are separated from the population of unmodified primary cells using flow cytometry.
106. The method of embodiment 105, wherein the flow cytometry comprises fluorescence-activated cell sorting (FACS).
107. The method of any one of embodiments 66 to 104, wherein the genetically modified primary cells are separated from the population of unmodified primary cells using magnetic bead separation.
108. The method of embodiment 107, wherein the magnetic bead separation comprises magnetic-activated cell sorting (MACS).
109. The method of any one of embodiments 66 to 108, wherein the expression of the selectable marker is about 10-fold to about 25-fold higher in the population of genetically modified primary cells compared to the population of primary cells to which only the homologous donor AAV vector has been introduced.
110. The method of any one of embodiments 66 to 109, wherein the enriched population of genetically modified primary cells has long-term repopulating capacity.
111. The method of any one of embodiments 66 to 110, wherein the method further comprises expanding the enriched population of genetically modified primary cells.
112. The method of any one of embodiments 66 to 111, wherein the method further comprises culturing the population of primary cells in a culture medium comprising a cytokine cocktail for 1 to 2 days prior to step (a).
113. The method of any one of embodiments 66 to 112, wherein step (b) further comprises culturing the population of primary cells in a culture medium comprising a cytokine cocktail.
114. The method of any one of embodiments 66 to 113, wherein the population of primary cells is isolated from a mammal prior to introducing the DNA nuclease and the homologous donor AAV vector into the population of primary cells.
115. The method of embodiment 114, wherein the enriched population of genetically modified primary cells is administered to the mammal.
116. An enriched population of genetically modified primary cells produced by the method of any one of embodiments 66 to 115.
117. A pharmaceutical composition comprising the enriched population of genetically modified primary cells of embodiment 116, and a pharmaceutically acceptable carrier.
118. A method for preventing or treating a disease in a subject in need thereof, the method comprising administering to the subject the enriched population of genetically modified primary cells of embodiment 116 or the pharmaceutical composition of embodiment 117 to prevent the disease or ameliorate one or more symptoms of the disease.
119. The method of embodiment 118, wherein administering comprises a delivery route selected from the group consisting of intravenous, intraperitoneal, intramuscular, intradermal, subcutaneous, intrathecal, intraosseous, and a combination thereof
120. The method of embodiment 118 or 119, wherein the disease is selected from the group consisting of a hemoglobinopathy, a viral infection, X-linked severe combined immune deficiency, Fanconi anemia, hemophilia, neoplasia, cancer, amyotrophic lateral sclerosis, Alzheimer's disease, Parkinson's disease, cystic fibrosis, blood diseases and disorders, inflammation, immune system diseases or disorders, metabolic diseases, liver diseases and disorders, kidney diseases and disorders, muscular diseases and disorders, bone or cartilage diseases and disorders, neurological and neuronal diseases and disorders, cardiovascular diseases and disorders, pulmonary diseases and disorders, and lysosomal storage disorders.
121. The method of embodiment 120, wherein the hemoglobinopathy is sickle cell disease, α-thalassemia, β-thalassemia, or δ-thalassemia.
122. The method of embodiment 120, wherein the viral infection is selected from the group consisting of a hepatitis B virus infection, hepatitis C virus infection, human papilloma virus infection, human immunodeficiency virus (HIV) infection, human T-lymphotrophic virus (HTLV) infection, Epstein-Barr virus infection, herpes virus infection, cytomegalovirus infection, and any other chronic viral infection.
123. The method of embodiment 120, wherein the muscular diseases and disorders are selected from the group consisting of Becker muscular dystrophy, Duchenne muscular dystrophy, Emery-Dreifuss muscular dystrophy, facioscapulohumeral muscular dystrophy, any other muscular dystrophy, and muscular atrophy.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described. All publications, patents, and patent applications cited in this specification are herein incorporated by reference as if each individual publication, patent, or patent application were specifically and individually indicated to be incorporated by reference.

What is claimed is:

1. A pharmaceutical composition comprising a population of primary hematopoietic stem and progenitor cells (HSPCs) isolated from an individual having sickle cell disease, wherein the population comprises:
 (a) a first plurality of primary HSPCs comprising an E6V mutation in an HBB gene;
 (b) a second plurality of primary HSPCs comprising at least one insertion and/or deletion (INDEL) within a target sequence formerly comprising SEQ ID NO:1 of an HBB gene comprising a nucleic acid sequence encoding an E6V mutation, wherein the INDEL is generated by introducing into a plurality of primary HSPCs:
   (i) a modified single guide RNA (sgRNA) comprising a first nucleotide sequence complementary to the target sequence and a second nucleotide sequence that interacts with a CRISPR-associated Cas polypeptide, wherein the first nucleotide sequence, the second nucleotide sequence, or both comprise a modified nucleotide; and
   (ii) the Cas polypeptide, a mRNA encoding the Cas polypeptide, or a recombinant expression vector comprising a nucleotide sequence encoding the Cas polypeptide,
   wherein the Cas polypeptide cleaves the target sequence in the HBB gene comprising the nucleic acid sequence encoding the E6V mutation, and wherein at least one INDEL is generated at the site of cleavage by non-homologous end-joining; and
 (c) a third plurality of primary HPSCs comprising a heterologous polynucleotide integrated into a target sequence formerly comprising SEQ ID NO:1 in an HBB gene comprising a nucleic acid sequence encoding an E6V mutation, wherein the heterologous polynucleotide comprises the nucleic acid sequence set forth in SEQ ID NO:73 and the heterologous polynucleotide corrects the nucleic acid sequence encoding the E6V mutation formerly in the HBB gene of the third plurality of primary HPSCs.

2. The pharmaceutical composition of claim 1, wherein the population of primary HSPCs comprises CD34+ HSPCs.

3. The pharmaceutical composition of claim 1, further comprising a pharmaceutically acceptable carrier.

4. The pharmaceutical composition of claim 1, wherein the modified nucleotide is selected from the group consisting of: a 2'-O-methyl nucleotide, a 2'-O-methyl 3'-phosphorothioate nucleotide, and a 2'-O-methyl 3'-thioPACE (MSP) nucleotide.

5. The pharmaceutical composition of claim 1, wherein the modified nucleotide comprises a 2'-O-methyl 3'-phosphorothioate nucleotide.

6. The pharmaceutical composition of claim 1, wherein a 5' end, a 3' end, or a combination thereof of the modified sgRNA comprises the modified nucleotide.

7. The pharmaceutical composition of claim 1, wherein the individual is human.

8. A pharmaceutical composition comprising a primary hematopoietic stem or progenitor cell isolated from an individual having sickle cell disease, wherein the hematopoietic stem or progenitor cell comprises a heterologous nucleic acid comprising SEQ ID NO:73 integrated into a target site formerly comprising SEQ ID NO:1 in an HBB gene formerly comprising a nucleic acid sequence encoding an E6V mutation.

9. The pharmaceutical composition of claim 8, further comprising a pharmaceutically acceptable carrier.

10. The pharmaceutical composition of claim 8, wherein the individual is human.

11. The pharmaceutical composition of claim 8, wherein the primary hematopoietic stem or progenitor cell is a CD34+ primary hematopoietic stem or progenitor cell.

12. The pharmaceutical composition of claim 2, wherein the CD34+ HSPCs comprise CD34+/CD38−/CD90+ HSPCs.

13. The pharmaceutical composition of claim 2, wherein the CD34+ HSPCs comprise CD34+/CD38−/CD90+/CD45RA− HSPCs.

14. The pharmaceutical composition of claim 11, wherein the CD34+ primary hematopoietic stem or progenitor cell is a HSPCs comprise CD34+/CD38−/CD90+ primary hematopoietic stem or progenitor cell.

15. The pharmaceutical composition of claim 11, wherein the CD34+ primary hematopoietic stem or progenitor cell is a CD34+/CD38−/CD90+/CD45RA− primary hematopoietic stem or progenitor cell.

* * * * *

```
                            SEQUENCE LISTING

<160> NUMBER OF SEQ ID NOS: 74

<210> SEQ ID NO 1
<211> LENGTH: 23
<212> TYPE: DNA
<213> ORGANISM: Artificial Sequence
<220> FEATURE:
<223> OTHER INFORMATION: Synthetic  Target DNA sequence, HBB gene locus

<400> SEQUENCE: 1
ccgttactgc cctgtggggc aag                                             23

<210> SEQ ID NO 2
<211> LENGTH: 22
<212> TYPE: DNA
<213> ORGANISM: Artificial Sequence
<220> FEATURE:
<223> OTHER INFORMATION: Synthetic  HBB on-target sgRNA target sequence

<400> SEQUENCE: 2
cttgcccaca gggcagtaac gg                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic HBB off-target sgRNA target sequence

<400> SEQUENCE: 3
tcagcccaca gggcagtaac gg                                              22

<210> SEQ ID NO 4
<211> LENGTH: 36
<212> TYPE: DNA
<213> ORGANISM: Artificial Sequence
<220> FEATURE:
<223> OTHER INFORMATION: Synthetic  rAAV6 HBB donor DNA sequence

<400> SEQUENCE: 4
gtcgagaagt ctgcagtcac tgctctatgg gggaag                               36

<210> SEQ ID NO 5
<211> LENGTH: 36
<212> TYPE: DNA
<213> ORGANISM: Artificial Sequence
<220> FEATURE:
<223> OTHER INFORMATION: Synthetic  Recombinant HBB sequence

<400> SEQUENCE: 5
gaggagaagt ctgccgttac tgccctgtgg ggcaag                               36

<210> SEQ ID NO 6
<211> LENGTH: 36
<212> TYPE: DNA
<213> ORGANISM: Artificial Sequence
<220> FEATURE:
<223> OTHER INFORMATION: Synthetic  Recombinant HBB sequence
```

```
<400> SEQUENCE: 6
gtcgagaagt ctgcagtcac tgctctstgg gggaaa                              36

<210> SEQ ID NO 7
<211> LENGTH: 36
<212> TYPE: DNA
<213> ORGANISM: Artificial Sequence
<220> FEATURE:
<223> OTHER INFORMATION: Synthetic Recombinant HBB sequence

<400> SEQUENCE: 7
gtcgagaagt ctgcagtcac tgccctgtgg ggcaag                              36

<210> SEQ ID NO 8
<211> LENGTH: 36
<212> TYPE: DNA
<213> ORGANISM: Artificial Sequence
<220> FEATURE:
<223> OTHER INFORMATION: Synthetic Recombinant HBB sequence

<400> SEQUENCE: 8
gaggagaagt ctgcagtcac tgctctatgg gggaaa                              36

<210> SEQ ID NO 9
<211> LENGTH: 36
<212> TYPE: DNA
<213> ORGANISM: Artificial Sequence
<220> FEATURE:
<223> OTHER INFORMATION: Synthetic Recombinant HBB sequence

<400> SEQUENCE: 9
gtcgagaagt ctgcagtcac tgctctatgg ggcaag                              36

<210> SEQ ID NO 10
<211> LENGTH: 24
<212> TYPE: DNA
<213> ORGANISM: Artificial Sequence
<220> FEATURE:
<223> OTHER INFORMATION: Synthetic Insert-3' homology arm for the HBB
      locus

<400> SEQUENCE: 10
acgtttcgcg cctgtggggc aagg                                           24

<210> SEQ ID NO 11
<211> LENGTH: 24
<212> TYPE: DNA
<213> ORGANISM: Artificial Sequence
<220> FEATURE:
<223> OTHER INFORMATION: Synthetic 3' homology arm-genomic locus for HBB

<400> SEQUENCE: 11
ctatgggacc cttgatgttt tctt                                           24

<210> SEQ ID NO 12
<211> LENGTH: 24
<212> TYPE: DNA
<213> ORGANISM: Artificial Sequence
<220> FEATURE:
<223> OTHER INFORMATION: Synthetic Insert-3' homology arm for the CCR5
      locus

<400> SEQUENCE: 12
tgggctacta gttgggctca ctat                                           24
```

```
<210> SEQ ID NO 13
<211> LENGTH: 24
<212> TYPE: DNA
<213> ORGANISM: Artificial Sequence
<220> FEATURE:
<223> OTHER INFORMATION: Synthetic 3' homology arm-genomic locus for
      CCR5

<400> SEQUENCE: 13
atctgtgggc ttgtgacacg gact                                            24

<210> SEQ ID NO 14
<211> LENGTH: 24
<212> TYPE: DNA
<213> ORGANISM: Artificial Sequence
<220> FEATURE:
<223> OTHER INFORMATION: Synthetic Insert-3' homology arm for the IL2RG
      locus

<400> SEQUENCE: 14
acgtttaaac actagtgaag agca                                            24

<210> SEQ ID NO 15
<211> LENGTH: 24
<212> TYPE: DNA
<213> ORGANISM: Artificial Sequence
<220> FEATURE:
<223> OTHER INFORMATION: Synthetic 3' homology arm-genomic locus for
      IL2RG

<400> SEQUENCE: 15
gtcataagtc ggttgagggg agat                                            24

<210> SEQ ID NO 16
<211> LENGTH: 22
<212> TYPE: DNA
<213> ORGANISM: Artificial Sequence
<220> FEATURE:
<223> OTHER INFORMATION: Synthetic HBB primer sequence

<400> SEQUENCE: 16
gaagatatgc ttagaaccga gg                                              22

<210> SEQ ID NO 17
<211> LENGTH: 22
<212> TYPE: DNA
<213> ORGANISM: Artificial Sequence
<220> FEATURE:
<223> OTHER INFORMATION: Synthetic HBB primer sequence

<400> SEQUENCE: 17
ccacatgccc agtttctatt gg                                              22

<210> SEQ ID NO 18
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 18
gtaccagcac gccttcaaga cc                                              22

<210> SEQ ID NO 19
<211> LENGTH: 21
<212> TYPE: DNA
```

```
<213> ORGANISM: Artificial Sequence
<220> FEATURE:
<223> OTHER INFORMATION: Synthetic CCR5 primer sequence

<400> SEQUENCE: 19
gcacagggtg gaacaagatg g                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic CCR5 primer sequence

<400> SEQUENCE: 20 aaggggagg attgggaaga c                                               21

<210> SEQ ID NO 21
<211> LENGTH: 25
<212> TYPE: DNA
<213> ORGANISM: Artificial Sequence
<220> FEATURE:
<223> OTHER INFORMATION: Synthetic CCR5 primer sequence

<400> SEQUENCE: 21
tcaagaatca gcaattctct gaggc                                          25

<210> SEQ ID NO 22
<211> LENGTH: 20
<212> TYPE: DNA
<213> ORGANISM: Artificial Sequence
<220> FEATURE:
<223> OTHER INFORMATION: Synthetic SFFV primer sequence

<400> SEQUENCE: 22
accgcagata tcctgtttgg                                                20

<210> SEQ ID NO 23
<211> LENGTH: 25
<212> TYPE: DNA
<213> ORGANISM: Artificial Sequence
<220> FEATURE:
<223> OTHER INFORMATION: Synthetic HBB primer sequence

<400> SEQUENCE: 23
gatcctgaga cttccacact gatgc                                          25

<210> SEQ ID NO 24
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 24
tcactagcaa cctcaaacag ac                                             22

<210> SEQ ID NO 25
<211> LENGTH: 18
<212> TYPE: DNA
<213> ORGANISM: Artificial Sequence
<220> FEATURE:
<223> OTHER INFORMATION: Synthetic primer sequence

<400> SEQUENCE: 25
atccacgttc accttgcc                                                  18
```

```
<210> SEQ ID NO 26
<211> LENGTH: 27
<212> TYPE: DNA
<213> ORGANISM: Artificial Sequence
<220> FEATURE:
<223> OTHER INFORMATION: Synthetic probe sequence

<400> SEQUENCE: 26
taacggcaga cttctccaca ggagtca                                    27

<210> SEQ ID NO 27
<211> LENGTH: 25
<212> TYPE: DNA
<213> ORGANISM: Artificial Sequence
<220> FEATURE:
<223> OTHER INFORMATION: Synthetic IL2RG primer sequence

<400> SEQUENCE: 27
cagatatcca gagcctagcc tcatc                                      25

<210> SEQ ID NO 28
<211> LENGTH: 30
<212> TYPE: DNA
<213> ORGANISM: Artificial Sequence
<220> FEATURE:
<223> OTHER INFORMATION: Synthetic IL2RG primer sequence

<400> SEQUENCE: 28
tcacacagca catatttgcc acccctctg                                  30

<210> SEQ ID NO 29
<211> LENGTH: 27
<212> TYPE: DNA
<213> ORGANISM: Artificial Sequence
<220> FEATURE:
<223> OTHER INFORMATION: Synthetic IL2RG primer sequence

<400> SEQUENCE: 29
tgcccacatg attgtaatgg ccagtgg                                    27

<210> SEQ ID NO 30
<211> LENGTH: 21
<212> TYPE: DNA
<213> ORGANISM: Artificial Sequence
<220> FEATURE:
<223> OTHER INFORMATION: Synthetic primer sequence

<400> SEQUENCE: 30
gggctttgac tttgggattt c                                          21

<210> SEQ ID NO 31
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 31
ttcgaaagct tcggcgacct ca                                         22

<210> SEQ ID NO 32
<211> LENGTH: 22
<212> TYPE: DNA
<213> ORGANISM: Artificial Sequence
<220> FEATURE:
```

<223> OTHER INFORMATION: Synthetic primer sequence

<400> SEQUENCE: 32
cggcatggac gagctgtaca ag         22

<210> SEQ ID NO 33
<211> LENGTH: 27
<212> TYPE: DNA
<213> ORGANISM: Artificial Sequence
<220> FEATURE:
<223> OTHER INFORMATION: Synthetic probe sequence

<400> SEQUENCE: 33
tgactgcgga tttttcctca ggagtca        27

<210> SEQ ID NO 34
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 34
gtgtatccct ggacacaaag at         22

<210> SEQ ID NO 35
<211> LENGTH: 23
<212> TYPE: DNA
<213> ORGANISM: Artificial Sequence
<220> FEATURE:
<223> OTHER INFORMATION: Synthetic CCR5 sgRNA target sequence

<400> SEQUENCE: 35
ggcagcatag tgagcccaga agg         23

<210> SEQ ID NO 36
<211> LENGTH: 2402
<212> TYPE: DNA
<213> ORGANISM: Artificial Sequence
<220> FEATURE:
<223> OTHER INFORMATION: Synthetic Sickle cell disease nucleotide
      correction donor sequence

<400> SEQUENCE: 36
aatttagtac aagggggaaaa agtacagggg gatgggagaa aggcgatcac gttgggaagc     60
tatagagaaa gaagagtaaa ttttagtaaa ggaggtttaa acaaacaaaa tataaagaga    120
aataggaact tgaatcaagg aaatgatttt aaaacgcagt attcttagtg gactagagga    180
aaaaaataat ctgagccaag tagaagacct tttcccctcc taccccctact ttctaagtca   240 cagaggcttt tgttccccc agacactctt gcagattagt ccaggcagaa acagttagat    300
gtccccagtt aacctcctat ttgacaccac tgattacccc attgatagtc acactttggg    360
ttgtaagtga ctttttattt atttgtattt ttgactgcat taagaggtct ctagtttttt    420
atctcttgtt tcccaaaacc taataagtaa ctaatgcaca gagcacattg atttgtattt    480
attctatttt tagacataat ttattagcat gcatgagcaa attaagaaaa acaacaacaa    540
atgaatgcat atatatgtat atgtatgtgt gtatatatac acacatatat atatatattt    600 tttctttttct taccagaagg ttttaatcca aataaggaga agatatgctt agaaccgagg    660
tagagttttc atccattctg tcctgtaagt attttgcata ttctggagac gcaggaagag    720
atccatctac atatcccaaa gctgaattat ggtagacaaa actcttccac ttttagtgca    780

```
tcaacttctt atttgtgtaa taagaaaatt gggaaaacga tcttcaatat gcttaccaag      840
ctgtgattcc aaatattacg taaatacact tgcaaaggag gatgttttta gtagcaattt      900
gtactgatgg tatggggcca agagatatat cttagaggga gggctgaggg tttgaagtcc      960
aactcctaag ccagtgccag aagagccaag gacaggtacg gctgtcatca cttagacctc     1020
accctgtgga gccacaccct agggttggcc aatctactcc caggagcagg gagggcagga     1080
gccagggctg ggcataaaag tcagggcaga gccatctatt gcttacattt gcttctgaca     1140
caactgtgtt cactagcaac ctcaaacaga caccatggtg cacctgactc ctgaggaaaa     1200
atccgcagtc actgccctgt ggggcaaggt gaacgtggat gaagttggtg gtgaggccct     1260
gggcaggttg gtatcaaggt tacaagacag gtttaaggag accaatagaa actgggcatg     1320
tggagacaga gaagactctt gggtttctga taggcactga ctctctctgc ctattggtct     1380
attttcccac ccttaggctg ctggtggtct acccttggac ccagaggttc tttgagtcct     1440
ttggggatct gtccactcct gatgctgtta tgggcaaccc taaggtgaag gctcatggca     1500
agaaagtgct cggtgccttt agtgatggcc tggctcacct ggacaacctc aagggcacct     1560
ttgccacact gagtgagctg cactgtgaca agctgcacgt ggatcctgag aacttcaggg     1620
tgagtctatg ggacgcttga tgttttcttt ccccttcttt tctatggtta agttcatgtc     1680
ataggaaggg gataagtaac agggtacagt ttagaatggg aaacagacga atgattgcat     1740
cagtgtggaa gtctcaggat cgtttagtt tcttttattt gctgttcata acaattgttt     1800
tcttttgttt aattcttgct ttcttttttt ttcttctccg caatttttac tattatactt     1860
aatgccttaa cattgtgtat aacaaaagga aatatctctg agatacatta agtaacttaa     1920
aaaaaaactt tacacagtct gcctagtaca ttactatttg gaatatatgt gtgcttattt     1980
gcatattcat aatctcccta ctttattttc tttttatttt aattgataca taatcattat     2040
acatatttat gggttaaagt gtaatgtttt aatatgtgta cacatattga ccaaatcagg     2100
gtaattttgc atttgtaatt ttaaaaaatg ctttcttctt ttaatatact ttttgttta     2160 tcttatttct aatactttcc ctaatctctt tctttcaggg caataatgat acaatgtatc     2220
atgcctcttt gcaccattct aaagaataac agtgataatt tctgggttaa ggcaatagca     2280
atatctctgc atataaatat ttctgcatat aaattgtaac tgatgtaaga ggtttcatat     2340
tgctaatagc agctacaatc cagctaccat tctgctttta ttttatggtt gggataaggc     2400
tg                                                                     2402
```

<210> SEQ ID NO 37
<211> LENGTH: 3720
<212> TYPE: DNA
<213> ORGANISM: Artificial Sequence
<220> FEATURE:
<223> OTHER INFORMATION: Synthetic Sickle cell disease HBB cDNA-tNGFR
      enrichment donor sequence

<400> SEQUENCE: 37

```
gtcctgtaag tattttgcat attctggaga cgcaggaaga gatccatcta catatcccaa       60
agctgaatta tggtagacaa aactcttcca cttttagtgc atcaacttct tatttgtgta      120
ataagaaaat tgggaaaacg atcttcaata tgcttaccaa gctgtgattc caaatattac      180
gtaaatacac ttgcaaagga ggatgttttt agtagcaatt tgtactgatg gtatggggcc      240
aagagatata tcttagaggg agggctgagg gtttgaagtc caactcctaa gccagtgcca      300
gaagagccaa ggacaggtac ggctgtcatc acttagacct caccctgtgg agccacaccc      360
```

```
tagggttggc caatctactc ccaggagcag ggagggcagg agccagggct gggcataaaa    420
gtcagggcag agccatctat tgcttacatt tgcttctgac acaactgtgt tcactagcaa    480
cctcaaacag acaccatggt gcacctgact cctgaagaaa aatccgctgt cacagccctc    540
tgggataagg tcaacgtcga tgccgtcggc ggcgaagctc tcggaagact cctcgtcgtg    600
tatccctgga cacaaagatt tttcgaaagc ttcggcgacc tcagcacccc cgacgccgtg    660
atgggaaatc ccaaagtcaa agcccacgga aaaaaggtcc tgggcgcttt cagcgacgga    720
ctcgcccatc tcgataatct gaaaggaaca ttcgctcagc tcagcgaact ccattgcgat    780
aaactccatg tcgaccccga aaattttaga ctgctcggaa atgtcctcgt gtgcgtcctc    840
gctcaccatt tcggaaagga gtttacaccc cctgtccaag ccgcttacca aaaggtcgtt    900
gccggcgtcg ccaacgctct cgctcataaa taccattgac tgtgccttct agttgccagc    960
catctgttgt ttgcccctcc cccgtgcctt ccttgaccct ggaaggtgcc actcccactg   1020
tcctttccta ataaaatgag gaaattgcat cgcattgtct gagtaggtgt cattctattc   1080
tggggggtgg ggtgggcag acagcaagg gggaggattg gaagacaat agcaggcatg   1140
ctggggatgc ggtgggctct atggggctcc ggtgccgtc agtgggcaga gcgcacatcg   1200
cccacagtcc ccgagaagtt gggggagg tcggcaatt gaaccggtgc ctagagaagg   1260
tggcgcgggg taaactggga aagtgatgtc gtgtactggc tccgcctttt tcccgagggt   1320
ggggagaac cgtatataag tgcagtagtc gccgtgaacg ttcttttcg caacgggttt   1380
gccgccagaa cacaggtaag tgccgtgtgt ggttcccgcg ggcctggcct ctttacgggt   1440
tatgcccctt gcgtgccttg aattacttcc acctggctgc agtacgtgat tcttgatccc   1500
gagcttcggg ttggaagtgg gtgggagagt tcgaggcctt gcgcttaagg agcccttcg   1560
cctcgtgctt gagttgaggc ctggcctggg cgctggggcc gccgcgtgcg aatctggtgg   1620
caccttcgcg cctgtctcgc tgctttcgat aagtctctag ccatttaaaa ttttttgatga  1680
cctgctgcga cgcttttttt ctggcaagat agtcttgtaa atgcgggcca agatctgcac   1740
actggtatt cggttttgg ggccgcgggc ggcgacgggg cccgtgcgtc ccagcgcaca   1800
tgttcgcga ggcggggcct gcgagcgcgg ccaccgagaa tcggacgggg gtagtctcaa   1860
gctggccggc ctgctctggt gcctggcctc gcgccgccgt gtatcgcccc gccctgggcg   1920
gcaaggctgg cccggtcggc accagttgcg tgagcggaaa gatggccgct tcccggccct  1980
gctgcaggga gctcaaaatg gaggacgcgg cgctcgggag agcgggcggg tgagtcaccc   2040
acacaaagga aaagggcctt tccgtcctca gccgtcgctt catgtgactc cacggagtac   2100
cgggcgccgt ccaggcacct cgattagttc tcgagctttt ggagtacgtc gtctttaggt   2160
tggggggagg ggttttatgc gatggagttt ccccacactg agtgggtgga gactgaagtt   2220
aggccagctt ggcacttgat gtaattctcc ttggaatttg ccctttttga gtttggatct   2280
tggttcattc tcaagcctca gacagtggtt caaagttttt ttcttccatt tcaggtgtcg   2340
tgacgccacc atggggcag gtgccaccgg ccgcgccatg gacgggccgc gcctgctgct   2400
gttgctgctt ctgggggtgt cccttggagg tgccaaggag gcatgcccca caggcctgta   2460
cacacacagc ggtgagtgct gcaaagcctg caacctgggc gagggtgtgg cccagccttg   2520
tggagccaac cagaccgtgt gtgagccctg cctggacagc gtgacgttct ccgacgtggt   2580
gagcgcgacc gagccgtgca agccgtgcac cgagtgcgtg gggctccaga gcatgtcggc   2640
gccatgcgtg gaggccgacg acgccgtgtg ccgctgcgcc tacggctact accaggatga   2700
gacgactggg cgctgcgagg cgtgccgcgt gtgcgaggcg ggctcgggcc tcgtgttctc   2760
```

```
ctgccaggac aagcagaaca ccgtgtgcga ggagtgcccc gacggcacgt attccgacga   2820
ggccaaccac gtggacccgt gcctgccctg caccgtgtgc gaggacaccg agcgccagct   2880
ccgcgagtgc acacgctggg ccgacgccga gtgcgaggag atccctggcc gttggattac   2940
acggtccaca cccccagagg gctcggacag cacagccccc agcacccagg agcctgaggc   3000
acctccagaa caagacctca tagccagcac ggtggcgggt gtggtgacca cagtgatggg   3060
cagctcccag cccgtggtga cccgaggcac caccgacaac ctcatccctg tctattgctc   3120
catcctggct gctgtggttg tgggtcttgt ggcctacata gccttcaaga ggtaaaactt   3180
gtttattgca gcttataatg gttacaaata aagcaatagc atcacaaatt tcacaaataa   3240
agcatttttt tcactgcatt ctagttgtgg tttgtccaaa ctcatcaatg tatcctgccc   3300 tgtgggcaa ggtgaacgtg gatgaagttg gtggtgaggc cctgggcagg ttggtatcaa   3360
ggttacaaga caggtttaag gagaccaata gaaactgggc atgtggagac agagaagact   3420
cttgggtttc tgataggcac tgactctctc tgcctattgg tctattttcc cacccttagg   3480
ctgctggtgg tctacccttg acccagagg ttctttgagt cctttgggga tctgtccact   3540
cctgatgctg ttatgggcaa ccctaaggtg aaggctcatg gcaagaaagt gctcggtgcc   3600
tttagtgatg gcctggctca cctggacaac ctcaagggca cctttgccac actgagtgag   3660
ctgcactgtg acaagctgca cgtggatcct gagaacttca gggtgagtct atgggacgct   3720
```

<210> SEQ ID NO 38
<211> LENGTH: 2469
<212> TYPE: DNA
<213> ORGANISM: Artificial Sequence
<220> FEATURE:
<223> OTHER INFORMATION: Synthetic HBB SFFV-GFP donor sequence

<400> SEQUENCE: 38

```
gtcctgtaag tattttgcat attctggaga cgcaggaaga gatccatcta catatcccaa     60
agctgaatta tggtagacaa aactcttcca cttttagtgc atcaacttct tatttgtgta    120
ataagaaaat tgggaaaacg atcttcaata tgcttaccaa gctgtgattc caaatattac    180
gtaaatacac ttgcaaagga ggatgttttt agtagcaatt tgtactgatg gtatgggcc     240 aagagatata tcttagaggg agggctgagg gtttgaagtc caactcctaa gccagtgcca    300 gaaagagccaa ggacaggtac ggctgtcatc acttagacct caccctgtgg agccacaccc    360
tagggttggc caatctactc ccaggagcag ggagggcagg agccagggct gggcataaaa    420
gtcagggcag agccatctat tgcttacatt tgcttctgac acaactgtgt tcactagcaa    480
cctcaaacag acaccatggt gcacctgact cctgaggaga agtctgccgt tactgcccat    540
taccctgtta tccctaccga taaaataaaa gattttattt agtctccaga aaagggggg    600 aatgaaagac cccacctgta ggtttggcaa gctagctgca gtaacgccat tttgcaaggc    660
atggaaaaat accaaaccaa gaatagaaa gttcagatca agggcgggta catgaaaata    720
gctaacgttg ggccaaacag gatatctgcg gtgagcagtt cggccccgg cccggggcca    780 agaacagatg gtcaccgcag tttcggcccc ggcccgaggc caagaacaga tggtcccag    840 atatggccca accctcagca gtttcttaag acccatcaga tgtttccagg ctcccccaag    900
gacctgaaat gaccctgcgc cttatttgaa ttaaccaatc agcctgcttc tcgcttctgt    960
tcgcgcgctt ctgcttcccg agctctataa aagagctcac aaccccctcac tcggcgcgcc   1020 agtcctccga cagactgagt cgcccggggg ggtaccgagc tcttcgaagg atccatcgcc   1080
```

```
accatgcccg ccatgaagat cgagtgccgc atcaccggca ccctgaacgg cgtggagttc      1140
gagctggtgg cggcggaga gggcaccccc gagcagggcc gcatgaccaa caagatgaag      1200
agcaccaaag gcgccctgac cttcagcccc tacctgctga gccacgtgat gggctacggc      1260
ttctaccact cggcacccta ccccagcggc tacgagaacc ccttcctgca cgccatcaac      1320
aacggcggct acaccaacac ccgcatcgag aagtacgagg acggcggcgt gctgacgtg       1380 agcttcagct accgctacga ggccggccgc gtgatcggcg acttcaaggt ggtgggcacc      1440
ggcttccccg aggacagcgt gatcttcacc gacaagatca tccgcagcaa cgccaccgtg      1500
gagcacctgc accccatggg cgataacgtg ctggtgggca gcttcgcccg caccttcagc      1560
ctgcgcgacg gcggctacta cagcttcgtg gtggacagcc acatgcactt caagagcgcc      1620
atccaccccc gcatcctgca gaacgggggc cccatgttcg ccttccgccg cgtggaggag      1680
ctgcacagca acaccgagct gggcatcgtg gagtaccagc acgccttcaa gacccccatc      1740
gccttcgcca gatctcgagt ctagctcgag ggcgcgcccg ctgatcagcc tcgacctgtg      1800
ccttctagtt gccagccatc tgttgtttgc ccctcccccg tgccttcctt gaccctggaa      1860
ggtgccactc ccactgtcct ttcctaataa aatgaggaaa ttgcatcgca ttgtctgagt      1920
aggtgtcatt ctattctggg gggtgggtg gggcaggaca gcaaggggga ggattgggaa       1980
gacaatagca ggcatgctgg ggatgcggtg ggctctatgg cttctgaggc ggaaagaacg      2040
tttcgcgcct gtggggcaag gtgaacgtgg atgaagttgg tggtgaggcc ctgggcaggt      2100
tggtatcaag gttacaagac aggtttaagg agaccaatag aaactgggca tgtggagaca      2160
gagaagactc ttgggtttct gataggcact gactctctct gcctattggt ctattttccc      2220
acccttaggc tgctggtggt ctaccctttgg acccagaggt tctttgagtc ctttggggat     2280
ctgtccactc ctgatgctgt tatgggcaac cctaaggtga aggctcatgg caagaaagtg      2340
ctcggtgcct ttagtgatgg cctggctcac ctggacaacc tcaagggcac ctttgccaca      2400
ctgagtgagc tgcactgtga caagctgcac gtggatcctg agaacttcag ggtgagtcta      2460
tgggacgct                                                              2469
```

<210> SEQ ID NO 39
<211> LENGTH: 2295
<212> TYPE: DNA
<213> ORGANISM: Artificial Sequence
<220> FEATURE:
<223> OTHER INFORMATION: Synthetic CCR5 SFFV-GFP donor sequence

<400> SEQUENCE: 39

```
aagagagtta attcaatgta gacatctatg taggcaatta aaaacctatt gatgtataaa       60
acagtttgca ttcatggagg gcaactaaat acattctagg actttataaa agatcacttt      120
ttatttatgc acagggtgga acaagatgga ttatcaagtg tcaagtccaa tctatgacat      180
caattattat acatcggagc cctgccaaaa aatcaatgtg aagcaaatcg cagcccgcct      240
cctgcctccg ctctactcac tggtgttcat ctttggtttt gtgggcaaca tgctggtcat      300
cctcatcctg ataaactgca aaaggctgaa gagcatgact gacatctacc tgctcaacct      360
ggccatctct gacctgtttt tccttcttac tgtccccttc tctagaccga taaaataaaa      420
gattttattt agtctccaga aaagggggg aatgaaagac cccacctgta ggtttggcaa      480
gctagctgca gtaacgccat tttgcaaggc atggaaaaat accaaaccaa gaatagagaa      540
gttcagatca agggcgggta catgaaaata gctaacgttg ggccaaacag gatatctgcg      600
gtgagcagtt tcggccccgg ccccggggcca agaacagatg gtcaccgcag tttcggcccc      660
```

```
ggcccgaggc caagaacaga tggtccccag atatggccca accctcagca gtttcttaag    720
acccatcaga tgtttccagg ctcccccaag gacctgaaat gaccctgcgc cttatttgaa    780
ttaaccaatc agcctgcttc tcgcttctgt tcgcgcgctt ctgcttcccg agctctataa    840
aagagctcac aacccctcac tcggcgcgcc agtcctccga cagactgagt cgcccgggtt    900
cgaaggatcc atcgccacca tggtgagcaa gggcgaggag ctgttcaccg gggtggtgcc    960
catcctggtc gagctggacg gcgacgtaaa cggccacaag ttcagcgtgt ccggcgaggg   1020
cgagggcgat gccacctacg gcaagctgac cctgaagttc atctgcacca ccggcaagct   1080
gcccgtgccc tggcccaccc tcgtgaccac cttcggctac ggcctgatgt gcttcgcccg   1140
ctaccccgac cacatgaagc agcacgactt cttcaagtcc gccatgcccg aaggctacgt   1200
ccaggagcgc accatcttct tcaaggacga cggcaactac aagacccgcg ccgaggtgaa   1260
gttcgagggc gacaccctgg tgaaccgcat cgagctgaag ggcatcgact tcaaggagga   1320
cggcaacatc ctggggcaca agctggagta caactacaac agccacaacg tctatatcat   1380
ggccgacaag cagaagaacg gcatcaaggt gaacttcaag atccgccaca acatcgagga   1440
cggcagcgtg cagctcgccg accactacca gcagaacacc cccatcggcg acggccccgt   1500
gctgctgccc gacaaccact acctgagcta ccagtccaag ctgagcaaag accccaacga   1560
gaagcgcgat cacatggtcc tgctggagtt cgtgaccgcc gccgggatca ctctcggcat   1620
ggacgagctg tacaagtaac tcgagggcgc gccccgctga tcagcctcga ctgtgccttc   1680
tagttgccag ccatctgttg tttgcccctc ccccgtgcct tccttgaccc tggaaggtgc   1740
cactcccact gtcctttcct aataaaatga ggaaattgca tcgcattgtc tgagtaggtg   1800
tcattctatt ctggggggtg gggtggggca ggacagcaag ggggaggatt gggaagacaa   1860
tagcaggcat gctggggatg cggtgggcta ctagttgggc tcactatgct gccgcccagt   1920
gggactttgg aaatacaatg tgtcaactct tgacagggct ctattttata ggcttcttct   1980
ctggaatctt cttcatcatc ctcctgacaa tcgataggta cctggctgtc gtccatgctg   2040
tgtttgcttt aaaagccagg acggtcacct ttggggtggt gacaagtgtg atcacttggg   2100
tggtggctgt gtttgcgtct ctcccaggaa tcatctttac cagatctcaa aaagaaggtc   2160
ttcattacac ctgcagctct cattttccat acagtcagta tcaattctgg aagaatttcc   2220
agacattaaa gatagtcatc ttggggctgg tcctgccgct gcttgtcatg gtcatctgct   2280
actcgggaat cctaa                                                    2295
```

<210> SEQ ID NO 40
<211> LENGTH: 3084
<212> TYPE: DNA
<213> ORGANISM: Artificial Sequence
<220> FEATURE:
<223> OTHER INFORMATION: Synthetic IL2RG SFFV-GFP donor (variant 1)

<400> SEQUENCE: 40

```
tgggagaaac accacagaag cagagtgggt tatattctct gggtgagaga ggggagaaa    60 ttgaagctga ttctgaggtt tcaagtctgg gtgactgaga gggtgacgat accattgact    120
gaggtgggga aggcaggaag agaagcagag ttggggaag atgggaagct tgaagctagt    180
attgttgttc ctccatttct agaatatttt tgtattataa gtcacacttc ctcgccagtc    240
tcaacaggga cccagctcag gcagcagcta agggtgggta ttctggtttg gattagatca    300
gaggaaagac agctgtatat gtgcccacag gagccaagac ggtattttcc atcctcccaa    360
```

```
aacagtagag ctttgacaga gatttaaggg tgaccaagtc aaggaagagg catggcatag    420
aacggtgatg tcgggggtgg gggttcagaa cttccattat agaaggtaat gatttagagg    480
agaaggtggt tgagaatggt gctagtggta gtgaacagat ccttcccagg atctaggtgg    540
gctgaggatt tttgagtctg tgacactatt gtatatccag ctttagtttc tgtttaccac    600
cttacagcag cacctaatct cctagaggac ttagcccgtg tcacacagca catatttgcc    660 acccctctg taaagccctg gtttataagg ttctttccac cggaagctat gacagaggaa    720
acgtgtgggt ggggaggggt agtgggtgag ggacccaggt tcctgacaca gacagactac    780
acccagggaa tgaagagcaa gcgcctctag aattaccctg ttatccctac cgataaaata    840
aaagatttta tttagtctcc agaaaaaggg gggaatgaaa gaccccacct gtaggtttgg    900
caagctagct gcagtaacgc cattttgcaa ggcatggaaa ataccaaac caagaataga    960 gaagttcaga tcaagggcgg gtacatgaaa atagctaacg ttgggccaaa caggatatct   1020
gcggtgagca gtttcggccc cggcccgggg ccaagaacag atggtcaccg cagtttcggc   1080
cccggcccga ggccaagaac agatggtccc cagatatggc ccaaccctca gcagtttctt   1140
aagacccatc agatgtttcc aggctccccc aaggacctga atgaccctg cgccttattt   1200 gaattaacca atcagcctgc ttctcgcttc tgttcgcgcg cttctgcttc ccgagctcta   1260 taaagagct cacaacccct cactcggcgc gccagtcctc cgacagactg agtcgcccgg   1320
gggatccatc gccaccatgc ccgccatgaa gatcgagtgc cgcatcaccg caccctgaa   1380 cggcgtggag ttcgagctgg tgggcggcgg agagggcacc cccgagcagg gccgcatgac   1440
caacaagatg aagagcacca aaggcgccct gaccttcagc ccctacctgc tgagccacgt   1500
gatgggctac ggcttctacc acttcggcac ctaccccagc ggctacgaga ccccttcct   1560 gcacgccatc aacaacggcg gctacaccaa cacccgcatc gagaagtacg aggacggcgg   1620
cgtgctgcac gtgagcttca gctaccgcta cgaggccggc cgcgtgatcg cgacttcaa   1680 ggtggtgggc accggcttcc ccgaggacag cgtgatcttc accgacaaga tcatccgcag   1740
caacgccacc gtgagcacc tgcaccccat gggcgataac gtgctggtgg cagcttcgc   1800 ccgcaccttc agcctgcgcg acggcggcta ctacagcttc gtggtggaca gccacatgca   1860
cttcaagagc gccatccacc ccagcatcct gcagaacggg ggccccatgt tcgccttccg   1920
ccgcgtggag gagctgcaca gcaacaccga gctgggcatc gtggagtacc agcacgcctt   1980 caagacccc atcgccttcg ccagatctcg agtctagctc gagggcgcgc cccgctgatc   2040
agcctcgact gtgccttcta gttgccagcc atctgttgtt tgcccctccc ccgtgccttc   2100
cttgaccctg gaaggtgcca ctcccactgt cctttcctaa taaaatgagg aaattgcatc   2160
gcattgtctg agtaggtgtc attctattct ggggggtggg gtgggcagg acagcaaggg   2220 ggaggattgg gaagacaata gcaggcatgc tggggatgcg gtgggctcta tggcttctga   2280
ggcggaaaga acgtttaaac actagtgaag agcaagcgcc atgttgaagc catcattacc   2340
attcacatcc ctcttattcc tgcagctgcc cctgctggga gtgggctga acacgacaat   2400 tctgacgccc aatgggaatg aagacaccac agctggtggg aaatctggga ctggaggggg   2460
ctggtgagaa gggtggctgt gggaagggc cgtacagaga tctggtgcct gccactggcc   2520
attacaatca tgtgggcaga attgaaaagt ggagtgggaa gggcaagggg gagggttccc   2580
tgcctcacgc tacttcttct ttctttcttg tttgtttgtt tctttctttc ttttgaggca   2640
gggtctcact atgttgccta ggctggtctc aaactcctgg cctctagtga tcctcctgcc   2700
tcagcctttc aaagcaccag gattacagac atgagccacc gtgcttggcc tcctccttct   2760
```

| | |
|---|---|
| gaccatcatt tctctttccc tccctgcctt cattttctcc ccaatctaga tttcttcctg | 2820 |
| accactatgc ccactgactc cctcagtgtt tccactctgc ccctcccaga ggttcagtgt | 2880 |
| tttgtgttca atgtcgagta catgaattgc acttggaaca gcagctctga gccccagcct | 2940 |
| accaacctca ctctgcatta ttggtatgag aagggacgag ggggagggga tgaagaagag | 3000 |
| gtgggttgga tcagagacca agagagaggg tagcaagtct cccaggtacc ccactgtttt | 3060 |
| ctcctggggt aagtcataag tcgg | 3084 |

<210> SEQ ID NO 41
<211> LENGTH: 2269
<212> TYPE: DNA
<213> ORGANISM: Artificial Sequence
<220> FEATURE:
<223> OTHER INFORMATION: Synthetic IL2RG SFFV-GFP donor (variant 2)

<400> SEQUENCE: 41

| | |
|---|---|
| gcatggcata gaacggtgat gtcggggtg ggggttcaga acttccatta tagaaggtaa | 60 |
| tgatttagag gagaaggtgg ttgagaatgg tgctagtggt agtgaacaga tccttcccag | 120 |
| gatctaggtg ggctgaggat ttttgagtct gtgacactat tgtatatcca gctttagttt | 180 |
| ctgtttacca ccttacagca gcacctaatc tcctagagga cttagcccgt gtcacacagc | 240 |
| acatatttgc cacaccctct gtaaagccct ggtttataag gttctttcca ccggaagcta | 300 |
| tgacagagga aacgtgtggg tggggagggg tagtgggtga gggacccagg ttcctgacac | 360 |
| agacagacta cacccaggga atgaagagca agcgccatgt agcgcccga taaaataaaa | 420 |
| gattttattt agtctccaga aaaggggggg aatgaaagac cccacctgta ggtttggcaa | 480 |
| gctagctgca gtaacgccat tttgcaaggc atggaaaaat accaaaccaa gaatagagaa | 540 |
| gttcagatca agggcgggta catgaaaata gctaacgttg gccaaacag gatatctgcg | 600 |
| gtgagcagtt tcggccccgg cccgggggcca agaacagatg gtcaccgcag tttcggcccc | 660 |
| ggcccgaggc caagaacaga tggtccccag atatggccca accctcagca gtttcttaag | 720 |
| acccatcaga tgtttccagg ctcccccaag gacctgaaat gaccctgcgc cttatttgaa | 780 |
| ttaaccaatc agcctgcttc tcgcttctgt tcgcgcgctt ctgcttcccg agctctataa | 840 |
| aagagctcac aacccctcac tcggcgcgcc agtcctccga cagactgagt cgcccggggg | 900 |
| ggtaccgagc tcttcgaagg atccatcgcc accatgcccg ccatgaagat cgagtgccgc | 960 |
| atcaccggca ccctgaacgg cgtggagttc gagctggtgg cggcggaga gggcacccc | 1020 |
| gagcagggcc gcatgaccaa caagatgaag agcaccaaag gcgccctgac cttcagcccc | 1080 |
| tacctgctga gccacgtgat gggctacggc ttctaccact tcggcaccta ccccagcggc | 1140 |
| tacgagaacc ccttcctgca cgccatcaac aacggcggct acaccaacac ccgcatcgag | 1200 |
| aagtacgagg acggcggcgt gctgcacgtg agcttcagct accgctacga ggccggccgc | 1260 |
| gtgatcggcg acttcaaggt ggtgggcacc ggcttccccg aggacagcgt gatcttcacc | 1320 |
| gacaagatca tccgcagcaa cgccaccgtg gagcacctgc acccatggg cgataacgtg | 1380 |
| ctggtgggca gcttcgcccg caccttcagc ctgcgcgacg gcggctacta cagcttcgtg | 1440 |
| gtggacagcc acatgcactt caagagcgcc atccacccca gcatcctgca gaacgggggc | 1500 |
| cccatgttcg ccttccgccg cgtggaggag ctgcacagca caccgagct gggcatcgtg | 1560 |
| gagtaccagc acgccttcaa gacccccatc gccttcgcca gatctcgagt ctagttaatt | 1620 |
| aactgtgcct tctagttgcc agccatctgt tgtttgcccc tcccccgtgc cttccttgac | 1680 |

```
cctggaaggt gccactccca ctgtcctttc ctaataaaat gaggaaattg catcgcattg   1740
tctgagtagg tgtcattcta ttctgggggg tggggtgggg caggacagca aggggagga    1800 ttgggaagac aatagcaggc atgctgggga tgcggtgggc tctatggcct gcaggtgaag   1860
ccatcattac cattcacatc cctcttattc ctgcagctgc ccctgctggg agtggggctg   1920
aacacgacaa ttctgacgcc caatgggaat gaagacacca cagctggtgg gaaatctggg   1980
actggagggg gctggtgaga agggtggctg tgggaagggg ccgtacagag atctggtgcc   2040
tgccactggc cattacaatc atgtgggcag aattgaaaag tggagtggga agggcaaggg   2100
ggagggttcc ctgcctcacg ctacttcttc tttctttctt gtttgtttgt ttctttcttt   2160
cttttgaggc agggtctcac tatgttgcct aggctggtct caaactcctg gcctctagtg   2220
atcctcctgc ctcagccttt caaagcacca ggattacaga catgagcca               2269
```

<210> SEQ ID NO 42
<211> LENGTH: 23
<212> TYPE: DNA
<213> ORGANISM: Artificial Sequence
<220> FEATURE:
<223> OTHER INFORMATION: Synthetic HBB sgRNA target sequence

<400> SEQUENCE: 42
cttgccccac agggcagtaa cgg                                              23

<210> SEQ ID NO 43
<211> LENGTH: 23
<212> TYPE: DNA
<213> ORGANISM: Artificial Sequence
<220> FEATURE:
<223> OTHER INFORMATION: Synthetic CCR5 sgRNA target sequence

<400> SEQUENCE: 43
gcagcatagt gagcccagaa ggg                                              23

<210> SEQ ID NO 44
<211> LENGTH: 23
<212> TYPE: DNA
<213> ORGANISM: Artificial Sequence
<220> FEATURE:
<223> OTHER INFORMATION: Synthetic IL2RG sgRNA target sequence

<400> SEQUENCE: 44
tggtaatgat ggcttcaaca tgg                                              23

<210> SEQ ID NO 45
<211> LENGTH: 23
<212> TYPE: DNA
<213> ORGANISM: Artificial Sequence
<220> FEATURE:
<223> OTHER INFORMATION: Synthetic HBB primer sequence

<400> SEQUENCE: 45
ggtgacaatt tctgccaatc agg                                              23

<210> SEQ ID NO 46
<211> LENGTH: 24
<212> TYPE: DNA
<213> ORGANISM: Artificial Sequence
<220> FEATURE:
<223> OTHER INFORMATION: Synthetic HBB primer sequence

<400> SEQUENCE: 46
gaatggtagc tggattgtag ctgc                                             24

<210> SEQ ID NO 47
<211> LENGTH: 23
<212> TYPE: DNA
<213> ORGANISM: Artificial Sequence
<220> FEATURE:
<223> OTHER INFORMATION: Synthetic HBB off-target sgRNA sequence

<400> SEQUENCE: 47
cttgccccac agggcagtaa cgg                                      23

<210> SEQ ID NO 48
<211> LENGTH: 36
<212> TYPE: DNA
<213> ORGANISM: Artificial Sequence
<220> FEATURE:
<223> OTHER INFORMATION: Synthetic HBB variant

<400> SEQUENCE: 48
gtcgagaagt ctgcagtcac tgctctatgg gggaaa                        36

<210> SEQ ID NO 49
<211> LENGTH: 23
<212> TYPE: DNA
<213> ORGANISM: Artificial Sequence
<220> FEATURE:
<223> OTHER INFORMATION: Synthetic HBB off-target site

<400> SEQUENCE: 49
tcagccccac agggcagtaa ggg                                      23

<210> SEQ ID NO 50
<211> LENGTH: 36
<212> TYPE: DNA
<213> ORGANISM: Artificial Sequence
<220> FEATURE:
<223> OTHER INFORMATION: Synthetic HBB allele that has undergone HR

<400> SEQUENCE: 50
gtcgagaagt ctgcagtcac tgctctatgg gggaaa                        36

<210> SEQ ID NO 51
<211> LENGTH: 98
<212> TYPE: DNA
<213> ORGANISM: Artificial Sequence
<220> FEATURE:
<223> OTHER INFORMATION: Synthetic wild-type HBB allele

<400> SEQUENCE: 51
tcaaacagac accatggtgc acctgactcc tgaggagaag tctgccgtta ctgccctgtg    60
gggcaagtga acgtggatga agttggtggt gaggccct                            98

<210> SEQ ID NO 52
<211> LENGTH: 95
<212> TYPE: DNA
<213> ORGANISM: Artificial Sequence
<220> FEATURE:
<223> OTHER INFORMATION: Synthetic HBB Variant

<400> SEQUENCE: 52
tcaaacagac accatggtgc acctgactcc tgaggagaag tctgccgtta ccctgtgggg    60
caagtgaacg tggatgaagt tggtggtgag gccct                               95

<210> SEQ ID NO 53

```
<211> LENGTH: 89
<212> TYPE: DNA
<213> ORGANISM: Artificial Sequence
<220> FEATURE:
<223> OTHER INFORMATION: Synthetic HBB Variant

<400> SEQUENCE: 53
tcaaacagac accatggtgc acctgactcc tgaggagaag tctgccctgt ggggcaagtg      60
aacgtggatg aagttggtgg tgaggccct                                        89

<210> SEQ ID NO 54
<211> LENGTH: 95
<212> TYPE: DNA
<213> ORGANISM: Artificial Sequence
<220> FEATURE:
<223> OTHER INFORMATION: Synthetic HBB Variant

<400> SEQUENCE: 54
tcaaacagac accatggtgc acctgactcc tgaggagaag tctgccgttta ccctgtgggg    60 caagtgaacg tggatgaagt tggtggtgag gccct                                 95

<210> SEQ ID NO 55
<211> LENGTH: 94
<212> TYPE: DNA
<213> ORGANISM: Artificial Sequence
<220> FEATURE:
<223> OTHER INFORMATION: Synthetic HBB Variant

<400> SEQUENCE: 55
tcaaacagac accatggtgc acctgactcc tgaggagaag tctgccgtgc cctgtggggc      60
aagtgaacgt ggatgaagtt ggtggtgagg ccct                                  94

<210> SEQ ID NO 56
<211> LENGTH: 95
<212> TYPE: DNA
<213> ORGANISM: Artificial Sequence
<220> FEATURE:
<223> OTHER INFORMATION: Synthetic HBB Variant

<400> SEQUENCE: 56
tcaaacagac accatggtgc acctgactcc tgaggagaag tctgccgttg ccctgtgggg      60
caagtgaacg tggatgaagt tggtggtgag gccct                                 95

<210> SEQ ID NO 57
<211> LENGTH: 90
<212> TYPE: DNA
<213> ORGANISM: Artificial Sequence
<220> FEATURE:
<223> OTHER INFORMATION: Synthetic HBB Variant

<400> SEQUENCE: 57
tcaaacagac accatggtgc acctgactcc tgaggagaag tctgccccctg tggggcaagt    60 gaacgtggat gaagttggtg gtgaggccct                                       90

<210> SEQ ID NO 58
<211> LENGTH: 85
<212> TYPE: DNA
<213> ORGANISM: Artificial Sequence
<220> FEATURE:
<223> OTHER INFORMATION: Synthetic HBB Variant
```

<400> SEQUENCE: 58
tcaaacagac accatggtgc acctgactcc tgaggagaag tctgccgtta caagtgaacg    60
tggatgaagt tggtggtgag gccct    85

<210> SEQ ID NO 59
<211> LENGTH: 97
<212> TYPE: DNA
<213> ORGANISM: Artificial Sequence
<220> FEATURE:
<223> OTHER INFORMATION: Synthetic HBB Variant

<400> SEQUENCE: 59
tcaaacagac accatggtgc acctgactcc tgaggagaag tctgccgtta tgccctgtgg    60
ggcaagtgaa cgtggatgaa gttggtggtg aggccct    97

<210> SEQ ID NO 60
<211> LENGTH: 97
<212> TYPE: DNA
<213> ORGANISM: Artificial Sequence
<220> FEATURE:
<223> OTHER INFORMATION: Synthetic HBB Variant

<400> SEQUENCE: 60
tcaaacagac accatggtgc acctgactcc tgaggagaag tctgccgtac tgccctgtgg    60
ggcaagtgaa cgtggatgaa gttggtggtg aggccct    97

<210> SEQ ID NO 61
<211> LENGTH: 87
<212> TYPE: DNA
<213> ORGANISM: Artificial Sequence
<220> FEATURE:
<223> OTHER INFORMATION: Synthetic HBB Variant

<400> SEQUENCE: 61
tcaaacagac accatggtgc acctgactcc tgaggagaag tctgccgtgg ggcaagtgaa    60
cgtggatgaa gttggtggtg aggccct    87

<210> SEQ ID NO 62
<211> LENGTH: 89
<212> TYPE: DNA
<213> ORGANISM: Artificial Sequence
<220> FEATURE:
<223> OTHER INFORMATION: Synthetic HBB Variant

<400> SEQUENCE: 62
tcaaacagac accatggtgc acctgactcc tgaggagaag tctgccctgt ggggcaagtg    60
aacgtggatg aagttggtgg tgaggccct    89

<210> SEQ ID NO 63
<211> LENGTH: 90
<212> TYPE: DNA
<213> ORGANISM: Artificial Sequence
<220> FEATURE:
<223> OTHER INFORMATION: Synthetic HBB Variant

<400> SEQUENCE: 63
tcaaacagac accatggtgc acctgactcc tgaggagaag tcttgccctg tggggcaagt    60
gaacgtggat gaagttggtg gtgaggccct    90

<210> SEQ ID NO 64

```
<211> LENGTH: 96
<212> TYPE: DNA
<213> ORGANISM: Artificial Sequence
<220> FEATURE:
<223> OTHER INFORMATION: Synthetic HBB Variant

<400> SEQUENCE: 64
tcaaacagac accatggtgc acctgactcc tgaggagaag tctgccgtta gccctgtggg    60
gcaagtgaac gtggatgaag ttggtggtga ggccct                              96

<210> SEQ ID NO 65
<211> LENGTH: 92
<212> TYPE: DNA
<213> ORGANISM: Artificial Sequence
<220> FEATURE:
<223> OTHER INFORMATION: Synthetic HBB Variant

<400> SEQUENCE: 65
tcaaacagac accatggtgc acctgactcc tgaggagaag tctgccgtta tgtggggcaa    60
gtgaacgtgg atgaagttgg tggtgaggcc ct                                  92

<210> SEQ ID NO 66
<211> LENGTH: 89
<212> TYPE: DNA
<213> ORGANISM: Artificial Sequence
<220> FEATURE:
<223> OTHER INFORMATION: Synthetic HBB Variant

<400> SEQUENCE: 66
tcaacagaca catggtgcac ctgactcctg aggagaagtc aatgcctgtg gggcaaggtg    60
aacgtggatg aagttggtgg tgaggccct                                      89

<210> SEQ ID NO 67
<211> LENGTH: 97
<212> TYPE: DNA
<213> ORGANISM: Artificial Sequence
<220> FEATURE:
<223> OTHER INFORMATION: Synthetic HBB Variant

<400> SEQUENCE: 67
tcaaacagac accatggtgc acctgactcc tgaggagaag tctgccgttc tgccctgtgg    60
ggcaagtgaa cgtggatgaa gttggtggtg aggccct                             97

<210> SEQ ID NO 68
<211> LENGTH: 92
<212> TYPE: DNA
<213> ORGANISM: Artificial Sequence
<220> FEATURE:
<223> OTHER INFORMATION: Synthetic HBB Variant

<400> SEQUENCE: 68
tcaaacagac accatggtgc acctgactcc tgaggagaag tctgctgccc tgtggggcaa    60
gtgaacgtgg atgaagttgg tggtgaggcc ct                                  92

<210> SEQ ID NO 69
<211> LENGTH: 97
<212> TYPE: DNA
<213> ORGANISM: Artificial Sequence
<220> FEATURE:
<223> OTHER INFORMATION: Synthetic HBB Variant
```

<400> SEQUENCE: 69
tcaacagaca ccatggtgca cctgactcct gaggagaact ctgccggctg ccctgtgggg    60
caaggtgaac gtggatgaag ttggtggtga ggcccct    97

<210> SEQ ID NO 70
<211> LENGTH: 29
<212> TYPE: DNA
<213> ORGANISM: Artificial Sequence
<220> FEATURE:
<223> OTHER INFORMATION: Synthetic Construct

<400> SEQUENCE: 70
tatttgtgta ataagaaaat tgggaaaac    29

<210> SEQ ID NO 71
<211> LENGTH: 31
<212> TYPE: DNA
<213> ORGANISM: Artificial Sequence
<220> FEATURE:
<223> OTHER INFORMATION: Synthetic Construct

<400> SEQUENCE: 71
gttactgccc attaccctgt tatccctacc g    31

<210> SEQ ID NO 72
<211> LENGTH: 36
<212> TYPE: DNA
<213> ORGANISM: Artificial Sequence
<220> FEATURE:
<223> OTHER INFORMATION: Synthetic Construct

<400> SEQUENCE: 72
gtggagaagt ctgccgttac tgccctgtgg ggcaag    36

<210> SEQ ID NO 73
<211> LENGTH: 36
<212> TYPE: DNA
<213> ORGANISM: Artificial Sequence
<220> FEATURE:
<223> OTHER INFORMATION: Synthetic Construct

<400> SEQUENCE: 73
gaggaaaaat ccgcagtcac tgccctgtgg ggcaag    36

<210> SEQ ID NO 74
<211> LENGTH: 455
<212> TYPE: DNA
<213> ORGANISM: Artificial Sequence
<220> FEATURE:
<223> OTHER INFORMATION: Synthetic Construct

<400> SEQUENCE: 74
catggtgcac ctgactcctg aagaaaaatc cgctgtcaca gccctctggg ataaggtcaa    60
cgtcgatgcc gtcggcggcg aagctctcgg aagactcctc ggtcgtgtat ccctggacac   120
aaagattttt cgaaagcttc ggcgacctca gcaccccga cgccgtgatg ggaaatccca   180
aagtcaaagc ccacggaaaa aaaggtcctg ggcgctttca gcgacggact cgcccatctc   240
gataatctga aggaacatt cgctcagctc agcgaactcc attgcgataa actccatgtc   300 gaccccgaa aatttagac tgctcggaaa tgtcctcgtg tgcgtcctcg ctcaccattt   360

```
cggaaaggag tttacacccc ctgtccaagc cgcttaccaa aagggtcgtt gccggcgtcg    420
ccaacgctct cgctcataaa taccattgac tgtgc                              455
```